(12) United States Patent
Wohlstadter et al.

(10) Patent No.: US 11,733,254 B2
(45) Date of Patent: Aug. 22, 2023

(54) INTEGRATED CONSUMABLE DATA MANAGEMENT SYSTEM AND PLATFORM

(71) Applicant: Meso Scale Technologies, LLC., Rockville, MD (US)

(72) Inventors: Jacob N. Wohlstadter, Potomac, MD (US); Peter J. Bosco, Rockville, MD (US); Kin Ng, New Carrollton, MD (US); Xinri Cong, Germantown, MD (US); Don E. Krueger, Stafford, VA (US); Pei-Ming Wu, Potomac, MD (US); Kim-Xuan Nguyen, Montgomery Village, MD (US); Louis W. Pang, Sandy Spring, MD (US); Michael L. Vock, Loveland, OH (US); Jon Willoughby, Potomac, MD (US); Lei Wang, Clarksville, MD (US)

(73) Assignee: MESO SCALE TECHNOLOGIES, LLC., Rockville, MD (US)

( * ) Notice: Subject to any disclaimer, the term of this patent is extended or adjusted under 35 U.S.C. 154(b) by 0 days.

(21) Appl. No.: 17/679,663

(22) Filed: Feb. 24, 2022

(65) Prior Publication Data
US 2022/0365106 A1    Nov. 17, 2022

Related U.S. Application Data

(63) Continuation of application No. 15/746,688, filed as application No. PCT/US2016/043755 on Jul. 22, 2016, now Pat. No. 11,300,579.
(Continued)

(51) Int. Cl.
*G01N 35/00* (2006.01)
*B01L 3/00* (2006.01)
(Continued)

(52) U.S. Cl.
CPC ...... *G01N 35/0099* (2013.01); *B01L 3/50853* (2013.01); *B01L 9/523* (2013.01);
(Continued)

(58) Field of Classification Search
None
See application file for complete search history.

(56) References Cited

U.S. PATENT DOCUMENTS

| 5,357,095 A | 10/1994 | Weyrauch et al. |
| 2004/0014097 A1 | 1/2004 | McGlennen et al. |

(Continued)

FOREIGN PATENT DOCUMENTS

| CN | 1157924 A | 8/1997 |
| CN | 1985173 A | 6/2007 |

(Continued)

OTHER PUBLICATIONS

O'Hara et al., "Ligand Binding Assays in the 21st Century Laboratory: Recommendations for Characterization and Supply of Critical Reagents," The AAPS Journal 14(2):316-328 (2012).
(Continued)

*Primary Examiner* — Kristy A Haupt
(74) *Attorney, Agent, or Firm* — Medler Ferro Woodhouse & Mills/MSD

(57) ABSTRACT

The present invention relates to methods, devices and systems for associating consumable data with an assay consumable used in a biological assay. Provided are assay systems and associated consumables, wherein the assay system adjusts one or more steps of an assay protocol based on consumable data specific for that consumable. Various types of consumable data are described, as well as methods of using such data in the conduct of an assay by an assay system. The present invention also relates to consumables (e.g., kits and reagent containers), software, data deployable
(Continued)

bundles, computer-readable media, loading carts, instruments, systems, and methods, for performing automated biological assays.

33 Claims, 150 Drawing Sheets

Related U.S. Application Data

(60) Provisional application No. 62/195,956, filed on Jul. 23, 2015.

(51) Int. Cl.
| | | |
|---|---|---|
| *B01L 9/00* | (2006.01) | |
| *G16H 40/67* | (2018.01) | |
| *G16H 10/40* | (2018.01) | |
| *G16H 40/40* | (2018.01) | |
| *F24F 11/30* | (2018.01) | |
| *G06K 7/14* | (2006.01) | |
| *G06Q 10/087* | (2023.01) | |
| *G06Q 10/10* | (2023.01) | |
| *H04B 1/3827* | (2015.01) | |

(52) U.S. Cl.
CPC ............ *F24F 11/30* (2018.01); *G06K 7/1413* (2013.01); *G06Q 10/087* (2013.01); *G06Q 10/10* (2013.01); *G16H 10/40* (2018.01); *G16H 40/40* (2018.01); *G16H 40/67* (2018.01); *B01L 2200/143* (2013.01); *B01L 2300/021* (2013.01); *G01N 2035/00356* (2013.01); *G05B 2219/40269* (2013.01); *H04B 1/3827* (2013.01)

(56) References Cited

U.S. PATENT DOCUMENTS

| | | |
|---|---|---|
| 2004/0072195 A1 | 4/2004 | Hunkapiller et al. |
| 2004/0151628 A1 | 8/2004 | Honkanen et al. |
| 2005/0072030 A1 | 4/2005 | Wu |
| 2007/0244897 A1 | 10/2007 | Voskuil et al. |
| 2009/0117620 A1 | 5/2009 | Fritchie et al. |
| 2010/0081583 A1 | 4/2010 | Shirazi |
| 2010/0322822 A1 | 12/2010 | Fritchie et al. |
| 2011/0009297 A1 | 1/2011 | Jones et al. |
| 2011/0022331 A1 | 1/2011 | Clinton et al. |
| 2011/0143947 A1 | 6/2011 | Chamberlin et al. |
| 2011/0223062 A1 | 9/2011 | Minemura et al. |
| 2012/0118954 A1 | 5/2012 | Hagen et al. |
| 2012/0190591 A1 | 7/2012 | Wohlstadter et al. |
| 2013/0092704 A1 | 4/2013 | Tincher et al. |
| 2014/0053952 A1 | 2/2014 | Genosar |
| 2014/0252088 A1* | 9/2014 | Cong ............... G01N 35/0099 235/382 |
| 2015/0057962 A1 | 2/2015 | Morita et al. |
| 2015/0093834 A1* | 4/2015 | Knecht ............. G01N 35/0099 422/63 |
| 2019/0391170 A1 | 12/2019 | Kochar et al. |

FOREIGN PATENT DOCUMENTS

| | | |
|---|---|---|
| CN | 203432984 U | 2/2014 |
| EP | 3329277 A1 | 6/2018 |
| JP | 60-20450 S | 2/1985 |
| JP | H08266267 A | 10/1996 |
| JP | H09127123 A | 5/1997 |
| JP | 2004-170159 A | 6/2004 |
| JP | 2004-219152 A | 8/2004 |
| JP | 2005-515785 A | 6/2005 |
| JP | 2009-510399 A | 3/2009 |
| JP | 2013-500496 A | 1/2013 |
| JP | 2013-532873 A | 8/2013 |
| JP | 2013-542450 A | 11/2013 |
| JP | 2013-545435 A | 12/2013 |
| JP | 2014-186038 A | 10/2014 |
| JP | 2015-514998 A | 5/2015 |
| JP | 2016-513975 A | 5/2016 |
| WO | 2010056903 A1 | 5/2010 |
| WO | 2012015809 A2 | 2/2012 |
| WO | 2013168441 A1 | 11/2013 |
| WO | 2015072941 A1 | 5/2015 |
| WO | 2015086313 A1 | 6/2015 |
| WO | 2016049571 A1 | 3/2016 |
| WO | 2017015636 A1 | 1/2017 |
| WO | 2018017156 A1 | 1/2018 |

OTHER PUBLICATIONS

Any reference or information that is not included with this Information Disclosure Statement can be found in U.S. Appl. No. 15/746,688 to which this application claims priority.

* cited by examiner

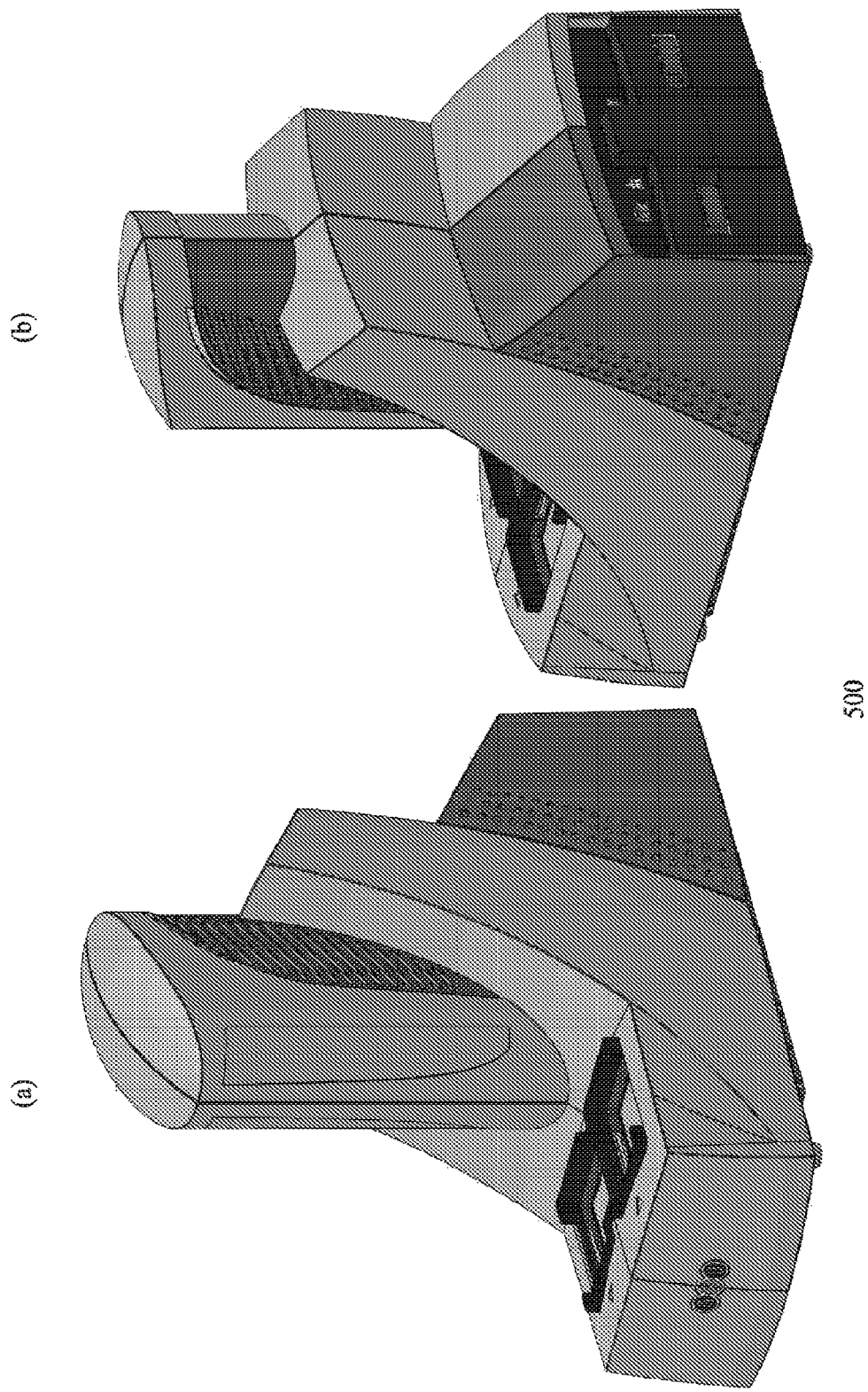
Fig. 5(a)-(b)

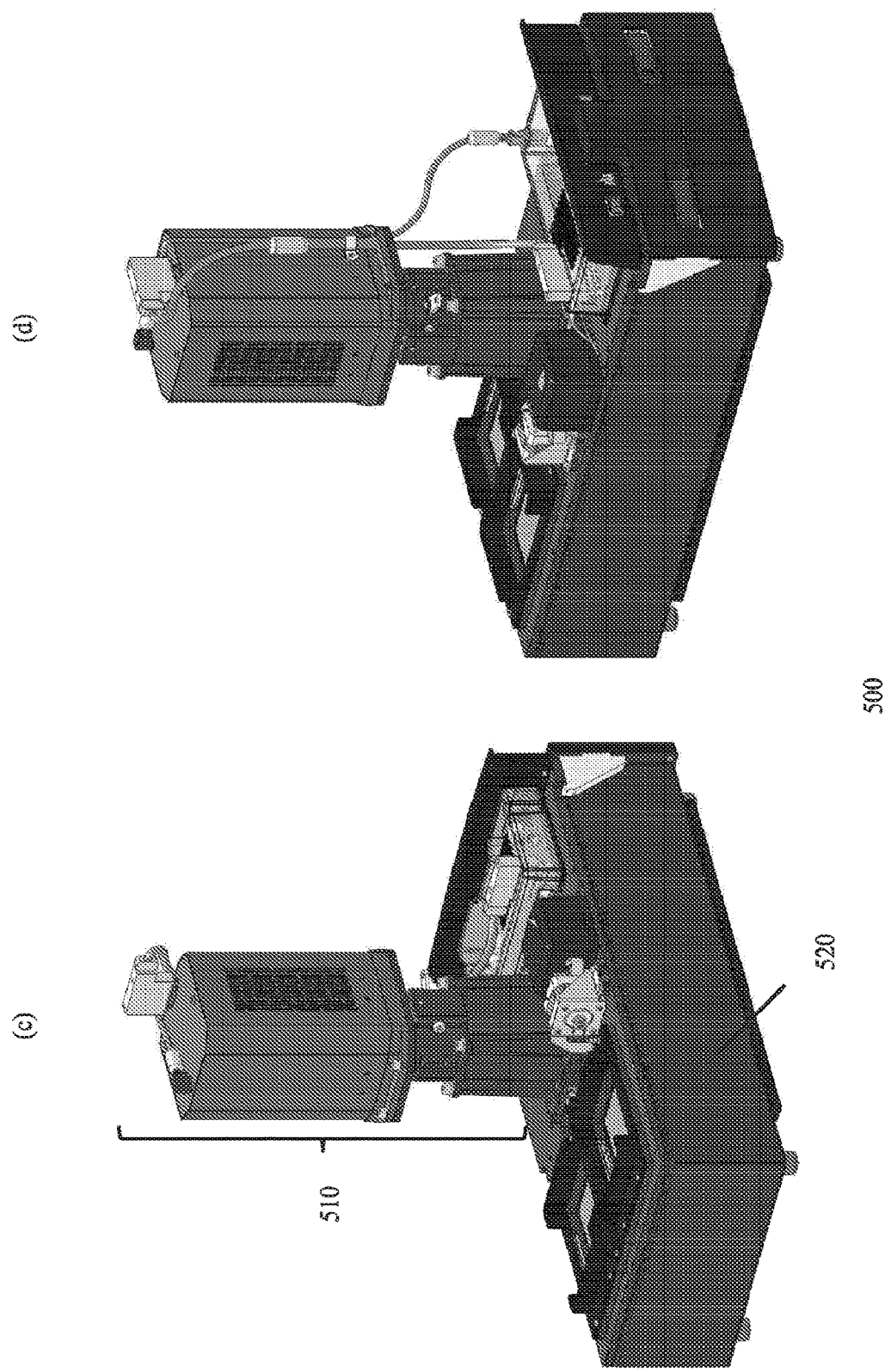
Fig. 5(c)-(d)

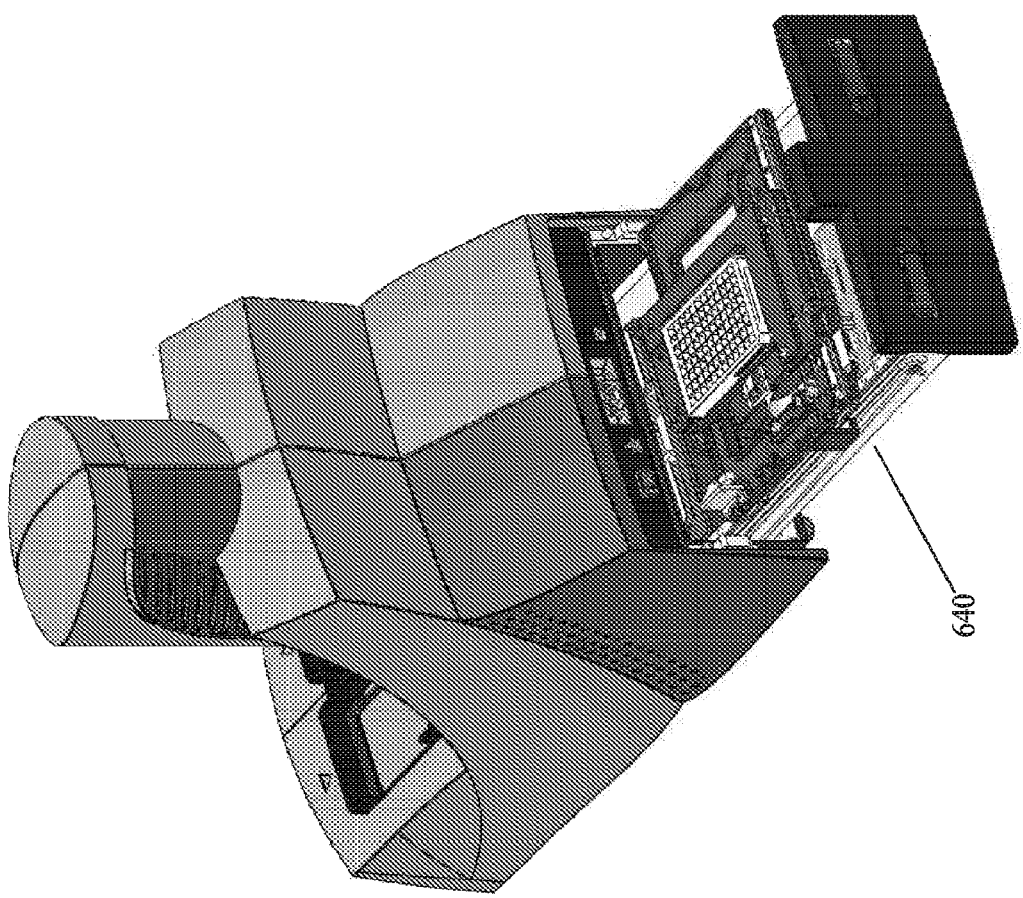

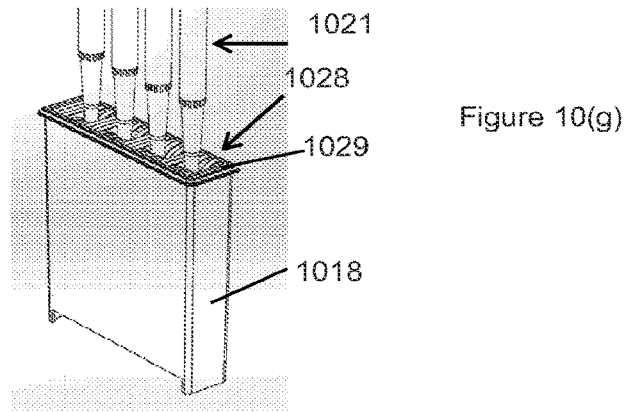
Figure 10(g)
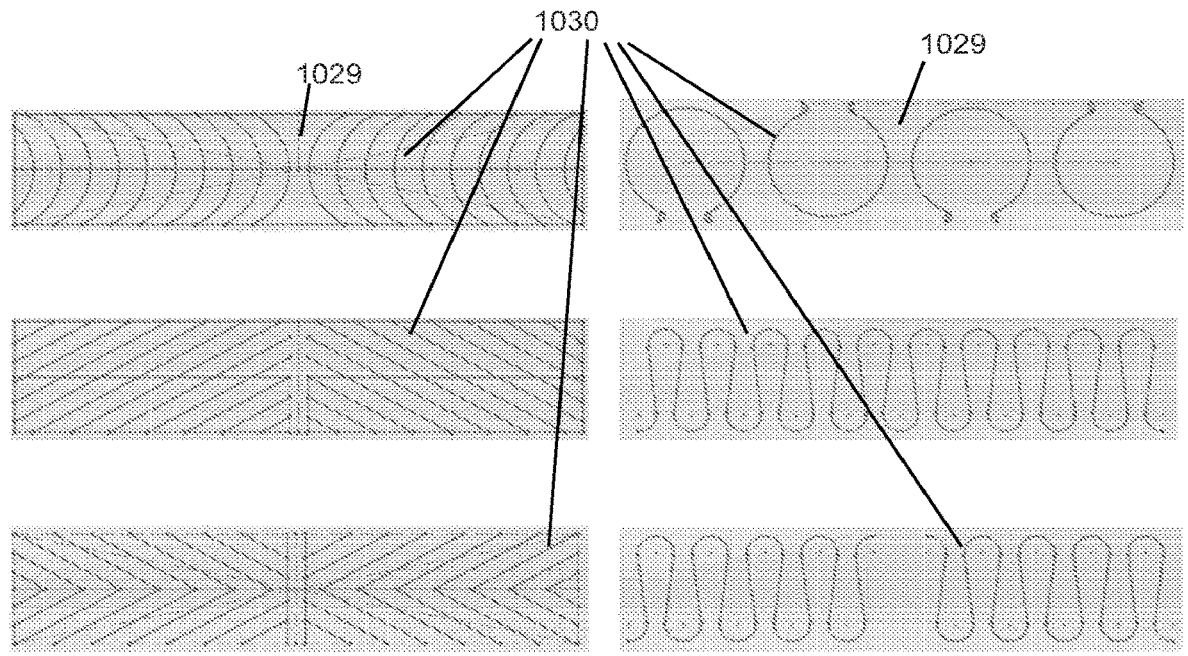
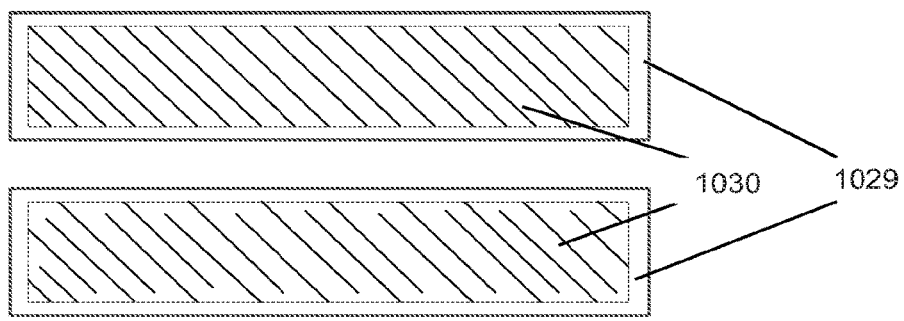
Figure 10(h)

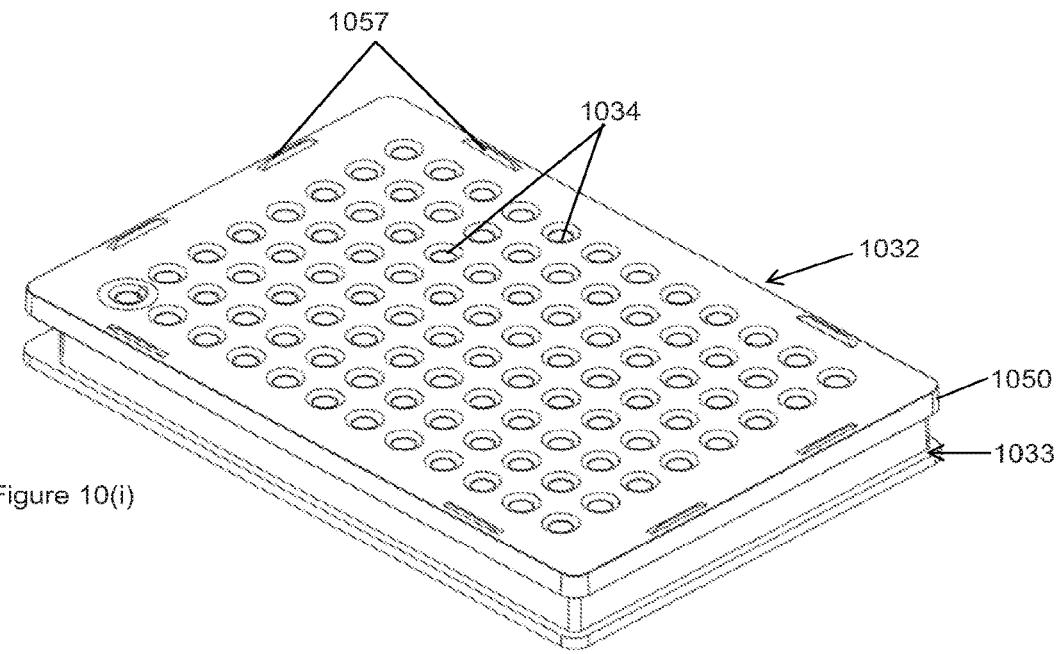
Figure 10(i)
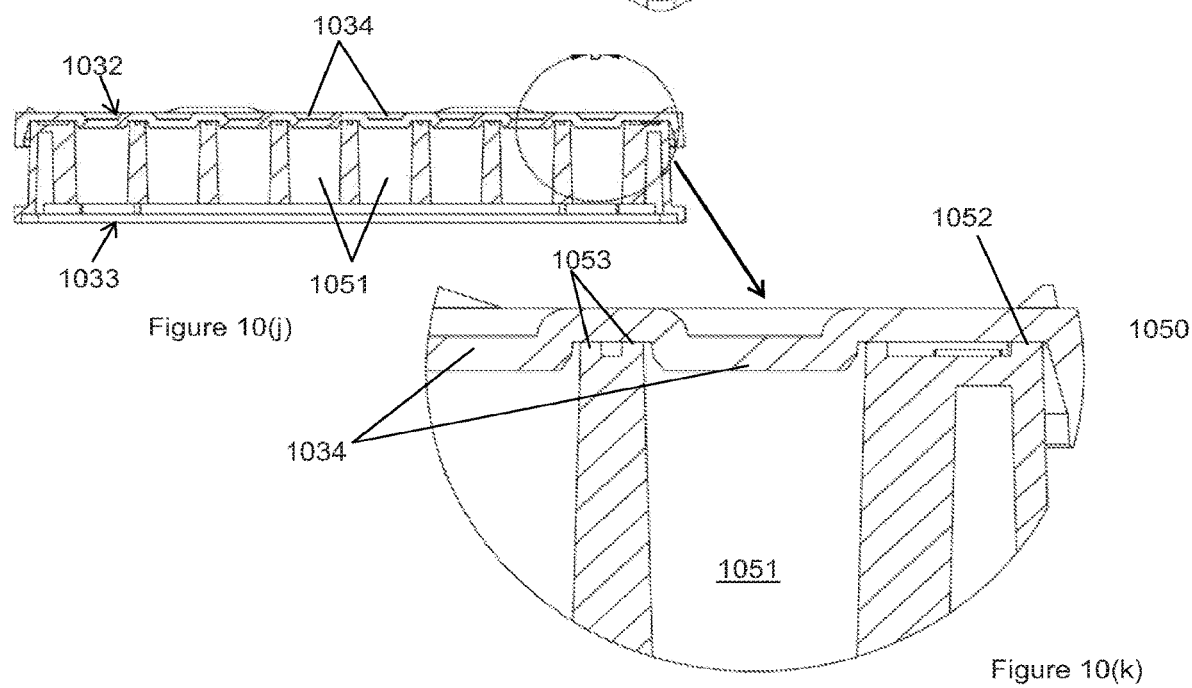
Figure 10(j)
Figure 10(k)

Figure 10(m) Side view

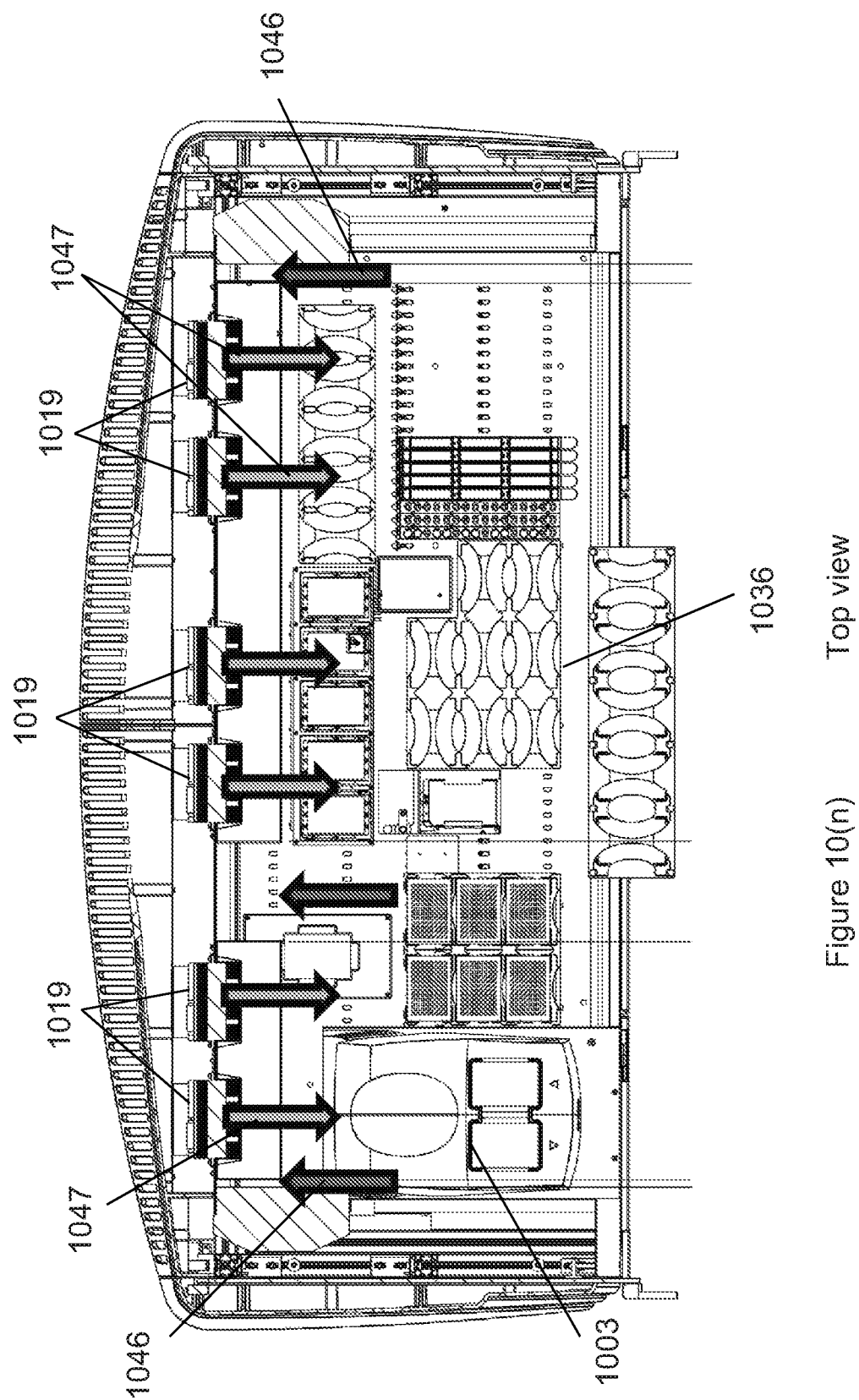
Figure 10(n) Top view

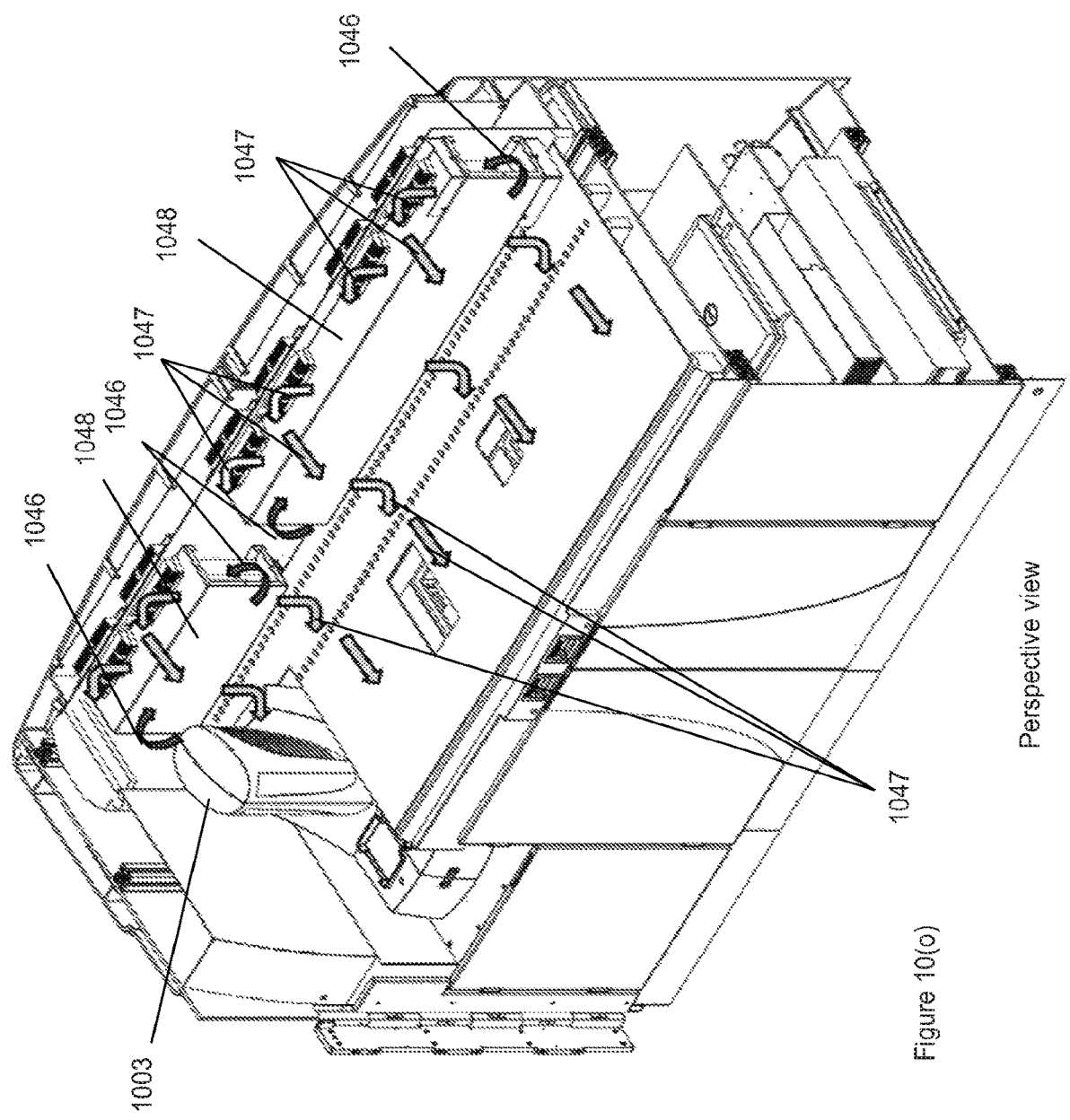
Figure 10(o) Perspective view

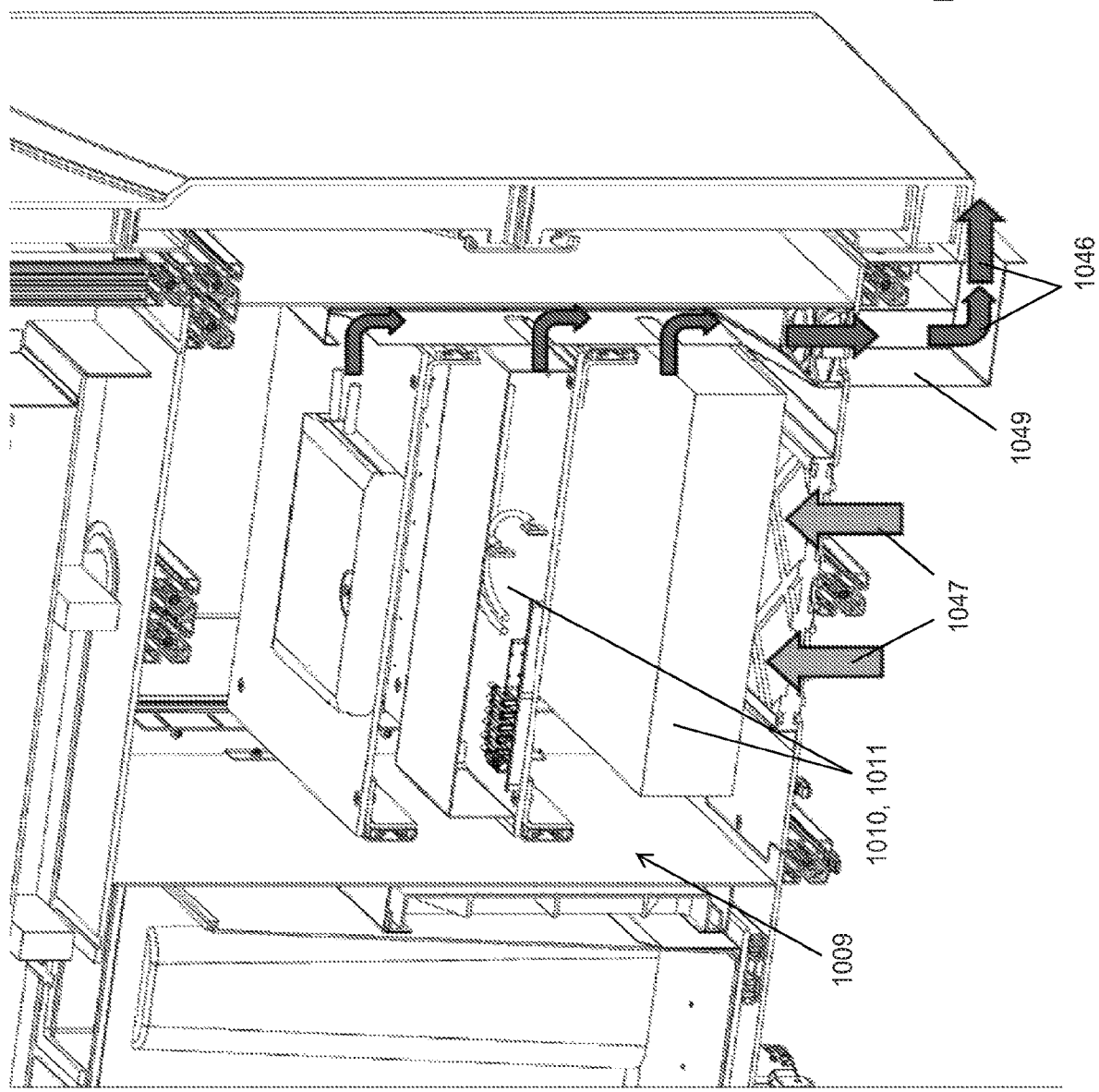

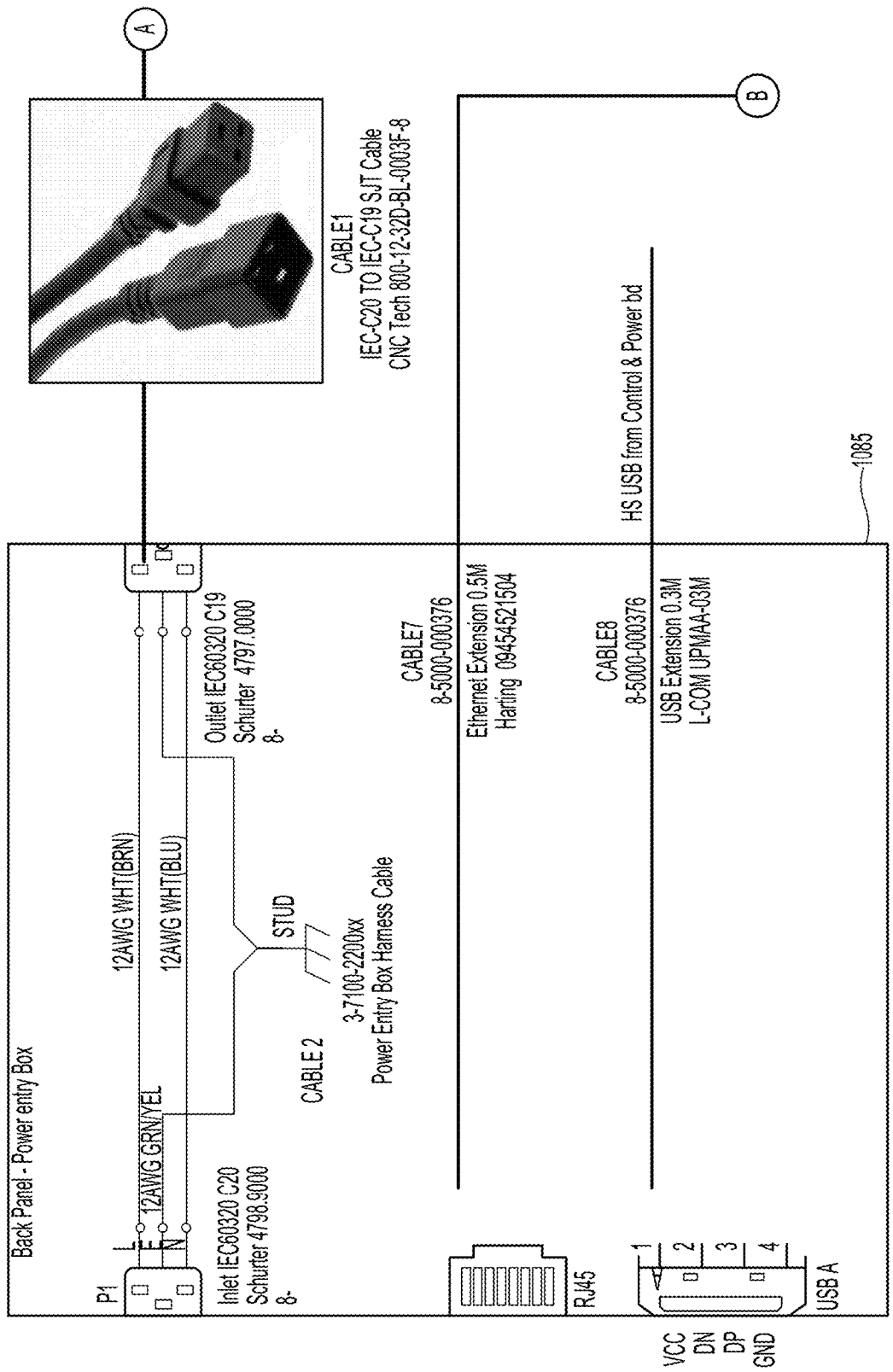
Fig. 10V-a

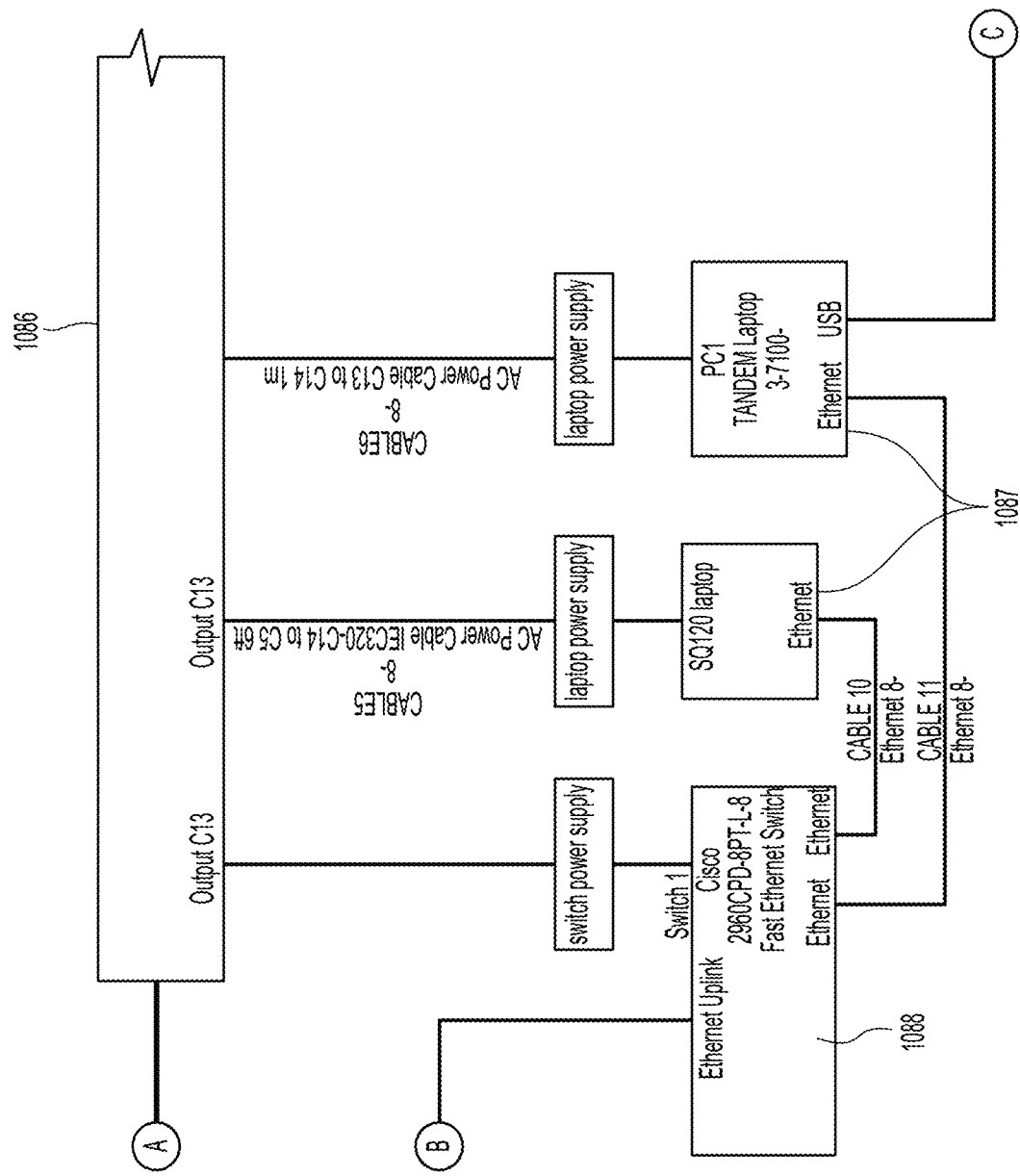
Fig. 10V-b

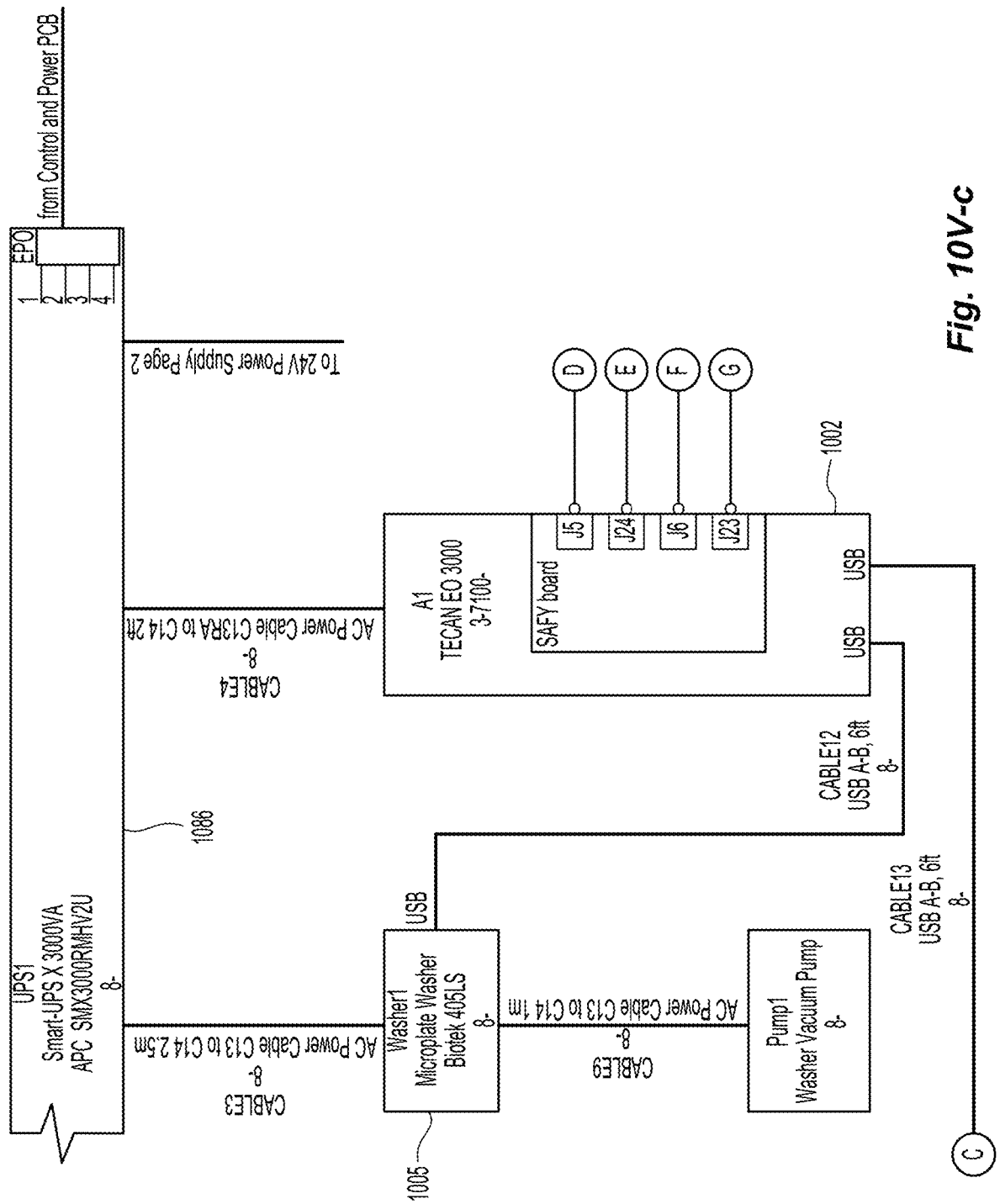
Fig. 10V-c

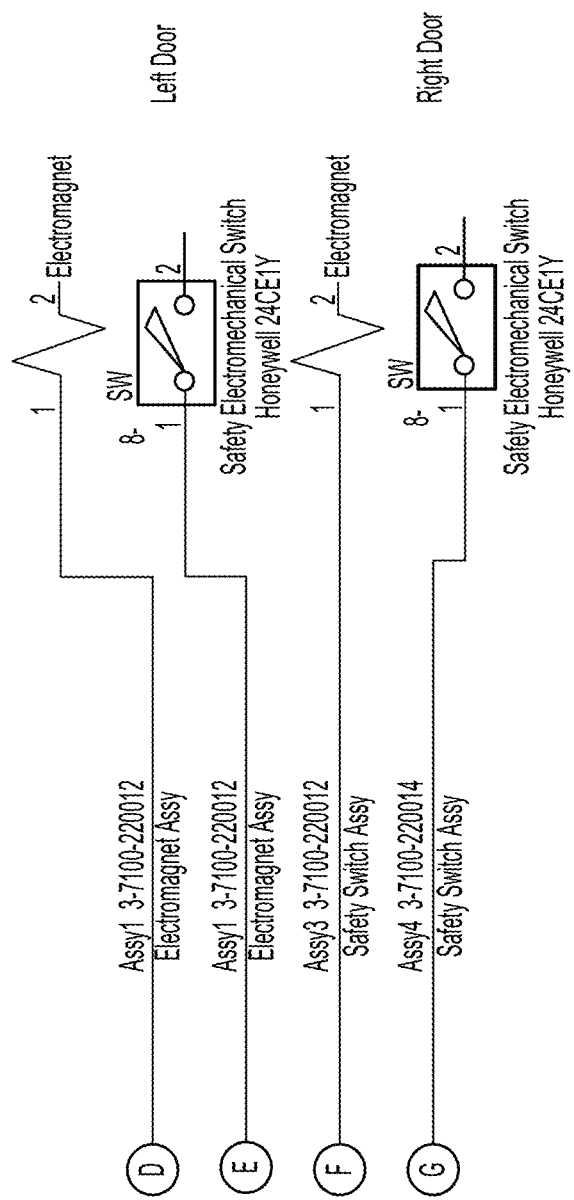
Fig. 10V-d

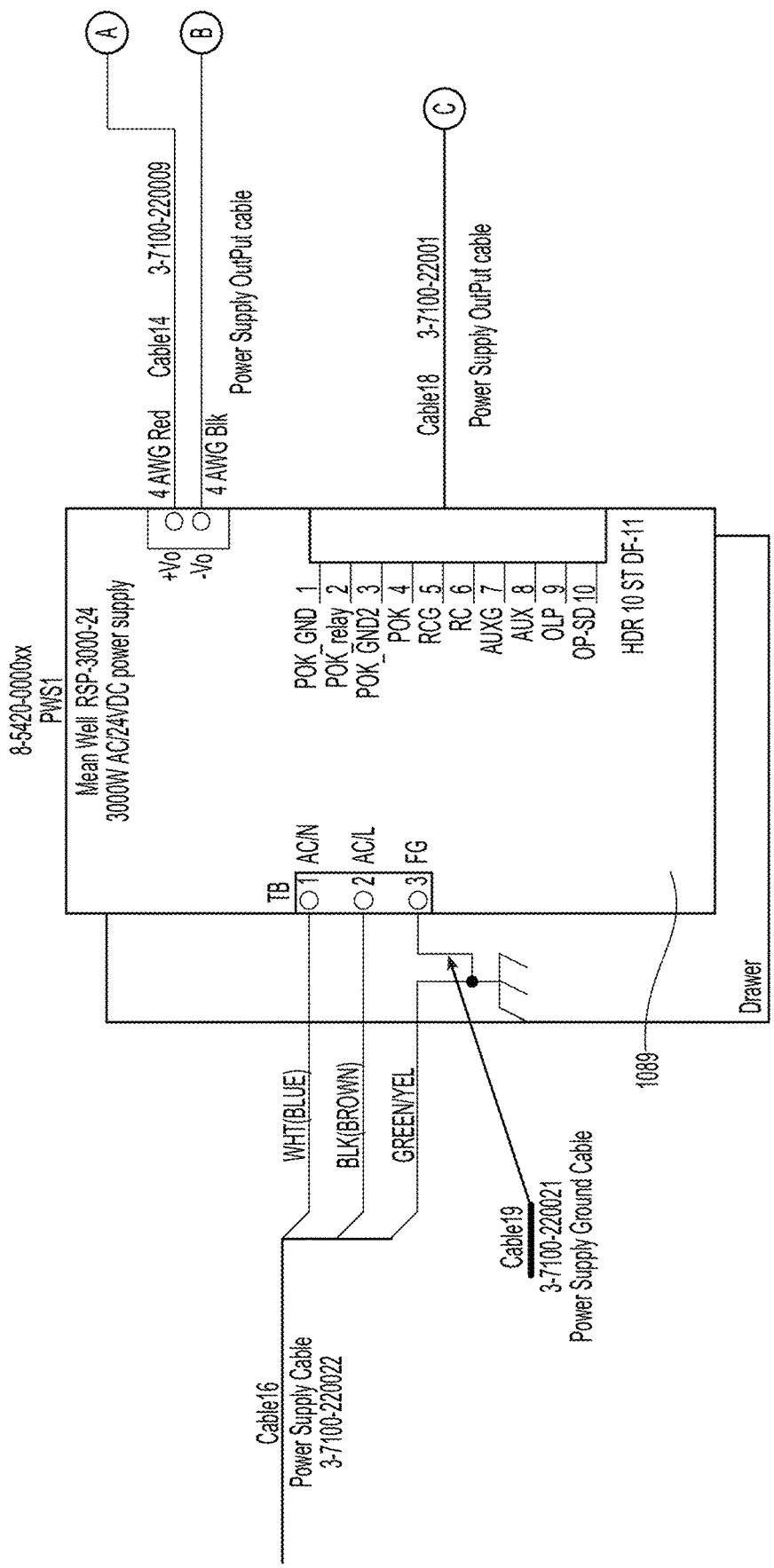
Fig. 10W-a

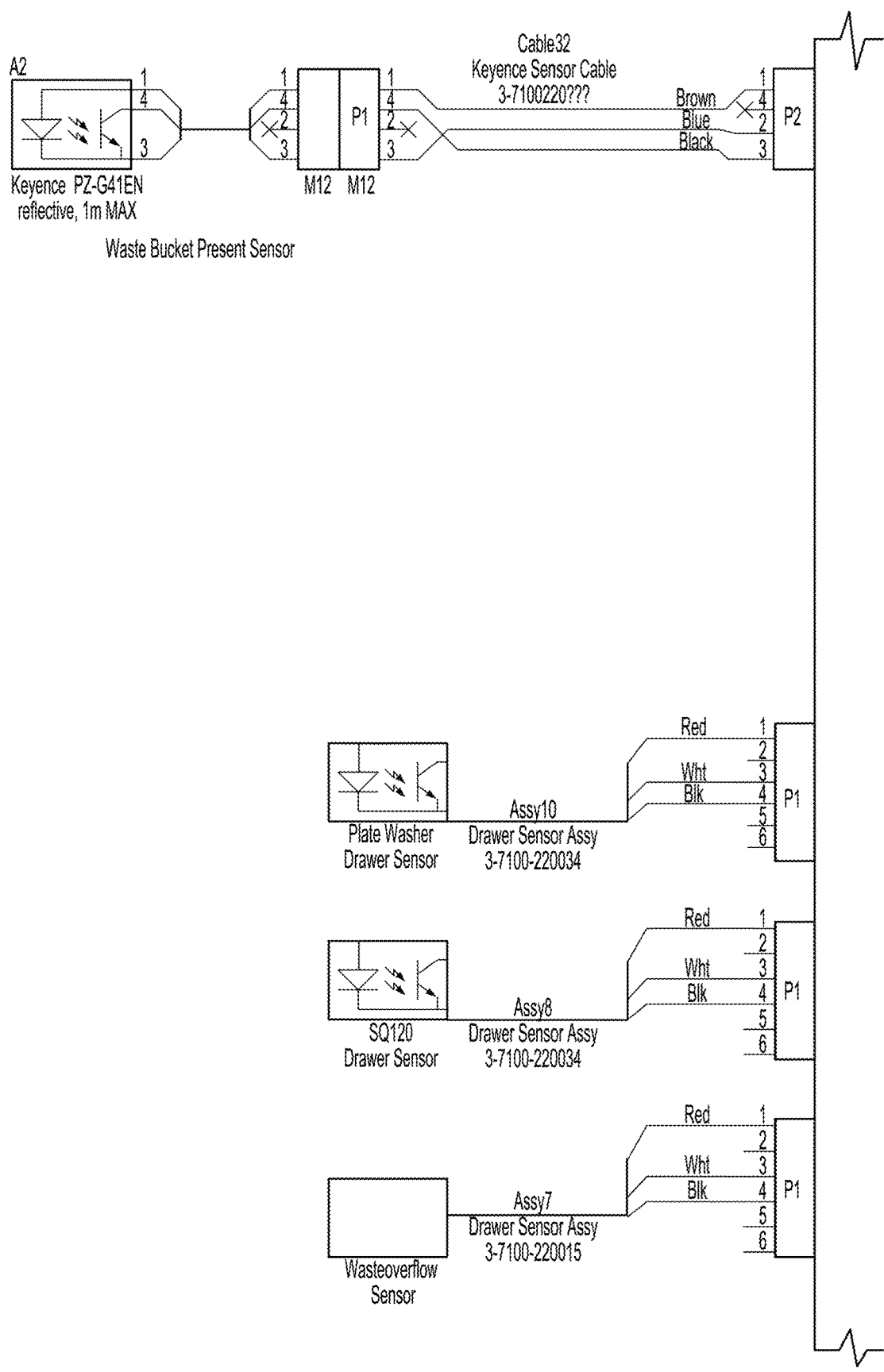
Fig. 10W-b

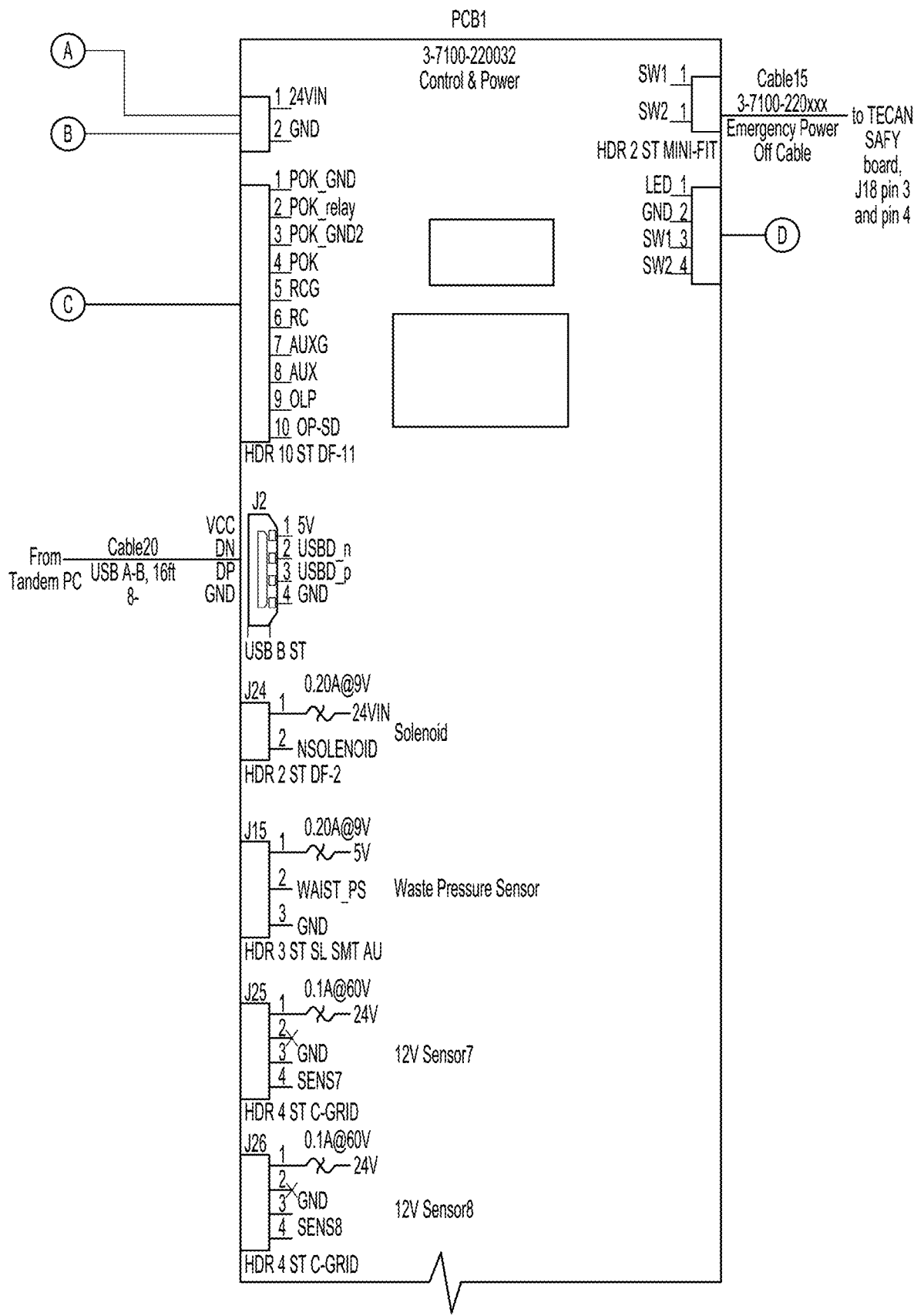
Fig. 10W-c

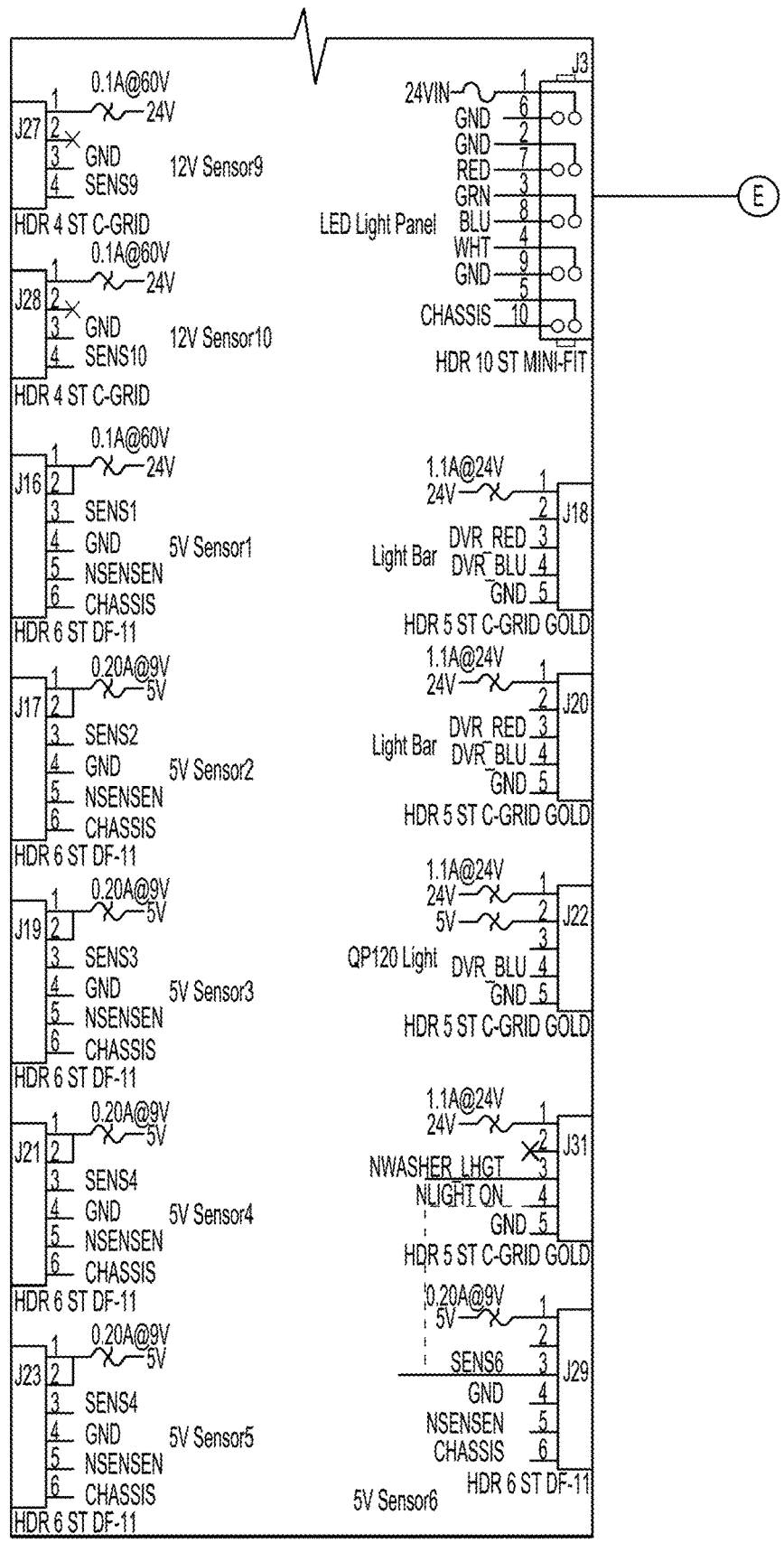
Fig. 10W-d

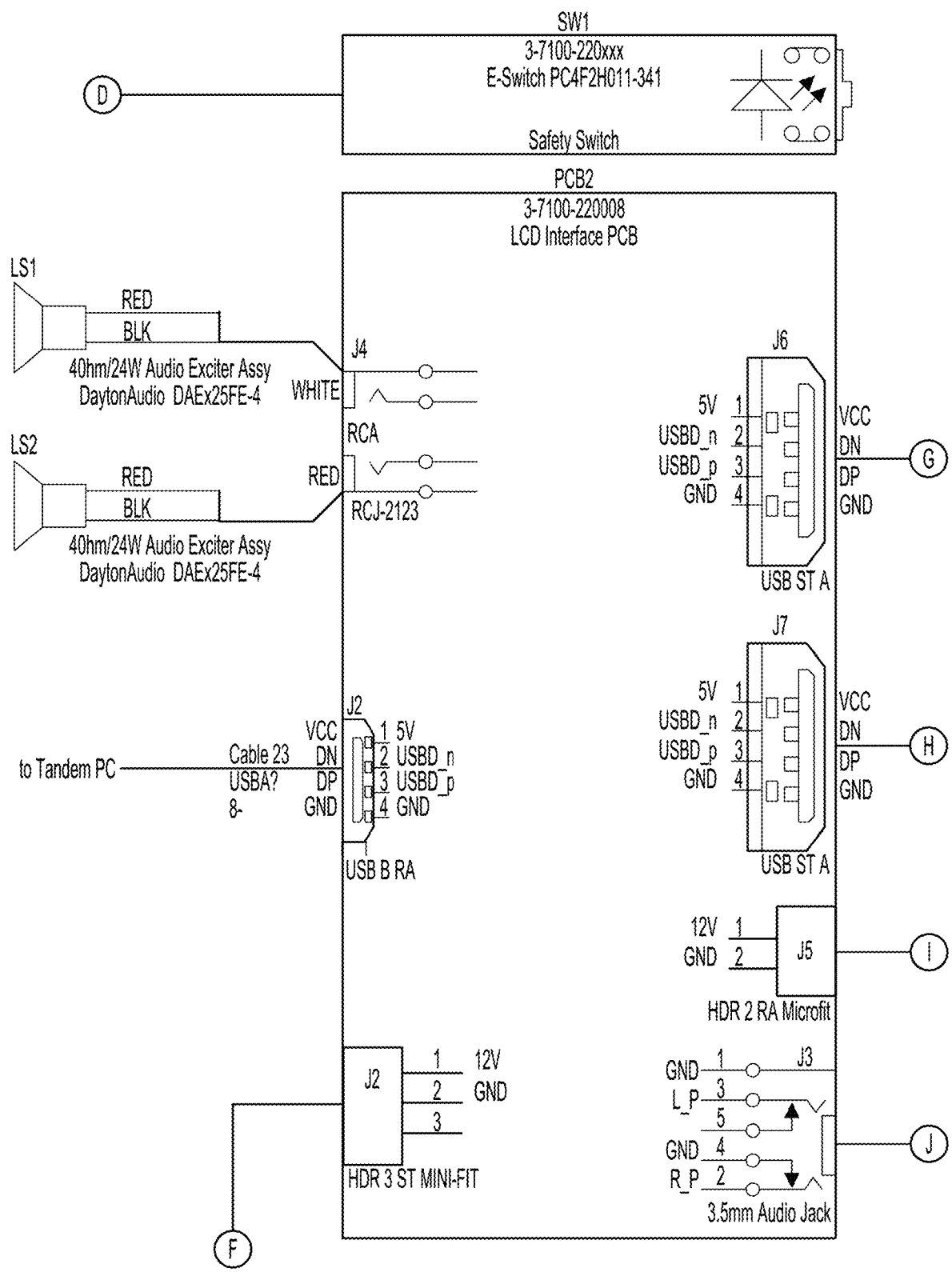
Fig. 10W-e

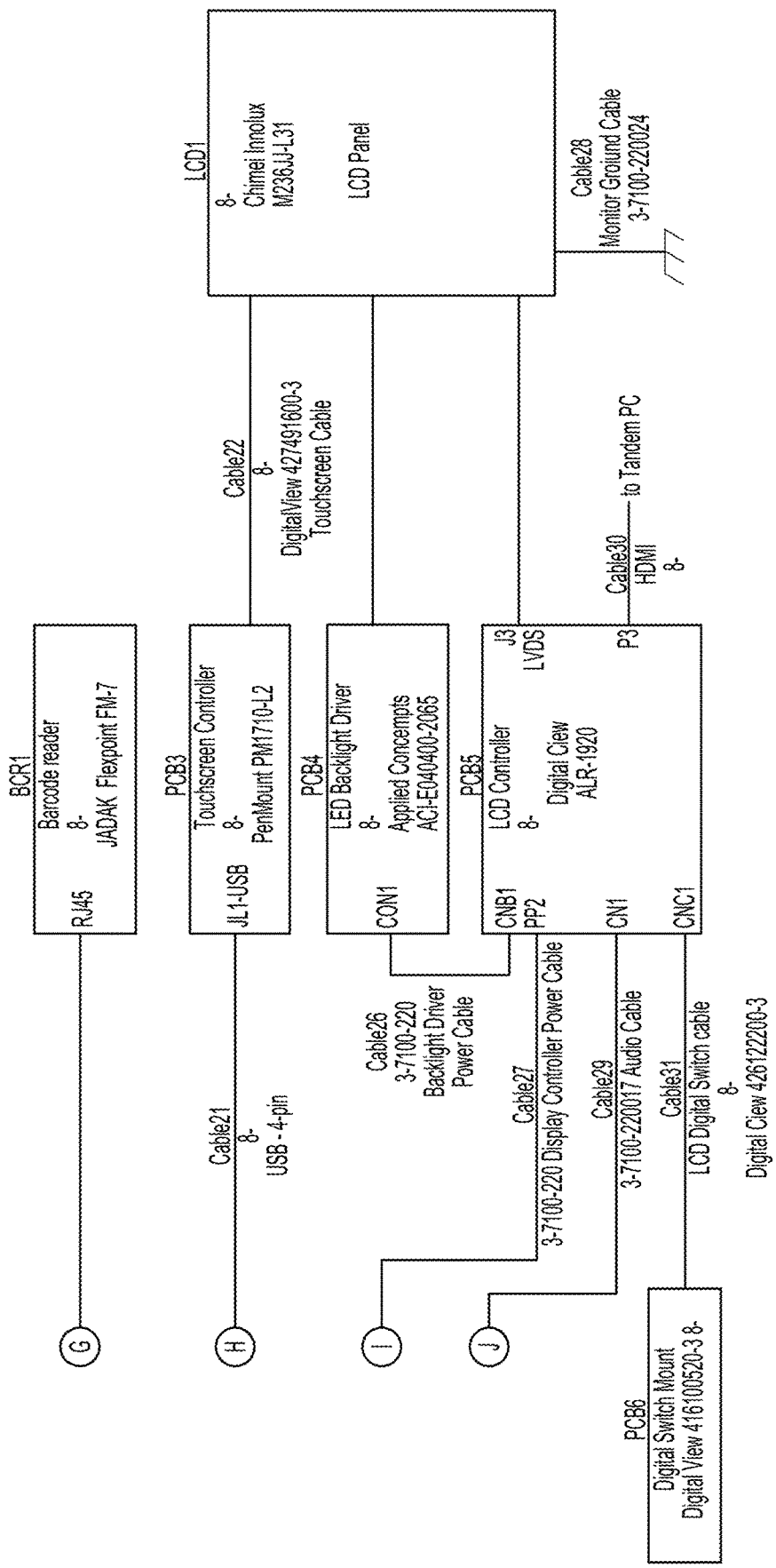
Fig. 10W-f

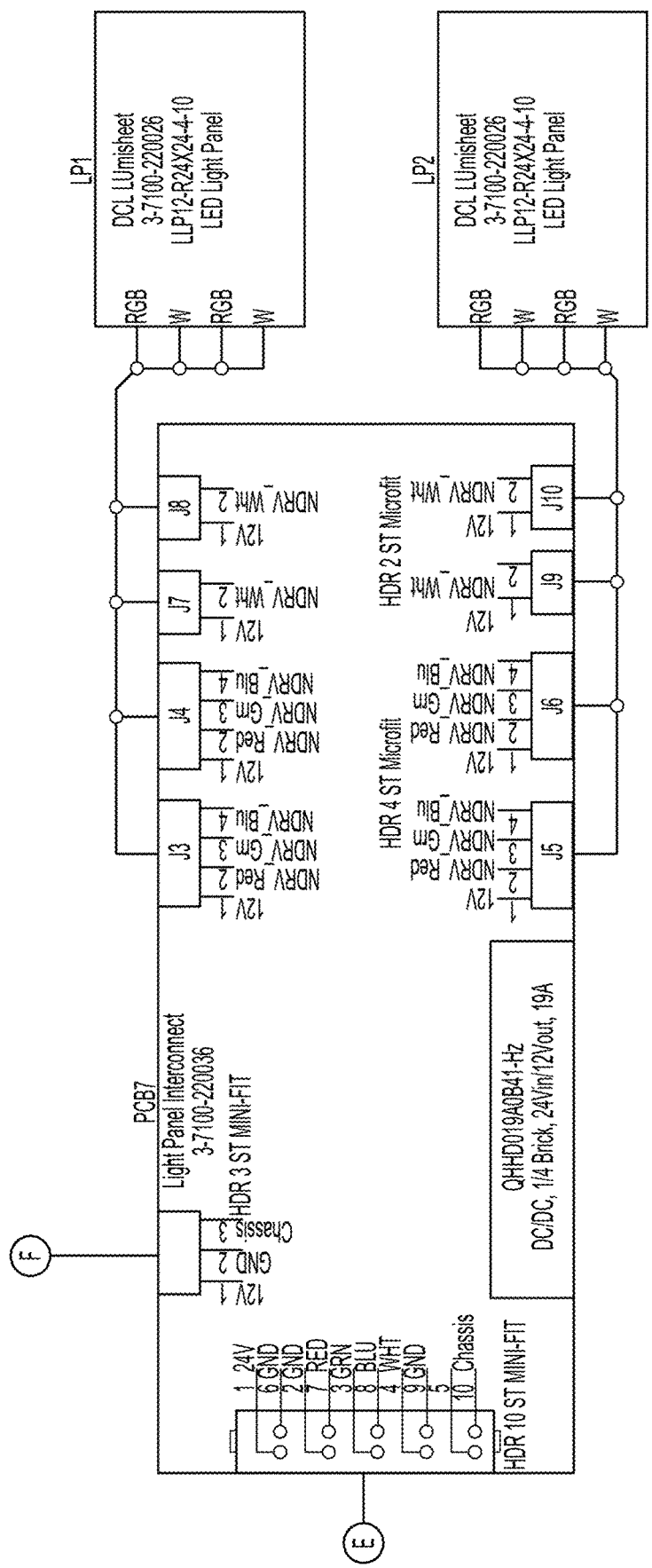
Fig. 10W-g

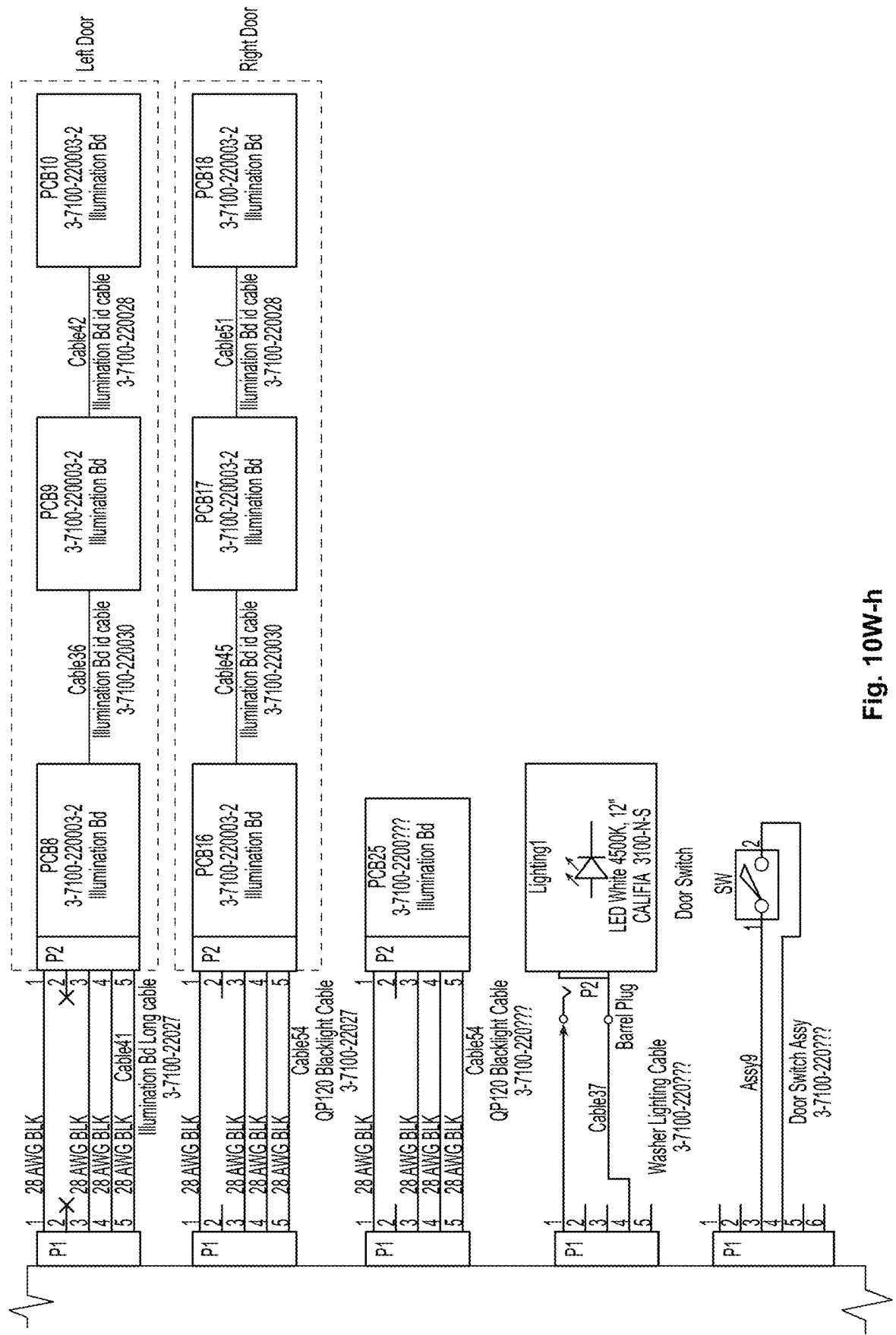
Fig. 10W-h

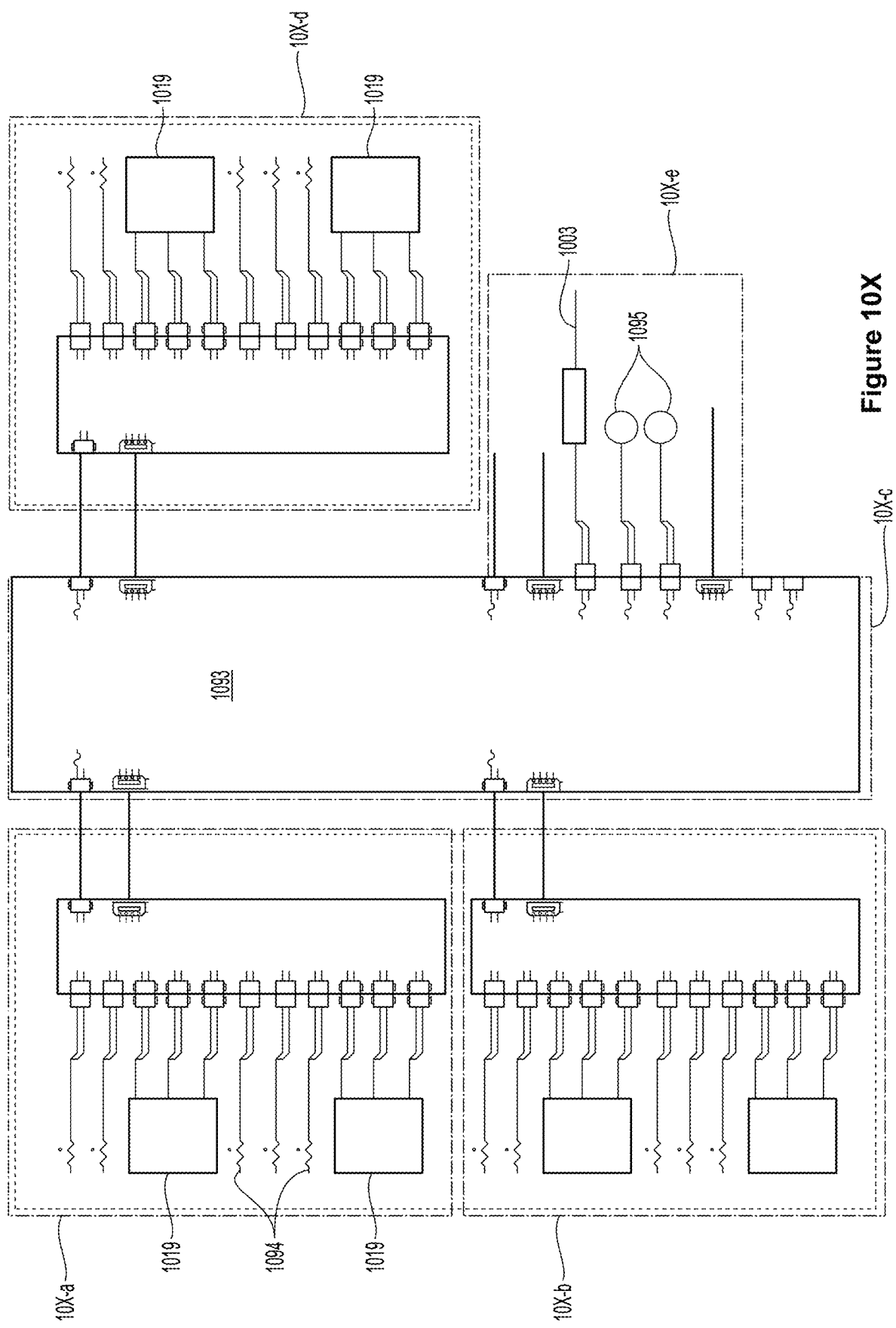

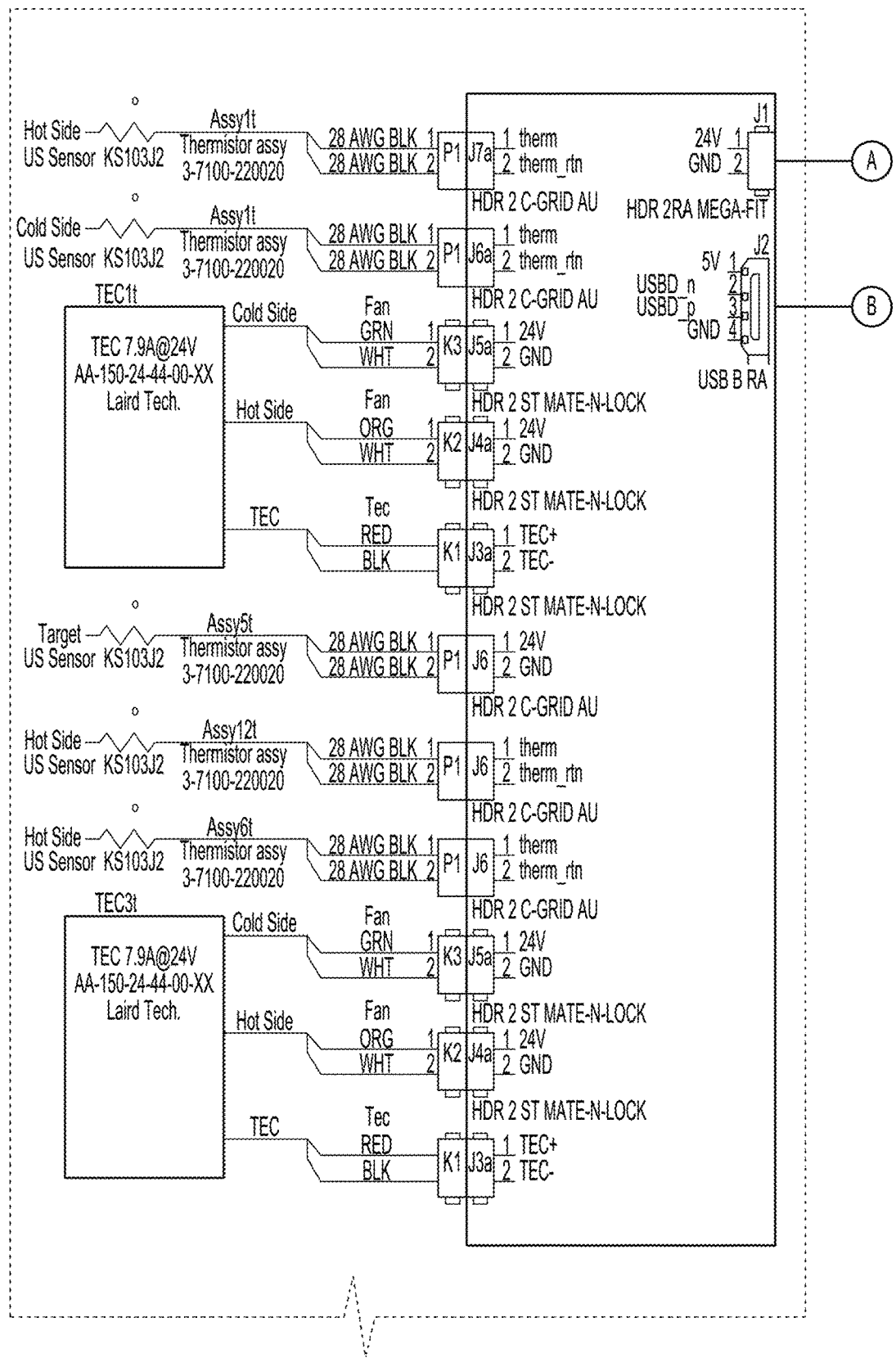
Figure 10X-a

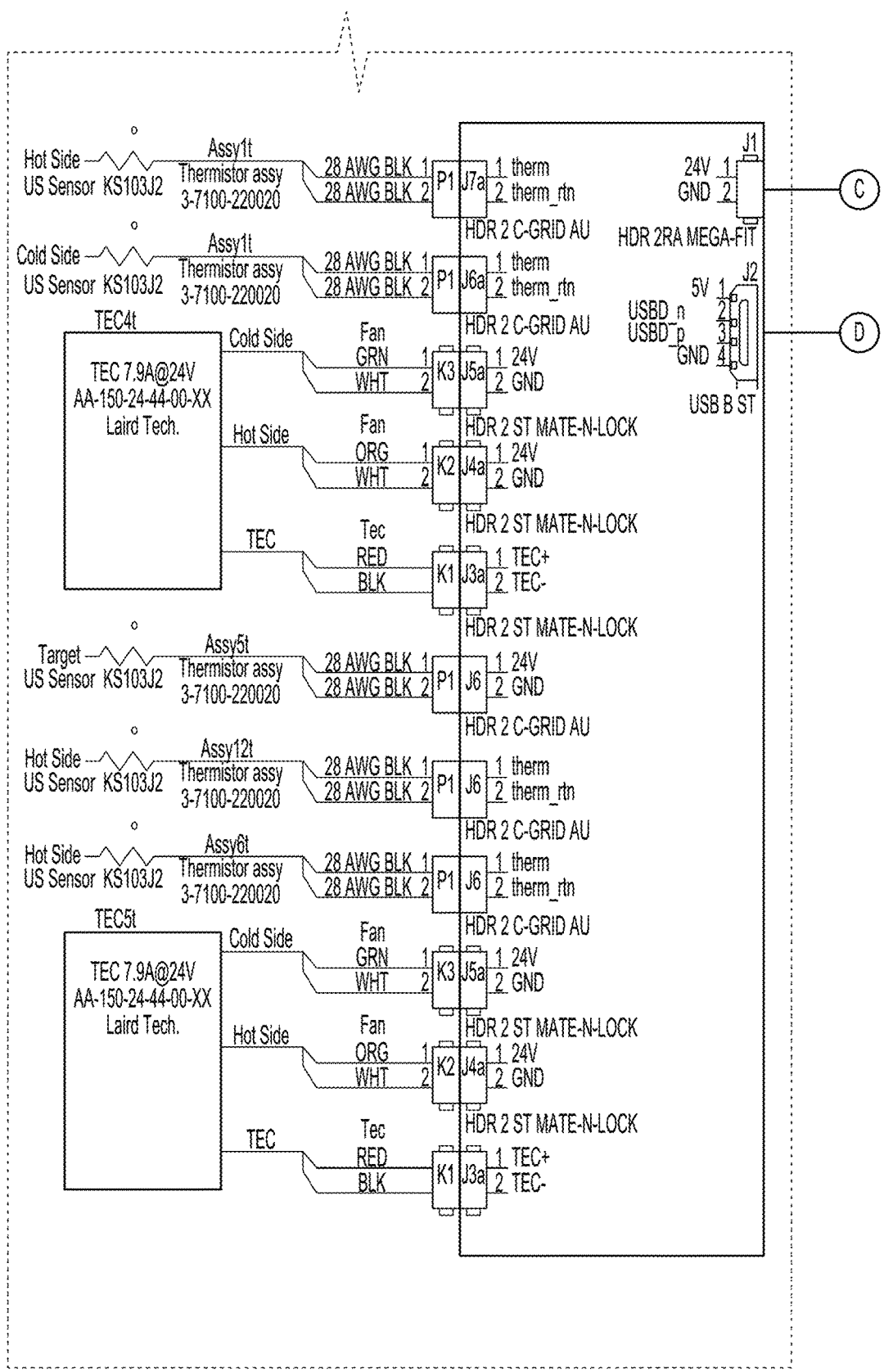
Figure 10X-b

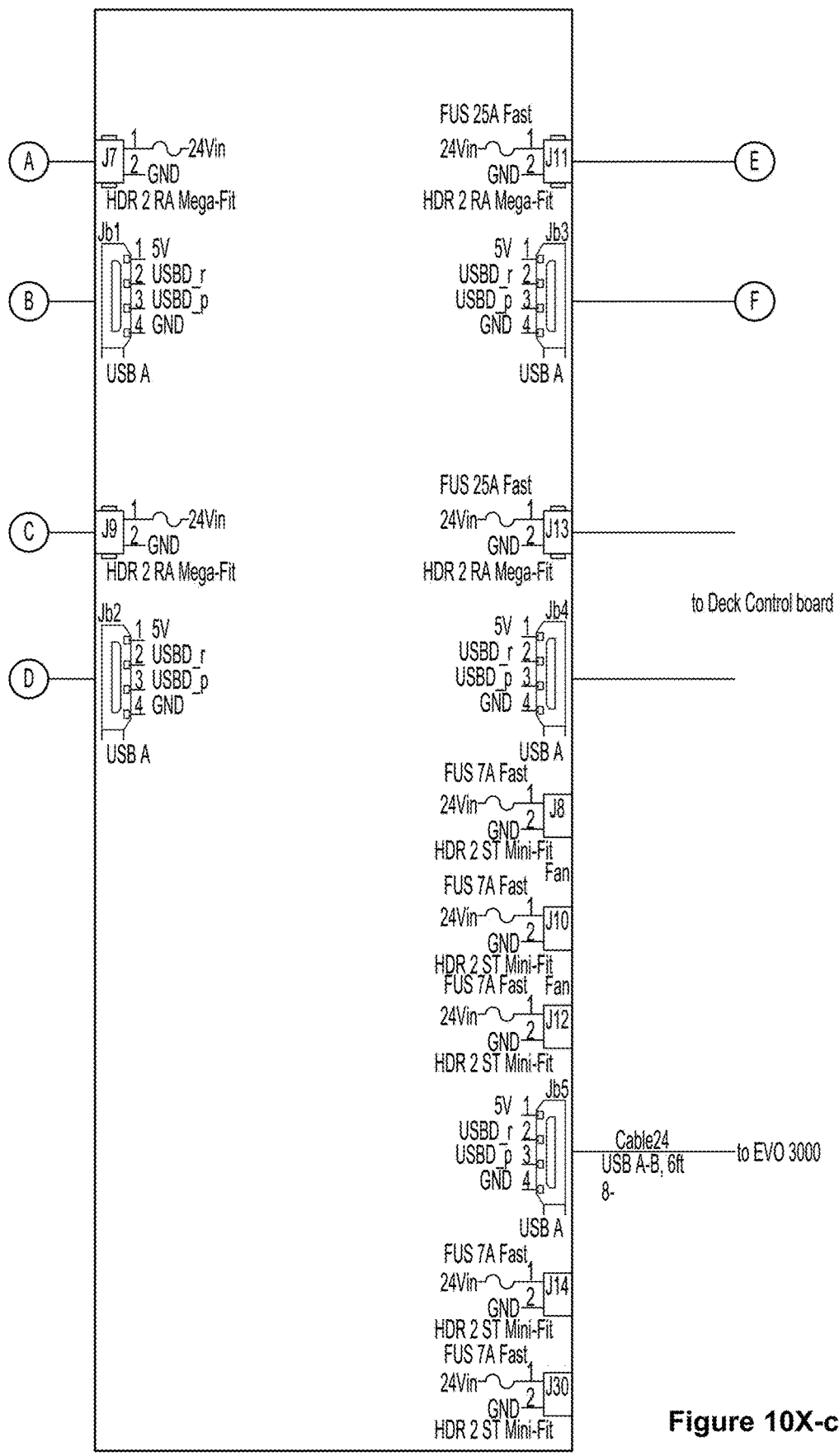
Figure 10X-c

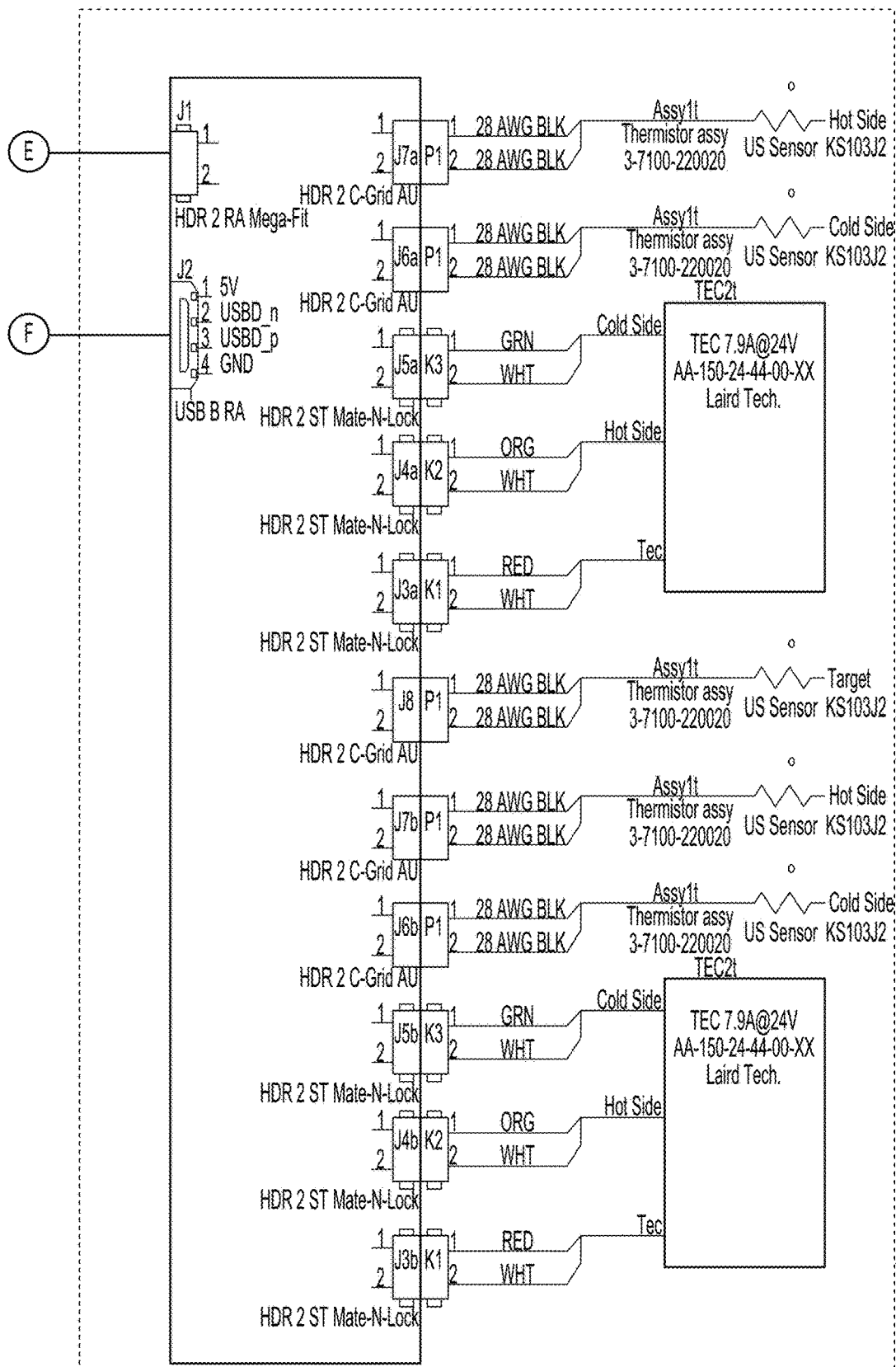
Figure 10X-d

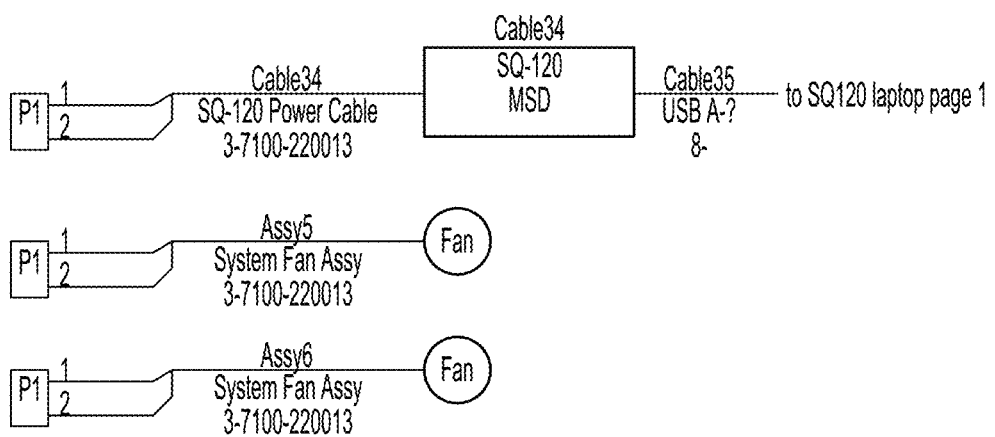
Figure 10X-e

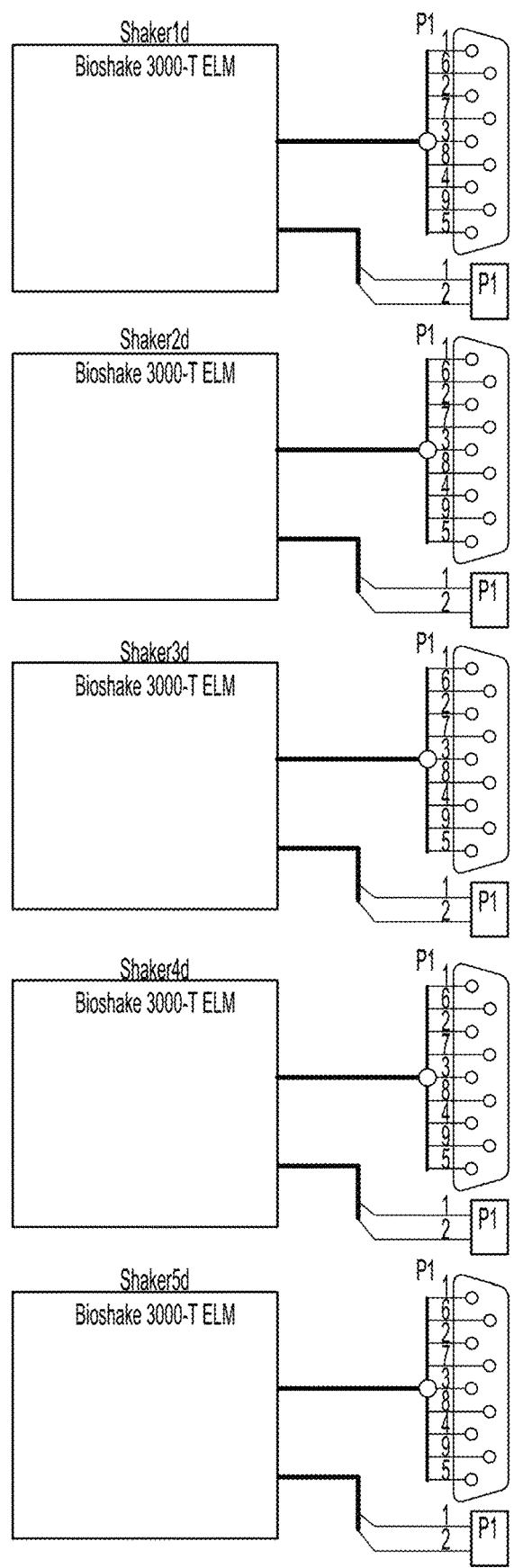
Figure 10Y-a

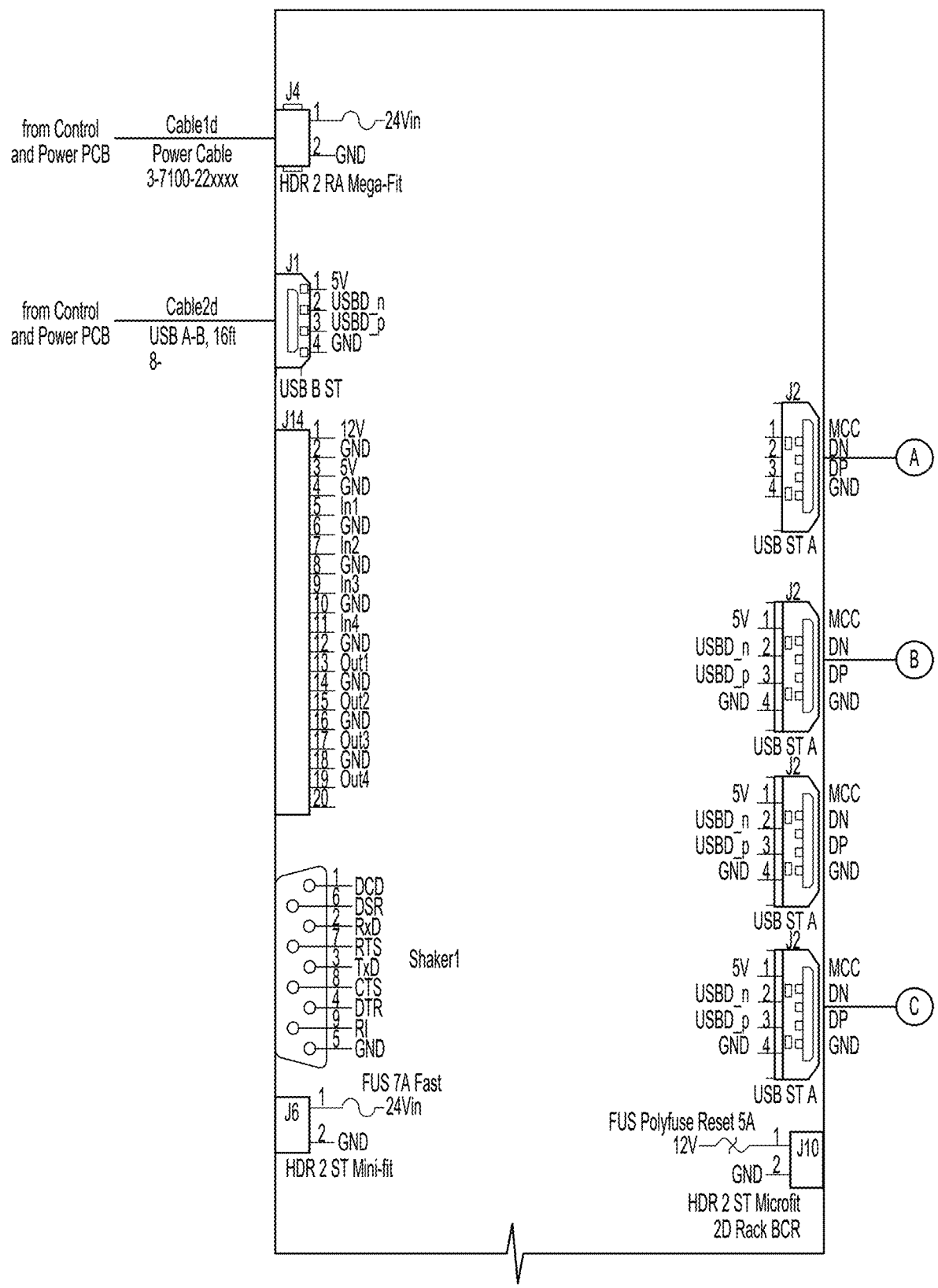
Figure 10Y-b

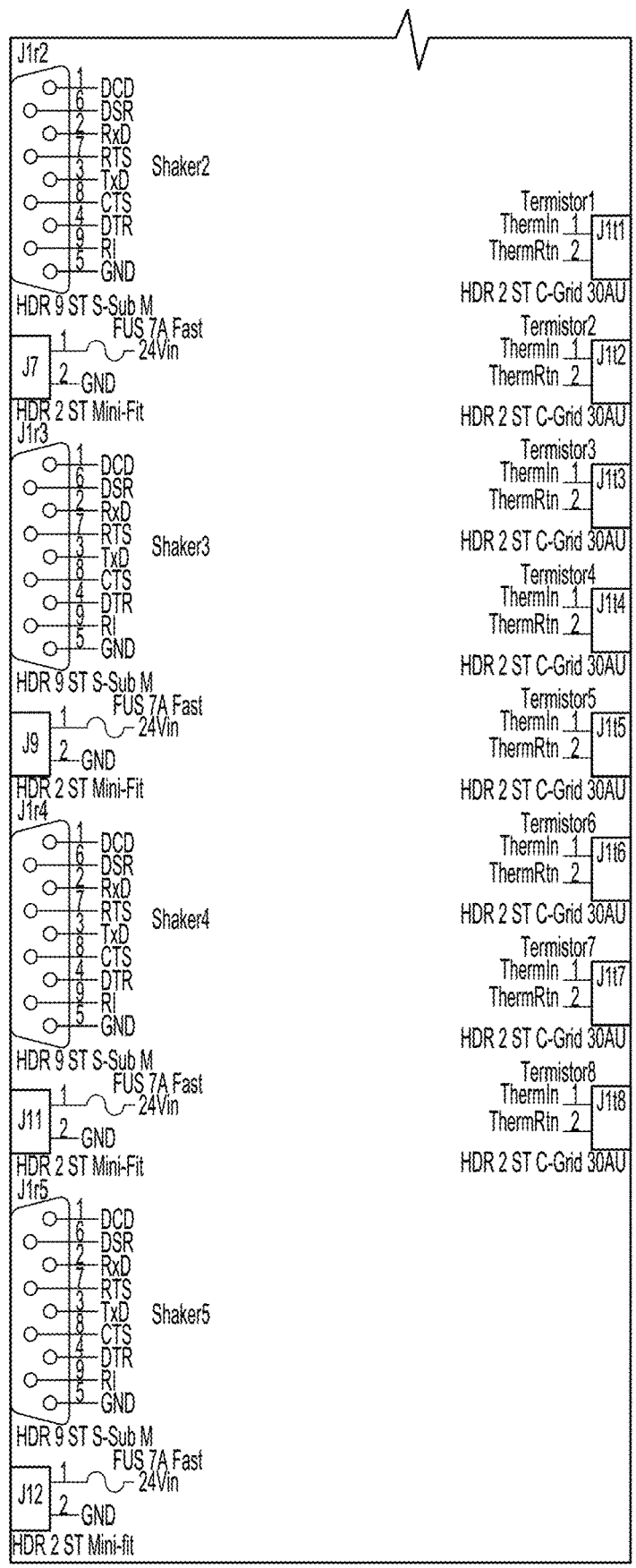
Figure 10Y-c

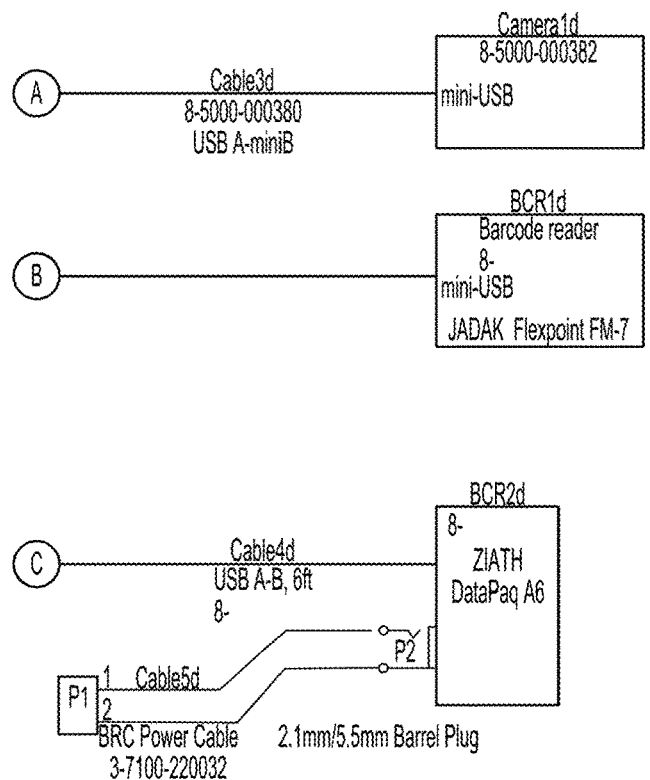
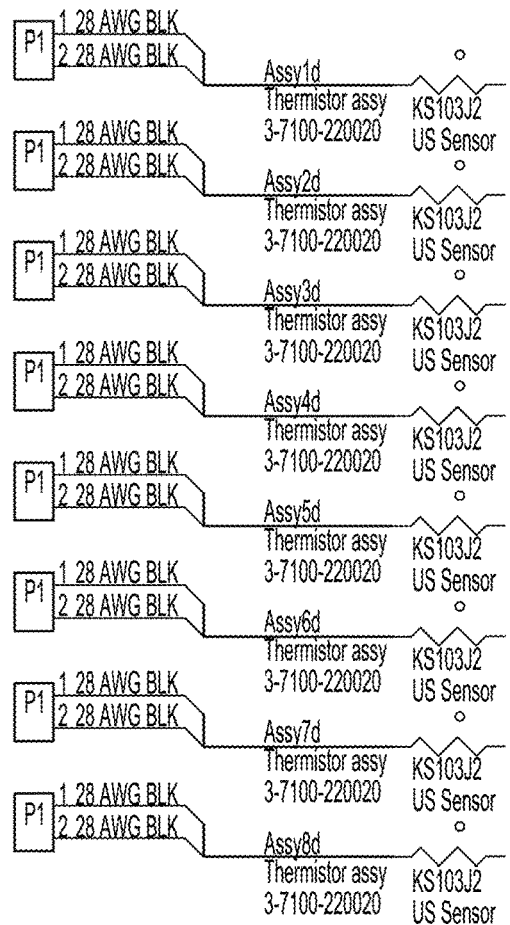
Figure 10Y-d

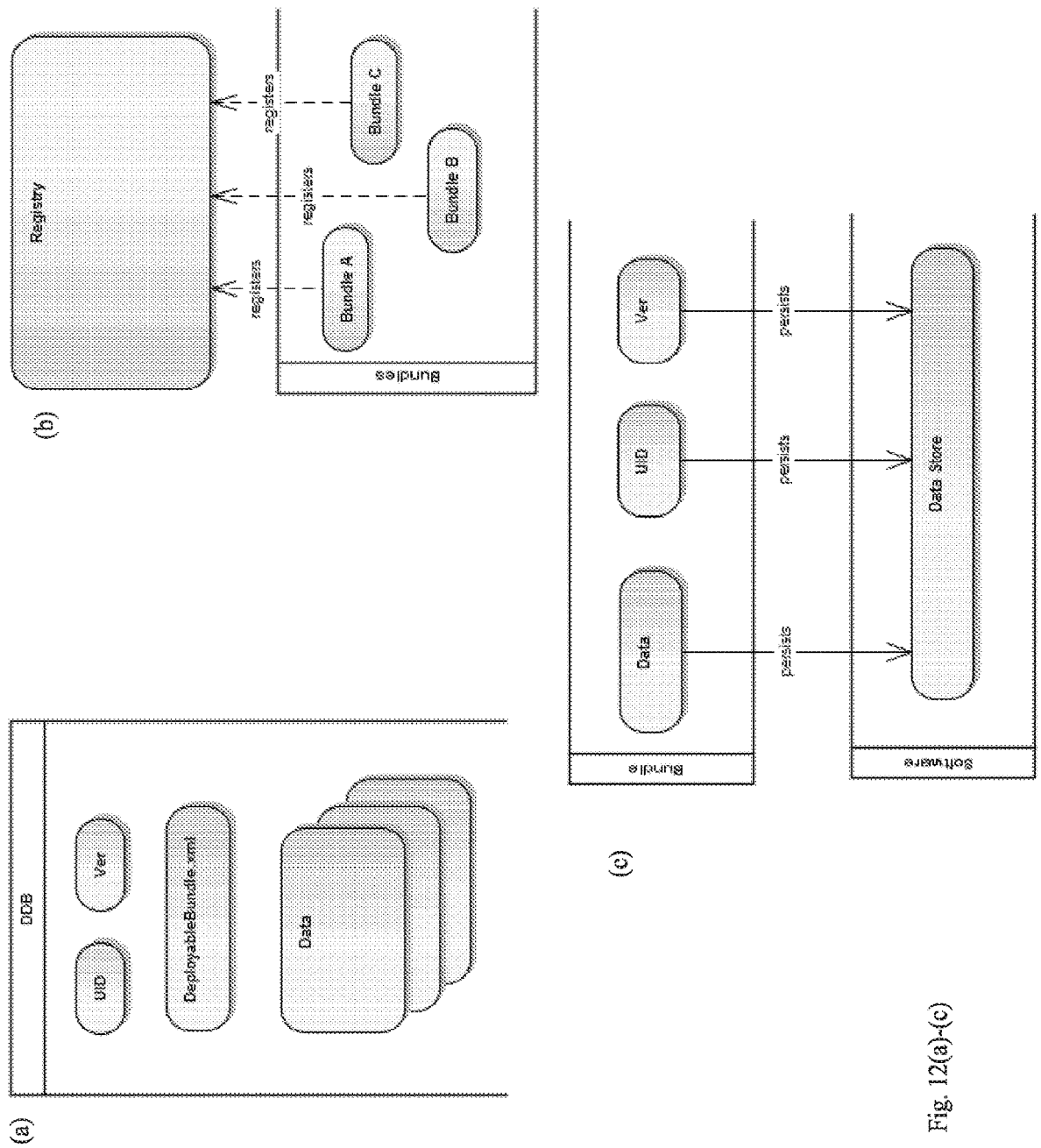
Fig. 12(a)-(c)

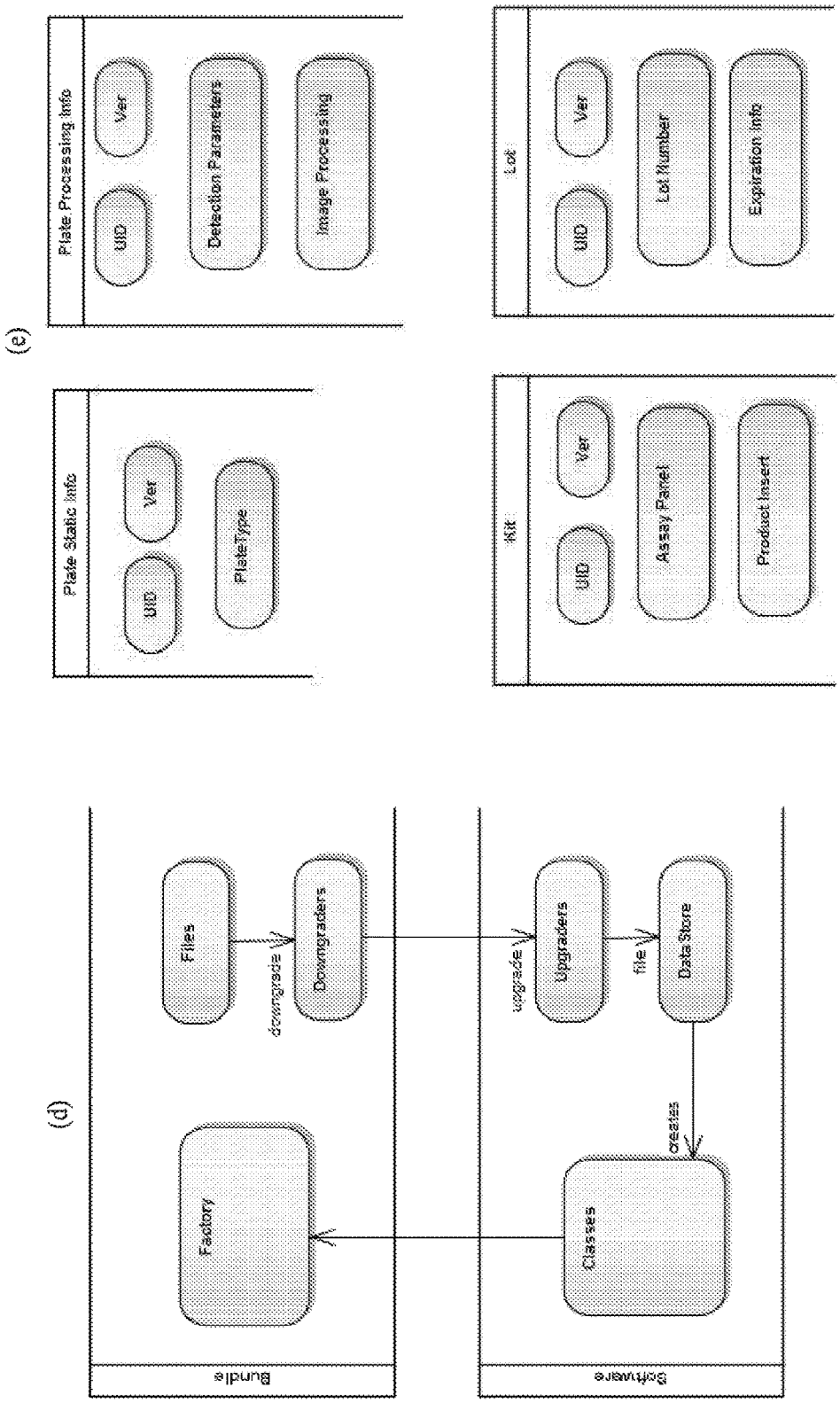
Fig. 12(d)-(e)

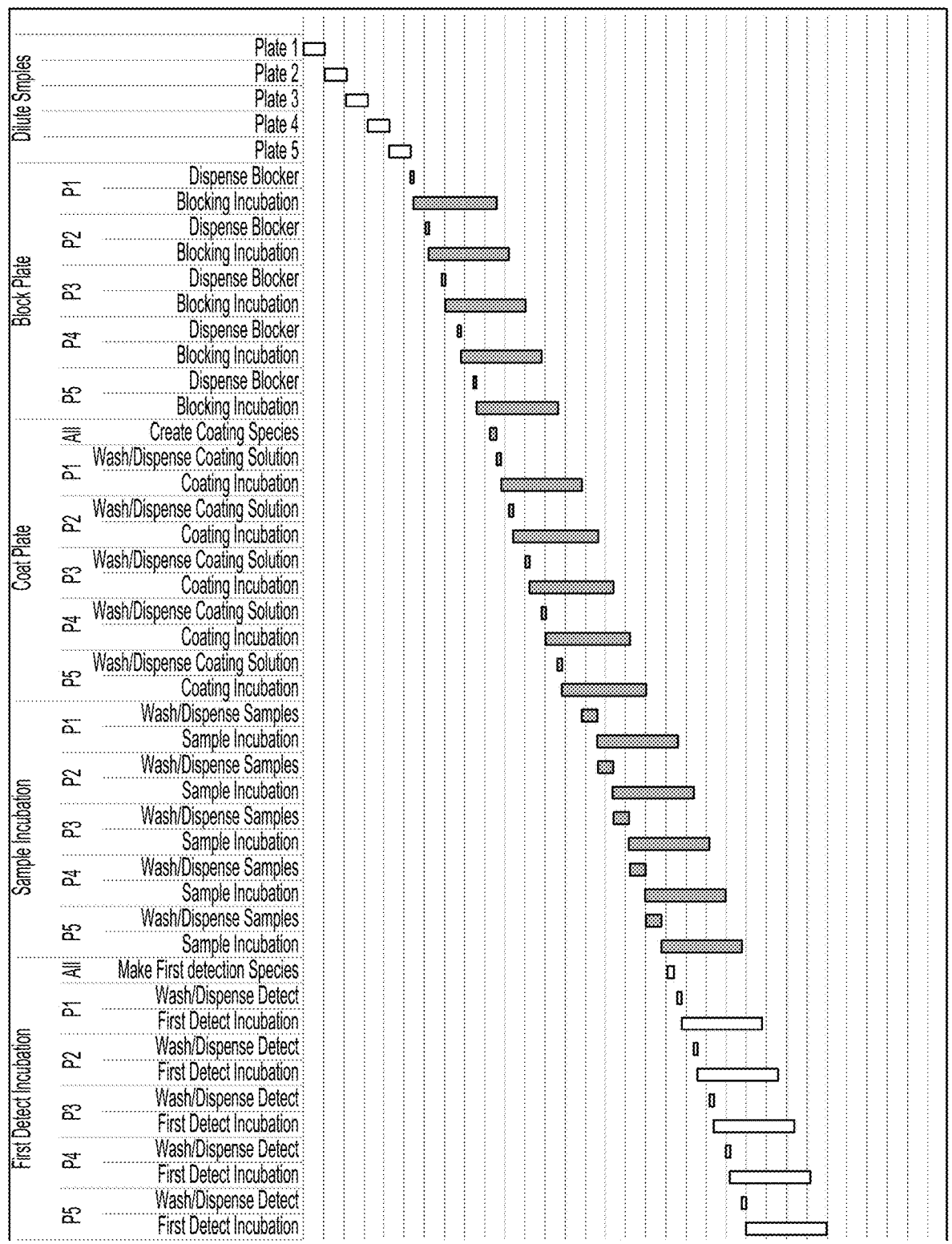
Figure 12M-a

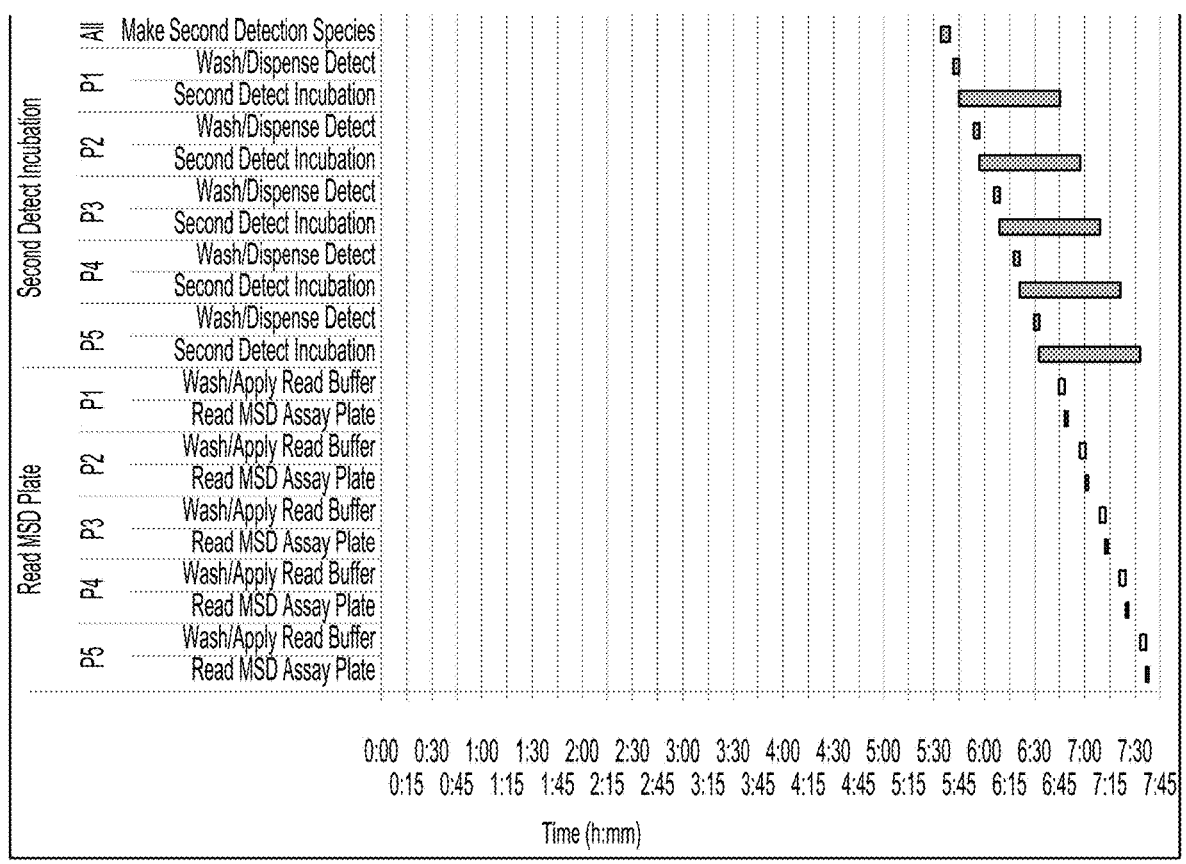
Figure 12M-b

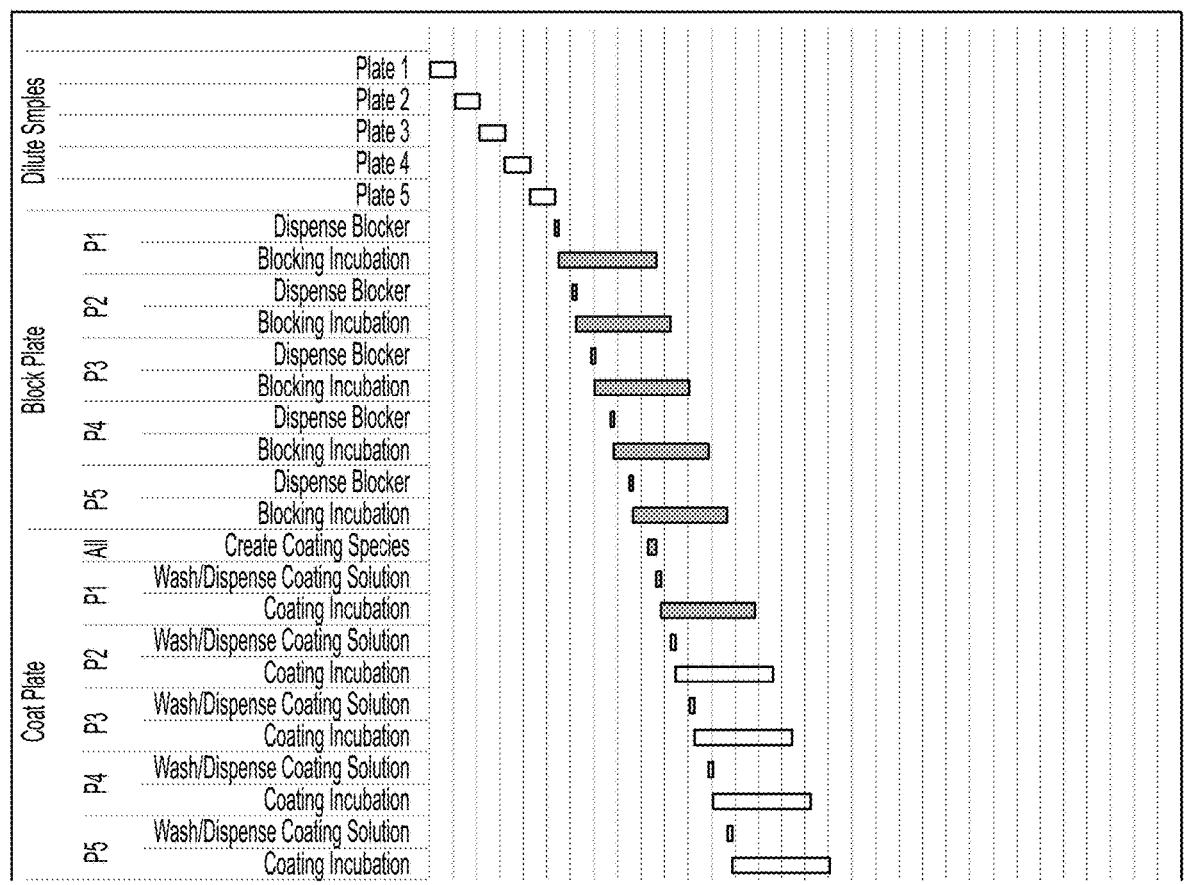
Figure 12N-a

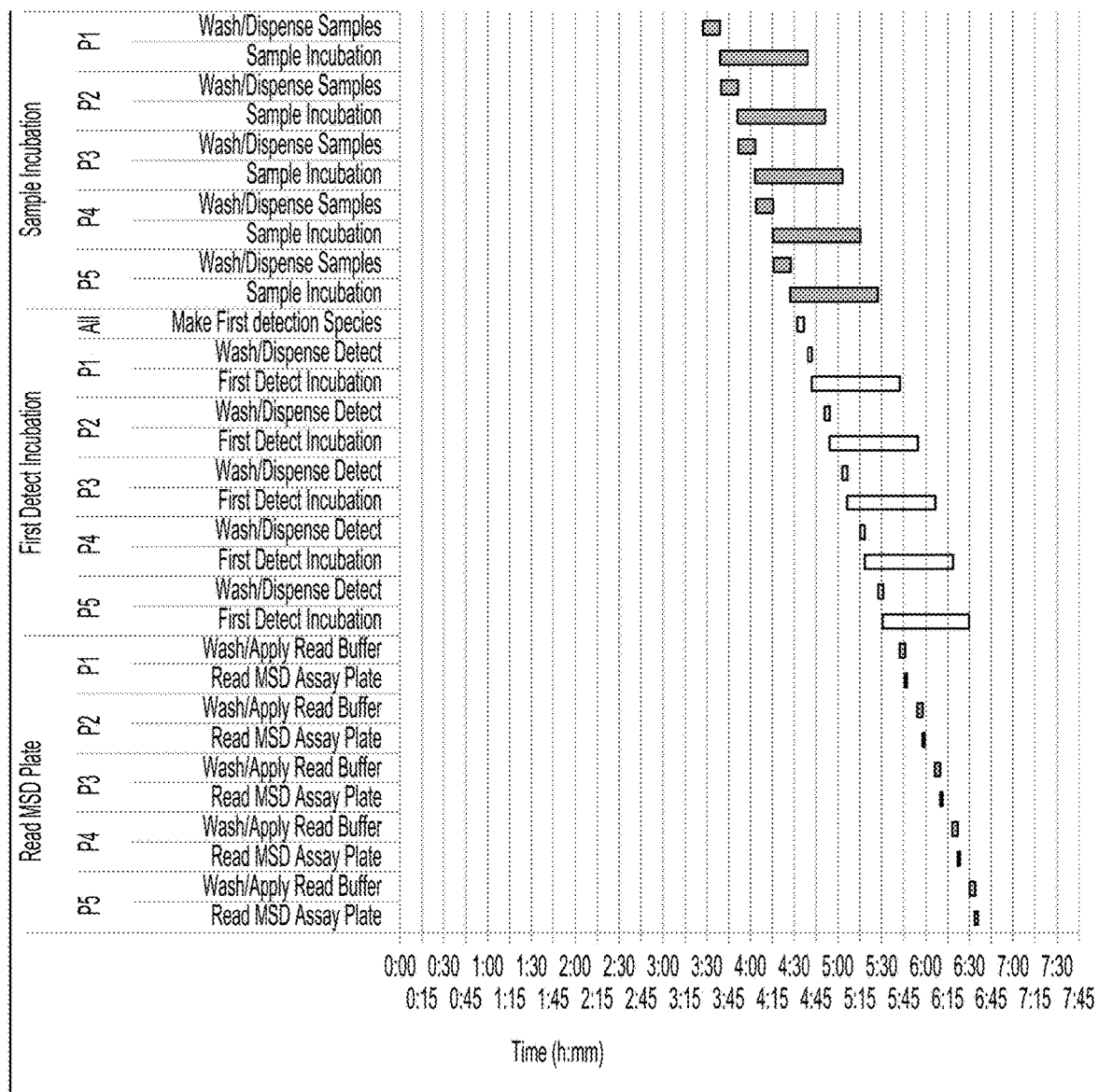
Figure 12N-b

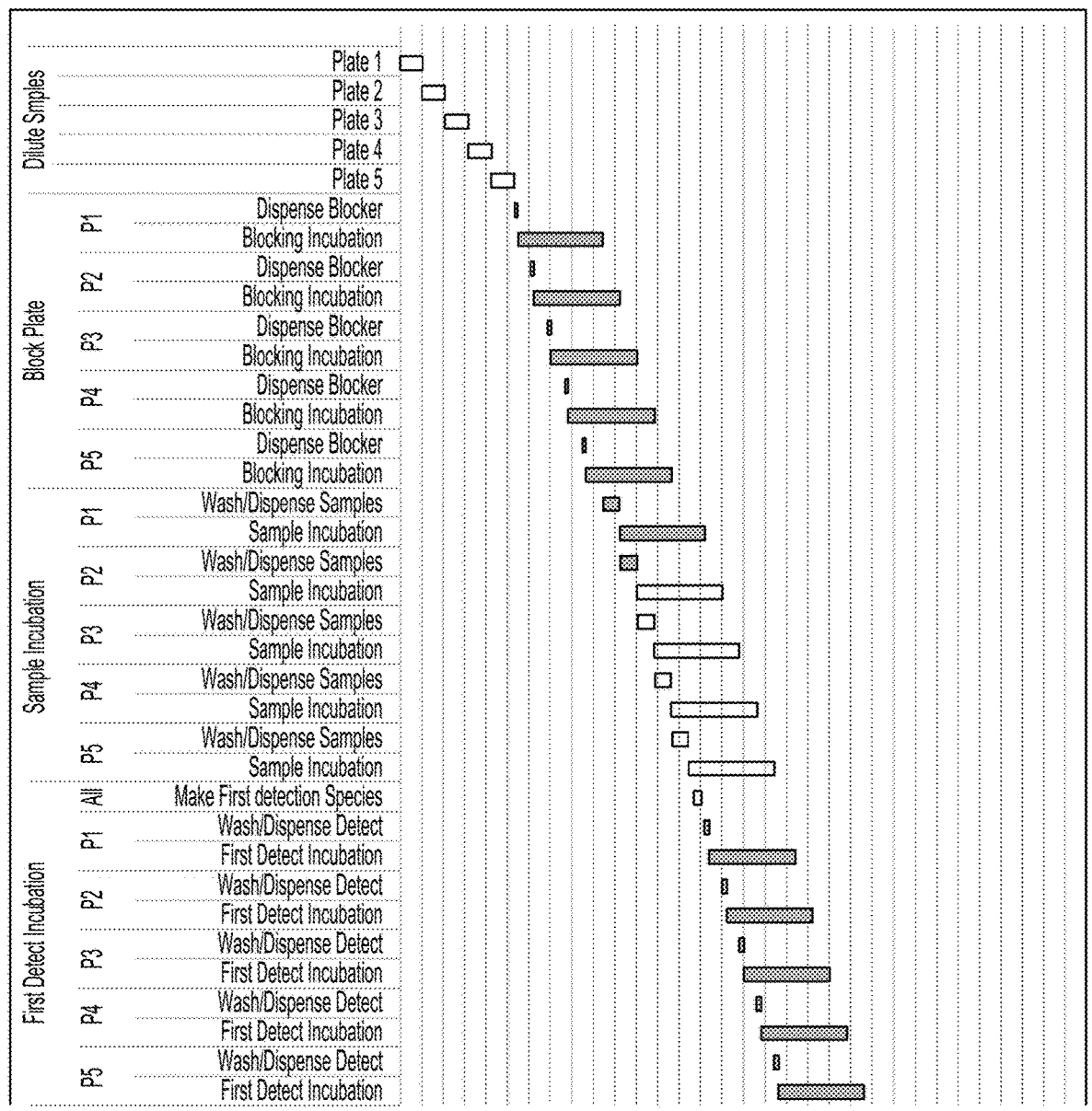
Figure 12O-a

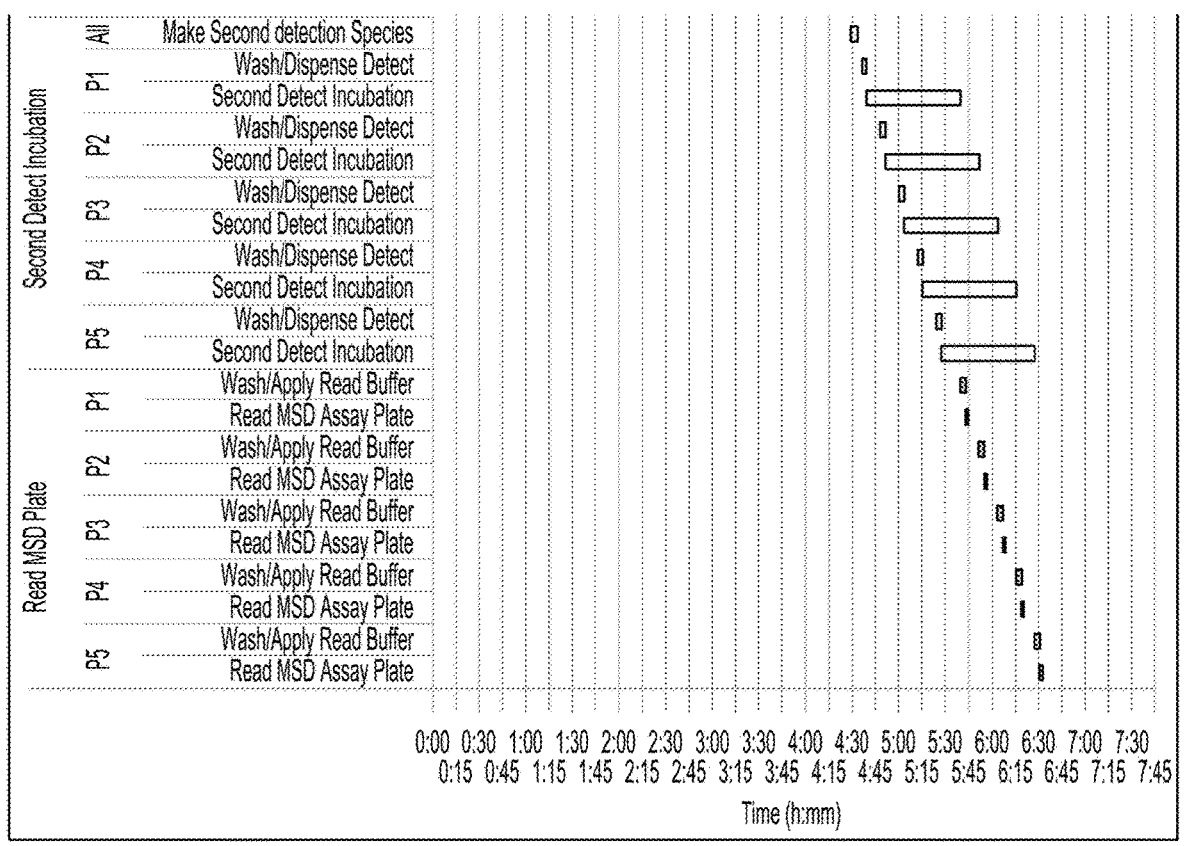
Figure 12O-b

```
18 script=VPLEX_Stepwise
19
20 com.mesoscale.lifesci.appsrv.inst.tandem.generator.gwl.DiluteControlsGWLGenerator.numberofAliquots=2
21 com.mesoscale.lifesci.appsrv.inst.tandem.generator.gwl.DiluteControlsGWLGenerator.dilutionFactor=2.0
22 com.mesoscale.lifesci.appsrv.inst.tandem.generator.gwl.DiluteControlsGWLGenerator.roundingMode=DILUTION_FACTOR
23
24 com.mesoscale.lifesci.appsrv.inst.tandem.generator.gwl.StandardCurveGWLGenerator.numberofAliquots=2
25 com.mesoscale.lifesci.appsrv.inst.tandem.generator.gwl.StandardCurveGWLGenerator.topDilutionFactor=1.0
26 com.mesoscale.lifesci.appsrv.inst.tandem.generator.gwl.StandardCurveGWLGenerator.dilutionFactor=4.0
27 com.mesoscale.lifesci.appsrv.inst.tandem.generator.gwl.StandardCurveGWLGenerator.roundingMode=DILUTIONFACTOR
28
29 com.mesoscale.lifesci.appsrv.inst.tandem.generator.gwl.DiluteSamplesGWLGenerator.numberofAliquots=2
30 com.mesoscale.lifesci.appsrv.inst.tandem.generator.gwl.DiluteSamplesGWLGenerator.dilutionFactor=2.0
31 com.mesoscale.lifesci.appsrv.inst.tandem.generator.gwl.DiluteSamplesGWLGenerator.roundingMode=DILUTIONFACTOR
32
33 com.mesoscale.lifesci.appsrv.inst.tandem.generator.gwl.DetectionAntibodyBlendGenerator.numberofAliquots=96
34 com.mesoscale.lifesci.appsrv.inst.tandem.generator.gwl.DetectionAntibodyBlendGenerator.dilutionFactor=50.0
35 com.mesoscale.lifesci.appsrv.inst.tandem.generator.gwl.DetectionAntibodyBlendGenerator.roundingMode=TO_NEAREST
36 com.mesoscale.lifesci.appsrv.inst.tandem.generator.gwl.DetectionAntibodyBlendGenerator.roundingToNearest=1000
37
38 blockingIncubationDuration=0
39 sampleIncubationDuration=20
40 detectionIncubationDuration=20
41 readBufferIncubationDuration=0
42
```

Figure 12q-a 43 blockingVolume=0.0
44 detectVolume=25.0
45 readBufferVolume=150.0
46
47 blendCalibratorIsEnabled=false
48 blockingIsEnabled=false
49 standardCurveISEnabled=true
50 diluteControlsEnabled=true
51 diluteControlVialsIsEnabled=false
52 diluteSamplesIsEnabled=true
53 assayTransferIsEnabled=true
54 blendDetectIsEnabled=true
55 dispenseDetectsIsEnabled=true
56 washpPlateIsEnabled=true
57 dispenseReadBufferIsEnabled=true
58 readPlateIsEnabled=true
59 washPreCaptureIsEnabled=true
60 washPostCaptureIsEnabled=true
61
62 assayVolume=50.0
63

Figure 12q-b

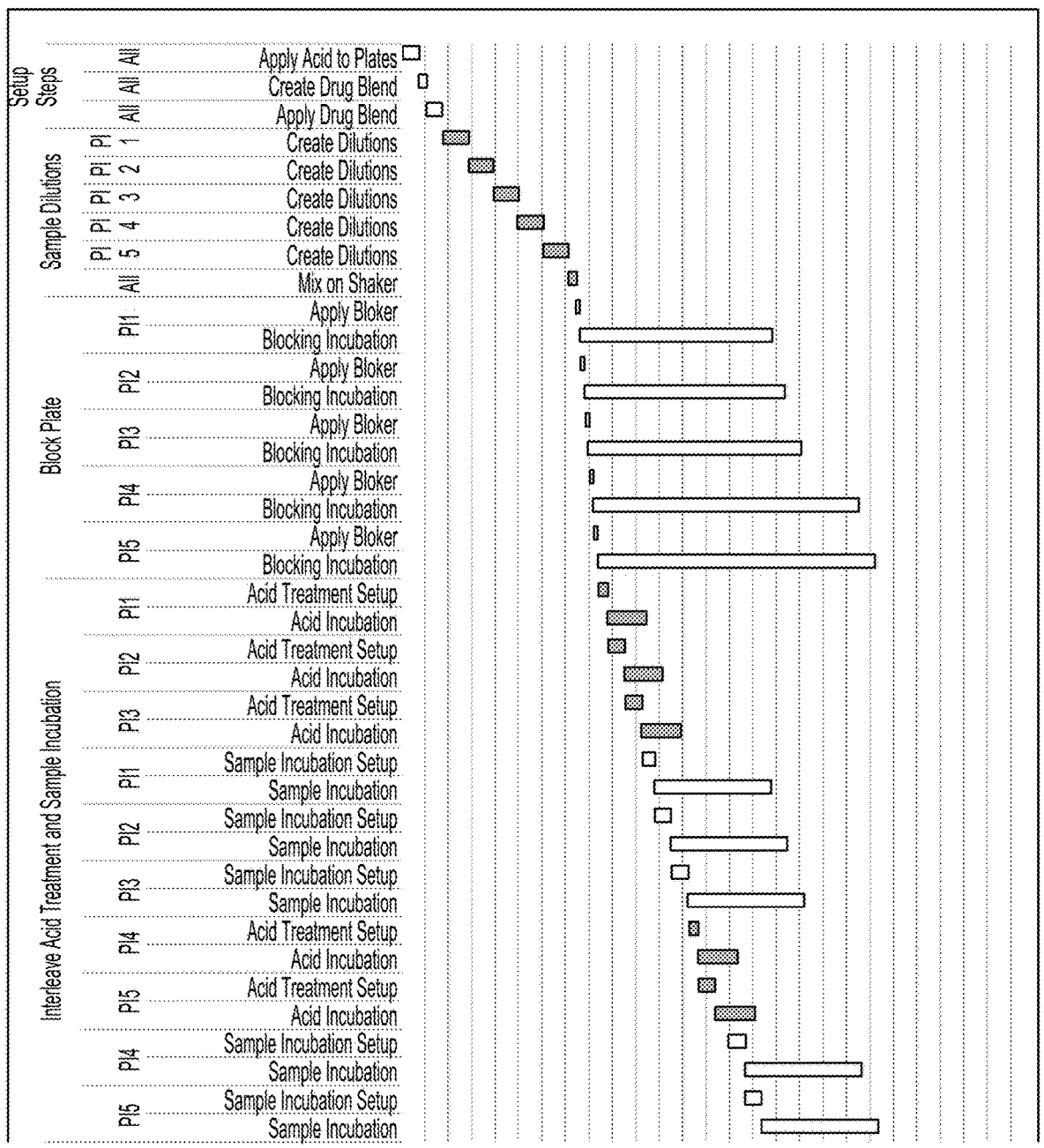
Figure 12R-a

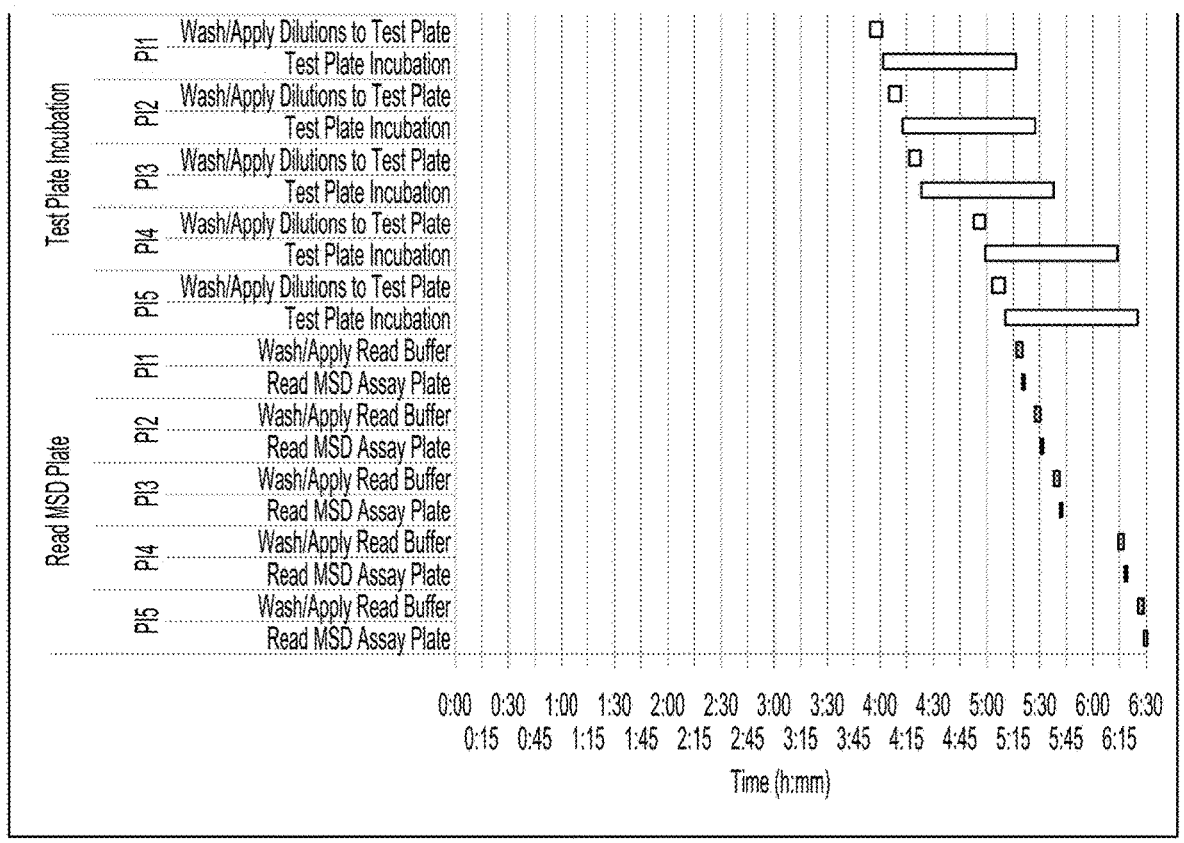
Figure 12R-b

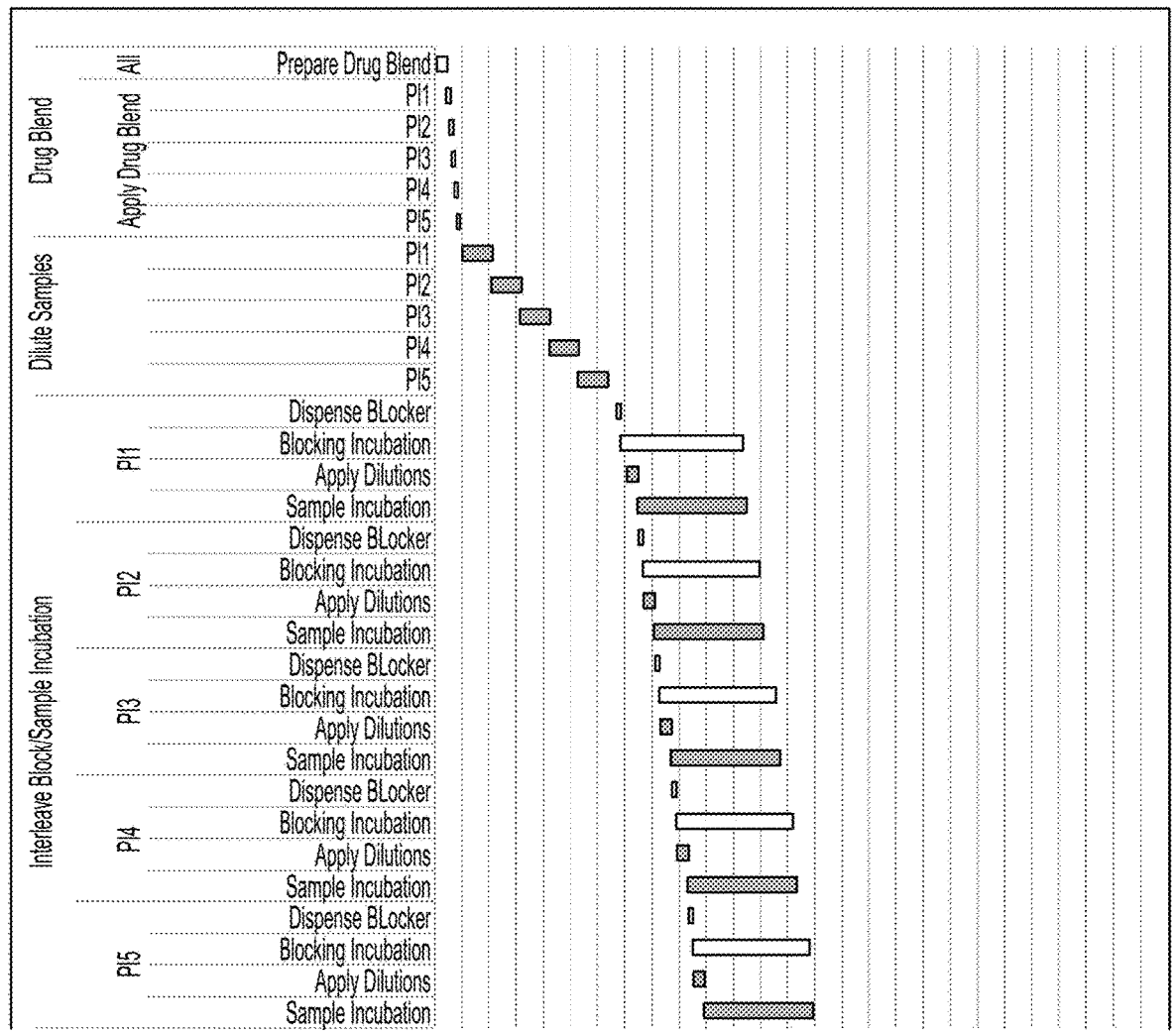
Figure 12S-a

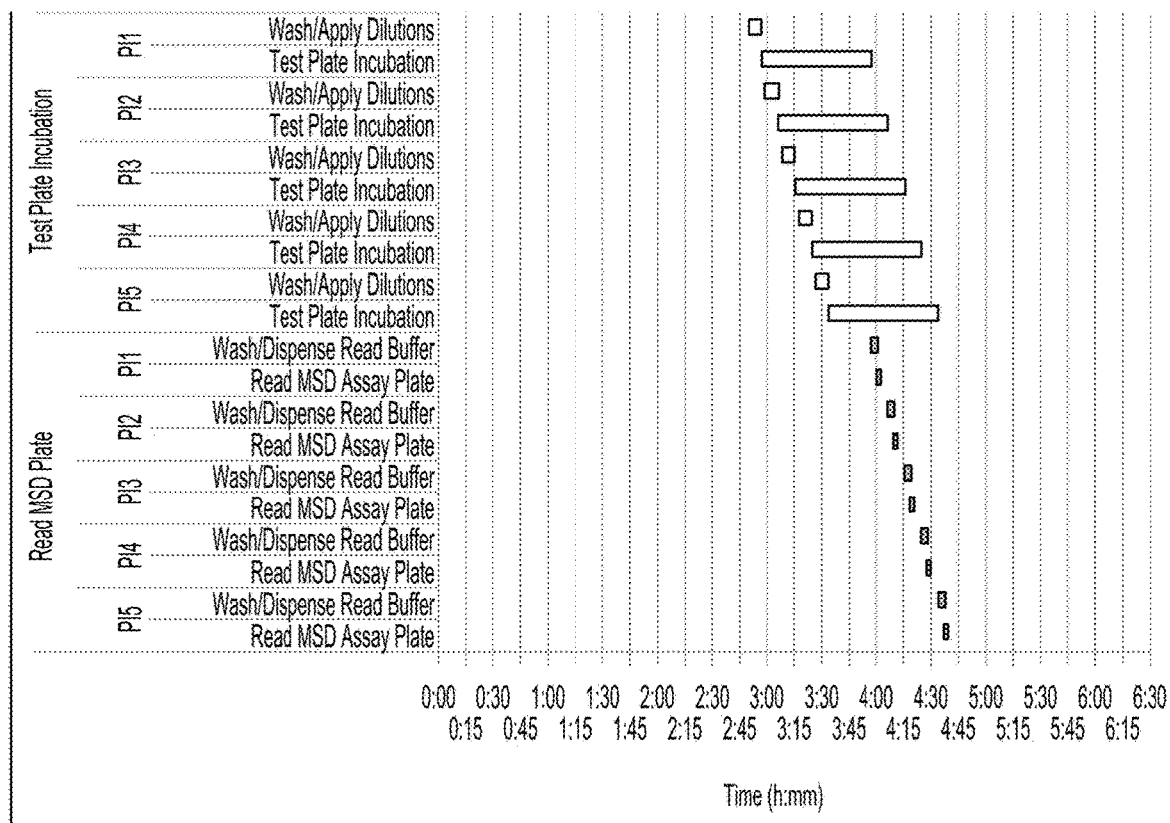
Figure 12S-b

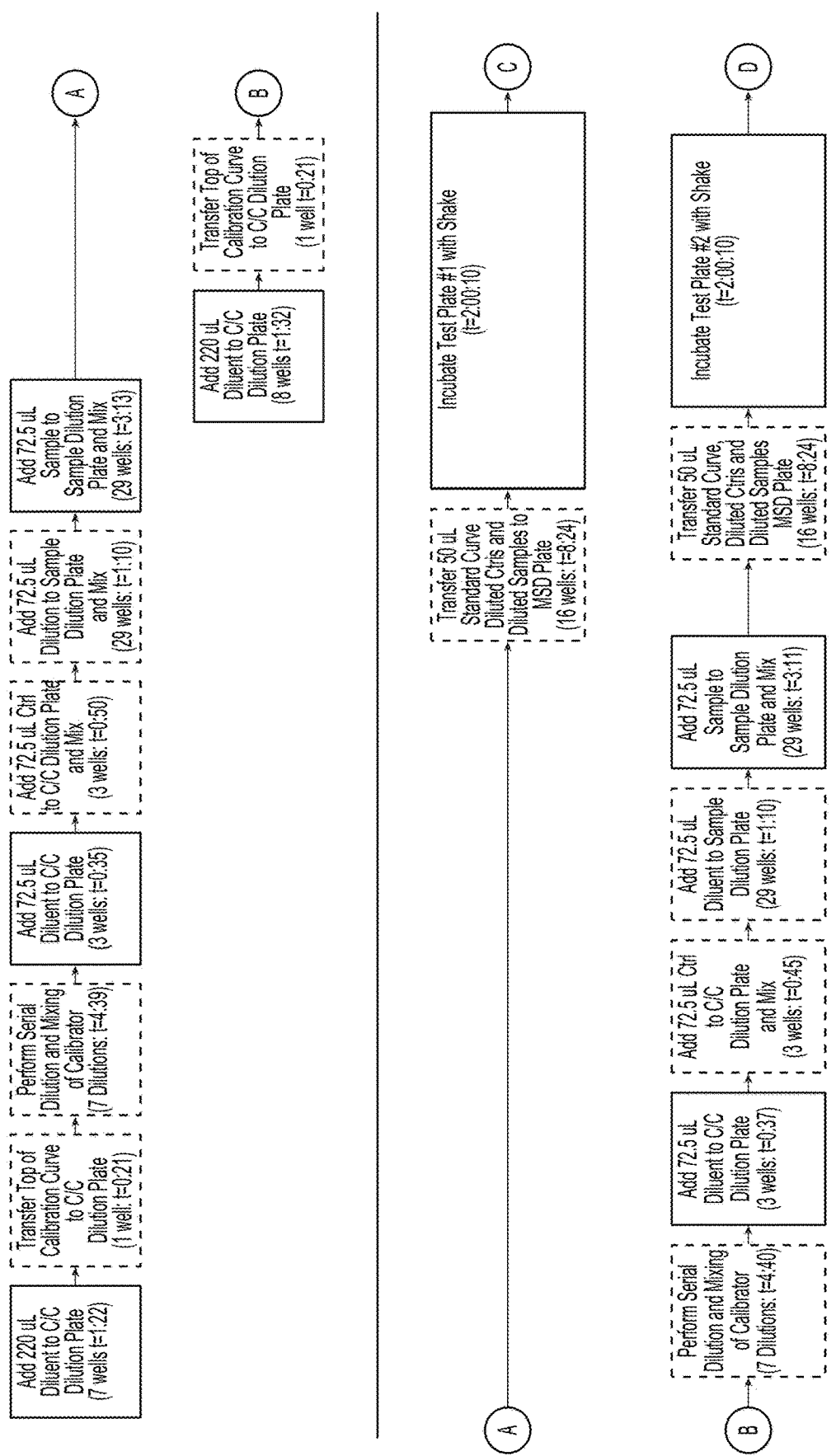
Figure 13D-a

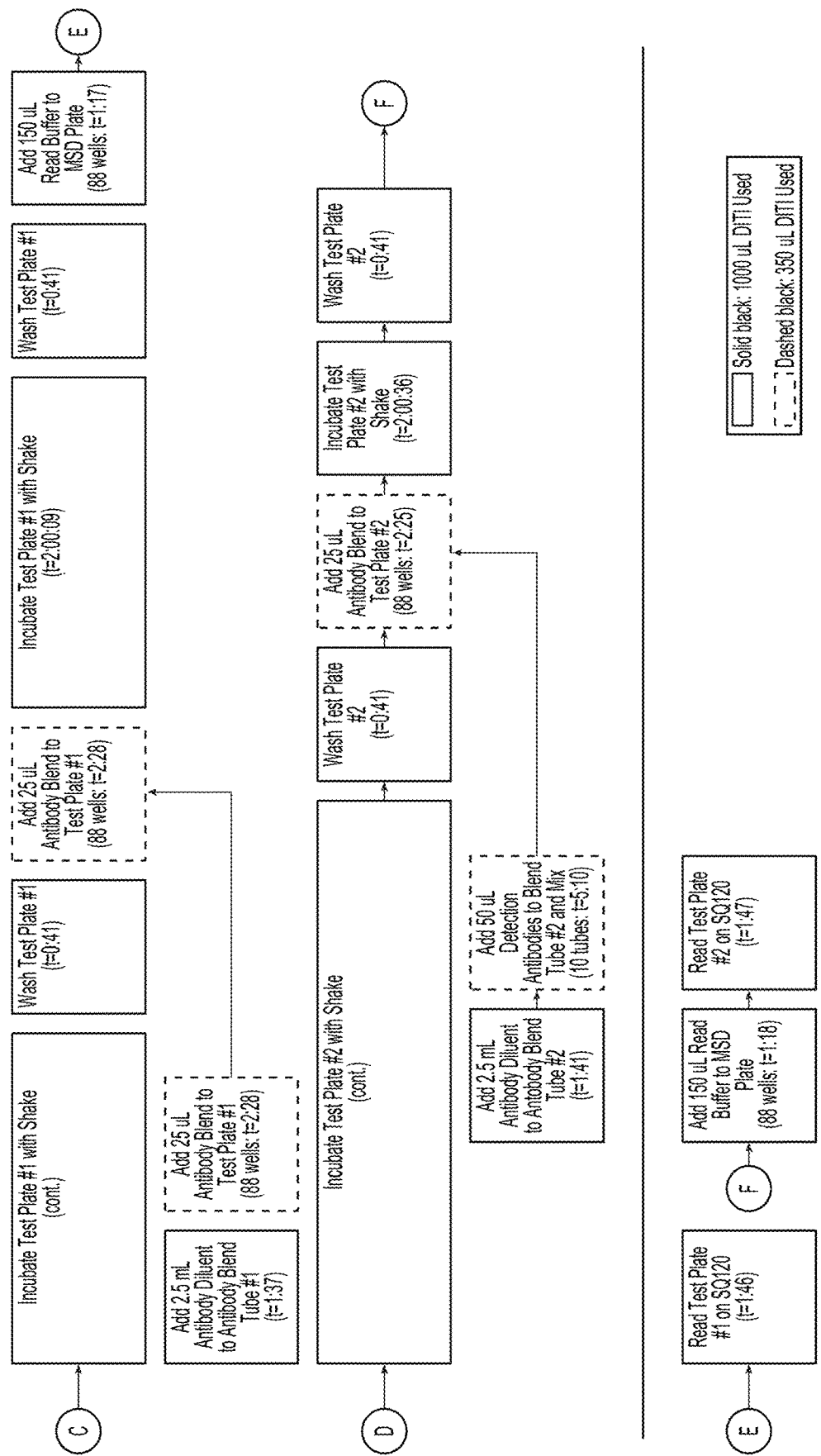
Figure 13D-b

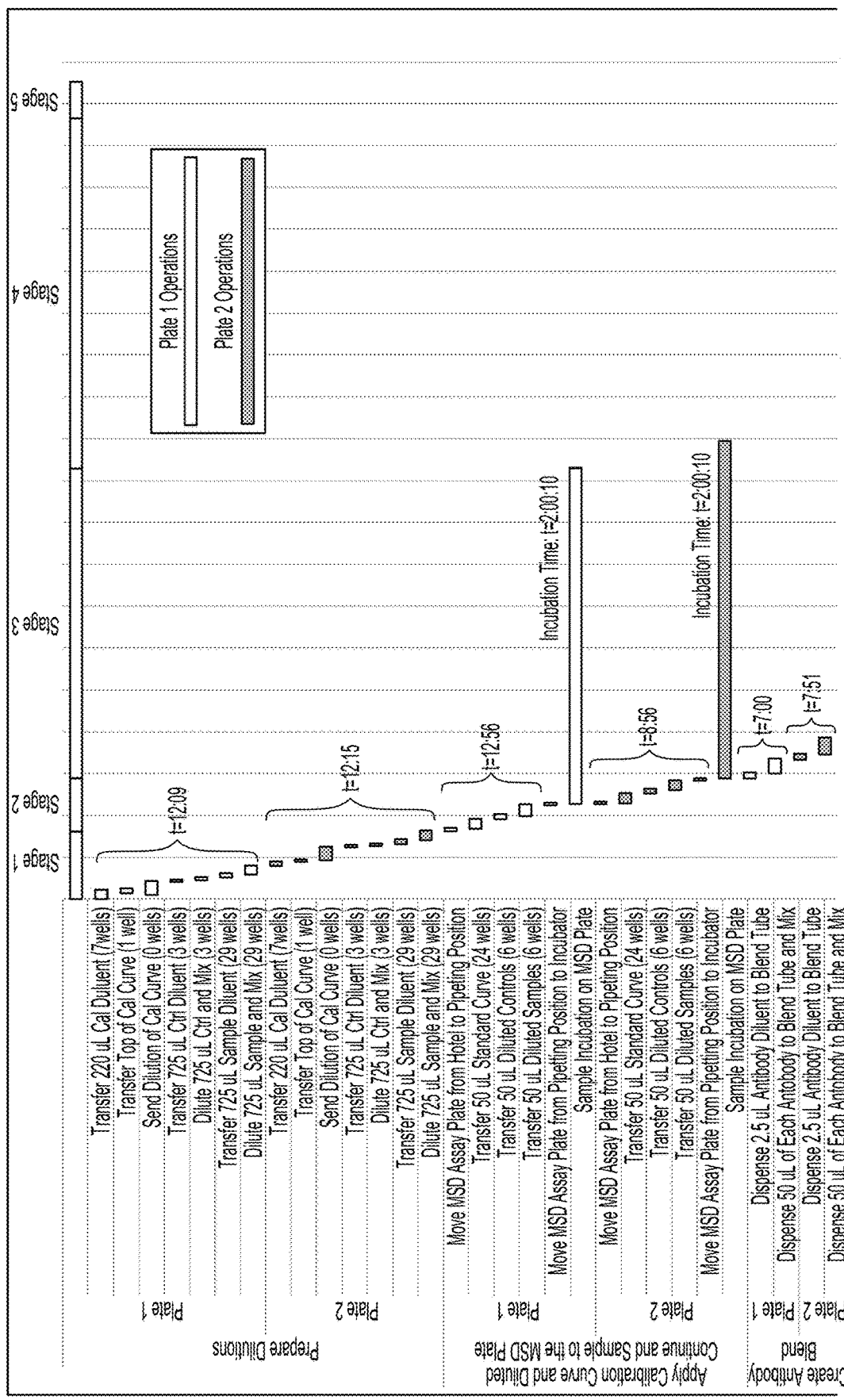
Figure 13E-a

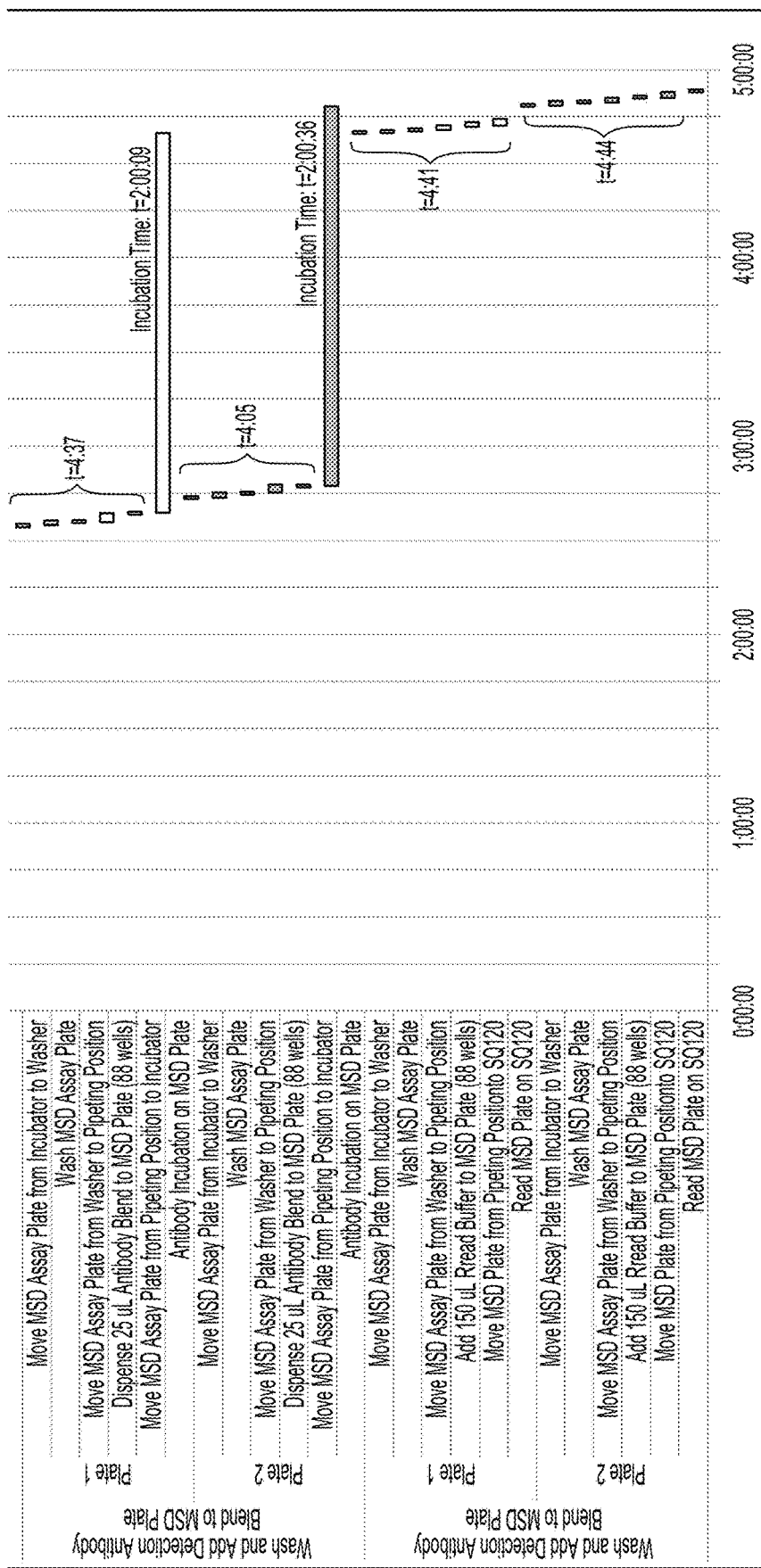
Figure 13E-b

| Stage | Description | Time to Complete Stage (hh:mm:ss) | | |
|---|---|---|---|---|
| | | Plate 1 | Plate 2 | Average |
| Stage 1 | Prepare Calibration Curve, Control Dilutions and Sample Dilutions | 00:12:09 | 00:12:15 | 00:12:12 |
| Stage 2 | Apply Calibration Curve and Diluted Controls and Samples to the MSD Plate | 00:09:56 | 00:08:56 | 00:09:26 |
| Incubation 1 | Sample Incubation on MSD Plate | 02:00:10 | 02:00:10 | 02:00:10 |
| Stage 3 | Create Antibody Blend (Occurs During Incubation 1) | 00:07:00 | 00:07:51 | 00:07:25 |
| Stage 4 | Move MSD Plate to Washer, Wash Plate and Return from Washer | 00:01:31 | 00:01:28 | 00:01:29 |
| | Add Detection Antibody Blend to MSD Plate | 00:03:06 | 00:02:37 | 00:02:52 |
| Incubation 2 | Detection Antibody Incubation on MSD Plate | 02:00:09 | 02:00:36 | 02:00:23 |
| Stage 5 | Move MSD Plate to Washer, Wash Plate and Return from Washer | 00:01:29 | 00:01:28 | 00:01:29 |
| | Add Read Buffer to MSD Plate and Read on SQ120 | 00:03:12 | 00:03:15 | 00:03:14 |
| Total Time to Complete the Run (hh:mm:ss) | | 04:42:43 | 04:40:42 | 04:41:27 |

Fig. 13(f)

| Reagent Rack 5 | MSD Plate 5 | Sample Input Plate 5 | Dilution Plate 5 | Empty | Empty |

| Reagent Rack 4 | MSD Plate 4 | Sample Input Plate 4 | Dilution Plate 4 | Empty | Empty |

| Reagent Rack 3 | MSD Plate 3 | Sample Input Plate 3 | Dilution Plate 3 | Empty | Empty |

| Reagent Rack 2 | MSD Plate 2 | Sample Input Plate 2 | Dilution Plate 2 | Empty | Empty |

| Reagent Rack 1 | MSD Plate 1 | Sample Input Plate 1 | Dilution Plate 1 | Empty | Empty |

Fig. 14(b)

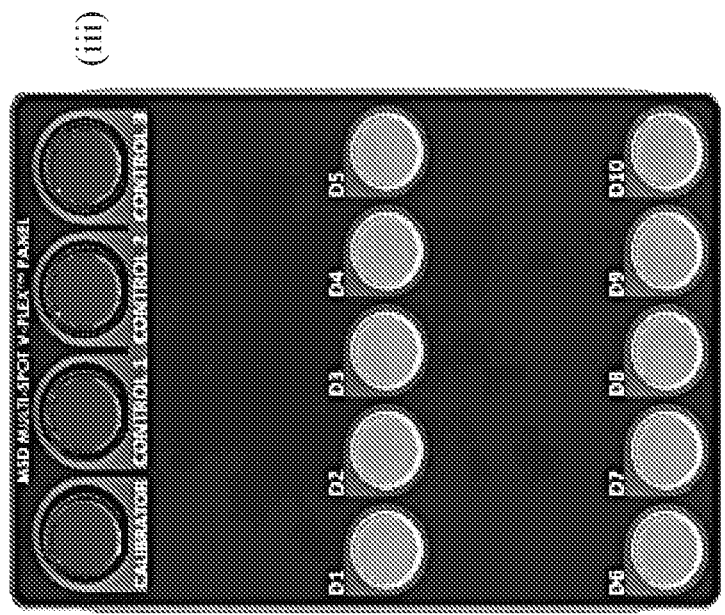
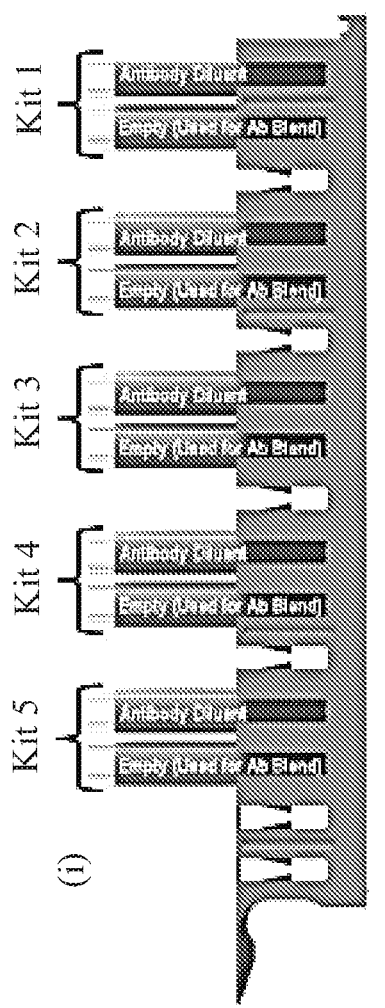
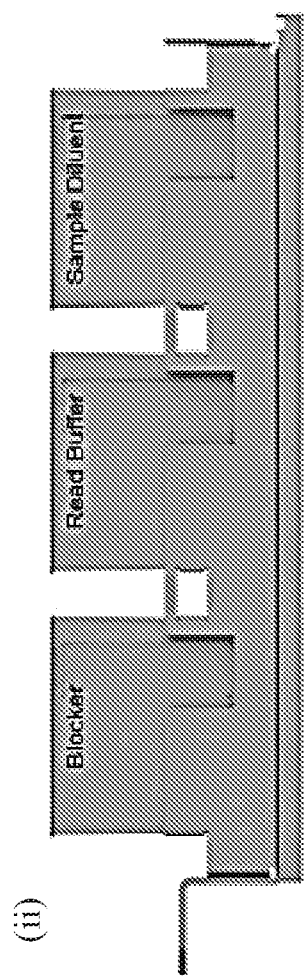
Fig. 14(c)

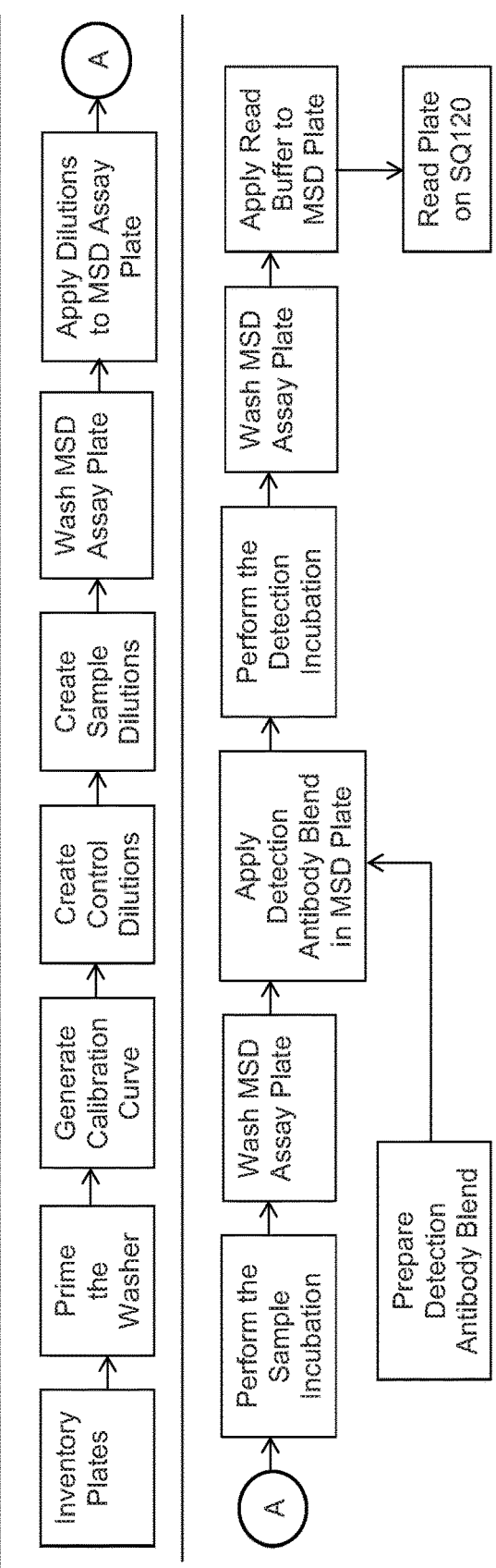

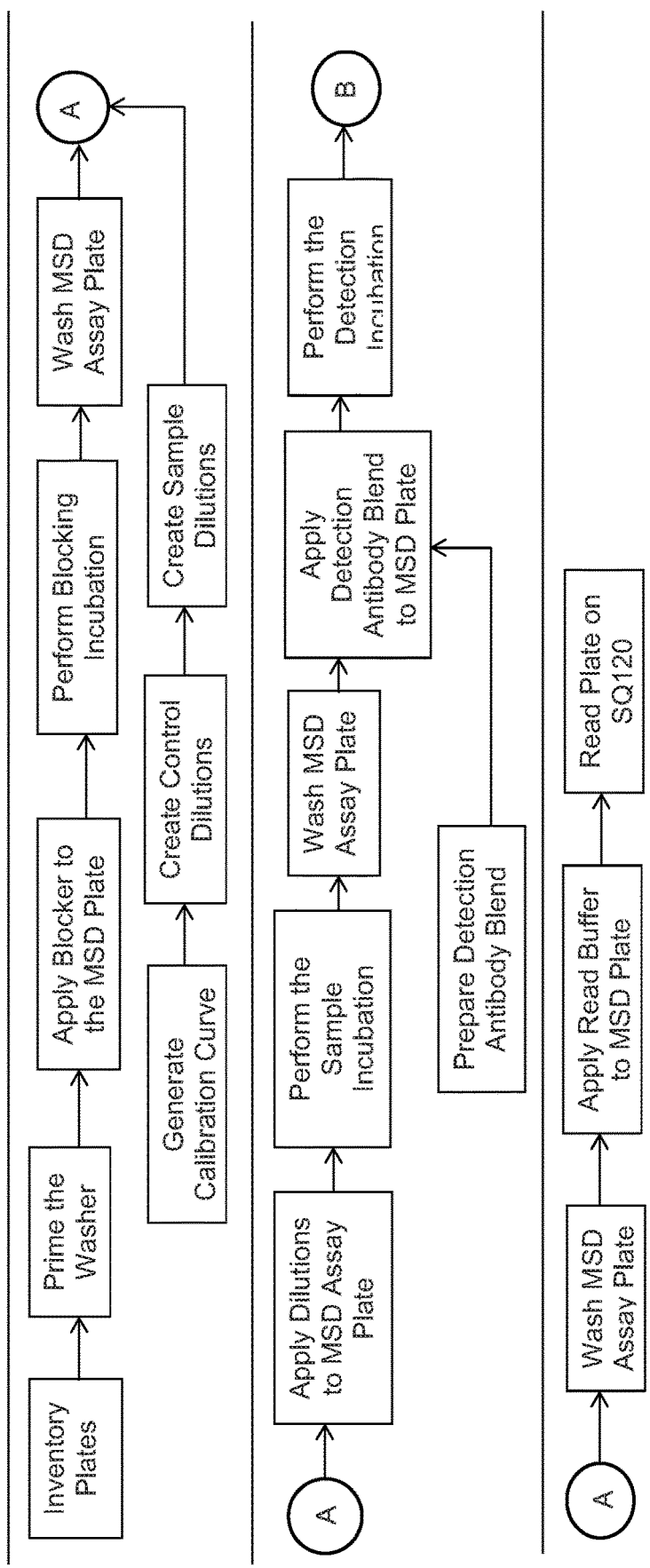

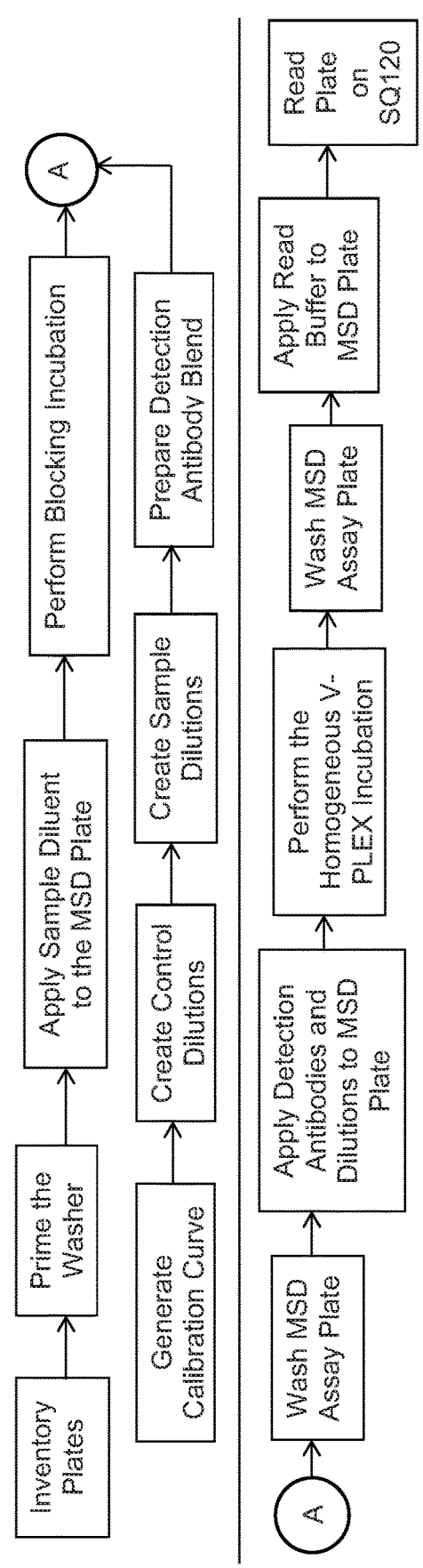

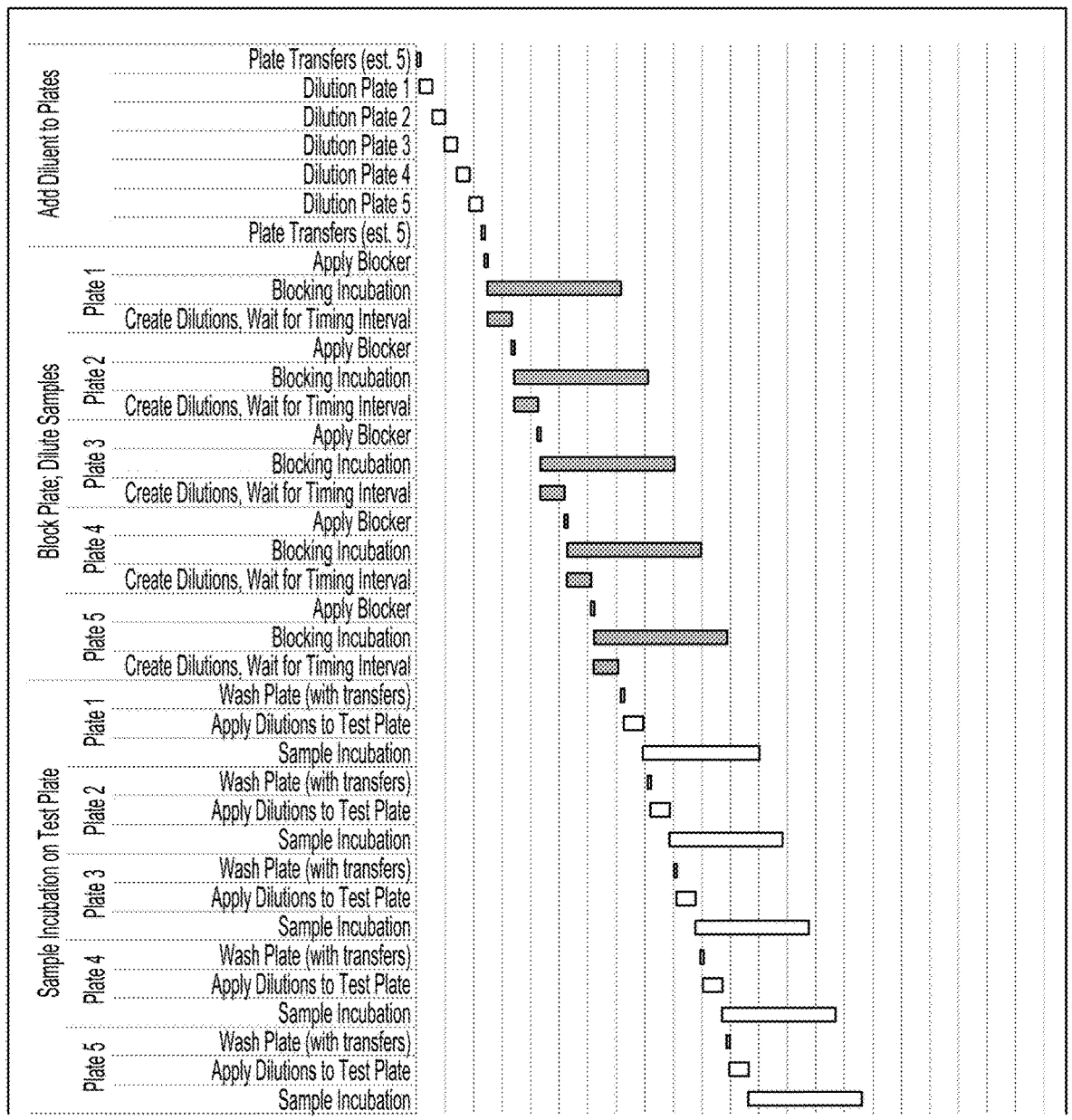
Figure 14J-a: V-PLEX Stepwise Assay, 5-Plate Run

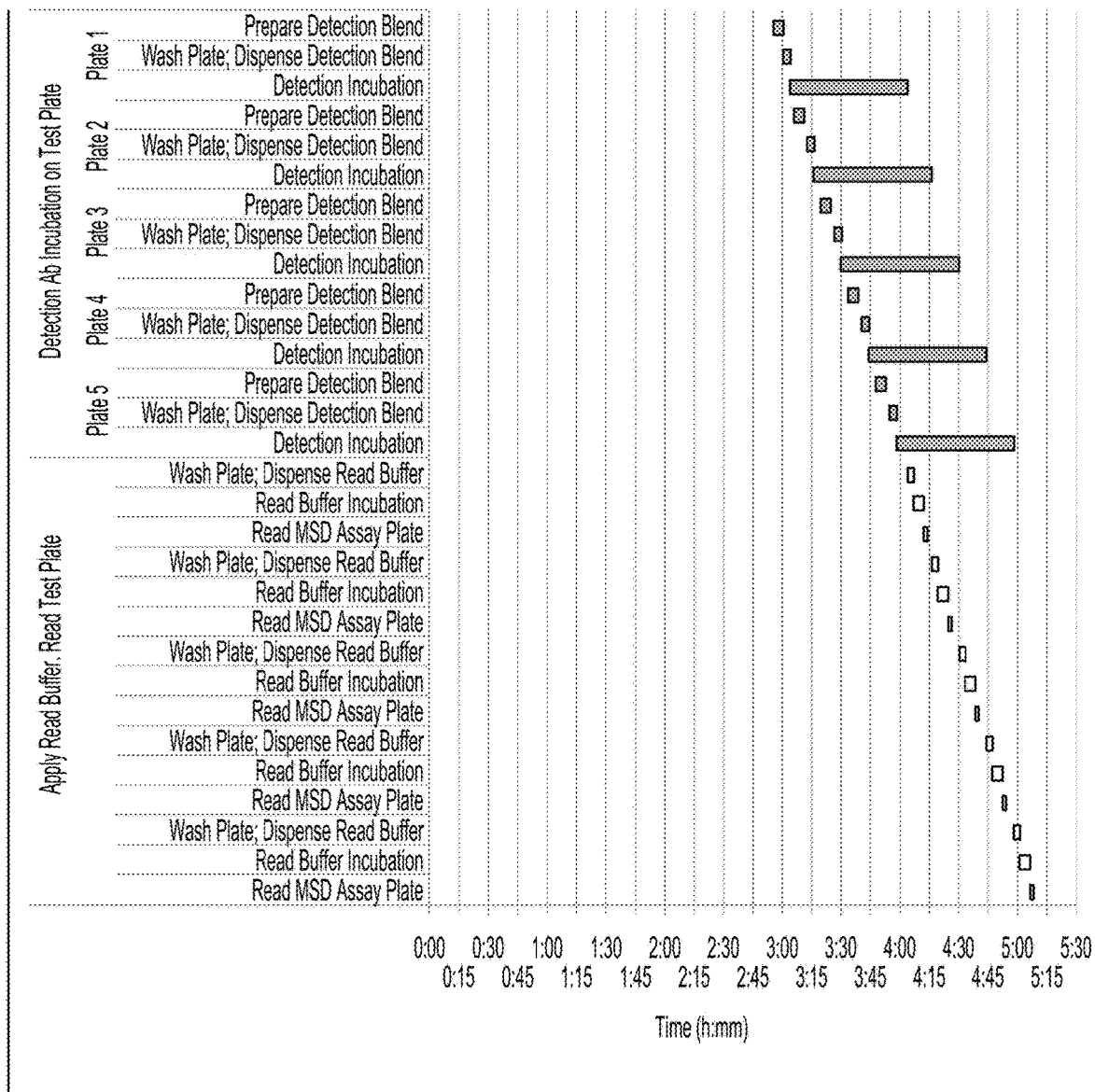
Figure 14J-b: V-PLEX Stepwise Assay, 5-Plate Run

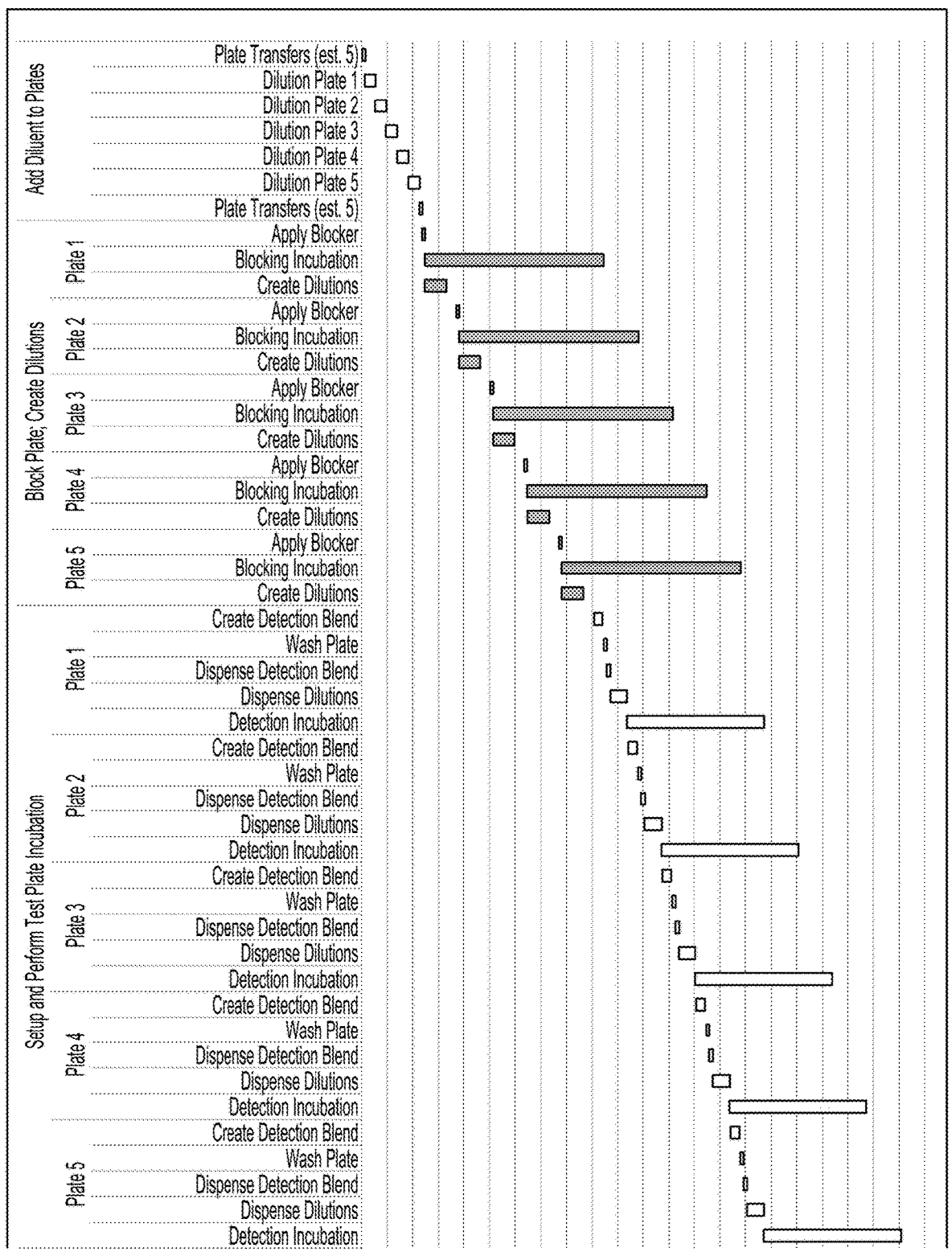
Figure 14K-a: V-PLEX Homogenous Assay, 5-Plate Run

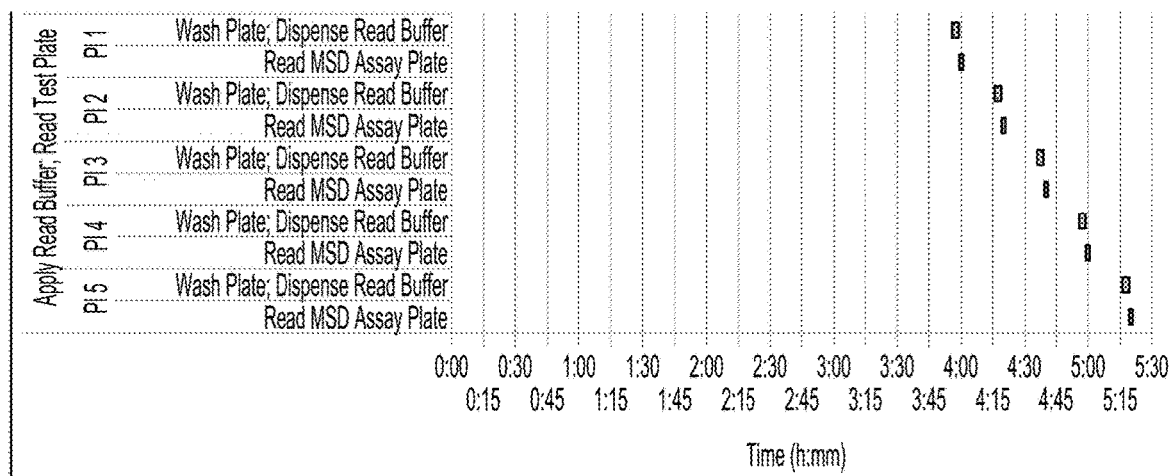
Figure 14K-b: V-PLEX Homogenous Assay, 5-Plate Run

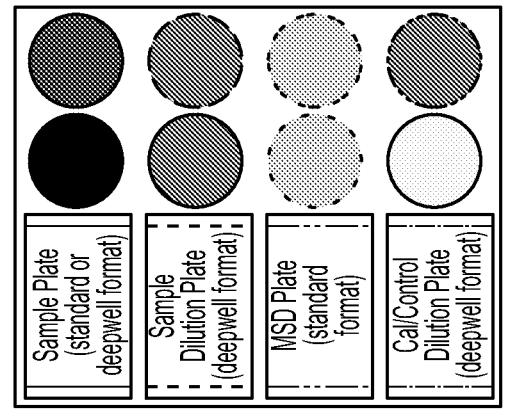
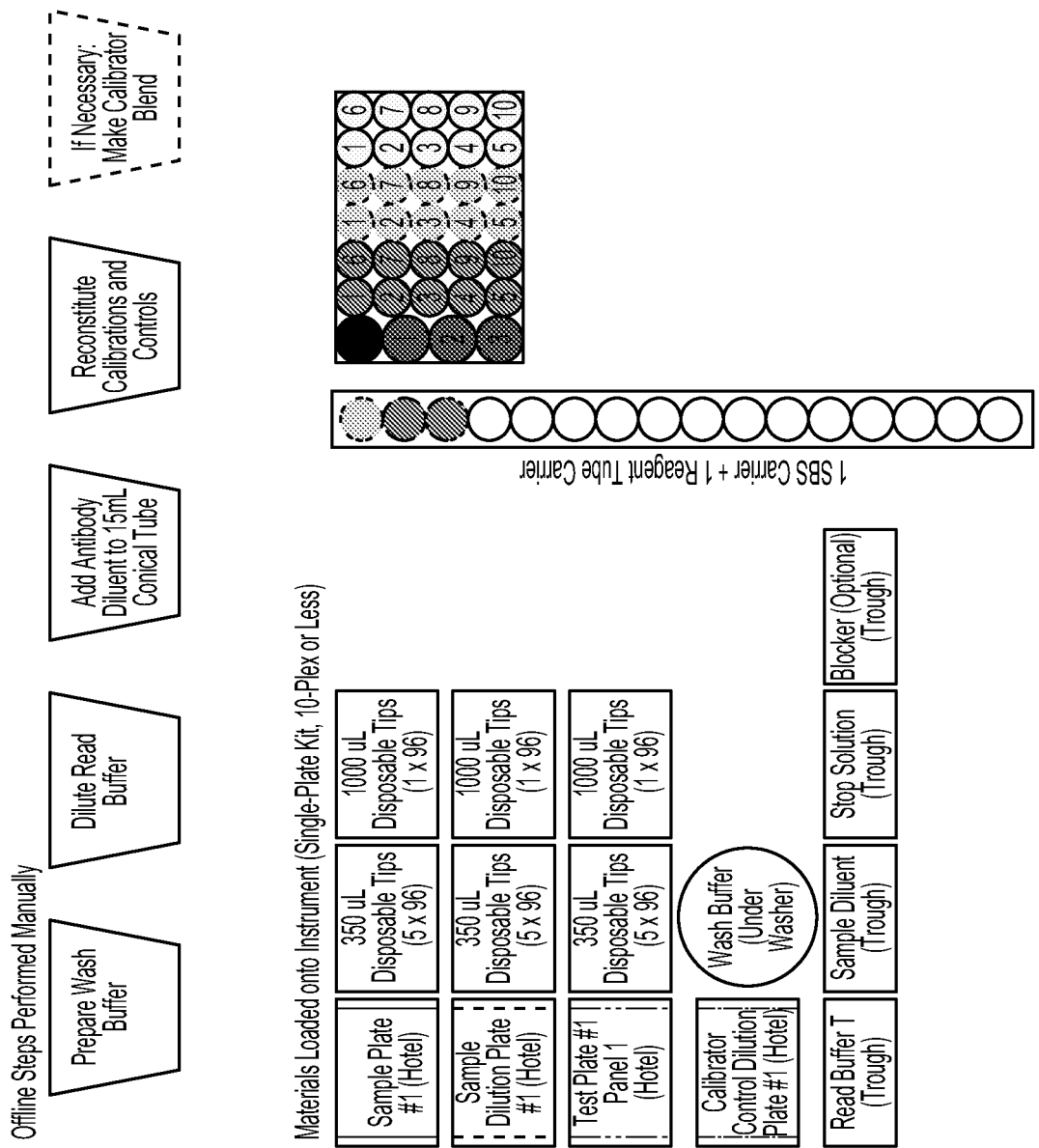
Figure 15A

Figure 15C-a

*Offline Steps and Instrument Loading: Multi-Plate U-Plex Kit*

*Offline Steps Performed Manually*

Prepare Wash Buffer → Dilute Read Buffer → Add Antibody Diluent to 15mL Conical Tube → Reconstitute Calibrations and Controls → If Necessary: Make Calibrator Blend

*Materials Loaded onto Instrument *Example for U-Plex Human Biomarker 40-Plex)*

| Sample Plate #1 (Hotel) | Sample Plate #2 (Hotel) | Sample Plate #3 (Hotel) | Sample Plate #4 (Hotel) | Sample Plate #5 (Hotel) |
|---|---|---|---|---|
| Sample Dilution Plate #1 (Hotel) | Sample Dilution Plate #2 (Hotel) | Sample Dilution Plate #3 (Hotel) | Sample Dilution Plate #4 (Hotel) | Sample Dilution Plate #5 (Hotel) |
| Test Plate #1 Panel 1 (Hotel) | Test Plate #2 Panel 2 (Hotel) | Test Plate #3 Panel 3 (Hotel) | Test Plate #4 Panel 4 (Hotel) | Test Plate #5 Panel 5 (Hotel) |
| Calibrator Control Dilution Plate #1 (Hotel) | | | | |

Wash Buffer (Under Washer)

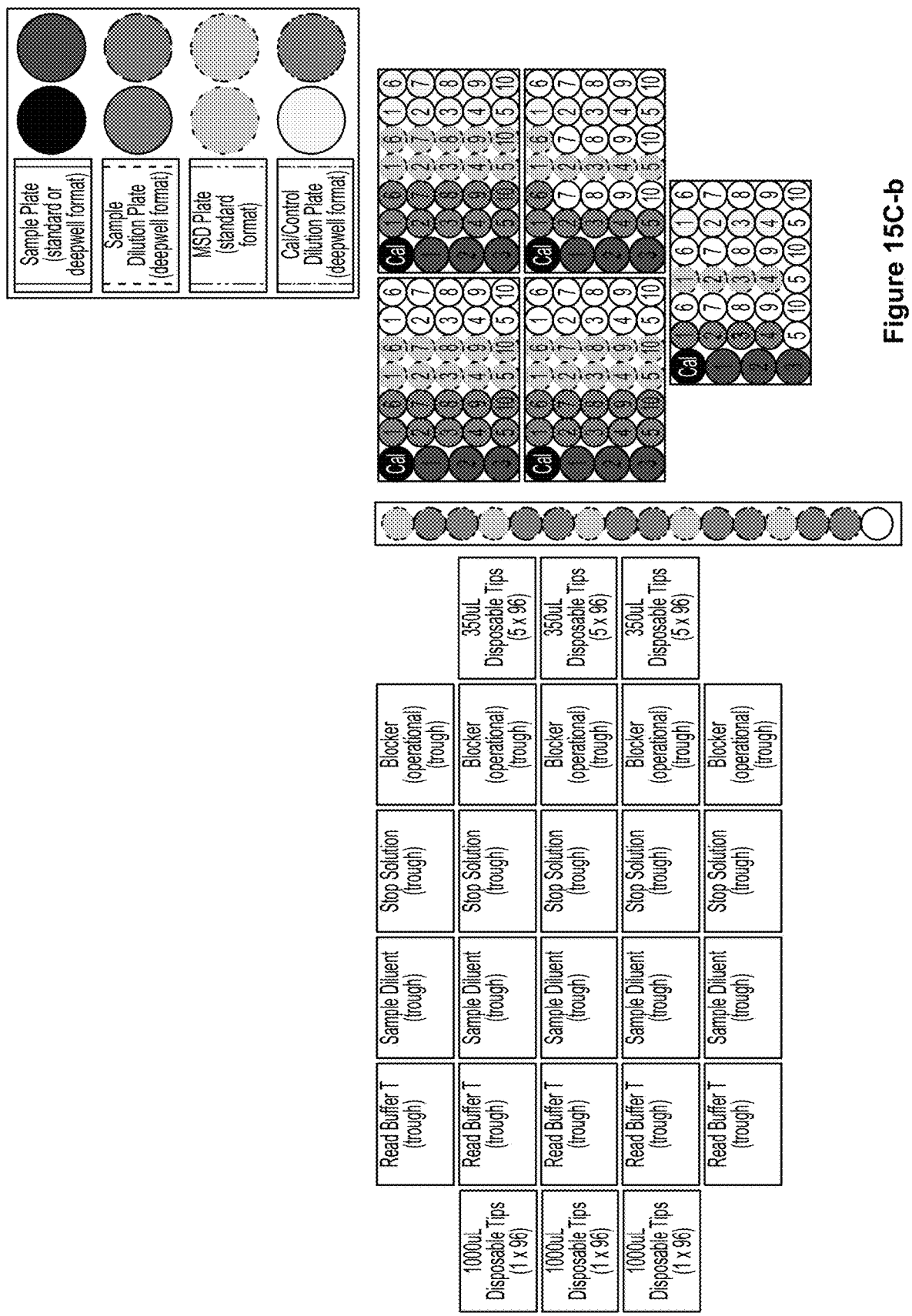
Figure 15C-b

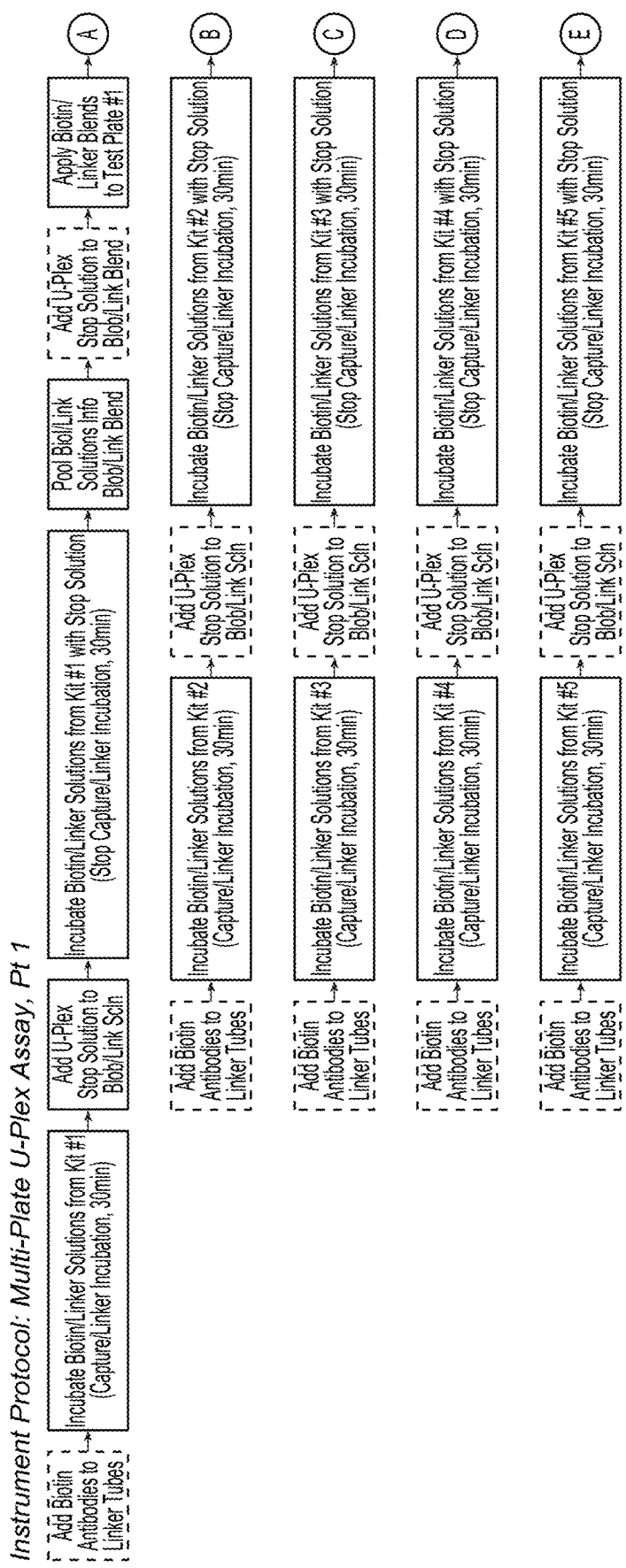
Figure 15D-a

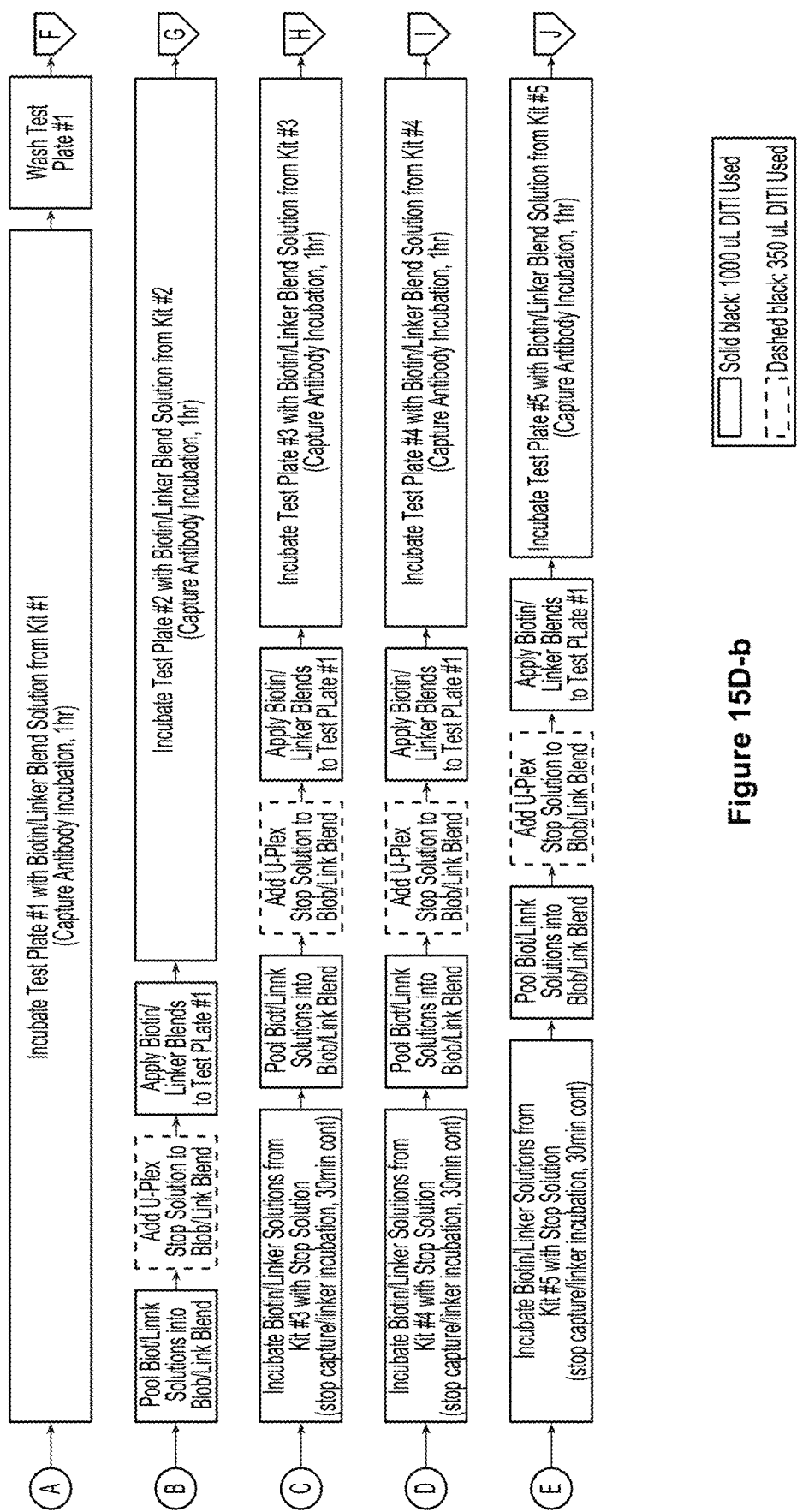
Figure 15D-b

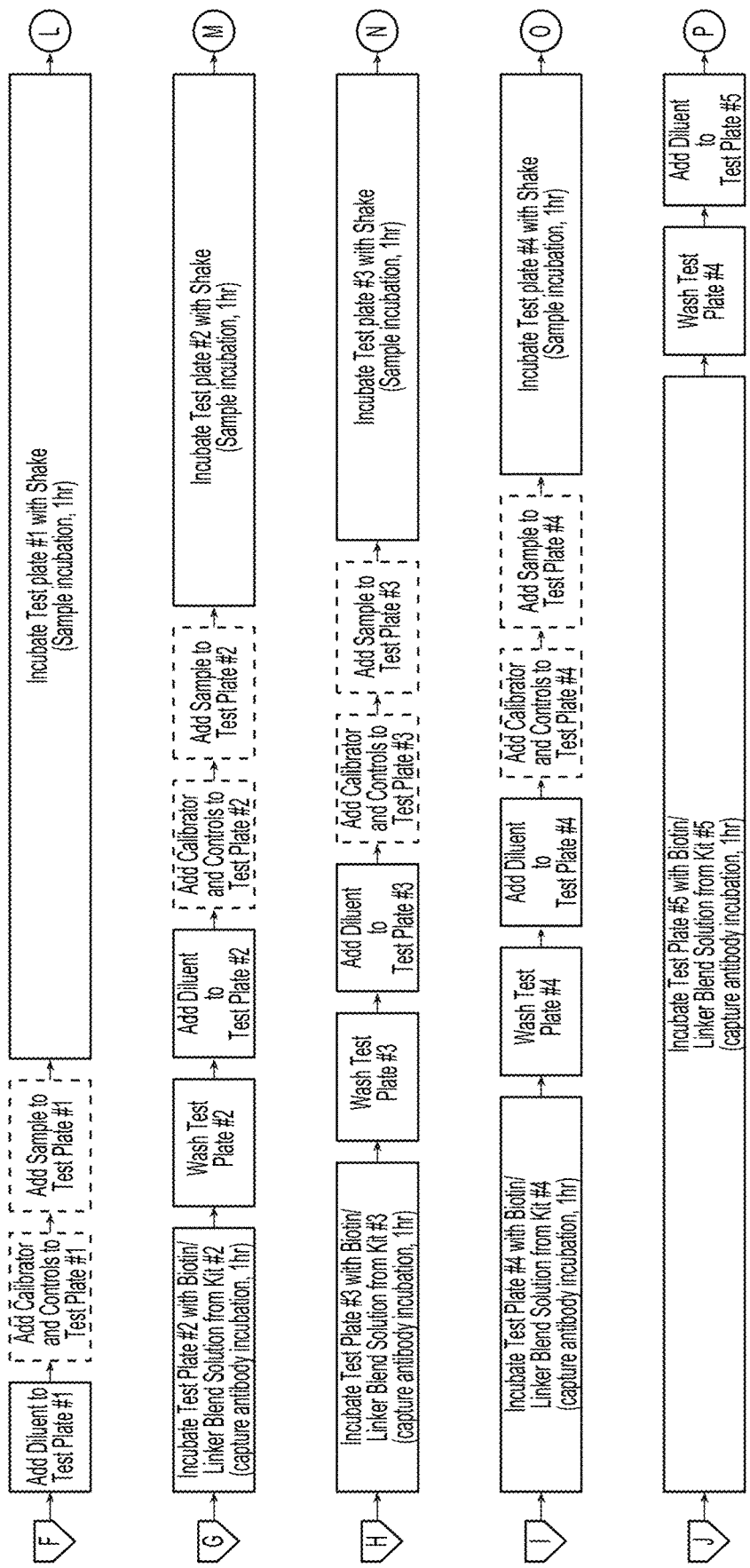
Figure 15E-a

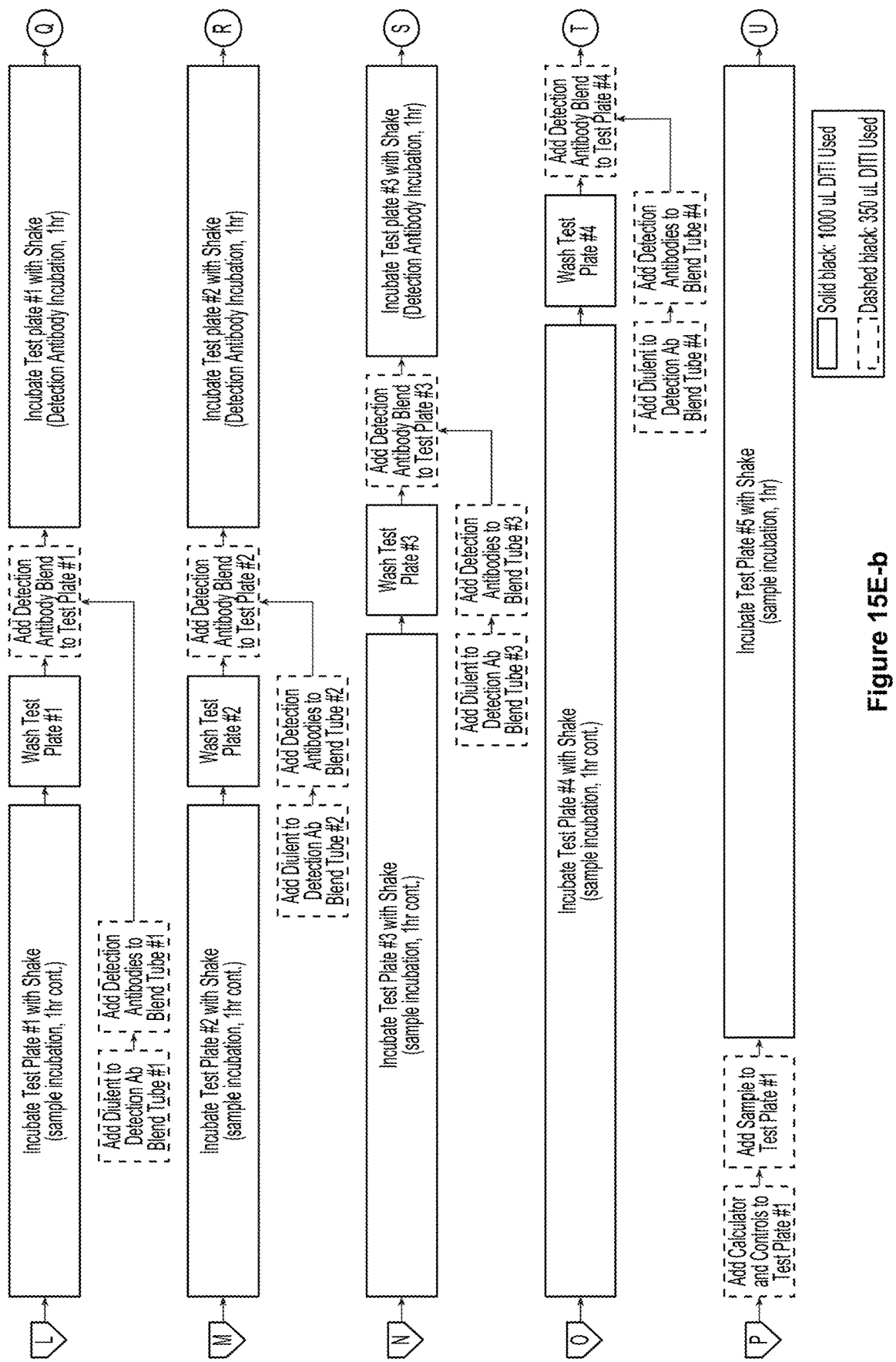
Figure 15E-b

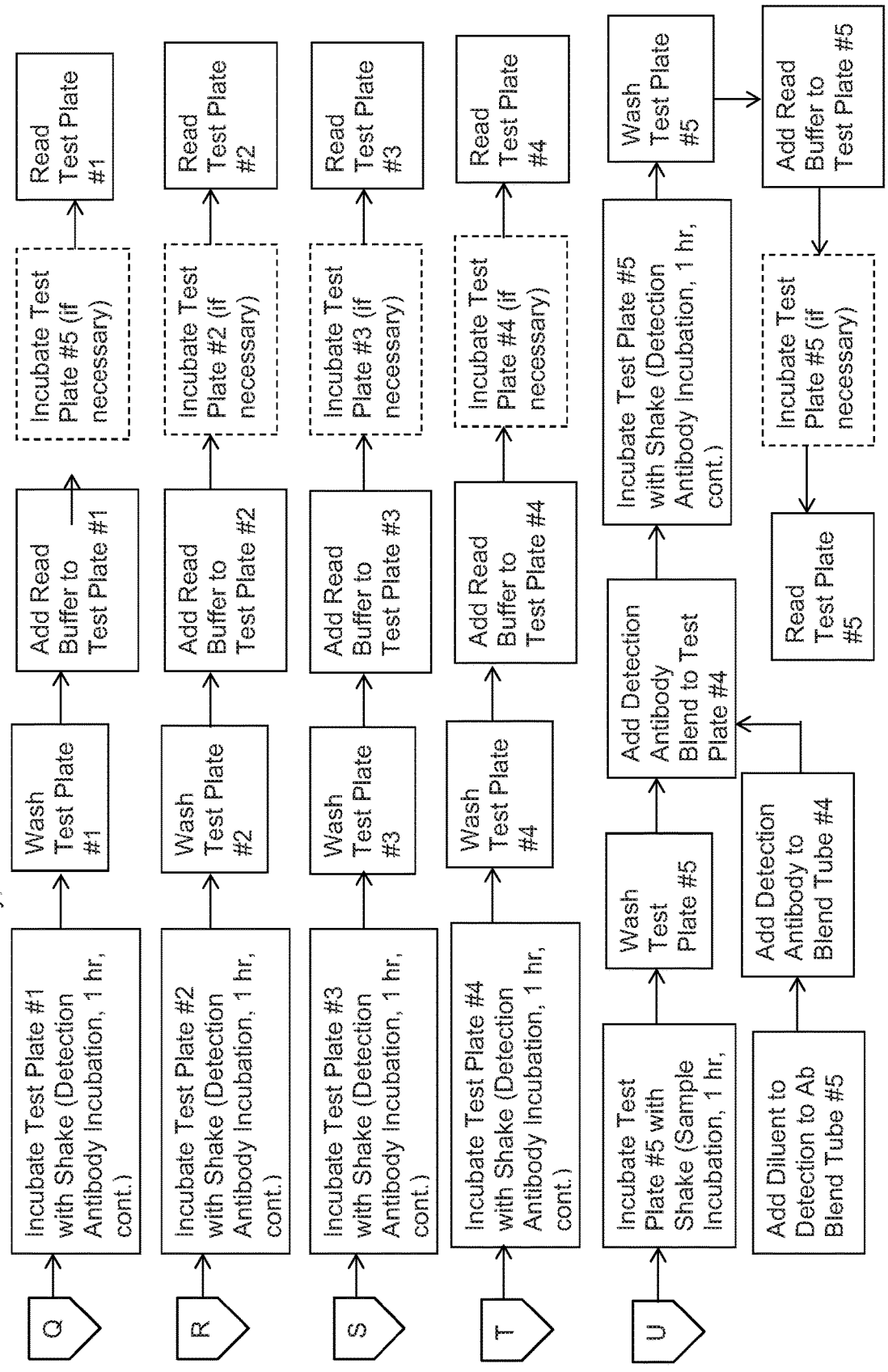

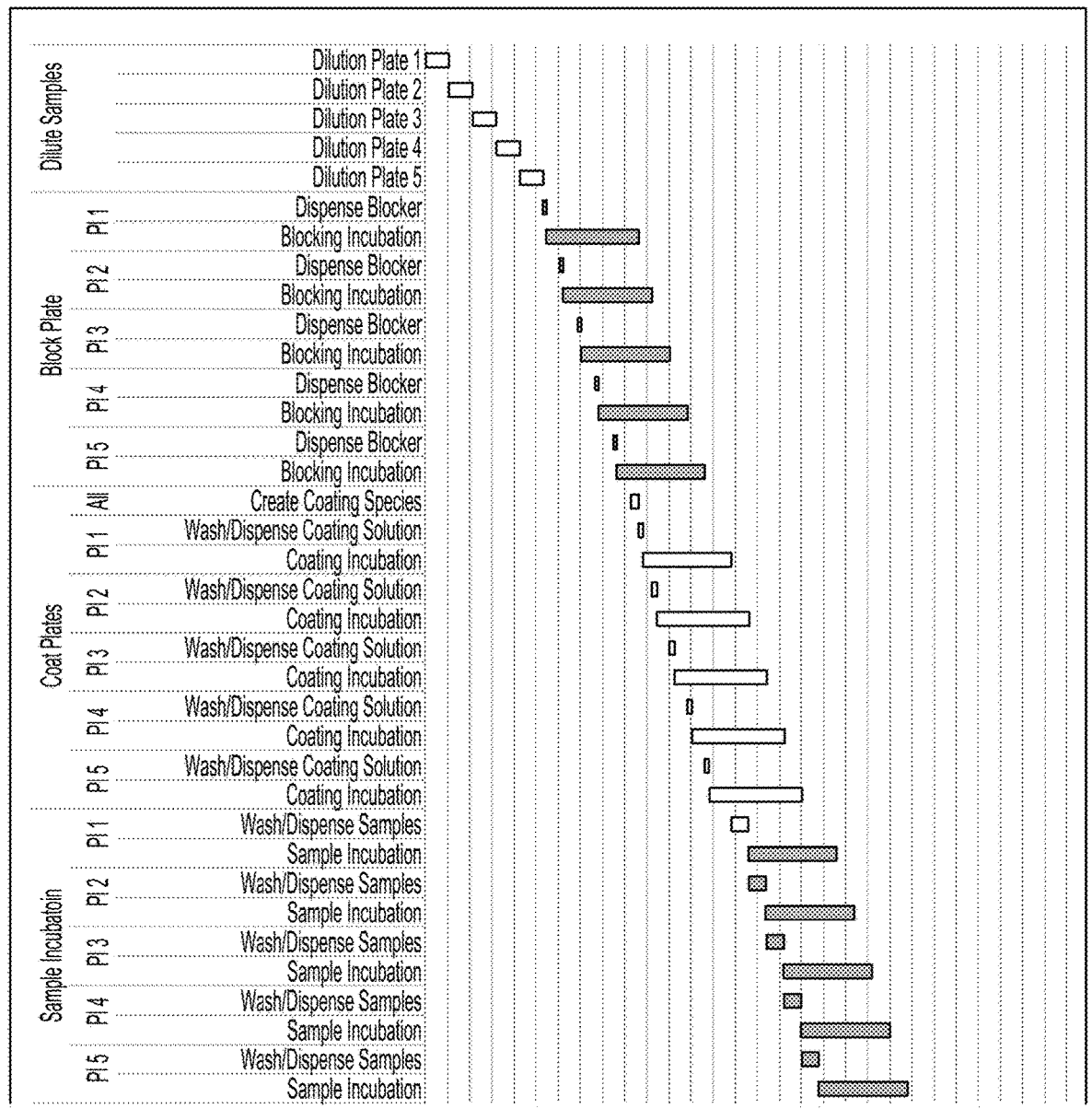
Figure 15G-a: U-PLEX Singleplex 5-Plate Run (Same as Custom Singleplex, Streptavidin Plate, Direct Assay)

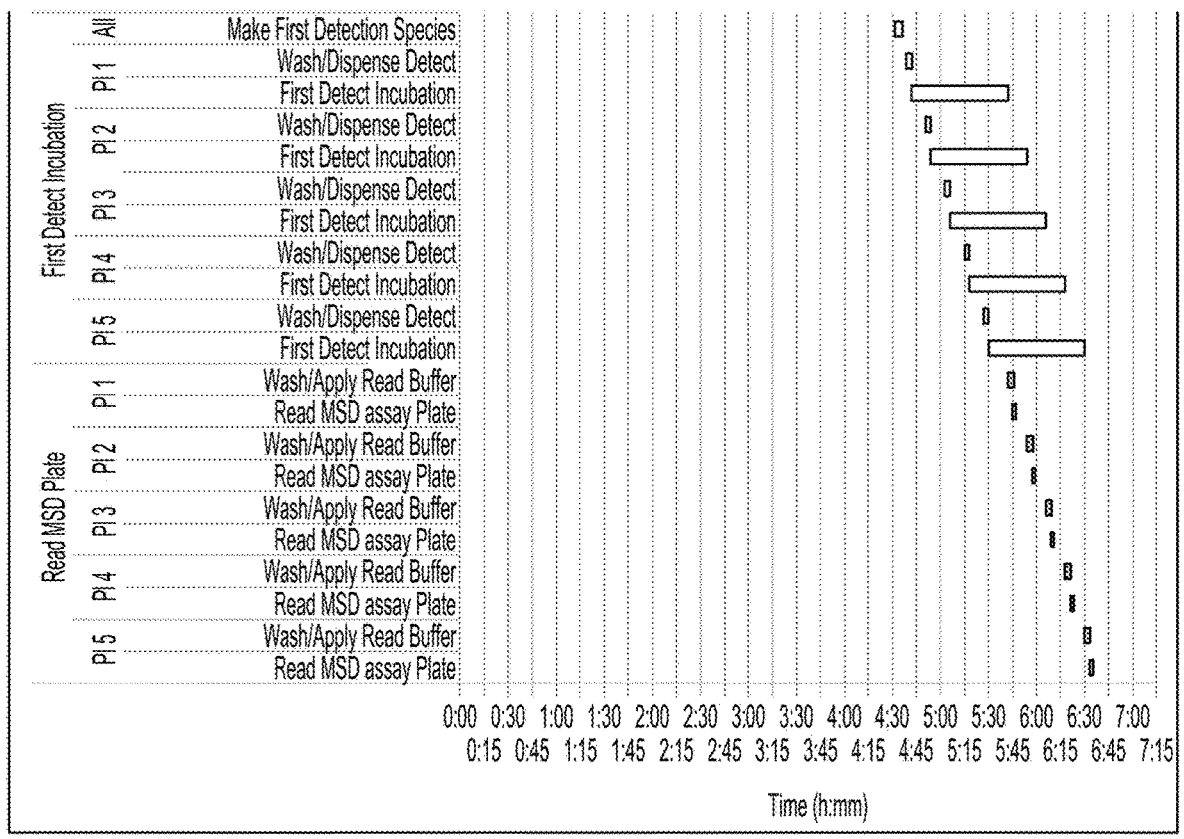
Figure 15G-b: U-PLEX Singleplex 5-Plate Run (Same as Custom Singleplex, Streptavidin Plate, Direct Assay)

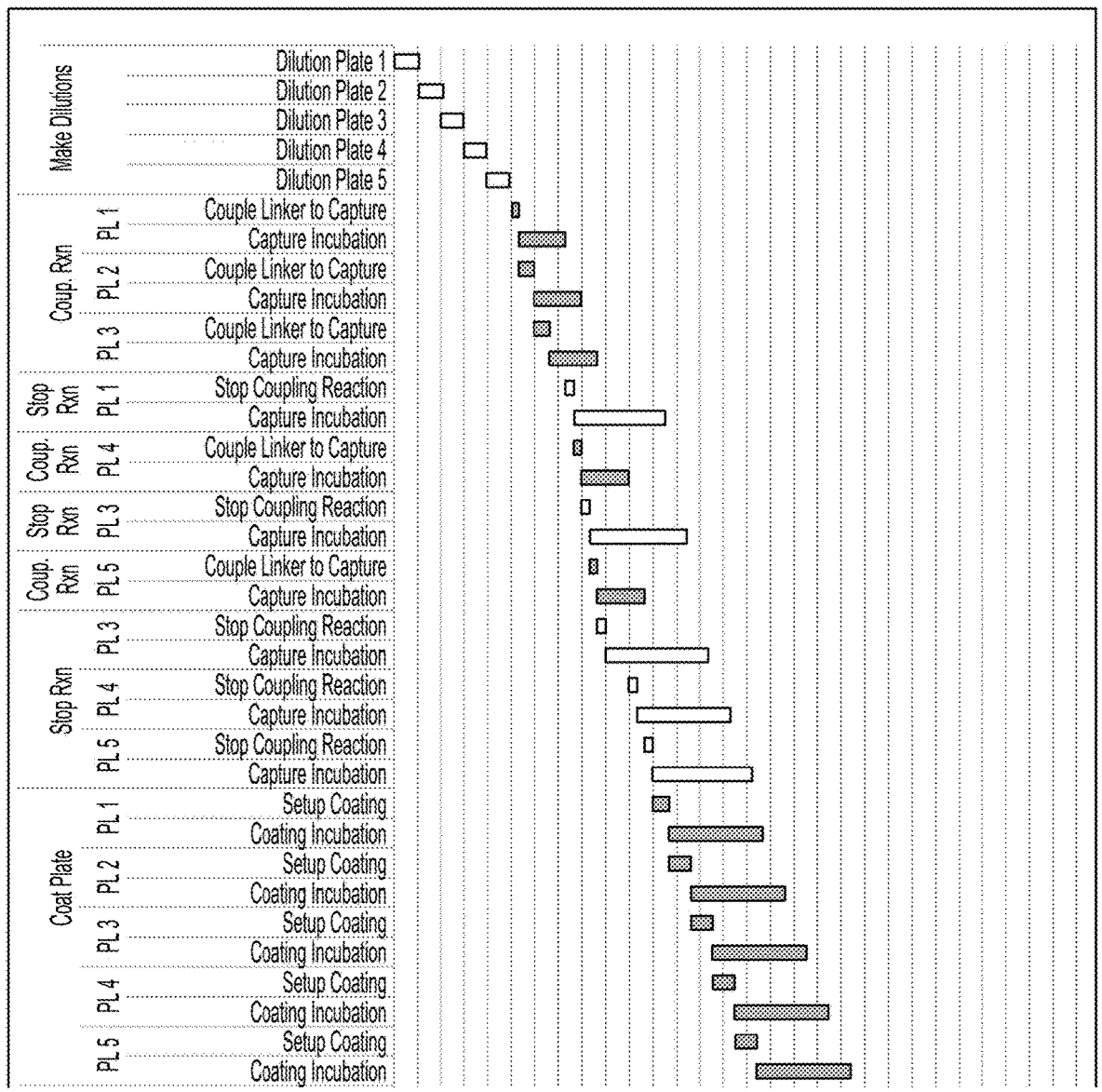
Figure 15H-a: U-PLEX 10-Plex Multiplex, 5-Plate Run

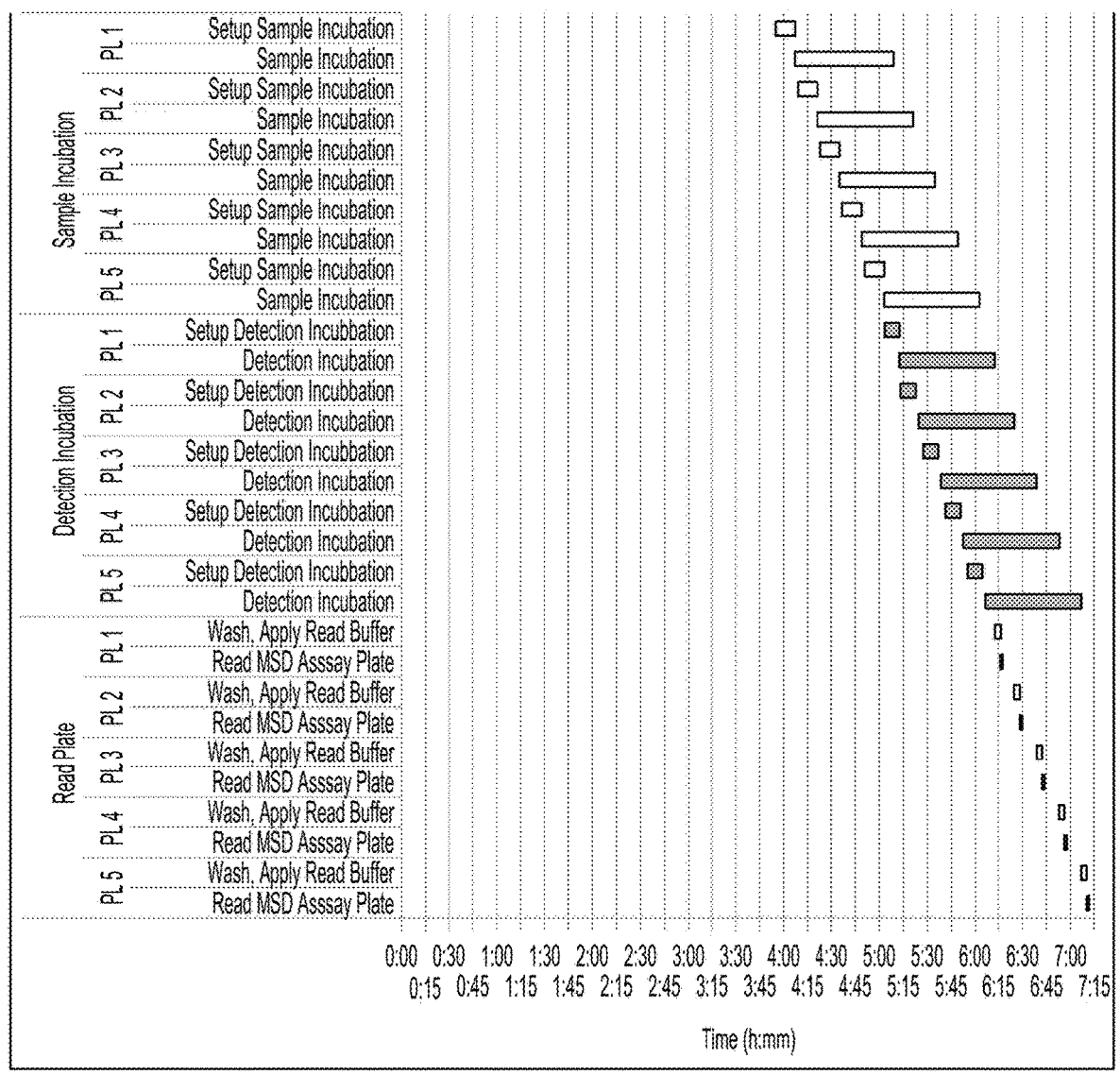
Figure 15H-b: U-PLEX 10-Plex Multiplex, 5-Plate Run

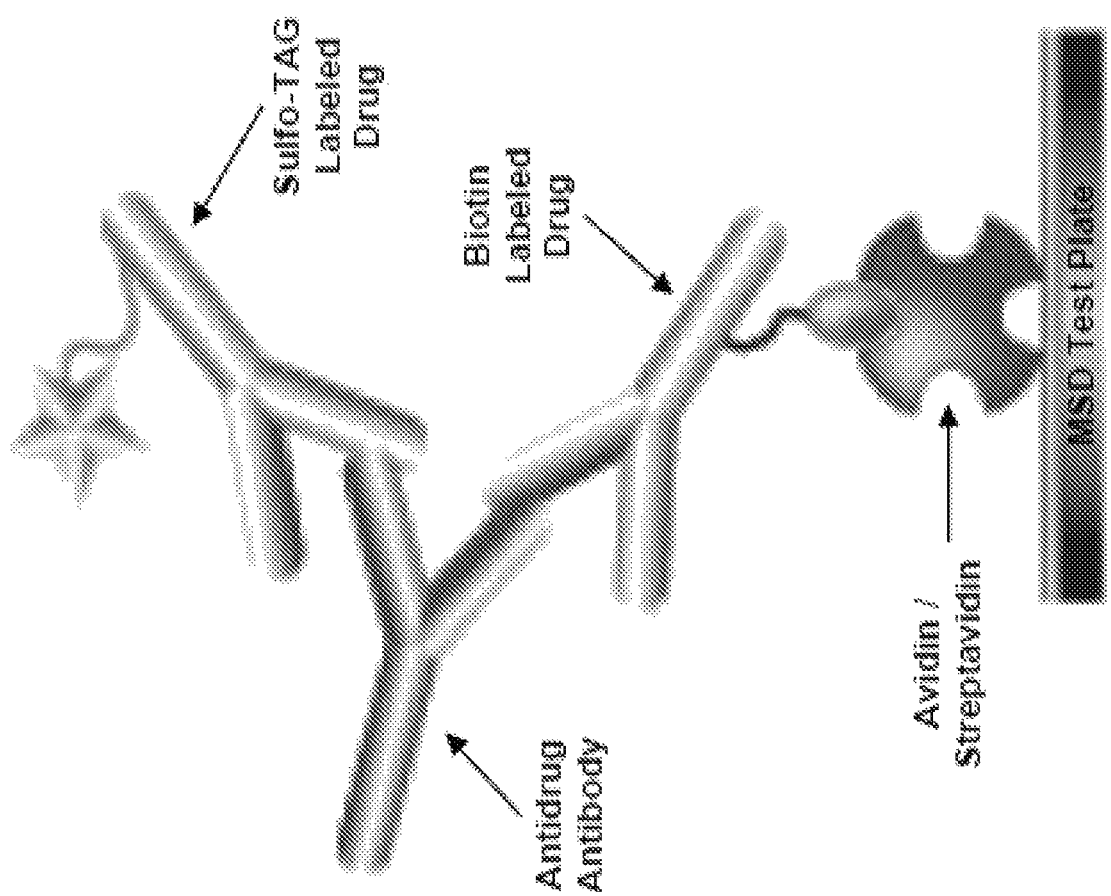

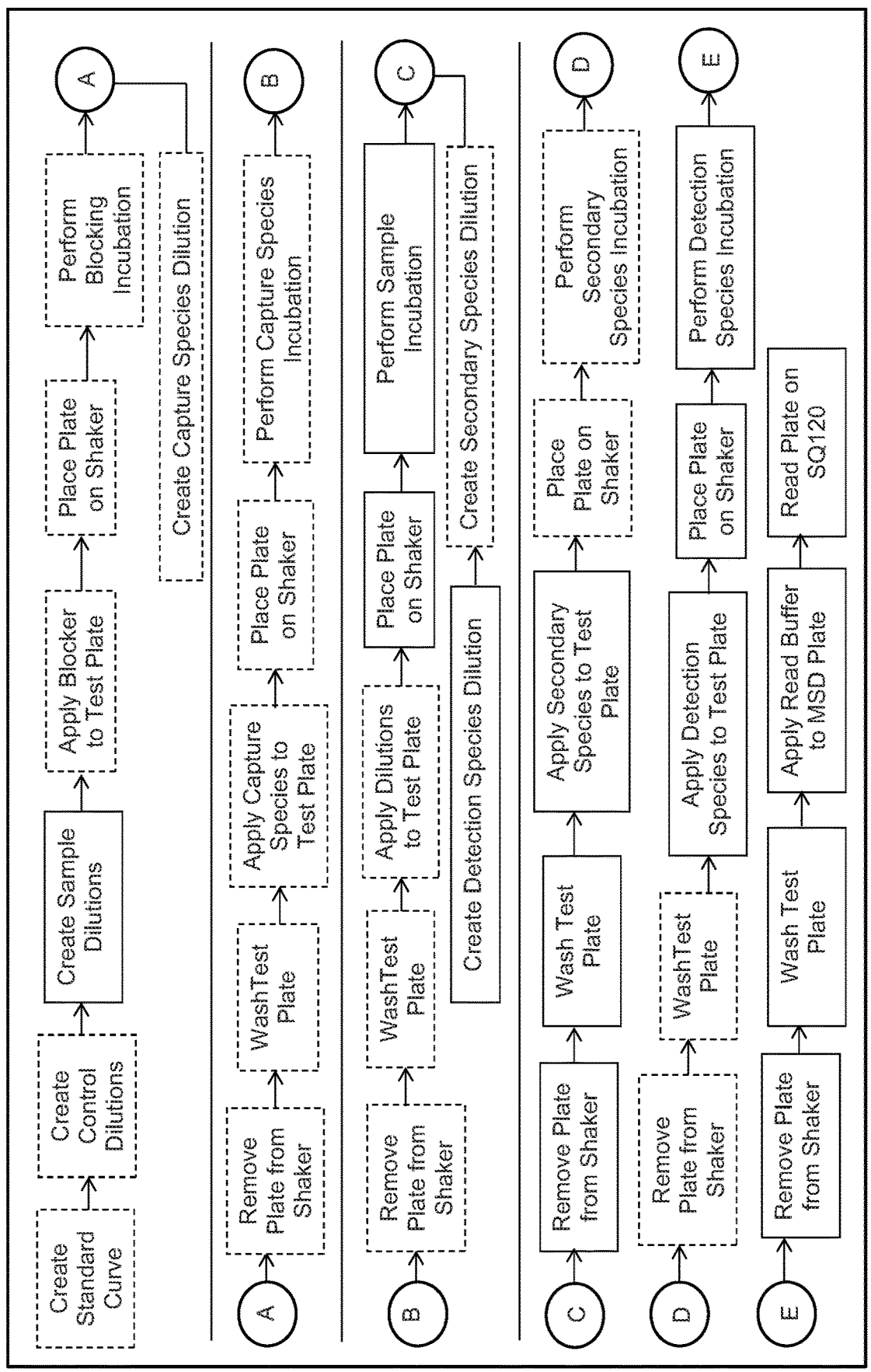
Figure 17(d). Custom Sandwich Immunoassays

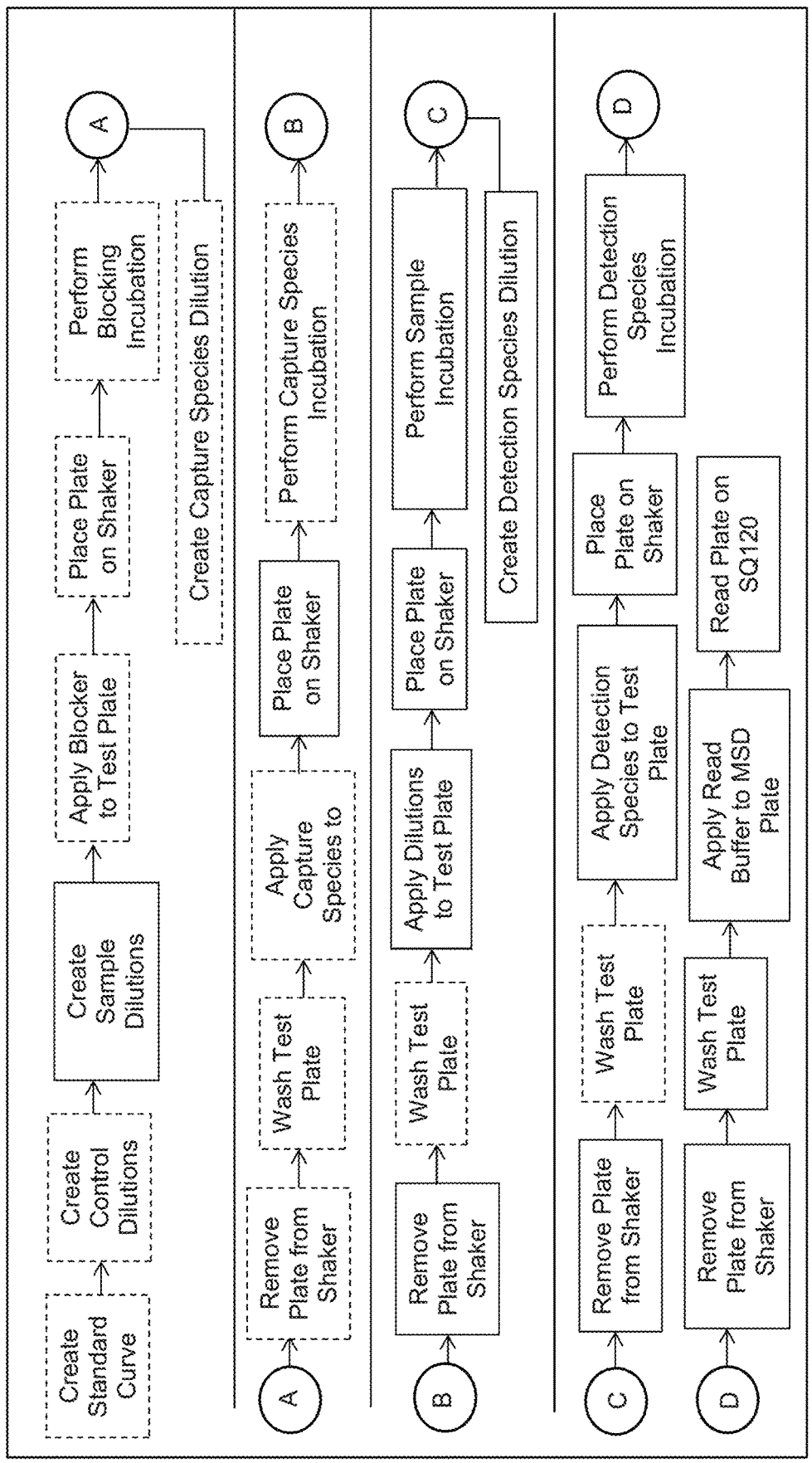
Figure 17(e)-a. Protocol for Direct Assay, Streptavidin or Avidin Plate and Reagent Rack

Figure 17(e)-b. Protocol for Direct Assay, Streptavidin or Avidin Plate and Reagent Rack

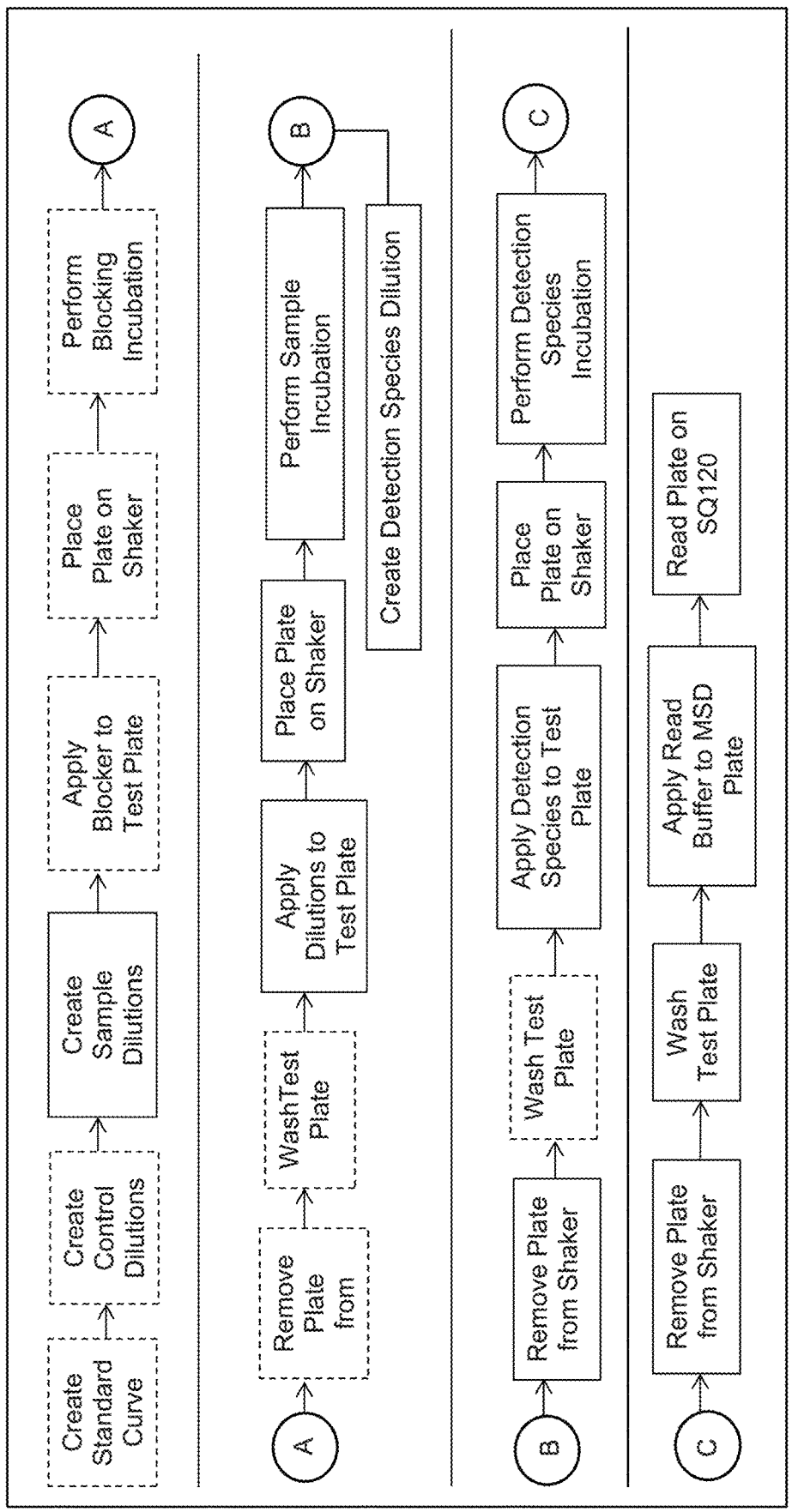
Figure 17(f)-a. Protocol for Direct Assay, Uncoated Plate and Reagent Rack

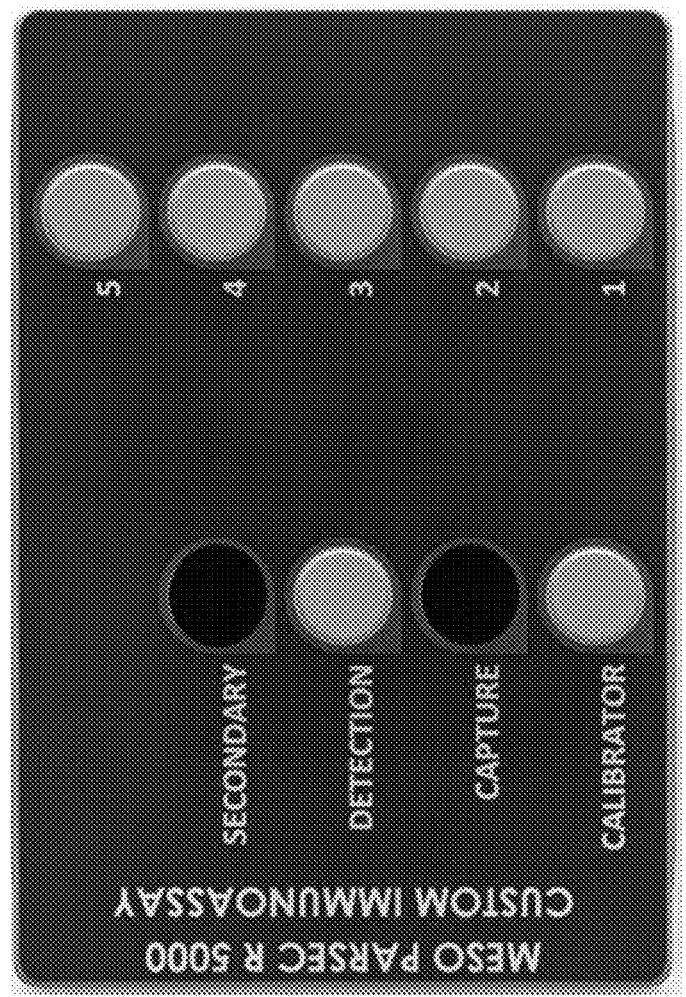
Figure 17(f)-b. Protocol for Direct Assay, Uncoated Plate and Reagent Rack

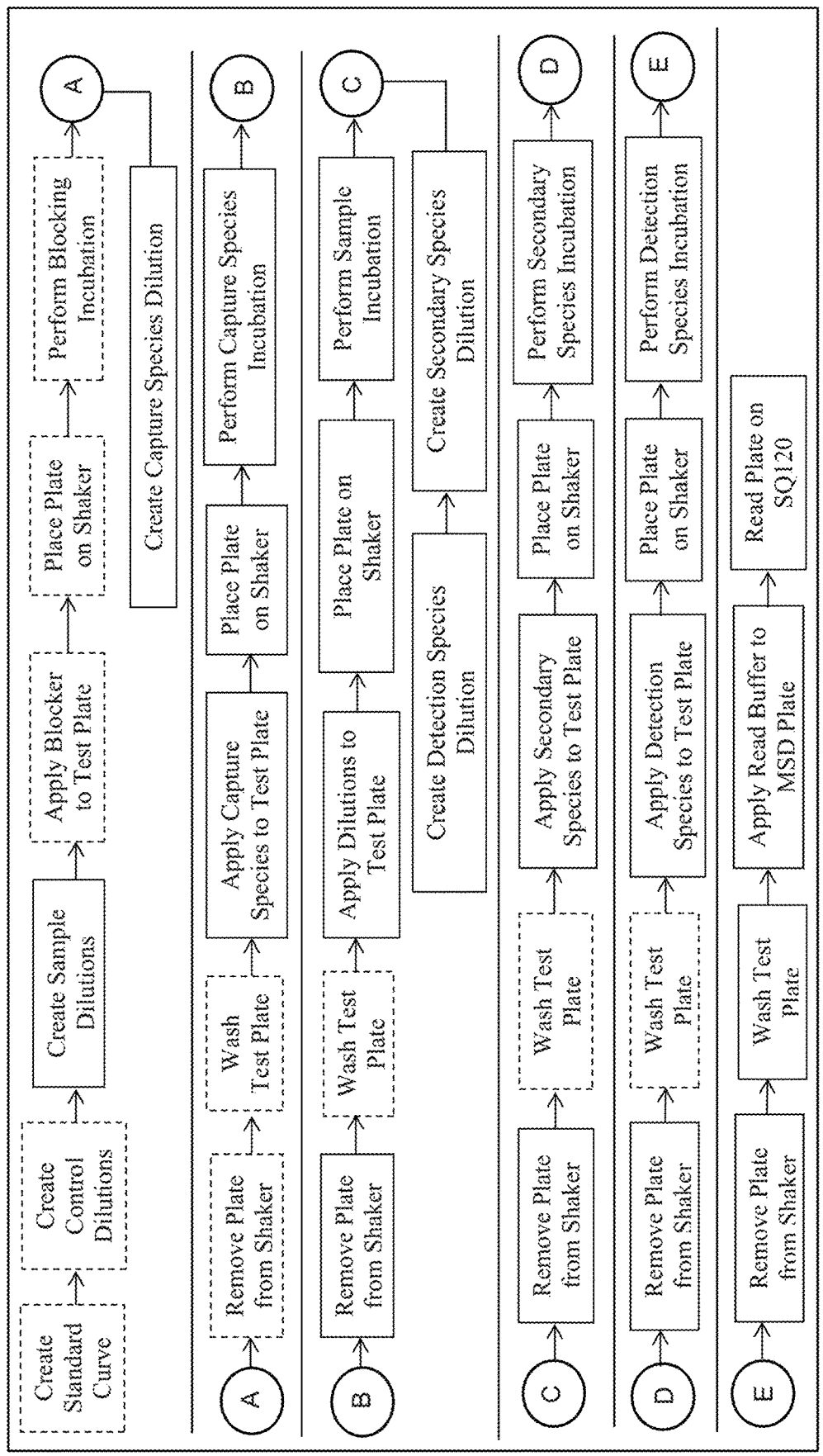
Figure 17(g)-a. Protocol for Indirect Assay, Streptavidin or Avidin Plate and Reagent Rack

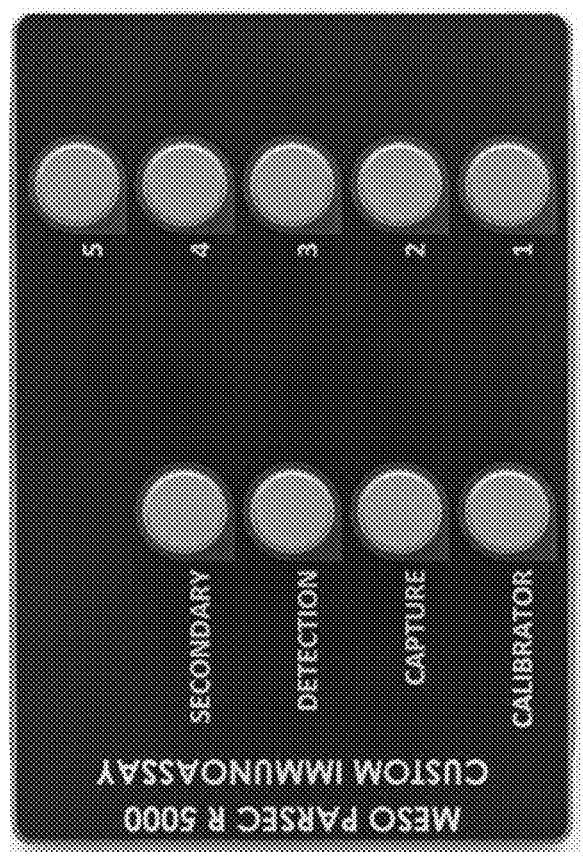
Figure 17(g)-b. Protocol for Indirect Assay, Streptavidin or Avidin Plate and Reagent Rack

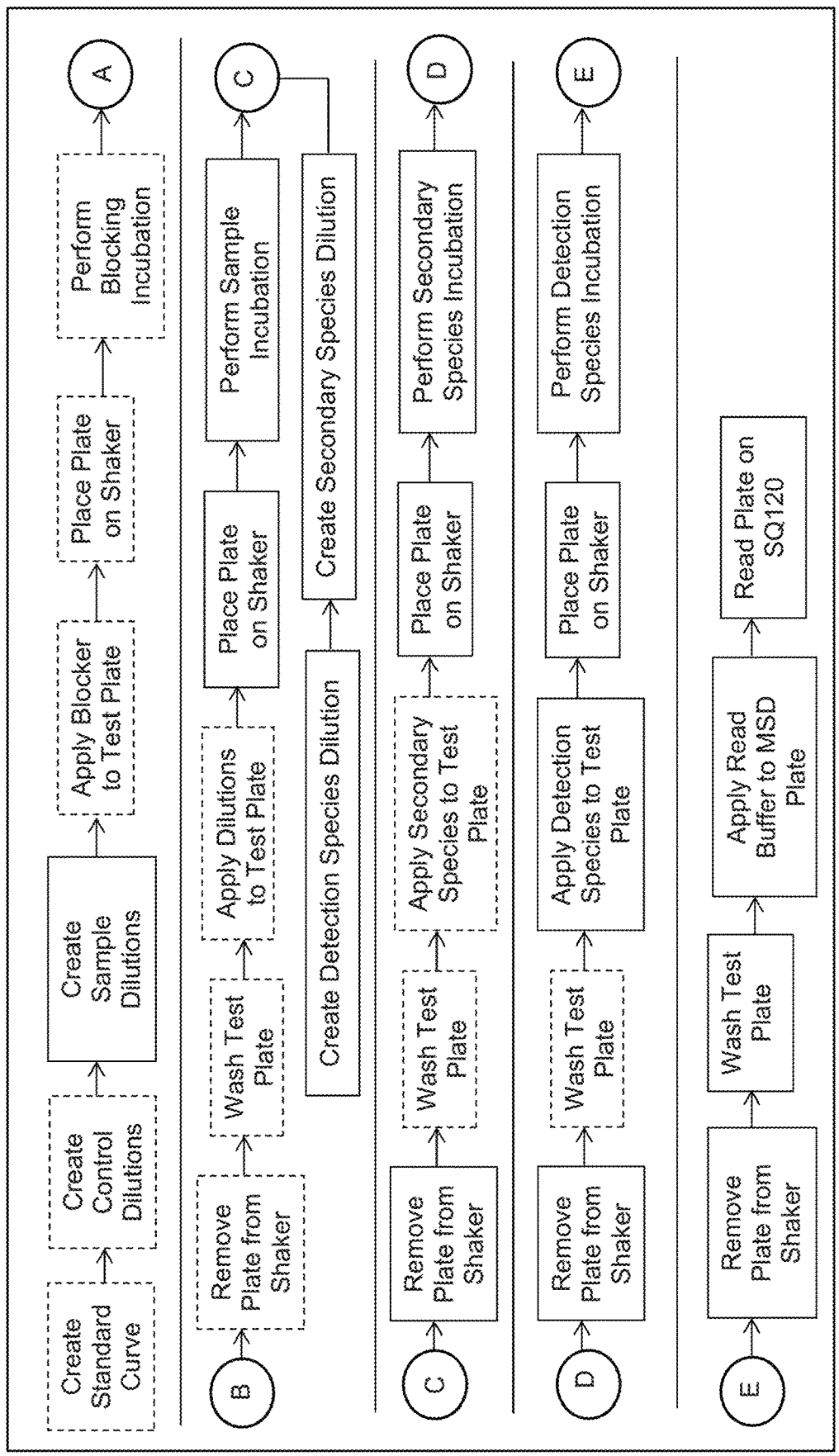
Figure 17(h)-a. Protocol for Indirect Assay, Uncoated Plate and Reagent Rack

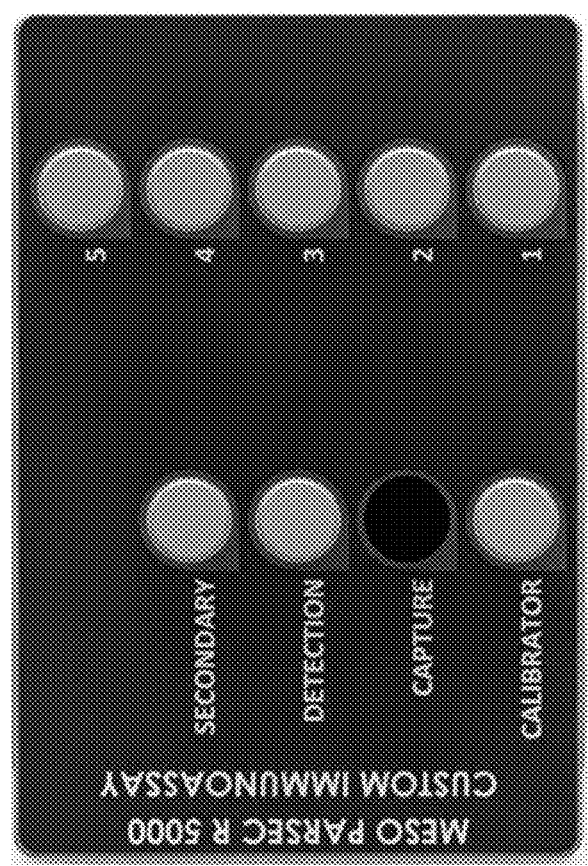
Figure 17(h)-b. Protocol for Indirect Assay, Uncoated Plate and Reagent Rack

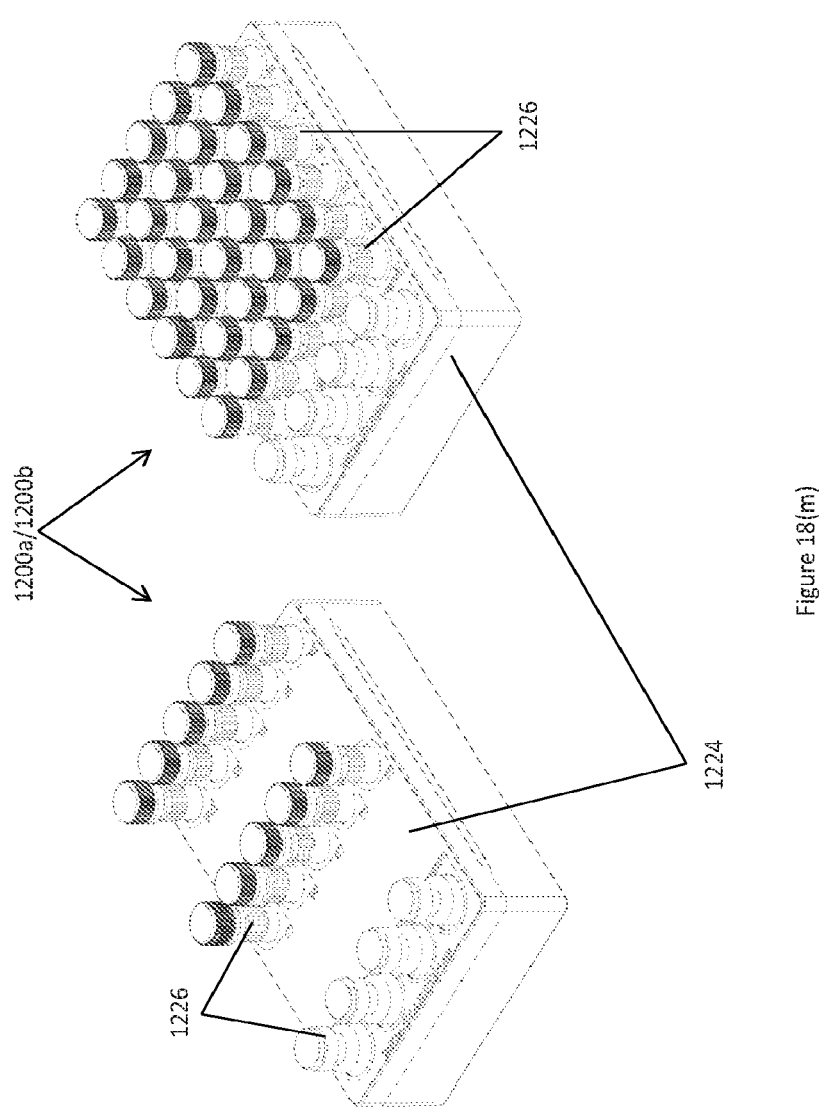

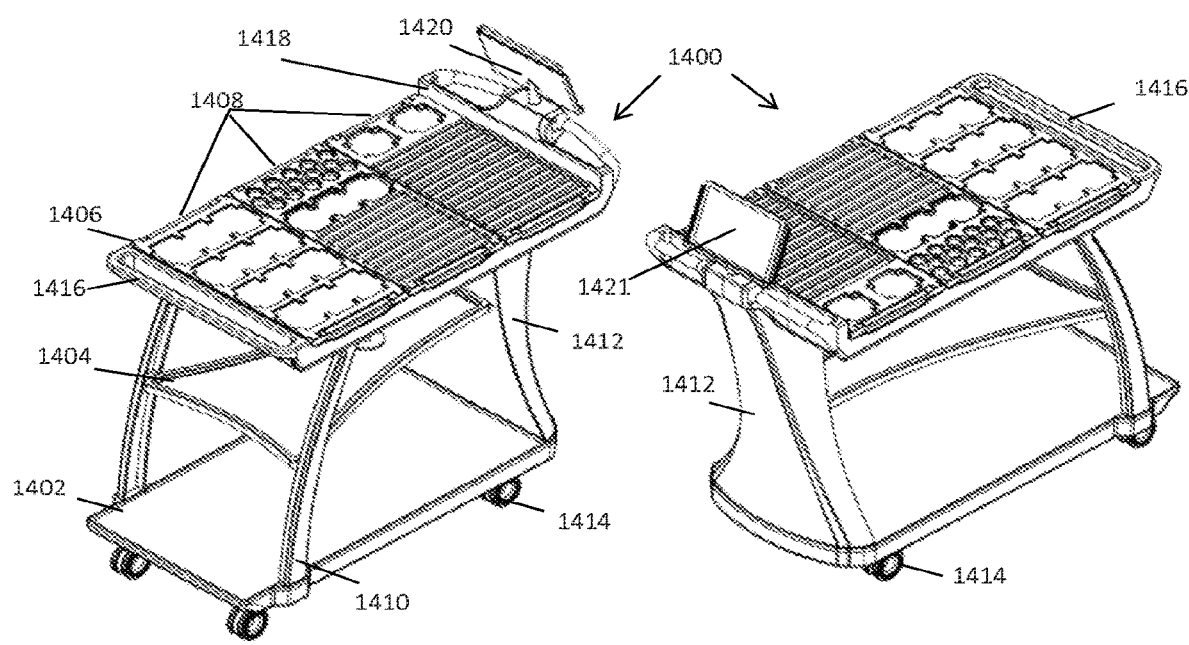
Figure 19(a)
Figure 19(b)
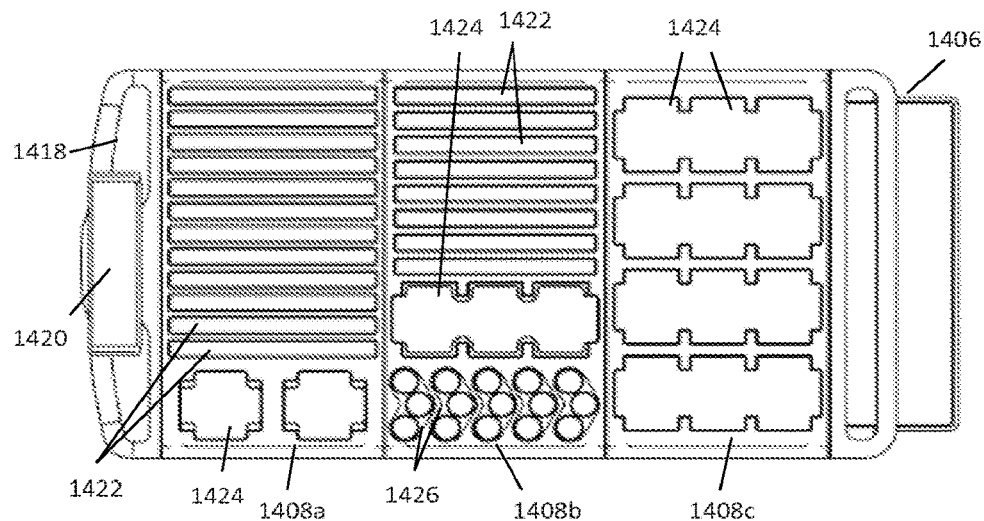
Figure 19(c)

|   | 1 | 2 | 3 | 4 | 5 | 6 | 7 | 8 | 9 | 10 | 11 | 12 |
|---|---|---|---|---|---|---|---|---|---|---|---|---|
| A |   |   |   |   |   |   |   |   |   |   |   |   |
| B |   |   |   |   |   |   |   |   |   |   |   |   |
| C |   |   |   |   |   |   |   |   |   |   |   |   |
| D | Read Buffer Addition 1 | Read Buffer Addition 2 | Read Buffer Addition 3 | Read Buffer Addition 4 | Read Buffer Addition 5 | Read Buffer Addition 6 | Read Buffer Addition 7 | Read Buffer Addition 8 | Read Buffer Addition 9 | Read Buffer Addition 10 | Read Buffer Addition 11 | Read Buffer Addition 12 |
| E |   |   |   |   |   |   |   |   |   |   |   |   |
| F |   |   |   |   |   |   |   |   |   |   |   |   |
| G |   |   |   |   |   |   |   |   |   |   |   |   |
| H |   |   |   |   |   |   |   |   |   |   |   |   |

Figure 20(a)

|   | 1 | 2 | 3 | 4 | 5 | 6 | 7 | 8 | 9 | 10 | 11 | 12 |
|---|---|---|---|---|---|---|---|---|---|---|---|---|
| A | 6 |   | 5 |   | 4 |   | 3 |   | 2 |   | 1 |   |
| B |   |   |   |   |   |   |   |   |   |   |   |   |
| C | 7 |   | 20 |   | 19 |   | 18 |   | 17 |   | 16 |   |
| D |   |   |   |   |   |   |   |   |   |   |   |   |
| E | 8 |   | 21 |   | 22 |   | 23 |   | 24 |   | 15 |   |
| F |   |   |   |   |   |   |   |   |   |   |   |   |
| G | 9 |   | 10 |   | 11 |   | 12 |   | 13 |   | 14 |   |
| H |   |   |   |   |   |   |   |   |   |   |   |   |

INTEGRATED CONSUMABLE DATA MANAGEMENT SYSTEM AND PLATFORM

CROSS-REFERENCE TO RELATED APPLICATION

The present international patent application claims priority to U.S. provisional patent application entitled "Integrated Consumable Data Management System and Platform" bearing Appl. No. 62/195,956 filed on Jul. 23, 2015.

Reference is also made to U.S. application Ser. No. 12/844,345, filed Jul. 27, 2010, U.S. Provisional Appl. Nos. 61/400,441, filed Jul. 27, 2010, and 61/462,024, filed Jan. 27, 2011. Reference is also made to U.S. application Ser. No. 13/191,000, filed Jul. 26, 2011, now U.S. Pat. No. 8,770,471, and U.S. application Ser. No. 14/719,818, filed May 22, 2015. The entire contents of each of these applications are incorporated herein by reference.

FIELD OF THE INVENTION

The present teaching relates to methods, devices and systems for associating consumable data with an assay consumable used in a biological assay. It also relates to consumables (e.g., kits and reagent containers), software, data deployable bundles, computer-readable media, loading carts, instruments, systems, and methods, for performing automated biological assays.

BACKGROUND OF THE INVENTION

Numerous methods and systems have been developed for conducting assays. These methods and systems are essential in a variety of applications including medical diagnostics, veterinary testing, food and beverage testing, environmental monitoring, manufacturing quality control, drug discovery, and basic scientific research. During the manufacture and use of reagents and other consumables used in biological assays, the reagents and consumables are typically coded and labeled by the manufacturer in order to track them. In addition, a myriad of analytical parameters must be tracked in order to understand the analytical results of any given assay, often requiring input from various parallel tracking systems supplied by the manufacturer, customer or both.

Automation of immunoassays presents a set of challenges. Repeatability and/or reproducibility remain goals for all automated assay systems.

SUMMARY OF THE INVENTION

One aspect of the present invention is an automated assay system for conducting biological assays, e.g., immunoassays, and more particularly electrochemiluminescent (ECL) immunoassays. The inventive automated assay system is capable of performing assay runs with reproducible results. Probable human or machine errors that may occur in the preparation for an assay run (e.g., sample or calibrator dilution), the loading of the assay consumables onto an instrument, and during an assay run have been identified and minimized. Other aspects include consumables, instruments, loading carts, software, data deployable bundles, computer-readable media, and methods, for performing biological assays.

Variables that have been minimized in the different aspects of the invention include one or more of the following. Variations in sample concentration among the wells within multi-well assay trays caused by evaporation of liquid during incubation are minimized. The positions and locations of the robotic system's gripper pads and pipettor for a particular assay system are trained by a precision training plate. Heat exchangers are provided to maintain a selected operating temperature in the assay system. Identical assay runs were completed substantially within the expected time period to ensure reproducibility. Consumables for specific assays are provided in kits to ensure that the proper consumables and amounts thereof are available for the assay runs. The loading of consumables to the assay system is standardized to minimized errors. Specialized assay consumable storage units on an assay instrument (e.g., a plate hotel, a plate carrier, a reserve pipet tip container carrier, a trough carrier) minimize loading and assay execution errors. For example, the configuration and position of the plate hotel minimize loading errors due to user safety, ergonomic, or consumable handling considerations. A user interface guides the users through the loading of the consumables and selection of the assay protocol to run. A loading cart is provided to serve as an intermediate consumable loading station to assist the users to properly load the consumables into the assay system. The inventive assay system's operational and performance qualifications have been automated and a validation kit is provided to ensure that the qualifications are properly executed and reproducible. Automated assay steps are carried out with tight timing tolerances to ensure run-to-run and plate-to-plate reproducibility. A specialized plate reader is configured to read the assay plates in an order than minimizes differences in timing between the addition of read buffer to the time of reading the signal from one well to another even within in a single plate. Various background signal noises in the ECL reader are measured and offset from the actual ECL readings. The ability of the pipettor and plate washer to dispense and/or aspirate are calibrated.

Other improvements include but are not limited to a software architecture that minimizes the revalidation of the software system when it receives a software update, and the creation of a generic protocol applicable to a plurality of assays paired with an instrument parameter file unique to a particular assay that turns specific components of the generic protocol ON or OFF to customize the protocol to the particular assay. Specialized lids are provided to minimize the loss of reagents from container through evaporation while maintaining the ability of a pipettor to access the reagents.

One embodiment of the invention is an assay system configured to use an assay consumable in the conduct of an assay, said assay consumable comprising an assay consumable identifier including an assay consumable identifier comprising a data deployable bundle (DDB) for said assay consumable, and said assay system comprises:
(a) a storage medium including a consumable data repository comprising local consumable data and a data registry;
(b) a consumable identifier controller adapted to read and install said DDB to said storage medium; and
(c) a consumable data service processor adapted to query said data registry and one or more remote consumable data databases to identify and download consumable data required for the conduct of an assay by the assay system using said assay consumable.

A further embodiment of the invention is a data deployable bundle (DDB) including one or more data files comprising consumable data related to an assay consumable and use thereof in an assay system, said one or more data files include a DDB unique identifier, DDB version, a DDB xml file, consumable static information, consumable processing information, and combinations thereof.

An additional embodiment includes a computer readable medium having stored thereon a computer program which, when executed by a computer system operatively connected to an assay system, causes the assay system to perform a method of conducting an assay on said assay system, wherein said assay system is configured to use an assay consumable in the conduct of said assay, said assay consumable comprising an assay consumable identifier including the DDB described herein, and said assay system comprises:

(a) a storage medium including a consumable data repository comprising local consumable data and a data registry;
(b) a consumable identifier controller adapted to read and install said DDB to said storage medium; and
(c) a consumable data service processor adapted to query said data registry and one or more remote consumable data databases to identify and download consumable data required for the conduct of an assay by the assay system using said assay consumable;

said method comprising the steps of:
(a) reading the DDB from said consumable identifier;
(b) storing the DDB to said consumable data repository;
(c) identifying consumable data from said consumable data repository and optionally, downloading consumable data from one or more remote consumable data databases;
(d) adjusting one or more operations performed by said system before, during and/or after the conduct of said assay based on said consumable data; and
(e) conducting said assay in said assay system using said assay consumable.

Another embodiment relates to a holder for assay reagents, comprising at least two areas configured to receive at least one or two reagent containers and at least one or two holes or windows configured to view at least one or two consumable identifier that are located on the bottom of the reagent containers. The areas can be at least two different sizes to receive at least two assay containers of different sizes. The areas and the holes or windows can be circular and the holes or windows may be smaller in diameter than the areas, or the areas and the holes or windows may be rectilinear and the holes or windows may be smaller in diameter than the areas.

The holder may comprise a frame, at least one optional insert, and at least one optional mask. The mask can be attached to the top of the frame, and the insert may be positioned within the frame and below the mask. The two areas of the holder may comprise columnar holes in the frame or the optional insert or both. The at least two areas may comprise holes in the mask. The at least two holes may be transparent plastic-coated holes in the frame.

The footprint dimensions of the container preferably comply with ANSI-SLAS dimensions for a multi-well plate. The height of the container may also comply with the ANSI-SLAS height for a multi-well plate.

In one embodiment the insert is foam and is inserted within the frame's at least two columnar holes for padding said at least two reagent containers. The insert may be positioned between a reagent container and an area that is larger than the reagent container. The insert can define the columnar holes of the assay reagent container, and fills the frame.

The mask may define a plurality of areas, wherein the number of mask areas can be the same or fewer than the number of areas in the container, frame, or insert and the mask can limit the number of assay containers received by the assay reagent container. Preferably, the mask comprises labels for reagents.

The holder may have an assay consumable identifier affixed thereon. The assay consumable identifier is located on a bottom, a side, or a top surface of the container. The holder may also comprise at least one reagent container. The reagent container comprises an assay reagent. The assay reagent can be a reagent for a V-PLEX, U-PLEX, immunogenicity (IG), pharmacokinetic (PK), or custom assay. The labels can define assay reagents for a V-PLEX, U-PLEX, immunogenicity (IG), pharmacokinetic (PK), or custom assay.

The assay reagent container or the frame can be made from conductive plastic. The holder may have a lid. The lid may be fully or mostly transparent. The assay containers may comprise assay consumable identifiers located on their bottoms, viewable from the bottom of the container. The areas are configured to accept at least one tube and at least one vial.

The holder may have (a) a frame with a bottom and sides, said bottom being roughly rectangular in shape and having dimensions compliant with ANSI-SLAS standards, and defining said holder holes or windows, (b) an insert that fits within said frame having insert holes sized to hold tubes or vials and arranged to align said tubes or vials with said holder holes or windows, (c) a mask located above said insert with mask holes aligned with said insert holes to allow for insertion of tubes or vials into the insert, said mask also providing identifying information about the tubes or vials, and (d) optionally, a lid to enclose said vials within said holder The consumable identifiers can be 2-D or 1-D bar codes. The 2-D or 1-D barcode can be printed on a plastic puck that is inserted into a recess of the bottom of said tube or vial, or printed on a foil disk that is heat sealed against a recess on the bottom of the tube or vial.

The assay tubes or vials include tubes or vials with one or more of the following assay reagents: (i) a calibration material; (ii) a control material; (iii) a capture reagent; (iv) a detection reagent; (v) a diluent or (vi) a linker reagent.

The invention is also related to an assay kit comprising any assay container discussed above in a cardboard container. Preferably, the kit has an assay consumable identifier on the cardboard container. The kit of may also have at least one assay consumable plate in said cardboard container. The assay consumable plate may be a multi-well assay plate and may have assay consumable identifier. The kit may also have at least one trough or tube or both.

The present invention is also related to a lid configured to cover a top surface of a multi-well plate, comprising a skirt dependent on a top portion of the lid, wherein the skirt is adapted to fit around an outer perimeter of the top surface of the multi-well plate, wherein the top surface of the plate is sized and dimensioned to contact the outer parameter of the multi-well plate, and the lid may also have a plurality of dimples extends from the top portion of the lid toward the multi-well plate. The plurality of dimples can correspond to the plurality of wells in the multi-well plate and is configured to extend into the plurality of wells. The top surface of the lid is adapted to contact at least one upper lip of the plurality of wells.

The lid can be not made of conformable plastic or elastomeric material, or is made of hard plastic or polystyrene.

The present invention is also related to a lid configured to cover a top surface of a multi-well plate, comprising a skirt dependent on a top portion of the lid, wherein the skirt is adapted to fit around an outer perimeter of the top surface of the multi-well plate, wherein the top surface of the plate is sized and dimensioned to contact the outer parameter of the multi-well plate. The lid is optionally hydrophobic. The lid can be made from a hydrophobic polymer, or bottom surface of the top portion of the lid can be rendered hydrophobic. The bottom surface can be microetched to create a roughen surface to trap air, such that the bottom surface exhibits Cassie-Baxter behavior as a barrier against moisture.

Alternatively, the bottom surface can be coated with a hydrophobic coating or a surfactant. The lid may also have a plurality of dimples extending from the top portion of the lid toward the multi-well plate. The plurality of dimples can correspond to the plurality of wells in the multi-well plate, and the plurality of dimples is configured to extend into the plurality of wells.

The present invention is also related to a lid configured to be attached to a reagent container and adapted to allow a probe to enter and exit, comprising a top surface, wherein the top surface comprises a pattern of cuts separating the top surface into segments, wherein the segments flex downward when the probe enters the reagent container and substantially return their original orientation when the probe exits. The probe can be at least one pipette tip.

The pattern of cuts may comprise at least one curvilinear line, at least one serpentine line, at least one substantially circular line or parallel linear lines. The lid can be made from non-elastomeric material or an elastomeric material. The lid can be used for covering a reagent trough.

The present invention is also related to a loading cart adapted to be used with an assay system, the loading cart comprising a computer screen and a mobile body comprising at least one shelf and a support for said computer screen, wherein said shelf comprises at least one tray, wherein a plurality of slots are defined on the tray and wherein the slots are sized and dimensioned to receive a plurality of consumables to conduct an assay. The computer screen is adapted to display a user interface that shows a first arrangement of the plurality of containers of consumables on the at least one tray.

The computer screen can be a screen of a tablet computer or be connected to a personal computer or a laptop computer. The computer screen can be controlled by a processor on the assay machine. The computer screen may connected to the processor on the assay machine by WiFi or blue tooth connection.

The plurality of slots on the loading cart can be defined on a top surface of the at least one tray or on both surfaces, i.e., the tray is reversible. The slots can be slots of different sizes adapted to receive the plurality of consumables of different sizes.

The support for the computer screen can be an adjustable support. The adjustable support can be rotatable substantially about a vertical axis and/or tiltable about an axis that is substantially orthogonal to the vertical axis. The at least one shelf is a top shelf. The cart may also have a bottom shelf and/or a middle shelf. The cart may have a compartment under the at least one tray or top tray and the compartment is adapted to store a coolant. The compartment may also have a drainage port, and the compartment's bottom surface may be concave. The mobile body of the curt should be supported by at least one caster wheel, and the caster wheel can be a hubless caster wheel.

The loading cart may hole a plurality of consumables, such as at least one multi-well plate, and the at least one multi-well plate may comprise at least one assay plate or at least one dilution plate. The plurality of consumables may comprise at least one container of a reagent. The plurality of consumables may comprise at least one tube or at least one trough. An example of the tray is illustrated in FIG. 19.

The present invention is also related to an assay preparation system for preparing assay components, the preparation system comprising:

(a) a assay system with a processor comprising information about the components needed to carry out an assay run;

(b) a loading cart comprising a shelf for assembling components that will be used in an assay and a support for holding a mobile computing device;

(c) a mobile computing device, which includes a computer screen;

wherein said mobile computing device includes networking capability to access said information on said processor and a graphical user interface to present that information on the computer screen to a user and guide the placement of assay components on the loading cart.

The loading cart can be the loading cart described above. The loading cart may also comprise a consumable identifier reader, and the graphical user interface is configured to accept identifier information provided by the user using the reader when placing assay components on the cart and to use that information to confirm the validity of the components and to transfer said identifying information to the processor.

The present invention is also related to a method of instructing a user to load consumables onto an assay system comprising using the loading cart discussed above. The method may comprise arranging a plurality of consumables on the loading station in accordance to a first arrangement displayed by a user interface on the screen.

The present invention is further related to a method for loading consumables to conduct an assay into an assay system, comprising steps of:

a. receiving a plurality of consumables, b. arranging the plurality of consumable on an intermediate consumable loading station in accordance to a first arrangement displayed by a user interface on a screen positioned on the intermediate consumable loading station, c. moving the intermediate consumable loading station to the assay system, d. transferring the plurality of consumables to the assay system in accordance with a second arrangement, wherein the first arrangement is substantially the same as the second arrangement.

Preferably, the intermediate consumable loading station comprises a mobile cart and the screen is a computer screen. The computer screen can be is movably attached to the cart, or is rotatable substantially about a vertical axis and/or tiltable relative to the vertical axis. This method may also comprise the step of cooling at least one consumable of the plurality of consumables. Step (b) may comprise the step of depositing the plurality of consumables into a plurality of slots defined on a top surface of the mobile cart. The plurality of consumables may comprise at least one multi-well plate or at least one container of reagent.

The present invention is also related to a plate sized and dimensioned to the size and dimensions of an ANSI-SLAS-format assay plate and comprising an outer rectangular perimeter and at least one support member connecting a first side of the rectangular perimeter to a second side of the perimeter, wherein at least one reference pad is located on a first major surface of the plate and corresponds to a location of at least one well in the ANSI-SLAS-format assay plate, wherein a location of the at least one reference pad in one dimension of a three-dimensional coordinate system is measurable by a probe of an assay system when the plate is positioned in a plate carrier in the assay system.

The probe can measure a capacitance between the probe and the at least one reference pad. The plate is preferably conductive. The ANSI-SLAS-format assay plate is a 8×12 multi-well plate and the at least one reference pad corresponds to a corner well on the ANSI-SLAS-format assay plate.

The plate may also have at least two opposite gripping areas located on the sides connecting the plate's two major surfaces, wherein the gripping areas are adapted to be gripped by a gripper arm of a robotic system. The outer rectangular perimeter proximate the first major surface is smaller than the outer rectangular perimeter proximate the second major surface, wherein the first and second major surfaces are substantially parallel.

The plate is preferably made of cast aluminum and/or is machined from cast aluminum.

A further aspect relates to a plate for teaching or training an automated instrument, the plate being sized and dimensioned to the size and dimensions of an ANSI-SLAS-format assay plate and comprising an outer rectangular perimeter and at least one support member connecting a first side of the rectangular perimeter to a second side of the perimeter, wherein at least one reference pad is located on a first major surface of the plate and corresponds to a location of at least one well in the ANSI-SLAS-format assay plate, wherein a location of the at least one reference pad in one dimension of a three-dimensional coordinate system is measurable by a probe of an assay system when the plate is positioned in a plate carrier in the assay system.

A further aspect relates to a method of training or teaching a robotic gripper or pipettor comprising using the plate described above.

Also relating to the an aspect of the invention is an assay consumable storage unit adapted to be attached to a platform in an assay system comprising a bottom base and a shelving assembly having a plurality of sets of vertically aligned storage units, wherein each storage unit is sized and dimensioned to receive a consumable for the conduct of an assay by the assay system, wherein the shelving assembly comprises a plurality of horizontal members connected by a plurality of upstanding vertical supports, wherein the bottom base is affixed in a cantilevered manner to the platform and the shelving assembly is removably attached to the bottom base by at least two locating pins and by at least one threaded connector with a finger-actuatable head.

A further aspect relates to assay systems. Such assays systems include an assay system configured to use an assay consumable in the conduct of an assay, said assay consumable comprising an assay consumable identifier associated with a data deployable bundle (DDB) for said assay consumable, and said assay system comprises:
    (a) a storage medium including a consumable data repository comprising local consumable data and a data registry;
    (b) a consumable identifier controller adapted to read and install said DDB to said storage medium; and
    (c) a consumable data service processor adapted to query said data registry and at least one remote consumable data database to identify and download consumable data required for the conduct of an assay by the assay system using said assay consumable.

Additional assays include an assay system comprising a housing, wherein the housing includes a continuous glass member, wherein a touch screen for a computer screen is formed by a first portion of the continuous glass member and an array of pressure transducers, and wherein a sound emitter is formed by a second portion of the continuous glass member and at least one sound exciter.

Further assays include an automated assay system adapted to receive consumables in the conduct of an assay, the assay system comprising a robotic controlled pipettor and a robotic controlled gripper arm, an assay reader, a plate washer and at least one optionally heatable shaker, at least one heat exchanger and at least one processor adapted to execute at least one instruction to minimize potential errors in loading of the consumables and in running the assay, wherein the consumables comprise at least one assay test plate, at least one dilution plate, at least one set of pipette tips, at least one sample plate, and a plurality of containers containing at least one of calibrator, diluent, and antibody, wherein the at least one instruction comprises at least one of the following:
    an instruction to a user interface to guide a user to load the consumables into the assay system,
    an instruction to the robotic gripper arm to place a lid on the at least one assay test plate when the at least one assay test plate is placed on the shaker,
    an instruction to the at least one heat exchanger to maintain a selected temperature within the assay system, and
    an instruction to run the assay for the at least one assay test plate, wherein the at least one assay plate comprises multiple assay test plates, wherein each assay test plate is completed in substantially a same time period.

A further aspect relates to a method for operating an automated assay system to minimize potential errors in loading consumables for an assay and running the assay, wherein said assay system comprises a robotic controlled pipettor and a robotic controlled gripper arm, an assay reader, a plate washer and at least one shaker and incubator, at least one heat exchanger and at least one processor wherein the assay system is adapted to receive consumables the consumables comprise at least one assay test plate, at least one dilution plate, at least one set of pipette tips, at least one sample plate, and a plurality of containers containing at least one of calibrator, control, diluents, antibodies, reagents and buffers, said method comprises at least one of the following steps:
    instructing a user interface to guide a user to load the consumables into the assay system,
    instructing the robotic gripper arm to place a lid on the at least one assay test plate when the at least one assay test plate is placed on the shaker and incubator,
    instructing the at least one heat exchanger to maintain a selected temperature within the assay system, and
    instructing the at least one processor to run the assay for the at least one assay test plate, wherein the at least one assay plate comprises multiple assay test plates, wherein each assay test plate is completed in substantially a same time period.

The invention also relates to an automated assay system configured to use assay consumables in the conduct of an assay, said assay system comprises at least one processor and at least one storage medium, wherein said storage medium stores instructions to conduct said assay by said processor, wherein said instructions are separated into a plurality of components, said plurality of components comprises:
    a security component,
    a user interface component, an instrument control component, and a data services component, wherein each component operates substantially independently of each other and has substantially no interaction with each other, wherein said components are connected to a master organizer and the master organizer instructs each component when to operate.

The invention further relates to an assay system configured to use assay consumables in the conduct of a first assay, wherein the first assay comprises a unique assay identifier, said assay system comprises a reader adapted to read the unique assay identifier and a processor that accesses a general protocol file and an instrument parameter file, wherein the general protocol file contains a general assay protocol comprising assaying steps that are applicable to a plurality of assays including the first assay, wherein the instrument parameter file contains a plurality of flags that are either ON or OFF, wherein the processor turns the assaying steps in the general assay protocol either ON or OFF according to said flags to conduct the first assay.

Additional assay systems relate to an automated assay system configured to minimize user, instrument, and assay method variations, the system comprising at least one of:

means for minimizing user error in system loading means for minimizing user error in selecting an automated workflow means for minimizing sample dilution error means for minimizing system plate handling error means for minimizing system pipetting error means for minimizing temperature variation means for minimizing evaporation or condensation within an assay consumable means for controlling the shaking frequency of at least one shaker, and means for minimizing complexity of maintenance procedures.

In a further aspect, the automated assay system is configured to minimize user, instrument, and assay method variations, the system comprising a robotic gripper arm and a robotic pipettor and also comprising software and an instrument component for at least one of:

performing sample dilution steps;

choosing and performing the correct assay workflow for a given assay;

controlling an air cooling and handling system and thereby maintaining a defined temperature in the assay workflow area of the system at a defined tolerance;

maintaining consistent timing between runs, plates, and wells; and s allowing users to perform different assay workflows without having to reconfigure or revalidate the workflow software.

Further aspects include an automated assay system comprising a robotic gripper arm and a robotic pipettor, and comprising at least the following additional components: (a) a plate carrier, (b) a tip box carrier, (c) five optionally heatable shakers, (d) an air cooling and handling system, (e) an assay consumable storage unit for assay reagents, (f) an assay consumable storage unit for immediate-use tips, (g) an assay consumable storage unit for reserve tips, (h) an assay consumable storage unit for plates, (i) positions for affixing assay consumable storage units for tubes and troughs, and (j) a platform or table or both; wherein said components (a)-(c) and (e)-(h) are located on said platform or table within the system in substantially the same position in relation to each other as shown in FIG. 10(*a*), (*b*), (*c*), (*l*), (*n*), or (*o*), and wherein component (d) is located on the back panel of the instrument substantially as shown in FIG. 10(*l*), (*m*), or (*n*).

In a further aspect, the invention relates to an automated assays system comprising (a) a single robotic controlled 8-channel pipettor (b) a single robotic controlled assay plate gripper arm (c) a single 96-channel channel assay plate washer (d) a single plate reader (e) one or more plate shakers with a total capacity of at least 5 plate shaking locations (f) a processor adapted to execute an assay process for analyzing a plurality of samples in 96-well plates wherein the following actions of a process are executed on in each well of said plates (i) a blocking step comprising addition of a blocking buffer with the pipettor, incubation for a blocking period (b) and washing with the plate washer (ii) a sample binding step comprising addition of one of said samples with the pipettor, incubation for a sample incubation period (s) while shaking on one of the plate shaking locations and washing with the plate washer (iii) a detector binding step comprising addition of a detection reagent with the pipettor, incubation for a detector incubation period (d) while shaking on one of the plate shaking locations and washing with the plate washer (iv) addition of a read buffer with the pipettor (v) measurement of an assay signal with the reader wherein, up to 5 plates can be processed in a run the steps are carried out as shown in FIGS. 9(*d*), 12(*m*)-(*p*), 12(*r*)-(*s*), 13(*d*)-(*f*), 14(*d*), (*f*)-(1), 15(*b*), 15(*d*)-(*h*), 16(*b*), 17(*b*), 17(*d*)-(*h*).

Additional automated assay systems relate to an automated assays system comprising (a) a processing deck for holding assay components providing a roughly rectangular surface with a front edge, a first side edge, a second side edge and a back edge; said deck supporting (i) an assay consumable hotel roughly centered and cantilevered over the front edge of the deck having a plurality of consumable slots sized to hold consumables with the meet the ANSI-SLAS specifications for width and length of 96-well assay plates (ii) a plurality of pipette tip locations for holding pipette tip containers located on a first side of the deck (iii) a plurality of plate shaker locations located along the back edge of the deck (iv) a set of processing locations located roughly in the center of the deck between the hotel and the shakers that are configured to hold consumables with ANSI-SLAS compliant dimensions (v) a bar code scanner located on the first side of the deck behind the pipette tip locations, the bar code scanner having a scanning surface large enough to scan the bottom surface of a consumable with ANSI-SLAS compliant dimensions (b) a plate washer located under the deck and accessible through an aperture in the deck between the pipette locations and the assay plate processing locations (c) a gantry located above the deck movably supporting a robotic plate gripper such that the gripper can move to access locations (i) through (v) and movable supporting a robotic 8 channel pipettor such that the pipettor can access locations (ii) and (iv)

(d) an assay reader located next to the first side of the deck on a platform that is at a lower vertical elevation than the deck, wherein the highest point on the reader is lower than the lowest point that the robotic grabber can move (e) an enclosure surrounding components (a) to (d) with a temperature controller for maintaining the components under temperature control and with a door providing user access to the front side of the deck and the consumable hotel located thereon A further aspect relates to an automated assay system comprising (a) a single robotic controlled 8-channel pipettor
(b) a single robotic controlled assay plate gripper arm
(c) a single 96-channel channel assay plate washer
(d) a single plate reader
(d) one or more plate shakers with a total capacity of at least 5 plate shaking locations
(e) a processor adapted to execute an assay process for analyzing a plurality of samples in 96-well plates wherein the following actions are executed on in each well of said plates
    (i) a blocking step comprising addition of a blocking buffer with the pipettor, incubation for a blocking period (b) and washing with the plate washer
    (ii) a sample binding step comprising addition of one of said samples with the pipettor, incubation for a sample incubation period (s) while shaking on one of the plate shaking locations and washing with the plate washer
    (iii) a detector binding step comprising addition of a detection reagent with the pipettor, incubation for a detector incubation period (d) while shaking on one of the plate shaking locations and washing with the plate washer
    (iv) addition of a read buffer with the pipettor
    (v) measurement of an assay signal with the reader
wherein,
up to 5 plates can be processed in a run.

BRIEF DESCRIPTION OF THE FIGURES

FIGS. 5(a)-(d) illustrate an assay reader described herein.

FIG. 7 illustrates an additional view of an assay reader described herein.

FIG. 10(g) is a perspective view showing pipette tips entering a lid of a reagent trough. FIG. 10(h) shows top views of various cut patterns of the lid shown in FIG. 10(g). FIG. 10(i) is a perspective view of a lid and assay plate. FIG. 10(j) is a cross sectional view of the lid and assay plate in FIG. 10(i). FIG. 10(k) is an enlarged portion of FIG. 10(j). FIGS. 10(m)-(o) show the cooling pattern within the assay system. FIG. 10(p) shows the cooling pattern of the electronic enclosure. FIGS. 10(v)-(y) show some of the wiring diagram of assay system (1000).

FIGS. 13(a)-(f) show one embodiment of the use of a data deployable bundle and consumable/system data to operate an assay system in the conduct of an assay.

FIGS. 14(a)-(l) illustrate the conduct of a V-PLEX assay on an assay system using the software described herein.

FIGS. 15(a)-(h) illustrate the conduct of a U-PLEX assay on an assay system using the software described herein.

FIGS. 16(a)-(d) illustrate the preparation, optimization, and execution of an immunogenicity assay in an assay system.

FIGS. 17(a)-(i) illustrate the preparation, optimization, and execution of a custom singleplex sandwich immunoassay or pharmacokinetic assay in an assay system.

FIGS. 19(a)-(b) are perspective views of an inventive loading cart designed for use with the assay systems described herein. FIG. 19(c) is a top view of the loading cart shown trays adapted to receive assay consumables.

FIGS. 20(a)-(e) show exemplary adjustments to the pipetting timing and ECL reading pattern for the inventive assay system.

DETAILED DESCRIPTION OF VARIOUS EMBODIMENTS

Figure 1:
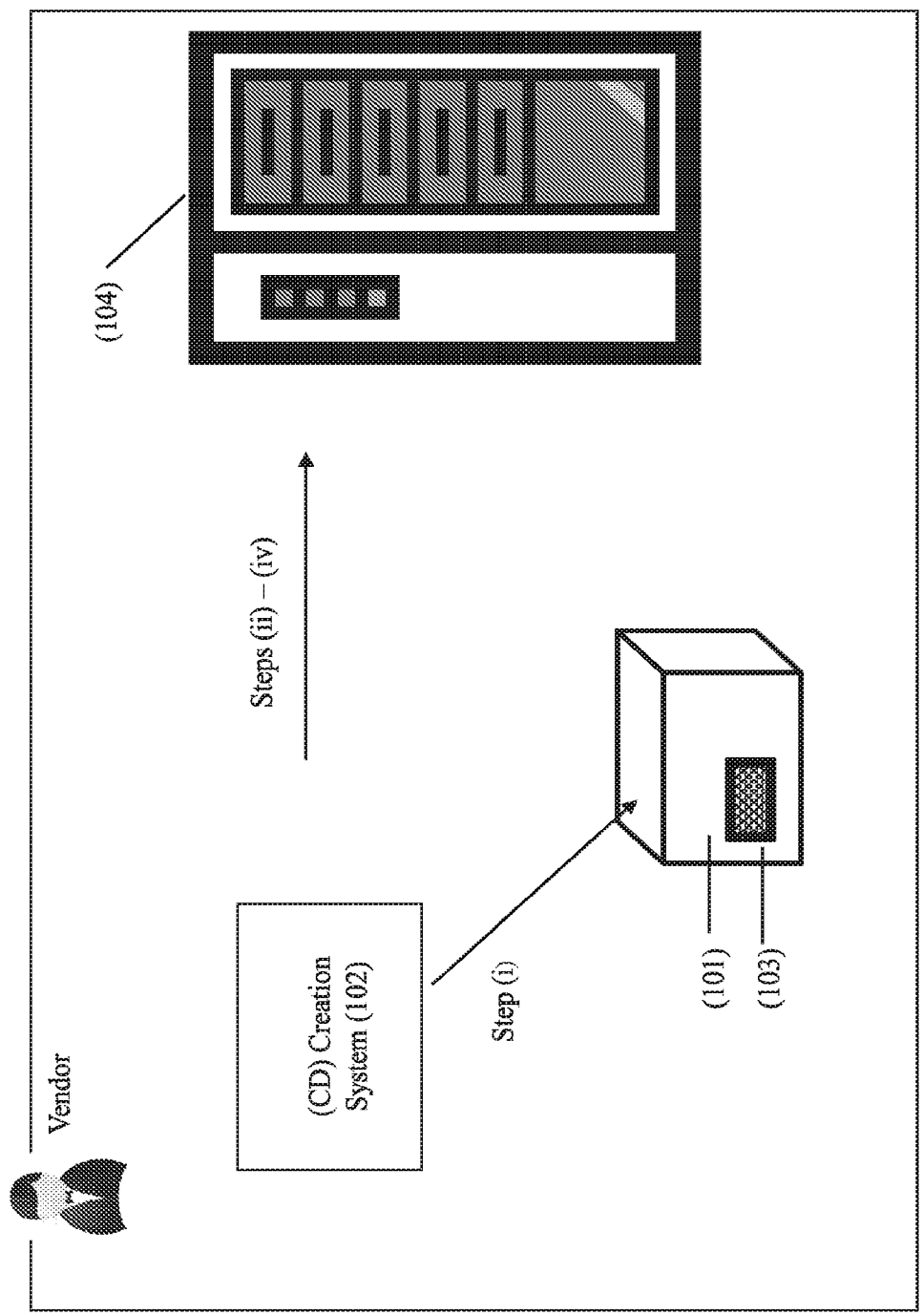
FIG. 1 illustrates the generation and storage of consumable data and consumable data by a consumable manufacturer.

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. The articles "a" and "an" are used herein to refer to one or to more than one (i.e., to at least one) of the grammatical object of the article. By way of example, "an element" means one element or more than one element.

As used herein, the term "sample" is intended to mean any biological fluid, cell, tissue, organ or combinations or portions thereof, which includes or potentially includes a biomarker of a disease of interest. For example, a sample can be a histologic section of a specimen obtained by biopsy, or cells that are placed in or adapted to tissue culture. A sample further can be a subcellular fraction or extract, or a crude or substantially pure nucleic acid molecule or protein preparation. In one embodiment, the samples that are analyzed in the assays of the present invention are blood, peripheral blood mononuclear cells (PBMC), isolated blood cells, serum and plasma. Other suitable samples include biopsy tissue, intestinal mucosa, saliva, cerebral spinal fluid, and urine.

The assay consumables and systems used in the present invention include a variety of devices and configurations. In one embodiment, the assay system used in the present invention includes an assay reader capable of conducting a biological assay using an assay consumable. The assay consumable comprises an identifier (referred to alternatively throughout the specification as an identifier, a consumable identifier, or an assay consumable identifier) and the assay system, assay reader or a component thereof comprises an identifier controller that interacts with the identifier. As described hereinbelow, the identifier is associated with information concerning the assay consumable, which can include but is not limited to, how the consumable is manufactured and handled prior to use and how the consumable is used in an assay system (referred to collectively as "consumable data"). Therefore, the assay system is configured to use an assay consumable in the conduct of an assay, and the assay system includes an identifier controller adapted to (i) read consumable data from an assay consumable identifier associated with the assay consumable; (ii) access consumable data associated with an assay consumable that is indexed by an assay consumable identifier, wherein the consumable data are stored locally on the assay system or assay reader or remotely on a vendor computing system; and optionally, (iii) erase consumable data associated with the assay consumable identifier; and/or (iv) write consumable data indexed to the consumable identifier to the assay system and/or a remote data table.

In a specific embodiment, the invention provides an assay system configured to use an assay consumable in the conduct of an assay, wherein the assay consumable includes an assay consumable identifier as described herein and the assay system includes (a) a storage medium comprising consumable data repository; and (b) an identifier controller adapted to read information from the consumable identifier. In one embodiment, the system comprises a storage medium including a consumable data repository comprising local consumable data. The local consumable data stored to the assay system includes consumable identification and/or configuration information and one or more steps of an assay protocol that can be applied by the system in the conduct of an assay using a consumable. For example, the assay consumable identifier includes information that can be used to identify a specific consumable, e.g., lot specific information for a given lot of consumables and/or information that is specific to an individual consumable, and the corresponding local consumable data stored to the assay system includes information that is used to identify a consumable associated with the system, e.g., as a member of a given lot or as an individual consumable within a lot and it also includes information that is used by the system once the consumable is identified to carry out an assay protocol using that consumable. Still further, the consumable data (and/or local consumable data) can include one or more analytical tools that can be applied by the system to analyze and interpret data generated using that consumable, system and/or consumable technical support information or combinations thereof. Moreover, the system can also be configured to receive updates to the consumable data repository from a remote storage medium, wherein those updates include additional consumable data, including but not limited to additional consumable identification and/or configuration information, assay protocol information, and one or more of the following: (x) one or more analytical tools that can be applied by the system to analyze data and interpreted results generated during and/or after the conduct of an assay, (y) assay system maintenance information, (z) system-consumable promotional information, and (xx) system and/or consumable technical support information.

One embodiment of the use of the identifier/consumable data in the system is illustrated in FIGS. 1-4. FIG. 1 shows how consumable data are generated, stored and used by the manufacturer, distributor, or supplier (referred to herein as "vendor"). First, the vendor generates a consumable and/or a set or lot of consumables (101) and for that consumable or lot of consumables, consumable data are generated using a consumable data (CD) creation system (102) and associated with a consumable identifier (103) indexed to the consumable or lot of consumables (step i). The consumable data are generated by the consumable vendor before, during and/or after the individual consumable and/or lot of consumables are made and/or distributed. The CD creation system generates a database of CD information for that consumable or lot, i.e., a CD database, to which consumable data are stored. The CD database is sent to a CD Server (104) which includes a master repository of all consumable data. In addition, the CD creation system stores information that is used to associate a given consumable identifier with consumable data in the master repository. The CD creation system and/or CD Server are located on a remote computing system, i.e., a computing system remote from the assay system and/or the customer or customer, e.g., a site maintained by the vendor. Therefore, as shown in FIG. 1, the vendor generates consumable data for a consumable or lot (a) and associates that information with a consumable identifier (b) indexed to that consumable or lot. The CD system also (step ii) generates a CD database; (step iii) stores consumable data to the CD database; and (step iv) sends the CD database to the CD Server (c), which includes a master repository of all consumable data.

Figure 2:
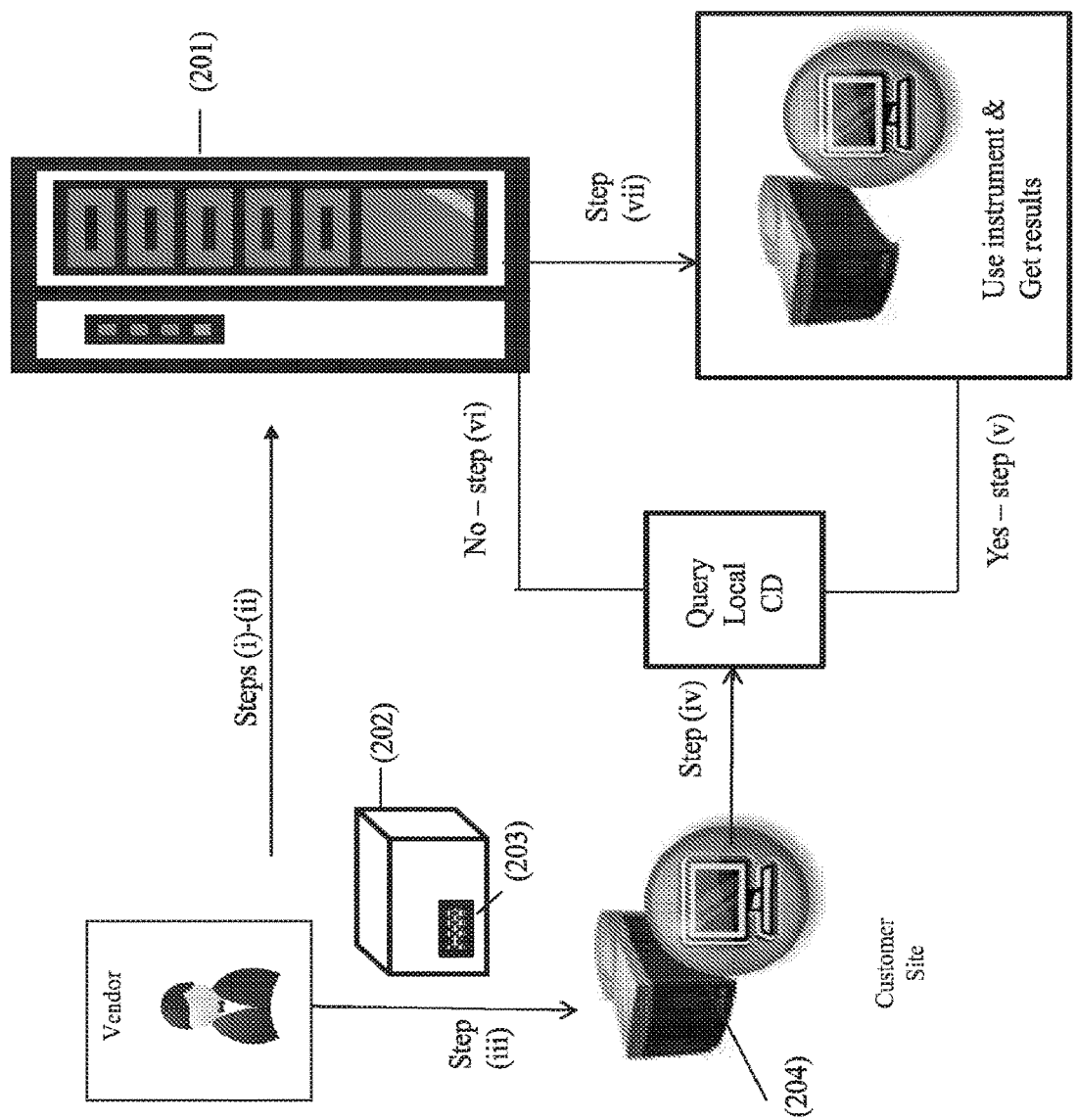
FIG. 2 illustrates the distribution of consumable data to a customer in response to a query for consumable data.

FIG. 2 illustrates one method of distributing consumable data to a customer or designated user of a customer (referred to collectively herein as a "customer"). Upon receipt of an order from a customer or when the consumable or lot is manufactured (step i), the vendor generates, stores and sends a CD database to the CD server (201) (step ii). The CD database can include order fulfillment information, i.e., a summary of the components of the order for a given customer so that the system can verify that all components of the order have been supplied to the customer. The customer receives the consumable (202), including consumable identifier (203), and contacts the consumable with the assay system (204) in preparation for the conduct of an assay (step iii), the system reads and/or accesses the data associated with the assay consumable identifier (203) and that information is used by the system to identify the consumable (202) (step iv). The system reviews the consumable data stored locally on the system in a local storage medium (referred to in FIG. 2 as "local CD") to identify that consumable data stored to the storage medium that can be used for the conduct of an assay using a given consumable. If the storage medium includes the consumable data for that consumable or lot, the consumables can be used in the system (step v). If the storage medium does not include consumable data for that particular consumable or lot of consumables, the system can query the customer for that consumable data and the customer can communicate with the vendor to receive the requisite consumable data, e.g., via email, compact diskette, memory card/stick, flash drive, web data storage service, etc. (step vi). The vendor sends consumable data binary files (including but not limited to encrypted XML files) to the customer, e.g., as an email attachment to a customer email account, the customer loads that file attachment to the assay system and the system software stores the consumable data to the local system consumable data repository. The consumable/lot of consumables can then be used in the instrument (step vii).

In an alternative embodiment, the CD server can be connected to the system via a direct interface which can automatically obtain the consumable data from the CD server if it is not available on the system locally. In this embodiment, the vendor generates, stores and sends a CD database to the CD server for a consumable order and/or lot of consumables, as shown in FIG. 2 and as described above. Thereafter the customer receives the consumable, order and/or lot and contacts the system with the consumable identifier to enable the system to identify the consumable or lot. The system software queries the system consumable data repository for the consumable data associated with that consumable identifier and if that consumable data are available locally on the system, the software will adjust the system based on the consumable data, if necessary. If the consumable data are not present in the system consumable data repository, the system will either (i) prompt the customer to manually obtain the consumable data from the vendor, or (ii) automatically, via a direct interface with the CD server, obtain the consumable data from the CD server and store that information locally on the system consumable data repository. Once the consumable data are available locally on the system, the software adjusts the system based on the consumable data, if necessary, and conducts an assay. Once the consumable data are available locally on the system, the consumable or lot can be used in the system to conduct an assay and display the assay results to the customer. In a specific embodiment, the system software adjusts the output to the customer based on the consumable data.

In addition, the CD server can periodically send consumable data for new lots of consumables/consumable types to a customer assay system, e.g., via email, CD, memory card/stick, flash drive and/or via a remote interface between the system and the CD server. The storage medium comprises a consumable data repository including the consumable data and the assay system is configured to receive updates to the repository from a remote storage medium, e.g., via email, CD, memory card/stick, flash drive and/or via a remote interface.

Figure 3:
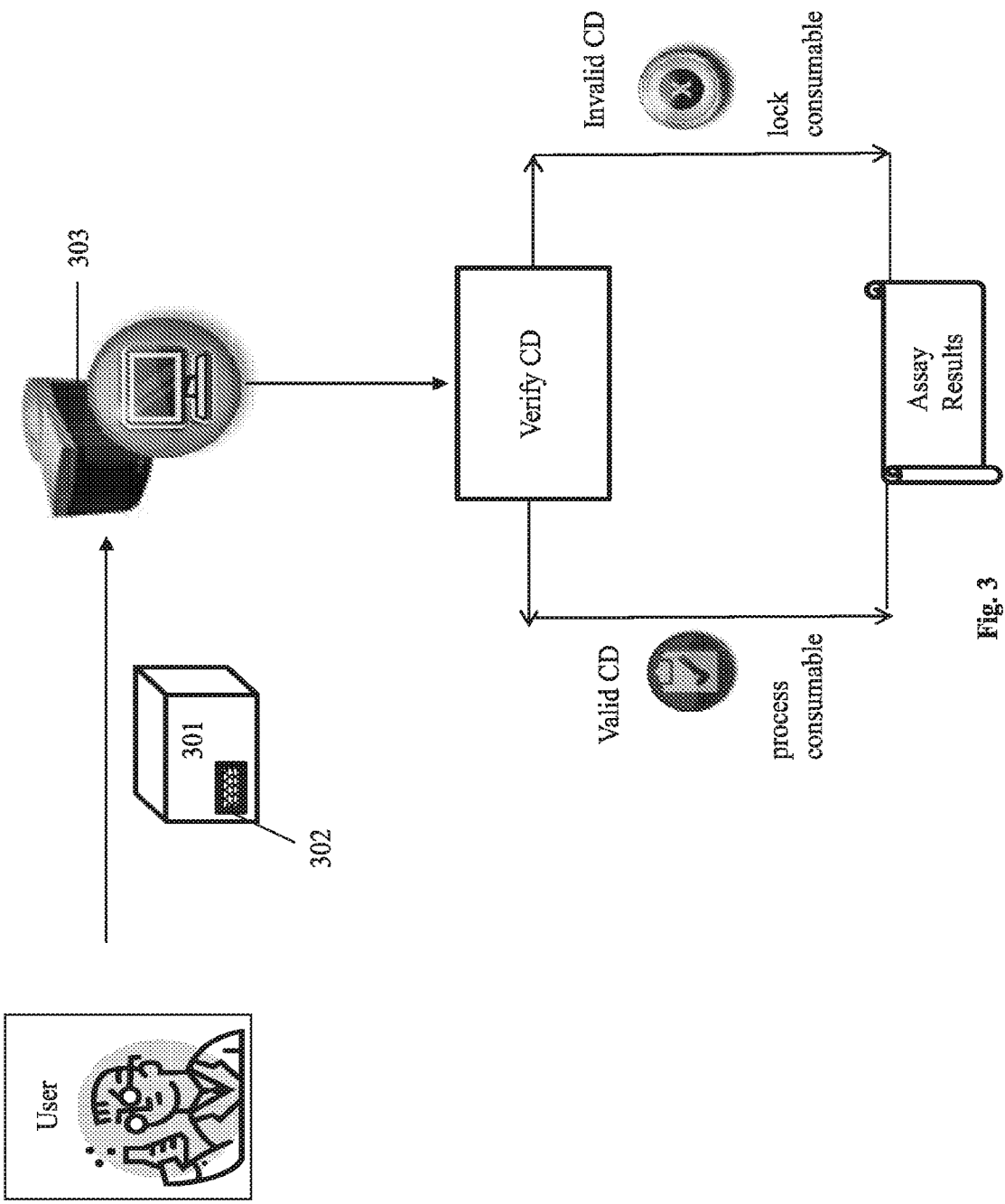
FIG. 3 illustrates the use of consumable data to verify authorized use of a consumable in an assay system.

FIG. 3 illustrates the verification of the consumable data by the system software and the consequences of that procedure. First, the customer inserts the consumable (301), with consumable identifier (302), into the system (303) (or otherwise contacts the consumable identifier with the controller on the system) and the system software identifies the consumable via the consumable identifier (302). The system will attempt to associate that identifier with the consumable data stored locally on the system repository. If the consumable data are verified and valid, the system will process the consumable and display the results of that processing step to the customer. But if the consumable data are invalid or unverifiable, although the consumable will be processed by the system, the results of that analysis will not be displayed or otherwise available to the customer until the consumable data are verified by the system software.

In addition, the invention provides a method of controlling customer access to an assay system and/or assay consumable by a vendor wherein the system comprises a system identifier, and the method includes receiving the system identifier from a customer, wherein the system identifier is sent to a vendor computing system; identifying the system identifier by the vendor; and performing an operation comprising:

(i) enabling full access to the apparatus and/or an assay consumable used in that apparatus;
(ii) enabling partial access to the apparatus and/or an assay consumable used in that apparatus; or
(iii) denying access to the apparatus and/or an assay consumable used in that apparatus.

The system identifier includes information that uniquely identifies the assay system, e.g., a serial number or other identification code that is generated and used by the vendor to identify the assay system. The system identifier is generated by the vendor during or after the manufacturing process and/or as the system is being prepared for shipment or transfer to a customer.

In one embodiment, the step of enabling access, either full or partial, includes the step of sending an access code from the vendor to the customer, thereby enabling access to the system. The access code can be a full or a partial access code that enables different functionalities in the system. In one embodiment, the access code is a partial access code that enables the system to operate in a demonstration mode. The partial access code can be time-limited. Alternatively, the access code can be a full access code that enables the system to be fully operational.

Figure 4:
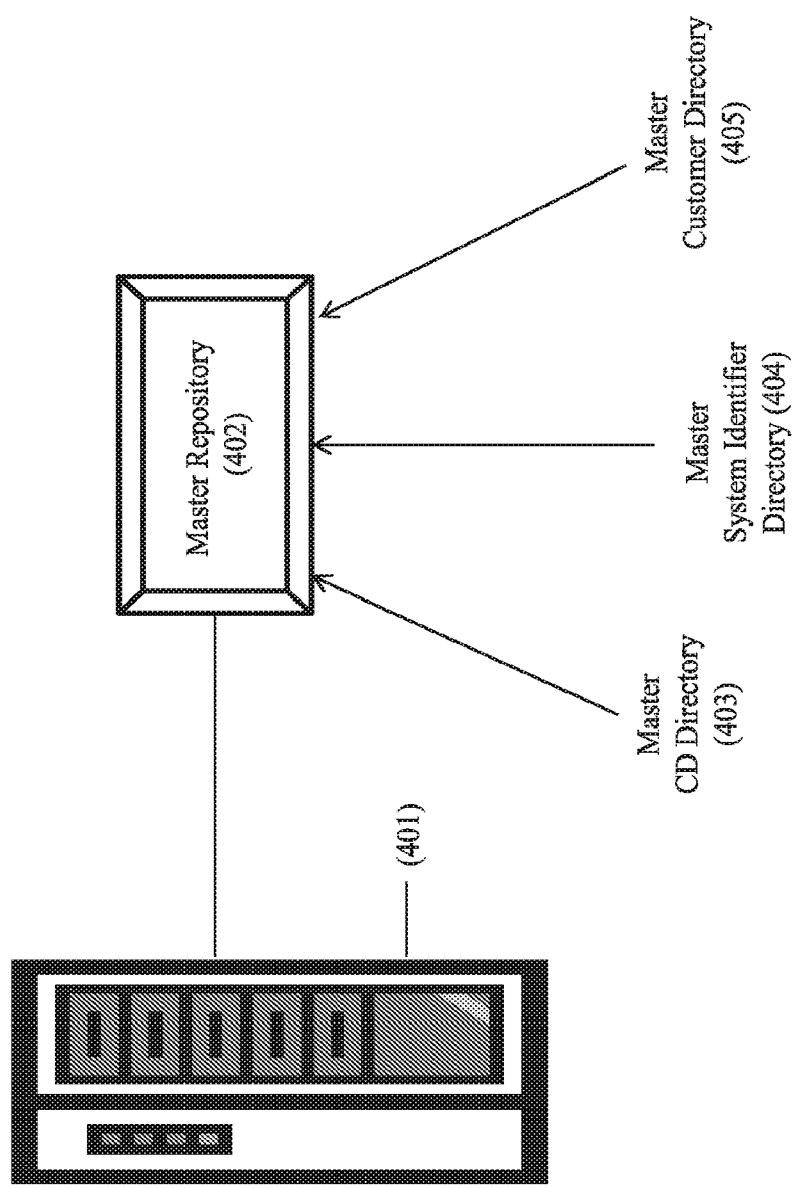
FIG. 4 illustrates the master repository on the CD server, its contents and/or interface with additional vendor directories.

As shown in FIG. 4, the CD server (401) includes a master repository (402) that comprises one or more directories of (i) consumable data; (ii) system data; and (iii) customer data. In addition or alternatively, the data contained in one or more of directories (i)-(iii) can be supplied to the master repository by an interface between the CD server and one or more supplemental vendor directories. In one embodiment, the master repository comprises (i) a master customer data directory (403); (ii) a master system identifier directory (404); and (iii) a master customer data directory (405). In a preferred embodiment, customer data are supplied to the CD server via an interface to a supplemental vendor-customer directory that maintains customer data. Customer data can be stored in one or more supplemental vendor-customer directories, each connected via an interface to the CD server. The master CD database comprises a plurality of CD directories, each generated for a consumable or lot of consumables. The master system identifier directory includes the unique system identifiers for each system manufactured and/or distributed by the vendor. And the master customer directory and/or supplemental vendor-customer directories that interface with the CD server include information related to each customer of the vendor, e.g., contact information for the customer and individual customers at that customer, billing information, pricing information, shipping information, order history, etc.

In a specific embodiment, when a system is manufactured and/or prepared for shipment, a vendor generates a system identifier for that system. The system identifier is stored in the master system identifier directory or available via an interface between a supplemental vendor directory to the CD server. If the system is ordered by a customer, order information, e.g., purchase order, a related quote, pricing, terms and conditions of sale or lease, related service agreements, etc., and customer information is stored to the master customer directory and/or to one or more supplemental vendor-customer directories that interface with the CD server. In this regard, the unique system identifier for that system is associated with the customer that has purchased that system in the master repository, as well as any information regarding related purchases by that customer. Shipping information for that system to the customer is also available in the customer directories(s) and once the system is shipped the customer receives a shipping confirmation, a copy of which is also stored in the customer directories. The customer receives the system and in a preferred embodiment, once installation and training on the system is completed, if required, the system software connects to the CD server via a remote interface between the system and the CD server to enable interaction between the two. The system initially connects to the CD server to confirm that system installation, and training is completed and successful and the CD server records that confirmation. Alternatively, if a remote connection is not enabled on the system, the customer receives a confirmation code, system login, and/or email address from the system once the system is installed and training is completed and the customer can login to the CD server via that confirmation code, system login and/or email, thereby providing a customer login to the CD server that provides a separate vendor-customer interface without a direct connection between the system and the CD server. The separate vendor-customer interface can be a portal on a vendor hosted customer accessible website via a password and/or the customer and the CD server can communicate via an email exchange server configured to send and receive emails between customers and the CD server (referred to collectively as an "indirect interface" between the customer and the CD server). Therefore, the vendor can communicate with the customer via a direct system-CD interface (referred to as a "direct interface") and/or via an indirect interface. As described above, the customer can then purchase consumables, the system will read the consumable identifier and confirm consumable data is stored locally, receive consumable data from the CD server, directly or indirectly, if necessary, and then the system will be enabled to use that consumable or lot.

Once the customer and vendor have a means of communicating via a direct or indirect interface, the customer and vendor can interact in a variety of ways and because the vendor has the ability to track customer-specific use information for the system and consumables purchase and/or used by the customer, communication between the parties can be more meaningful and productive. For example, the customer can browse and/or purchase vendor products, receive customer assistance, schedule service calls, etc. via the direct or indirect interface. Because the vendor is able to track customer activity and purchases so closely via the consumable identifier/CD server, the vendor can tailor its interactions with the customer based on that information. For example, because the vendor is aware of the customer's order history, the vendor can send the customer promotional materials for products related to those products the customer has purchased/used in the past. Similarly, because the vendor tracks information related to the customer's system, the vendor can send the customer preventative maintenance tips and reminders, general or specific customer training and seminars based on the customer's unique needs (and informed by tracking consumable data for that customer), and information regarding system service, warranty repairs, service contract information and reminders, etc.

In one embodiment, the vendor tracks use of consumables by an assay customer and the consumable data stored to the assay system includes system-consumable use information. To facilitate consumable use tracking, the assay system is configured to send system-consumable use information directly or indirectly to the CD server. If a direct interface is enabled between the system and the CD server, system-consumable use information can be sent automatically. If, however, the direct interface is not enabled, system-consumable use information can be provided indirectly by the customer to the CD server. In this embodiment, the system can periodically prompt the customer to provide system-consumable use information to the vendor via the indirect interface. The vendor can maintain a directory of customer consumable information to track consumable use and information from that directory is used to send consumable data, via the direct or indirect interface, which can be relevant to a customer based on prior consumable and/or system use. If the direct interface is enabled, the assay system can be configured to receive assay system maintenance and/or promotional information from a vendor computing system related to an individual customer's prior consumable and/or system use.

The vendor can also track and/or convey system maintenance information to the customer, e.g., monitoring system and/or system components usage, service history, system troubleshooting information, the results of diagnostics run on the system, control charting, periodic maintenance scheduling, warranty information regarding the system and/or a components thereof, or combinations thereof. The system software can be programmed to monitor various components of the system and automatically or when prompted, send monitoring reports to a remote computing system and/or to a service technician. If a direct interface is not enabled, the system can prompt the customer to send monitoring reports to the CD server via an indirect interface. In addition or alternatively, such system monitoring reports can be accessed by a service technician charged with the task of maintaining and/or servicing the system on site or remotely. In a specific embodiment in which a direct interface is enabled, the CD server monitors system component usage and/or warranty information and based on standard system component lifetimes and/or warranty terms, schedules periodic system/component maintenance and/or upgrades by a service technician. In addition, the CD server can maintain a log of the service history for a given assay system and schedule a service call by a service technician (this can be done using either a direct or indirect interface). The remote computing system can also send an individual assay system software upgrades via a direct or indirect interface.

In addition, one or more of the following system components and/or actions can be monitored by the system software including, but not limited to, expected motor positions during normal usage, positional errors for each expected motor position, corrective actions and/or attempted corrective actions taken by the system in the event of a motor positioning error, and error frequencies; component usage, e.g., the approximate time the component has been powered on in the system, and in a preferred embodiment, the system also tracks the relative lifespan of that component under normal use conditions; locking mechanisms attempts, re-attempts, and failures; bar code identifier controller attempts, re-attempts, and failures; approximate temperature of one or more components in the system, error warnings, database performance and capacity, instrument hard disk capacity, software and firmware version and patches, customer login/logout, system startup and shutdown, and the like. In a particularly preferred embodiment involving a system designed to conduct electrochemiluminescence measurements using assay consumables, the system software can also be programmed to monitor the time the analyzer camera has been powered on and approximate temperature, the use cycle of latches within the system, bar code identifier controller attempts, re-attempts, and failures, consumable locking and unlocking events, ECL waveform voltage and integrated current, image processing analysis accuracies and failures, consumable type, kit, owner, consumable identifier (e.g. bar code), and time stamp for each consumable run in the system, or combinations thereof. Still further, the system software can also monitor experiments conducted in the system, e.g., when, by whom, and which type of consumable(s) were used in that experiment. Such system-use monitoring information can be sent via a direct and/or indirect interface, to the CD server to enable the vendor to schedule appropriate support, service and/or maintenance on the system.

In another embodiment, by tracking use of an assay system, a vendor can provide use and/or purchasing assistance. For example, a vendor can track consumable use and purchase history and based on the consumable data for a given lot or consumable, the vendor can monitor the expiration data of a given lot or consumable and notify the customer of an approaching expiration date for a lot or consumable. Tracking use of an assay system/consumable type can also enable a vendor to track a relative schedule/frequency of consumable use and notify the customer that the customer's consumable supply needs to be replenished. If a direct interface is enabled, the system can also be configured to order/re-order consumables and the system can be further configured to track and confirm consumable orders from a vendor. If a direct interface is not enabled, the system can monitor consumable use and inventory and prompt the customer to replenish a supply of one or more consumables. (In this regard, when a system receives lot size information via the consumable identifier and by monitoring consumable usage, it can prompt the customer when the available consumable supply in a given lot has been diminished to a minimum level.) Moreover, by tracking consumable use, the vendor can send the customer information regarding custom assay design services for a specific custom consumable type based on the customer's order/consumable use history. A direct or indirect interface can also provide customer training modules, consulting services, and/or live customer service assistance capabilities to facilitate the customer experience (i.e., live-chatting) (referred to collectively as system and/or consumable technical support information).

In another embodiment, tracking consumable/system use enables the vendor to send promotional material to the customer, e.g., when a new type or lot of consumables historically used by a given end-customer, the vendor computing system sends consumable data to the customer regarding those new products. Such promotional materials can also relate to new assay systems that might be of interest to the customer based on that customer's prior usage. The remote computing system can also send a customer literature references that can relate to one or more consumables/systems used by a given customer.

These and other specific examples of consumable data are described in more detail hereinbelow.

A. Assay Systems, Consumables & Methods of Use

The assay systems contemplated by the present invention are used to conduct any type of diagnostic or analytical method known in the art. Such analytical methods include but are not limited to clinical chemistry assays (e.g., measurements of pH, ions, gases and metabolites), hematological measurements, nucleic acid amplification assays (e.g., polymerase chain reaction (PCR) and ligase chain reaction assays), immunoassays (e.g., direct, sandwich and/or competitive immunoassays and serological assays), oligonucleotide ligation assays, and nucleic acid hybridization assays. Any biological reagent that might be used in such analytical methods can be used in such systems, including but not limited to nucleic acids, nucleotides, oligonucleotides, DNA, RNA, PNA, primers, probes, antibodies or fragments thereof, antigens, small molecules, e.g., drugs or prodrugs, streptavidin, avidin, and biotin.

These systems can be portable, e.g., hand-held, and/or operated within a fixed laboratory or field setting, alone or in combination with one or more additional components, assay devices or systems. These systems can be used in a variety of applications, from field operations to laboratory settings, in a wide variety of industries, including but not limited to, medical, clinical, forensic, pharmaceutical, environmental, veterinary, biological, chemical, agricultural, waste management, hazardous chemical, drug testing, and in defense applications, e.g., for the detection of biological warfare agents. The assay systems, assay readers, and consumables used in the present invention can detect an analyte of interest by any suitable method, including but not limited to, optical, electromechanical, radiowave, electromagnetic, colorimetric, fluorimetric, chemiluminescent, electrochemiluminescent, radiochemical, nuclear magnetic resonance, enzymatic, fluorescent, particle-count, and cell-count based detection.

(i) Specific Embodiments of Assay Consumables

The assay consumable includes devices in which one or more steps of an assay process are conducted and such devices can include one or more test sites where an assay measurement is conducted. In one embodiment, the assay consumable includes at least one assay test site for an assay. A test site can include a plurality of distinct assay domains, at least two of the domains including reagents for measuring different analytes. Still further, the consumable can include a plurality of test sites for a plurality of individual assays. Alternatively, the assay consumable can be a component that provides a reagent or other assay component that is used by the system to conduct an assay. For example, the assay consumable can be a container with one or more compartments for holding assay reagents. The assay consumable (or test sites therein) can be single use or it can be reusable. The assay consumable can be configured to conduct one test or multiple tests (sequentially or in parallel).

Test sites, as used herein, refer to regions of a consumable that hold, contact and/or interrogate a sample. A test site can include a plurality of distinct assay domains, at least two such domains include reagents for measuring different analytes. Consumables can comprise multiple test sites which can hold, contact or otherwise interrogate distinct volumes (aliquots) of the same sample and/or volumes of different samples. A sector of an assay consumable refers to grouping of two or more test sites of the consumable. Each test site can be used to conduct a single measurement or multiple measurements on a volume of sample (for example, the measurement of multiple different analytes in a multiplexed assay format). Depending on the specific requirements of an application, a consumable with multiple test sites can be configured to use all of its test sites in parallel, to use its test sites at different times (e.g., assigning unused test sites to be used as new samples are delivered to the assay system), or a combination of both modes of operation can be enabled.

The assay consumable can be any structure useful in diagnostic applications and that structure can be dictated by the particular assay format or detection method employed by the device. Examples of assay consumables suitable for use with the invention include, but are not limited to, test tubes, cuvettes, flow cells, assay cartridges and cassettes (which can include integrated fluidics for assay processing), multi-well plates, slides, assay chips, lateral flow devices (e.g., strip tests), flow-through devices (e.g., dot blots), pipette tips, solid phase supports for biological reagents and the like. In certain embodiments, test sites in the assay consumable are defined by compartments in the assay consumable, e.g., wells, chambers, channels, flow cells and the like. The assay consumable and/or test sites can include one or more components used to carry out an assay measurement according to one or more specific detection methodologies. Depending on the function of the consumable and the detection modalities employed by the assay system, examples of such components can include, but are not limited to, lateral flow matrices, filtration matrices, optical windows, sensors (e.g., electrochemical and optical sensors), solid phase supports for binding reactions (e.g., coated slides, chips, beads, pins, coated filtration or lateral flow matrices, tubes and the like), reagents (dry or in liquid form), electrodes, analyte selective membranes and the like.

In one embodiment, the assay consumable can be a device that incorporates a conventional lateral flow test strip, e.g., an immunoassay test strip, as an assay medium. In this example, the device is molded to include an identifier or the identifier is affixed to the device without any modification to the structure of the device and/or the assay medium. In one embodiment, the device is placed within the analytical system, i.e., the assay system, for analysis and before, during or after the performance of the assay, the identifier controller within, affixed to or associated with the assay system reads the data contained on the identifier and uses that data in the assay or after the assay is completed by the system.

In another embodiment, the assay consumable and accompanying assay system or assay reader is capable of performing a multiplex assay. A multiplex assay is a type of assay in which multiple measurements are performed on a single sample, e.g., by distributing samples across multiple test sites and/or by carrying out multiple measurements on volumes of samples in individual test sites. The multiple measurements can include, but are not limited to, (i) multiple replicates of a measurement for an analyte; (ii) multiple measurements of a certain analyte (i.e., multiple non-identical measurements for the same analyte, e.g., measurements that differ in format or in the identity of the assay reagents that are employed); and/or (iii) measurements of multiple different analytes. In one specific embodiment, an assay consumable is configured to carry out, in one or more test sites, multiplex measurements that include at least two assays for two different analytes.

The invention is not restricted to specific approaches for conducting multiplex measurements in a test site and can employ any of the numerous techniques that have been developed for carrying out multiplex measurements. Multiplex measurements that can be used with the invention include, but are not limited to, multiplex measurements (i) that involve the use of multiple sensors; (ii) that use discrete assay domains on a surface (e.g., an array) that are distinguishable based on location on the surface; (iii) that involve the use of reagents coated on particles that are distinguishable based on a particle property, such as size, shape, color, etc.; (iv) that produce assay signals that are distinguishable based on optical properties (e.g., absorbance or emission spectrum), (v) that are based on temporal properties of an assay signal (e.g., time, frequency or phase of a signal), and/or (vi) that are based on some other assay characteristic. Accordingly, interpretation of multiplexed assay results can involve the use of multiplexing information, such as the identity of the assays carried out in each test site and, within a test site, any assay characteristics (identity of specific sensors, location and identity of assay domains, etc.) that are used to distinguish assays carried out in a test site and/or that are used to tie a specific assay identity to the corresponding assay signal.

In one embodiment, an assay test site comprises a plurality of distinct assay domains and each domain comprises one or more reagents for measuring a different analyte. Multiplexing information, including the location, identity, and composition of each assay domain, is used to identify the assay signal generated at each domain and connect it to a determination of the presence or amount of the corresponding analyte (a process which can include the application of additional consumable data such as signal thresholds and/or calibration parameters). Such multiplexing information can be provided as consumable data and/or associated with the consumable identifier.

A test site can be configured to carry out a plurality of multiplexed measurements (e.g., it can include a plurality of distinct assay domains, wherein each domain comprises reagents for measuring a different analyte). In one embodiment, the assay consumable can include a plurality of test sites. Information regarding the exact configuration of the one or more test sites, assay domains, and/or one or more sectors in a consumable can be included in the information saved to the assay consumable identifier and/or provided as consumable data. This information can include the location and identity of the test sites, assay domains, and/or one or more sectors as well as multiplexing information (as described above) including the number, identity and differentiating characteristics of the individual measurements within a test site, assay domain, and/or sector (e.g., the specific locations, identities and/or assay reagents of assay domains within each test site). In addition, the use of a test site, assay domain, and/or sector in an assay consumable can also be recorded to the identifier to track the use of the consumable in an assay system. The identifier and/or consumable data can also include information concerning the assay format and specific processing steps to be used for an assay consumable or test site, assay domain, and/or sector of an assay consumable. The identifier and/or consumable data can also include information concerning analytical methods that should be applied by the system once an assay is conducted to analyze the output of an assay in a given test site, assay domain, and/or sector and, optionally, to provide results that combine the output from multiple assays in a test site, assay domain, and/or sectors.

The test sites can be configured in any suitable configuration, depending on the geometry of the consumable and/or the type of assay conducted with the consumable. In one embodiment, the test sites are configured as wells and/or chambers in the assay consumable. For example, the assay consumable of the present invention can be a multi-well plate (e.g., a 24-, 96, 384- or 1536-well plate), and the wells of the plate can further comprise a plurality (e.g., 2 or more, 4 or more, 7 or more, 25 or more, 64 or more, 100 or more, etc.) of distinct assay domains. Multi-domain multi-well plates that are adapted to allow assay measurements to be conducted using electrode induced luminescence measurements (e.g., electrochemiluminescence measurements) are described in U.S. application Ser. No. 10/238,391, entitled "Methods and Reader for Conducting Multiple Measurements on a Sample", filed on Sep. 10, 2002, hereby incorporated by reference. The exact configuration of the domains, test sites, and/or sectors in an assay consumable, as well as the specific identity of each domain, test site, and/or sector and the reagents bound to that domain/test site/sector can be included in the information saved to the assay consumable identifier and/or provided as consumable data. In addition, the use of a given domain, test site, and/or sector in an assay consumable can also be recorded to the identifier to track the use of the consumable in an assay system.

Assay consumables can be used in a plurality of diverse assays and this diversity leads to a variety of suitable configurations of the associated consumable. In one assay format, the same analyte is measured at different assay domains within a test site, the different assay domains being designed to measure a different property or activity of the analyte. Information concerning the assay format that can be used in an assay consumable, test site and/or assay domain can also be saved to the assay consumable identifier and/or provided as consumable data. The identifier and/or consumable data can also include information concerning analytical methods that should be applied by the system once an assay is conducted to analyze the output of an assay in a given test site and/or domain and compare that output to an assay in a separate test site and/or domain.

One example of a multiplex assay consumable is described in U.S. 2004/0022677, the disclosure of which is incorporated herein by reference in its entirety. Such assay consumables include one or more, and in one embodiment, a plurality of test sites and/or assay domains for conducting one or more assay measurements simultaneously or sequentially. For example, the test sites can be configured as wells and/or chambers. These test sites and/or assay domains comprise one or more electrodes for inducing luminescence from materials in the test sites and/or assay domains. The assay consumables can further comprise assay reagents in liquid or dry form, e.g., in the test sites, e.g., wells or chambers, of the consumable.

In addition to the test sites and assay domains, an assay consumable or multi-well assay plate can include several additional elements, e.g., a plate top, plate bottom, wells, working electrodes, counter electrodes, reference electrodes, dielectric materials, electrical connections, and assay reagents. The wells of the plate can be defined by holes or openings in the plate top, or as indentations or dimples on a surface of a plate. The plates can have any number of wells of any size or shape, arranged in any pattern or configuration and can be composed of a variety of different materials. Exemplary embodiments of consumables that can be used in the present invention include industry standard formats for the number, size, shape and configuration of the plate and wells, e.g., 96-, 384-, and 1536-well plates, with the wells configured in two-dimensional arrays. Other formats can include single well plates, 2-well plates, 6-well plates, 24-well plates, and 6144-well plates. Multi-well assay plates can be used once or can be used multiple times and are well suited to applications where the plates are disposable. Various configurations for suitable assay plates can be used in the present invention, including but not limited to those depicted in FIGS. 11A, 12A, 13A, 13B, 14A, 15, and 16A of U.S. application Ser. No. 2004/0022677, each of which are incorporated herein by reference. As stated above, the specific configuration and identity of assay test sites, domains, and/or sectors of an assay consumable can be included in the information saved to the assay consumable identifier and/or provided as consumable data.

(ii) Specific Embodiments of Assay Readers

Assay consumables can be used in an assay reader that can be used to induce and measure luminescence, e.g., electrode induced luminescence or electrochemiluminescence, in assays conducted in or on assay consumables, e.g., multi-well assay plates. The assay reader can also induce and/or measure current and/or voltage, for example, at an electrode. The assay reader can incorporate, for example, one or more photodetectors; a light tight enclosure; mechanisms to transport the assay plates into and out of the assay reader (and in particular, into and out of a light tight enclosure); mechanisms to align and orient the assay plates with the photodetector(s) and/or with electrical contacts; additional mechanisms to track and identify plates (e.g. bar code identifier controllers); mechanisms to make electrical connections to plates, one or more sources of electrical energy for inducing luminescence, and appropriate devices, electronics and/or software. The assay reader can also include mechanisms to store, stack, move and/or distribute one or more multi-well assay plates (e.g. plate stackers and/or plate conveyors). The assay reader can be configured to measure light from multi-well assay plates by measuring light sequentially from a plurality of sectors or regions of the plate (i.e., a grouping of a plurality of adjacent assay domains within a plate) and/or from the entire plate substantially simultaneously or simultaneously. The assay reader can also incorporate additional microprocessors and computers to control certain functions within the system and to aid in the storage, analysis and presentation of data. Various configurations for suitable assay readers can be used in the present invention, including but not limited to those depicted in FIGS. 17 to 23 of U.S. application Ser. No. 2004/0022677, incorporated herein by reference.

In a specific embodiment, the assay reader is an apparatus described and claimed in U.S. application Ser. No. 14/147,216, published as US 2014/0191109 and WO 2014/107576, the disclosure of which is incorporated herein by reference. Particular embodiments of the assay reader are illustrated in the Figures of U.S. Ser. No. 14/147,216 and certain of those figures are reproduced herein. FIGS. 5(*a*)-(*b*) show a front and rear view, respectively, of apparatus 500 with a stylized cover, and FIGS. 5(*c*)-(*d*) show the corresponding front and rear views, respectively, of the apparatus without the cover.

Figure 6A:
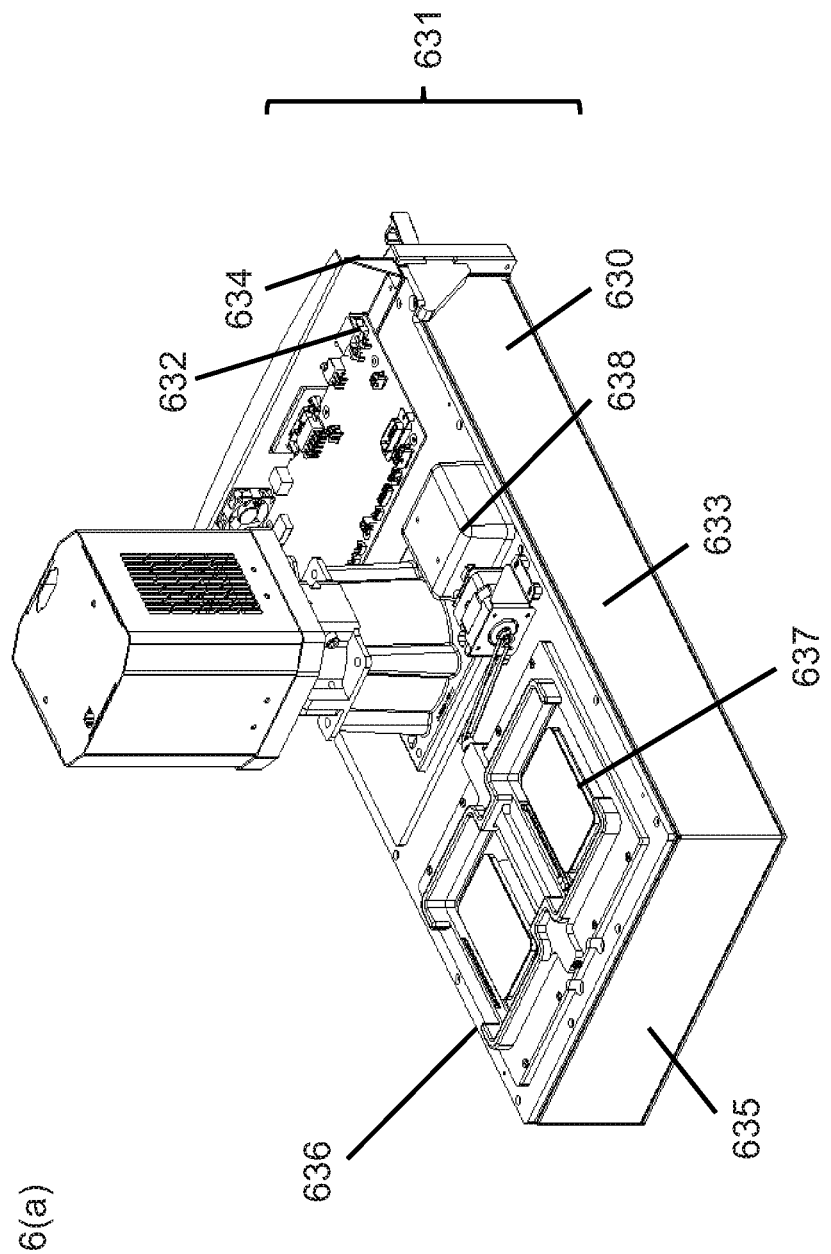
FIGS. 6(a)-(c) illustrate several alternative views of an assay reader described herein.
Figure 6B:
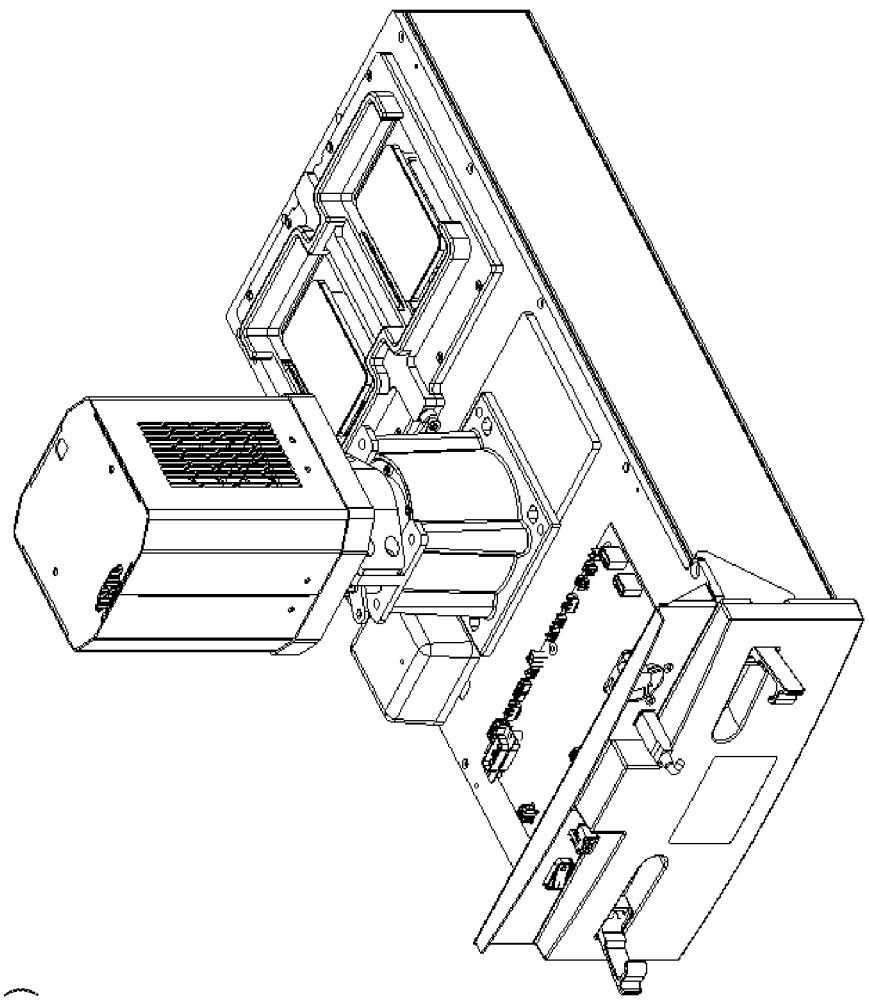
Figure 6C:
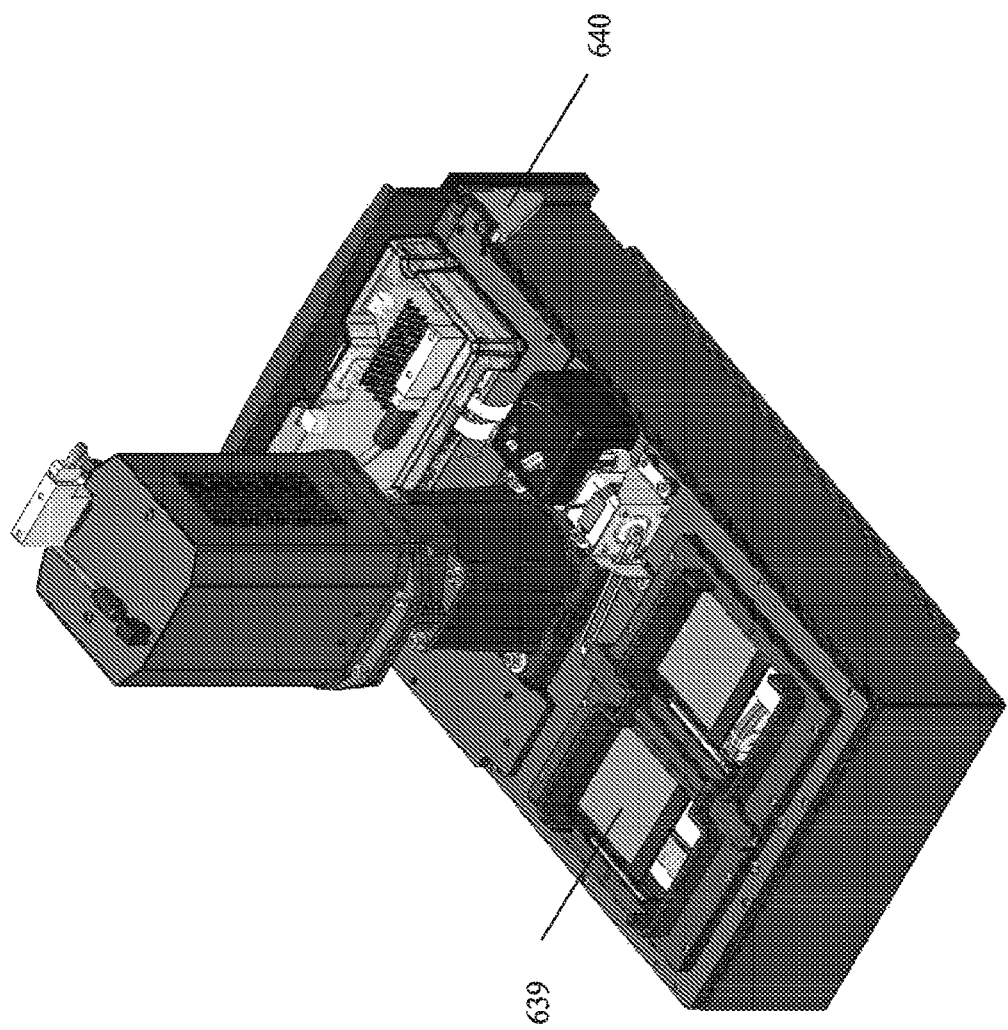

As shown, e.g., in FIG. 5(c), the apparatus includes a light detection subsystem 510 and a plate handling subsystem 520. A more detailed view is provided in FIGS. 6(a)-(b). The plate handling subsystem 620 includes a light tight enclosure 630 comprising a housing 631 having a housing top 632, bottom 633, front 634, and rear 635. The housing also includes a plurality of alignment features and the housing is adapted to receive a removable drawer. The removable drawer 640 is shown in FIG. 7, being in the partially opened or closed position. Referring to FIG. 6(a), the housing top 632 also includes one or more plate introduction (and ejection) apertures, 636 and 637, respectively, through which plates are lowered onto or removed from the plate translation stage (manually or mechanically). A sliding light-tight door (shown in FIG. 6(c) as 639) is used to seal the plate introduction apertures 636, 637 from environmental light prior to carrying out luminescence measurements. Moreover, the housing top also includes an identifier controller to read and process data associated with an identifier on the plates. In one embodiment, the identifier controller is a bar code reader (638) mounted via a light-tight seal over an aperture in the housing top, where the bar code reader is configured to read consumable identifiers (e.g. bar codes) on plates placed on the plate translation stage within the housing. In a preferred embodiment, the consumable identifier (e.g. bar code) on a plate is read once the plate has been lowered into the drawer. In an alternative or additional embodiment, an identifier controller can be provided separately from the apparatus.

In a further specific embodiment, the assay reader is a MESO QuickPlex SQ 120, available from Meso Scale Discovery, Rockville, Md.

(iii) Specific Embodiments of Assay Systems

Figure 8:
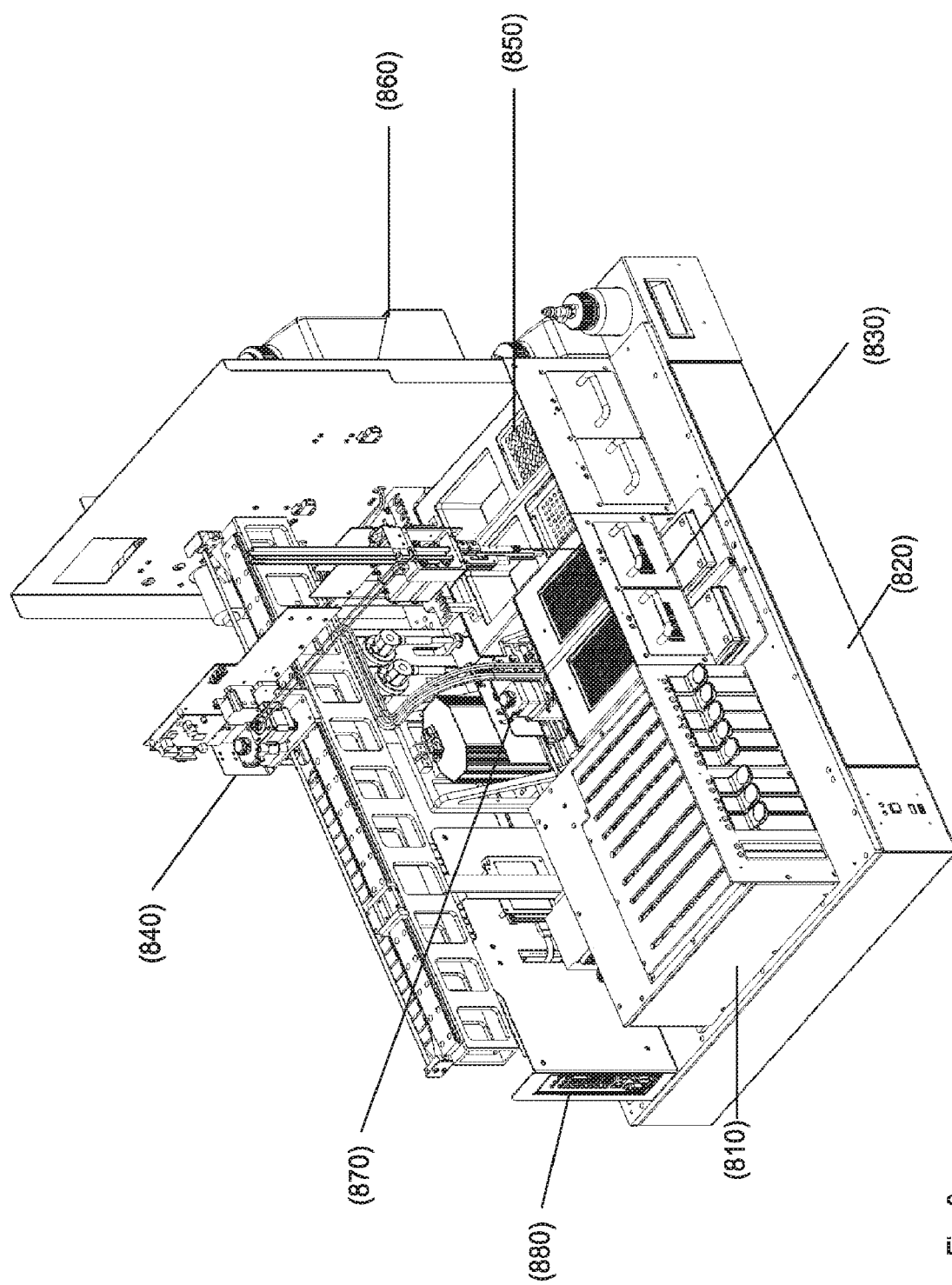
FIG. 8 illustrates an assay system described herein.

One embodiment of an assay system that can be used in the present invention is illustrated in U.S. application Ser. No. 12/844,440, published as US 2011/0143947, which is hereby incorporated herein by reference. In particular, as shown in FIG. 8, an assay system can include the following components: (i) a sample rack subassembly (810); (ii) a light-tight enclosure (820); (iii) an auxiliary plate subassembly (830); (iv) a pipettor subassembly (840); (v) a pipetting tip storage/disposal compartment (850); (vi) a liquid reagent subassembly (860); (vii) a well-wash subassembly (870); and (viii) a power supply (880). The apparatus is also attached to a computer through a user interface (not shown). This system enables fully automated random access analysis of samples using array-based multiplexed multi-well plate consumables. The apparatus achieves enhanced sensitivity and high sample throughput. It may be adapted for use with any of a variety of detection techniques, e.g., changes in optical absorbance, emission of luminescence or radiation, changes in light scattering and/or changes in a magnetic field. In one embodiment, the apparatus is configured to detect the emission of luminescence, e.g., fluorescence, phosphorescence, chemiluminescence and electrochemiluminescence (ECL). In a particular embodiment, the apparatus is configured to detect ECL. All the biological reagents required for an assay are provided in the apparatus, thus minimizing the consumable and reagent requirements for the apparatus. The apparatus depicted in FIG. 8 further comprises one or more consumable identifier controllers (not shown), either incorporated within the housing of the apparatus and/or positioned outside of the apparatus housing.

Figure 9A:
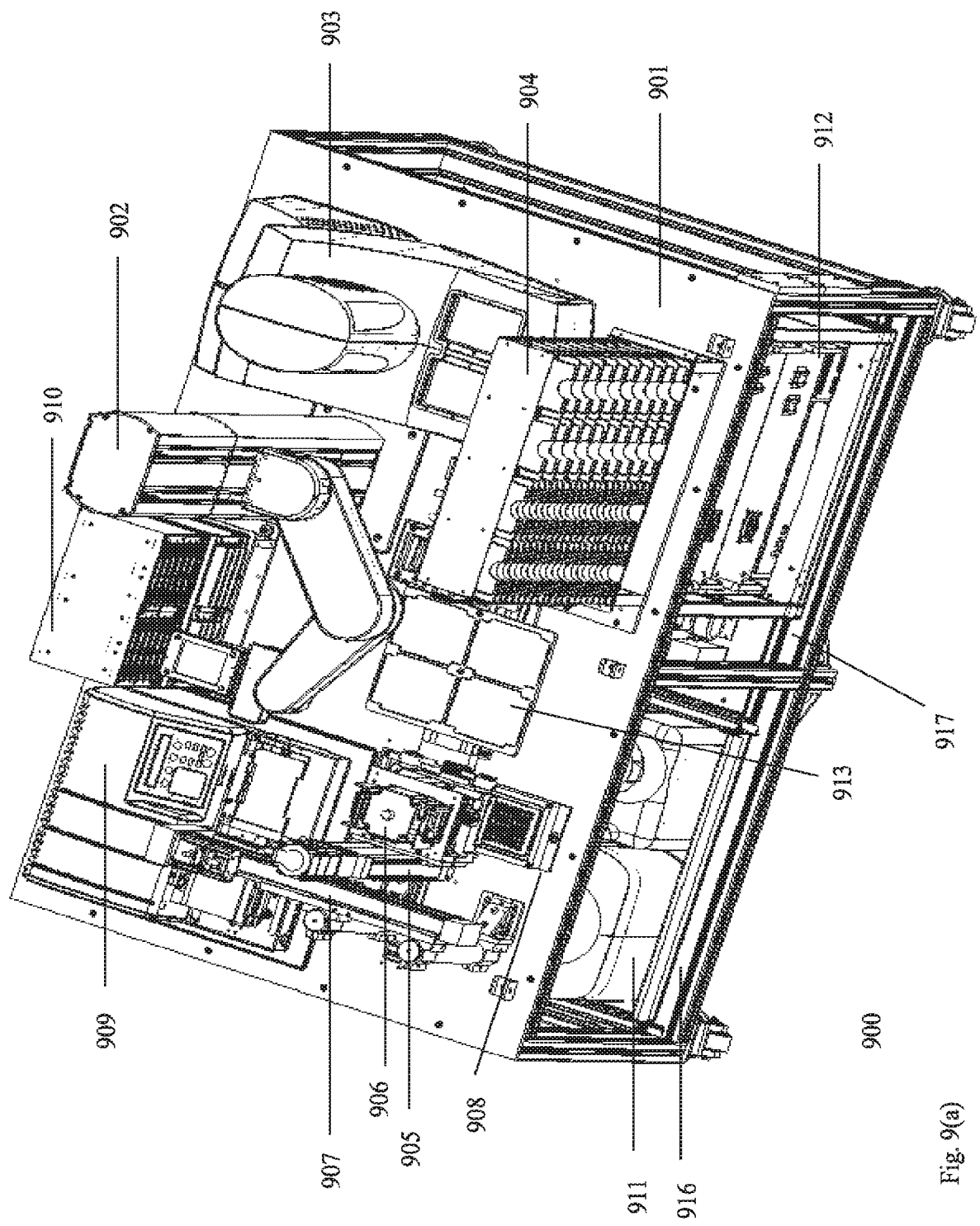
FIGS. 9(a)-(c) illustrate an assay system and various subsystems included in that system. In particular, the system includes a plurality of subsystems positioned on a table or platform, wherein each subsystem is operatively connected to a robotic subsystem configured to access and move one or more consumables, e.g., multi-well assay plates, from one subsystem of the assay system to another.
Figure 9B:
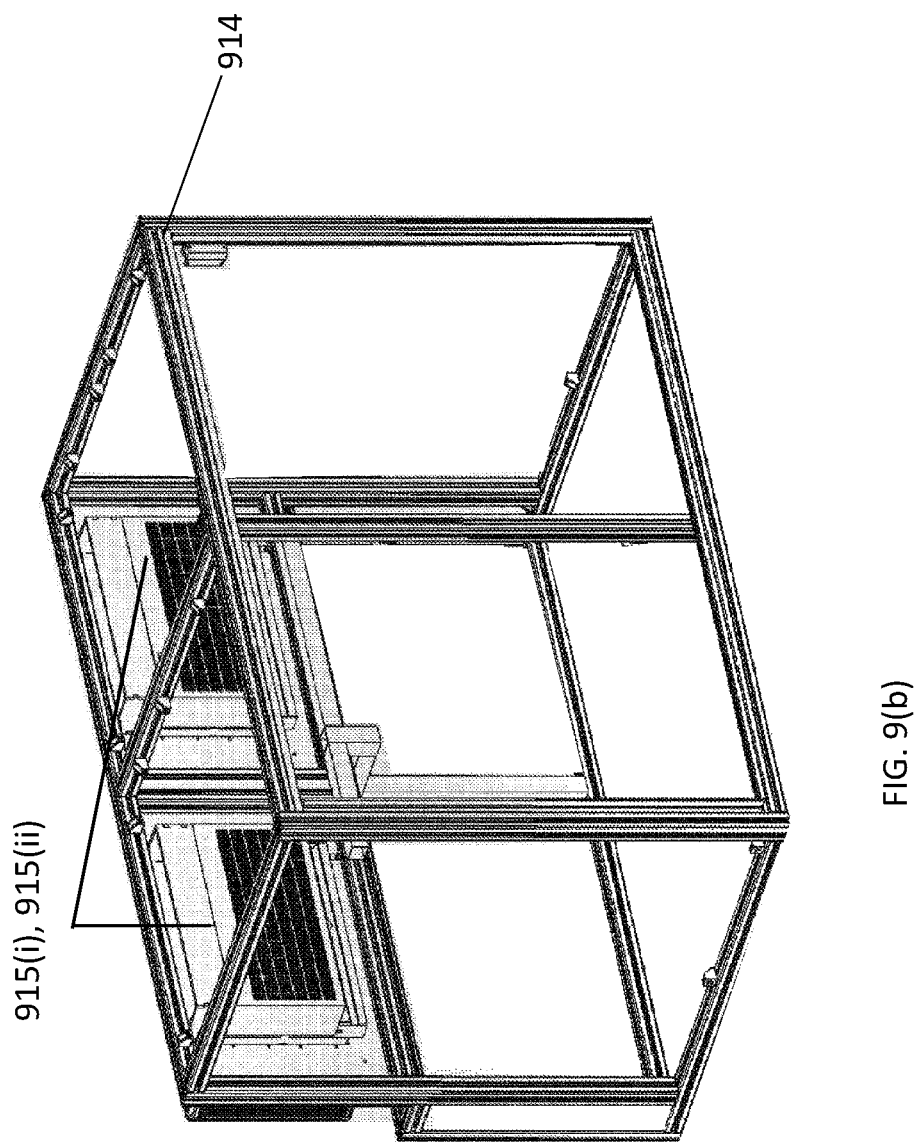
Figure 9C:
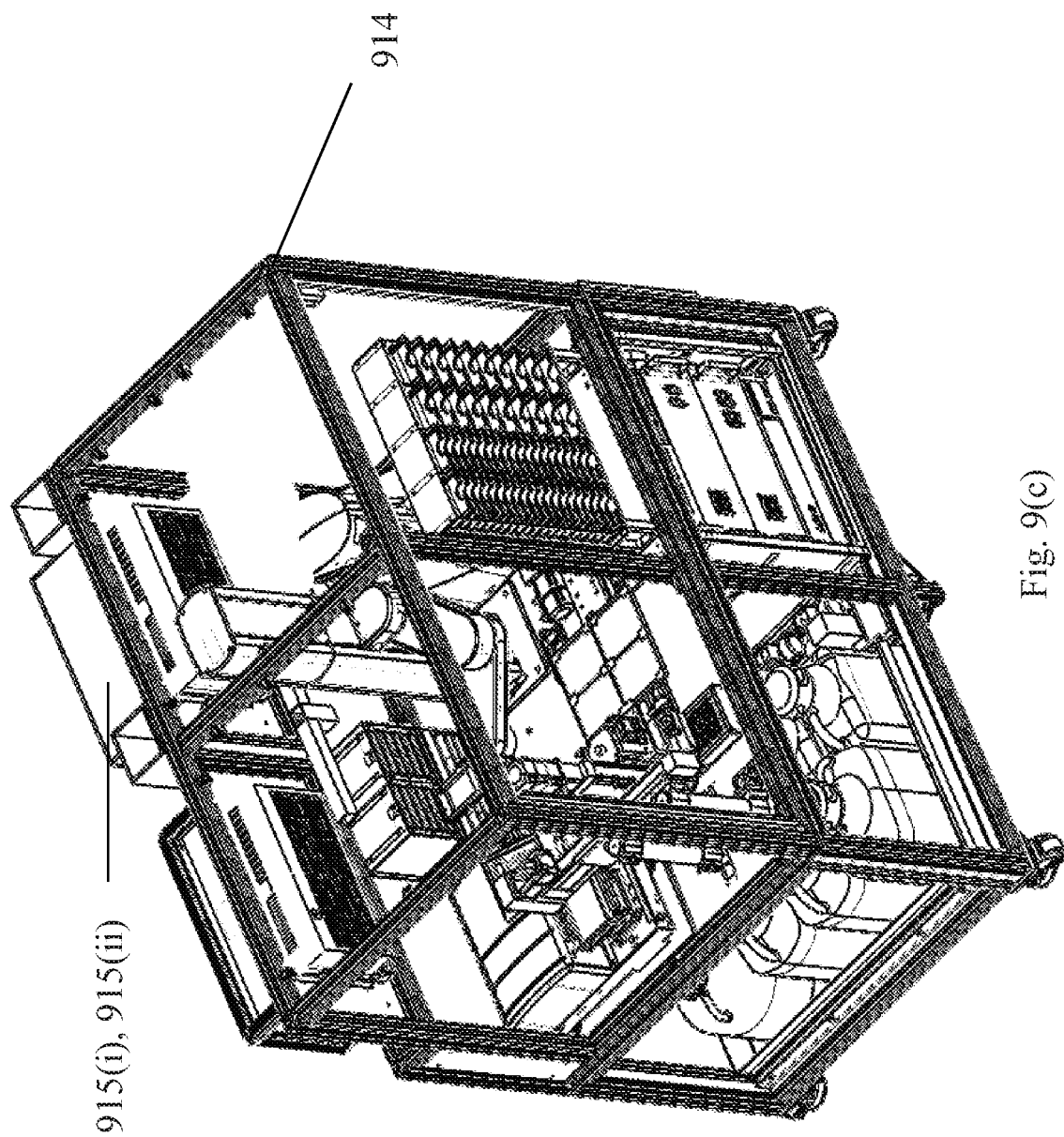

A further embodiment of an assay system of the invention is shown in FIG. 9(a). The assay system (900) includes a plurality of subsystems positioned on a table or platform (901), wherein each subsystem is operatively connected to a robotic subsystem (902) configured to access and move one or more consumables, e.g., multi-well assay plates, from one subsystem of the assay system to another. The plurality of subsystems include an assay reader (903); an assay consumable storage unit (904); a pipetting subassembly (905) comprising at least one pipetting probe (906) affixed to a pipetting head gantry (907) that provides X, Y, and Z motion of the probe to and from a pipetting tip washing station (908) and a plate washing subassembly (909)); an orbital shaking subassembly (910); a liquid reagent subassembly (911); and an electronic subassembly, including a computer (912). The computer also includes a user interface (not shown). The assay system can also include a multi-well plate preparation platform (913) positioned on the table (901) and configured to enable pipetting of liquids to and/or from one or more wells of a multi-well assay plate positioned on the preparation platform. Optionally, the platform (913) is positioned on a linear track that enables movement of the platform in a direction parallel to the plane of the table to and/or from the pipetting subassembly (905). Alternatively or additionally, the platform and/or one or more subcomponents of the pipetting subassembly are configured to move in the X, Y, and/or Z direction relative to one another. The robotic subsystem is configured to move one or more plates to and/or from the plate preparation platform, the plate washing subassembly, the orbital shaking subasssembly, the assay reader, and the consumable storage unit. As shown in FIGS. 9(b)-(c), the assay system can further comprise an enclosure (914) including one or more environmental control units, e.g., thermoelectric cooling units (915(i) and 915(ii) respectively), disposed within the enclosure. In one embodiment, the enclosure is configured to encase the assay system in order to maintain the internal temperature within the enclosure to approximately 20-30° C.

The assay system depicted in FIG. 9(a) is configured to process multi-well assay plates that have been subjected to an offline sample preparation step, which can be performed manually, using an automated sample preparation system, or using an automated sample preparation system integrated with the assay system via an additional robotic subsystem. In addition, the reagents used in the conduct of an assay in the assay plates can be provided in one or more additional assay plate, e.g., a reagent plate and/or a dilution plate, i.e., a plate including a specific reagent used in the conduct of an assay. In a specific embodiment, sample can be added offline to a sample plate, the system uses one or more diluents and reagents that can be stored in a diluent plate and/or reagent plate, respectively, and the assay can be conducted in a test plate, i.e., a plate to which sample and/or reagents are added during one or more processing steps by the system.

Figure 9D:
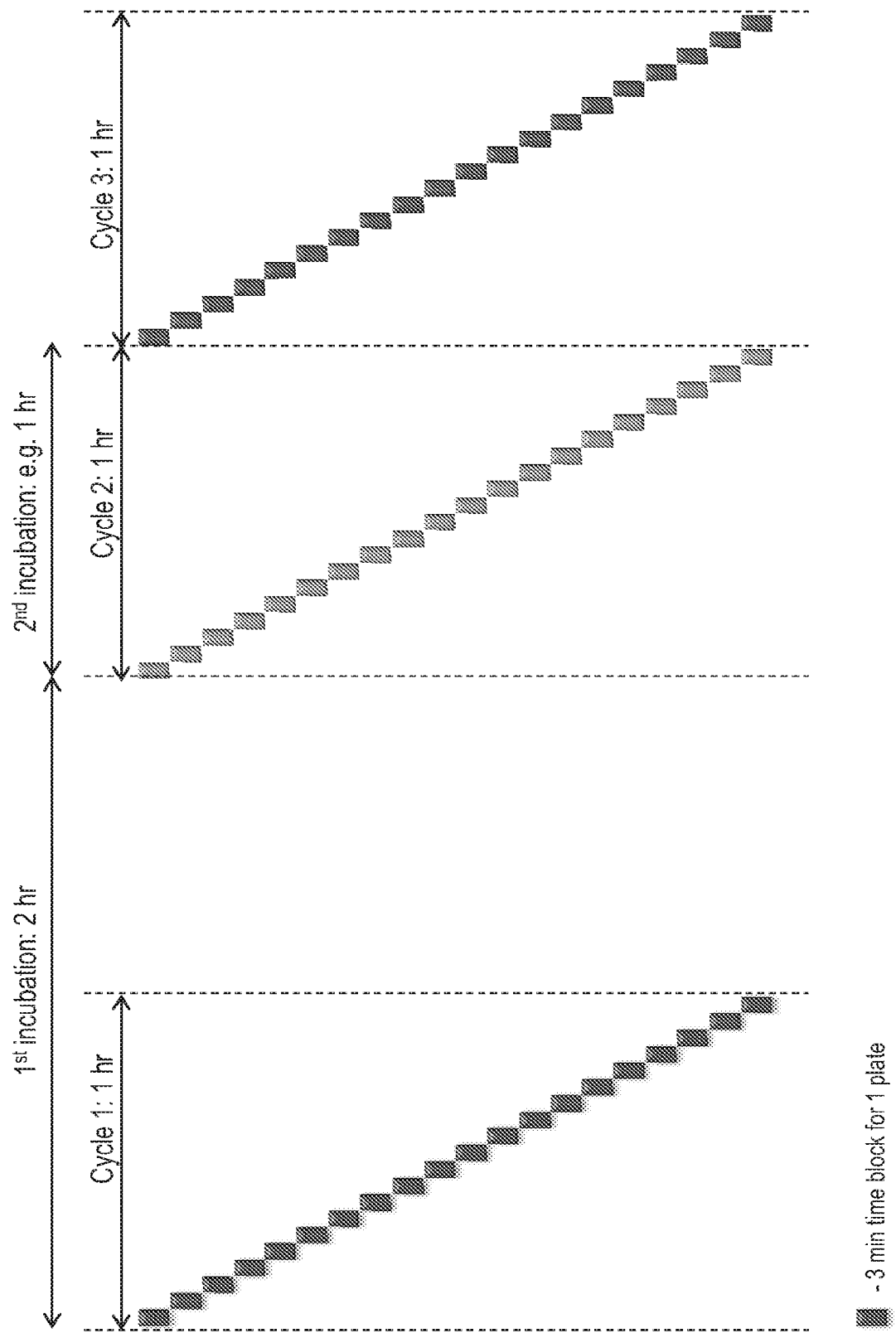
FIG. 9(d) shows the scheduling of operations conducted in the system during the conduct of an assay.

In a specific embodiment, the system processes plates in batch-mode, i.e., all wells of a plate are operated on or processed simultaneously by the system before moving to the next step and/or the next plate. For example, if the system is configured to use 96-well multi-well plates, all 96 wells of a plate are subjected to each processing step in the assay system simultaneously before the system moves to the next step and/or the next plate. FIG. 9(d) shows the sequence of operations of the assay system operating in batch mode. In this example, a first system operation cycle (Cycle 1) includes the following steps: (a) one set of plates is moved into the storage unit of the assay system, the set including a sample plate, a diluent plate, and a test plate; (b) diluent and sample are taken from the diluent and sample plates, respectively, and added to the test plate; and (c) the test plate is moved to the orbital shaking subassembly and the sample and diluent plates are returned to the storage unit. Cycle 1 is completed when the first test plate of the set has completed a first incubation. The second system operation cycle (Cycle 2) includes the steps of (a) moving the test plate to the plate washing subsystem and washing the test plate; (b) moving the test plate and a detection antibody solution plate to the plate preparation platform; (c) adding detection antibody solution to the test plate; and (d) moving the test plate to the orbital shaking subassembly and returning the detection antibody solution plate to the storage unit. Cycle 2 is completed when the first test plate has completed the second incubation. The third system operation cycle (Cycle 3) includes the following steps: (a) move a test plate to the plate washing subsystem and wash the test plate; (b) move the test plate and a read buffer plate to the plate preparation platform; (c) add read buffer to the test plate; (d) move the test plate to the assay reader and return the read buffer plate to the storage unit; (e) read a signal from the assay reader and move the test plate from the assay reader to the storage unit. Throughout Cycles 1-3, the assay system is configured to move a plate from one subsystem to another up to every three minutes (3 min/plate).

In one embodiment, the assay reader integrated with the assay system 900 is an assay reader as described herein, e.g., apparatus 500, illustrated in FIGS. 5-7. In a specific embodiment, the assay reader is the apparatus described and claimed in U.S. application Ser. No. 14/147,216, the disclosure of which is incorporated herein by reference. In a further specific embodiment, the assay reader is a MESO QuickPlex SQ 120, available from Meso Scale Discovery, Rockville, Md. Alternatively, the assay reader is a MESO SECTOR S600, available from Meso Scale Discovery, Rockville, Md.

The assay consumable storage unit (904) can be configured to store any type of consumable used in the conduct of an assay in the assay reader. In a specific embodiment, the storage unit is a multi-well plate storage unit configured to store a plurality of multi-well assay plates. In one embodiment, the plate storage assembly is configured as a shelving subassembly comprising a plurality of shelving units each sized to accommodate a multi-well assay plate. The shelving subassembly comprises a housing including a housing top, housing back, left and right housing walls and a plurality of storage units disposed within the housing, wherein each storage unit includes a plate introduction aperture. The shelving subassembly can comprise an M×N rectilinear array of storage units, wherein M and N are integers, e.g., a 2×1, 2×2, 3×3, or 4×4 array. In one embodiment, the subassembly comprises a 2×1 array of storage units. And in a specific embodiment, the shelving subassembly is a 2×1 array of twenty storage units.

As described above, the pipetting subassembly (alone or in combination with the platform) provides for independent X, Y, and Z motion of a probe so as to allow it to access sample plates, reagent plates, and/or test plates (as required). The pipetting subassembly can also include the appropriate pumps and valves for controlling the pipettors and/or probes (not shown). A pump is used to drive fluids through the pipetting subassembly. One skilled in the art will be able to select appropriate pumps for use in the apparatus including, but not limited to diaphragm pumps, peristaltic pumps, and syringe (or piston) pumps. The pump also includes a multi-port valve to allow the pump to push and pull fluids from different fluidic lines. Alternatively, multiple pumps can be used to independently control fluidics in different fluidic lines.

In one embodiment, the pipetting probe can use fixed or disposable pipetting tips. In a specific embodiment, the pipetting probe uses fixed pipetting tips. Alternatively, if disposable tips are used, disposable pipetting tips can be stored in a pipetting tip storage/disposal compartment (not shown). The arm/track of the pipettor subassembly allows for access of the probe to the tip storage/disposal compartment for tip loading on the pipetting probe and tip removal after use. In addition to transferring reagents and samples from one well to another, the fluidic lines connected to the pipetting probes may also be connected to working fluids or diluents so that the probes can be used to deliver these fluids/diluents to wells. Optionally, the pipetting probes may include fluid sensing capability, e.g., using capacitive sensors to detect when the probes contact fluid in a tube or well. In a specific embodiment, the pipetting probe includes a multi-channel pipetting probe enabling simultaneous fluid transfer to a plurality of wells of a multi-well plate. For example, the pipetting probe includes a 96-channel pipetting head capable of simultaneous fluid transfer to a 96 well plate. In one embodiment, the pipetting head and corresponding fixed pipetting tips are available from Apricot Designs, Covena, Calif. In general, if fixed pipetting tips are used, they are supplied by the supplier of the pipetting probe, e.g., Apricot Designs, Covena, Calif. If disposable pipetting tips are used, the tips can be stored and disposed of in a tip compartment, including a housing for one or more individual drawers that can accommodate a standard disposable tip box (available from Axygen, Qiagen or Rainin) and a removable waste container for used pipetting tips. To remove tips, the pipettor probe is translated horizontally to locate the shaft in the slot and then translated vertically until the pipette tip is pulled off by the bracket. During operation, the specific slot that is used is chosen using a set pattern or a random pattern such that the used pipette tips are distributed evenly along the width of the waste container. The dimensions of the tips vary according to the dimensions of the pipetting probe, the volume of the sample/reagents dispensed and/or the dimensions of the plates within which the tip is placed. In one embodiment, the tip volume ranges from approximately 100 μL, to 550 μL. In another embodiment, the tip volume ranges from about 100 μL, to 250 μL.

The plate washing subassembly can be any suitable commercial microtitre plate washing system, e.g., a plate washing subassembly available from BioTek Instruments, Inc., Winooski, Vt., including but not limited to the 405 Touch Washer, 405 LS Washer, Elc405× Select Deep Well Washer, or the Elx50 Washer. Likewise, the robotic subsystem can be any suitable tabletop commercial robotic system, e.g., systems available from Precise Automation, Inc., Fremont, Calif.

The liquid reagent subassembly includes a plurality of liquid reagent and waste compartments and for use in one or more steps of an assay conducted in the apparatus. A reagent/waste compartment comprises a compartment body that encloses an internal volume and a reagent or waste port for delivering reagent or receiving waste. The volume of the compartments in the subassembly are adjustable such that the relative proportion of the volume of the compartment body occupied by reagent and waste can be adjusted, e.g., as reagent is consumed in assays and returned to a compartment as waste. The total internal volume of the compartment body may be less than about 2, less than about 1.75, less than about 1.5, or less than about 1.25 times the volume of liquid stored in the body, e.g., the volume of reagent originally provided in the compartment, thus minimizing the space required for waste and reagent storage, and allowing for convenient one-step reagent replenishment and waste removal. In certain embodiments, the apparatus has a reagent compartment slot configured to receive the compartment, and provide fluidic connection to the waste and reagent ports, optionally via "push-to-connect" or "quick connect" fittings.

Optionally, the reagent and/or waste compartments are removable. In one embodiment, the reagent and/or waste compartments are removable and the apparatus further includes a sensor, e.g., an optical sensor, to monitor the fluid level(s) in the reagent and/or waste compartments. Alternatively, the liquid reagent subassembly may include electronic scales to monitor the weight of fluid in the reagent and waste reservoirs for real-time tracking of reagent use and availability. Once the reagent and/or waste compartments reach a certain minimal or maximal capacity, as detected by the sensor or scale, the apparatus alerts the user to remove the reagent or waste compartment to replenish and/or empty the contents. In one embodiment, the motor of the pipetting probe is in communication with the sensor or scale and when the reagent and/or waste compartments reach the minimal or maximal capacity, the pipetting probe motor is disabled by the apparatus, e.g., the probe sensor relays information regarding the capacity of the compartment to the instrument software, which then halts further pipetting action.

The reagent and waste compartments may be provided as collapsible bags located in the subassembly body. One of the reagent and waste compartments may be provided as a collapsible bag and the other may be provided as the compartment body itself (i.e., the volume in the compartment body excluding the volume defined by any collapsible bags in the compartment body). In addition to the first reagent and waste compartments, the reagent cartridge may further comprise one or more additional collapsible reagent and/or waste compartments connected to one or more additional reagent and/or waste ports. Alternatively, one or the other of the reagent and waste compartments may be constructed from blow-molded plastic. Additionally or alternatively, waste can be pumped to an external drain or container. In one embodiment, the liquid reagent subassembly also includes a reagent reservoir that is used during the conduct of an assay in the apparatus. In one specific embodiment, each reagent compartment is connected via a fluidic line to a reagent reservoir that houses a volume of reagent used during the assay. Fluidic lines to the pipettor subassembly lead directly from the reagent reservoir. In practice, reagent is stored in a reagent compartment and a predetermined volume of reagent is dispensed from the reagent compartment to the reagent reservoir. The apparatus draws fluids for use in an assay from the reagent reservoir. The reagent compartment and reagent reservoir can be each connected to an independent fluid sensor. The fluid sensor in the reservoir monitors the internal volume within the reservoir and if the internal volume decreases below a predetermined level, reagent is dispensed from the reagent compartment to the reservoir. Likewise, if the internal volume of the reagent compartment decreases below a predetermined level, the fluid sensor signals to the operator to replace or refill the reagent container. The dual reagent compartment/reservoir assembly enables the apparatus to continually supply fluid to an assay as the assay is conducted by the apparatus as fluid is replaced in the reagent compartment without interrupting the assay processing by the instrument.

In one embodiment, the orbital shaking subassembly (910) is a counterbalanced assay consumable shaking apparatus as described and claimed in U.S. Ser. No. 62/143,557, filed Apr. 6, 2015, the disclosure of which is hereby incorporated herein by reference in its entirety. In particular, the orbital shaking apparatus comprises (a) an orbital shaker assembly comprising a horizontal orbiting platform, and (b) an assay consumable storage assembly positioned on the platform. The storage assembly comprises (i) a shelving subassembly comprising a plurality of sets of vertically aligned storage units, within each storage unit is sized to accommodate a consumable and comprises a consumable latching mechanism; and (ii) a counterweight positioned within the storage assembly at a height corresponding to the center of mass of the storage assembly and the orbiting platform. The orbital shaking apparatus further comprises a rotating axle extending from the shaker assembly to the storage assembly in a vertical direction and the counterweight is operatively connected to the rotating axle.

The assay system illustrated in FIG. 9 can include a table or platform, e.g., 901, or the system can be built and configured on a laboratory benchtop. In the system depicted in FIG. 9(a), the assay system is positioned on a table including one or more shelving units (916 and 917, respectively) positioned below the table top (901) and configured to house one or more elements or subsystems of the assay system. In an embodiment of the system positioned on a laboratory benchtop, the various subsystems can be distributed across the benchtop in the same X-Y plane (not shown).

The assay system (900) illustrated in FIGS. 9(a)-9(d), including orbital shaker (910), is described in U.S. provisional patent application Ser. No. 62/311,752 filed on Mar. 22, 2016 and in international patent application serial No. PCT/US 2016/026242 filed on Apr. 6, 2016, which are incorporated herein in their entireties.

A further embodiment of an assay system of the invention is shown in FIG. 10 and its subparts. The assay system (1000) includes a plurality of subsystems positioned on a table (1001), wherein each subsystem is operatively connected to a robotic subsystem (1002) configured to access and move one or more consumables, e.g., multi-well assay plates, from one subsystem of the assay system to another. The robotic subsystem of the instrument depicted in FIG. 10 and its subparts includes one or more pipetting subsystem (1021), each including one or more pipetting tip head(s), e.g., a multi-channel pipetting tip head, which is used to dispense/draw fluids to/from wells of a multi-well plate. The pipetting subsystem is affixed to a gantry (1022) within the robotic system that enables the pipetting tip head to move throughout the assay system in the X, Y, and Z direction. The plurality of subsystems within the assay system includes an assay reader (1003); an assay consumable storage unit (1004); a plate washing subassembly (1005)); a plate shaking subassembly (1006) comprising one or more independent plate shaking apparatuses (e.g., as described above in reference to FIG. 9, element 910 except that shaker 910 has its own assay consumable storage unit and can shake and incubate a number of plates at the same time); a liquid reagent subassembly (1007); a solid waste storage unit (1008) and a liquid waste storage unit (1020); and an electronic enclosure (1009) configured to house a system control computer, keyboard, display, wireless router, and a power supply (not shown). Electronic components are designated as elements (1010, 1011), which is shown in FIG. 10(a) to be under reader (1003) can also be positioned in electronic enclosure (1009). The assay system can also include a platform (1012) positioned on a table (1001) and configured to enable pipetting of liquids to and/or from one or more wells of a multi-well assay plate positioned on the preparation platform. The robotic subsystem is configured to move one or more plates to and/or from the platform, the plate washing subassembly, the shaking subasssembly, the assay reader, and the consumable storage unit. The platform comprises a consumable identifier controller (e.g., a bar code reader (1013)) configured to read assay consumable identifiers, e.g., positioned on a multi-well plate, e.g., positioned on the bottom of a plate or tubes placed in a reagent rack or tube holder; a pipetting tip storage compartment (1014) configured to house pipetting tip boxes of varying size tips, as needed (e.g., 1015 and 1016, 1000 µl and 350 µl tips, respectively); one or more sample/reagent tube carriers (1017) and one or more reagent troughs positioned in one or more corresponding carriers (1018). Optionally, the system includes a second consumable identifier controller (1023) positioned above the platform and configured to read an identifier on the side of a plate(s) and/or reagent rack; and a third consumable identifier controller (not shown) configured to read an identifier on a consumable box located outside of the system housing (not shown). In one embodiment, the third consumable identifier controller is remote from the assay system, affixed to the outer housing of the assay system, or positioned on a front or side panel of the housing of the assay system and configured to enable the user to contact a consumable identifier, e.g., on a plate or kit, with the third consumable identifier controller before the consumable is used in the system. The assay system can further include one or more environmental control units, e.g., thermoelectric cooling units or TECs (1019), disposed within the assay system. Although TECs are illustrated with assay system (1000), any environmental control systems, heat exchangers or cooling devices can be used.

Unlike the assay system depicted in FIG. 9(*a*), the instrument shown in FIG. 10 and its subparts is configured to conduct all sample processing steps on-board as well as all assay processing steps required in the conduct of an assay. In addition, the user-interface of the assay system of FIG. 10 and its subparts is configured to display to the user stepwise instructions for appropriate sample/reagent preparation steps that should be performed manually before the system conducts the assay. The sample/reagent preparation steps and individual assay steps performed by one or more subsystems of the assay system may differ from one assay protocol to another. Detailed examples of various assays performed by an assay system of FIG. 10 and its subparts are described hereinbelow, including but not limited to, the conduct of a cytokine, V-PLEX, U-PLEX, S-PLEX, pharmacokinetic (PK), immunogenicity (IG) assays and custom sandwich immunoassays (available from Meso Scale Discovery, Rockville, Md.), as well as optimization of PK, IG and custom sandwich immunoassays.

Another iteration of the inventive assay system (1000) is illustrated in FIG. 10(*c*). Some of the components shown in FIGS. 10(*a*)-(*b*) are omitted for clarity. This iteration contains one or more catching trays (1024) positioned below platform (1012) and above table (1001) to catch and hold liquid spilled from the various reagents, diluents, buffers during the operations of assay system (1000). Catching trays (1024) preferably have flow channels (1025) defined thereon to direct the flow of spilled liquid from trays (1024) toward waste storage unit (1008). Preferably, the flow channels include a perimeter channel (1025*b*) to lead liquid away from the edges of trays (1024) and internal flow channels (1025*a*) leading to waste assembly (1008). Optionally, flow channels (1025) have absorbent materials disposed therein to absorb spilled liquids and/or wick the liquids towards waste assembly (1020), as best illustrated in FIG. 10(*d*). Alternatively, flow channels (1025) may be coated with a surfactant to reduce flow resistance.

Additionally, platform (1012) also contains additional raised podiums (1026), which are designed to hold extra disposable tips or to host additional components such as individual shakers (1006) thereby illustrating the expandable nature of assay system (1000). A plurality of holes (1027) is provided on platform (1012) to receive additional labwares or other functional components.

In one embodiment, the assay reader used in assay system 1000 is an assay reader as described herein, e.g., apparatus 500, illustrated in FIGS. 5-7. In a specific embodiment, the assay reader is the apparatus described and claimed in U.S. application Ser. No. 14/147,216, the disclosure of which is incorporated herein by reference. In a further specific embodiment, the assay reader is a MESO QuickPlex SQ 120, available from Meso Scale Discovery, Rockville, Md. Alternatively, the assay reader is a MESO SECTOR 5600, available from Meso Scale Discovery, Rockville, Md.

The assay consumable storage unit (1004) can be configured to store any type of consumable used in the conduct of an assay in the assay reader. In a specific embodiment, the storage unit is a multi-well plate storage unit configured to store a plurality of multi-well assay plates. In one embodiment, the plate storage assembly is configured as a shelving subassembly comprising a plurality of shelving units each sized to accommodate a multi-well assay plate. The shelving subassembly comprises a housing including a housing top, housing back, housing left and right housing walls and a plurality of storage units disposed within the housing, wherein each storage unit includes a plate introduction aperture. The shelving subassembly can comprise an M×N rectilinear array of storage units, wherein M and N are integers, e.g., a 2×1, 2×2, 3×3, 4×4, 5×6 or 6×5 array. In one embodiment, the subassembly comprises a 2×1 array of storage units. In a specific embodiment the storage subassembly comprises a 2×1 array of twenty storage units.

In the iteration of FIG. 10(*c*), assay consumable storage unit (1004) is redesigned to have both ornamental as well as functional aspects. In this iteration, the assay consumable storage unit is a single integral unit with a number of parallel shelfing surfaces (1072) connected by a number of vertical supports (1074), as shown in FIG. 10(*r*). Each storage unit on the top row comprises raised corners (1076), which are sized and dimensioned to retain the lids of reagent or kitted racks, illustrated in FIG. 18 and its subparts below, when a technician or robotic system (1002) places an assay plate or rack thereon. As shown in FIG. 10(*c*), preferably the bottom horizontal shelf of assay consumable storage unit is securely bolted by itself in a cantilever manner to platform (1012). The upper assembly of the assay consumable storage unit is secured to the bottom horizontal shelf using a plurality, preferably two or more, alignment pins are used to maintain consistent positioning of the upper assembly. Preferably, the alignment pins are located off of the X and/or Y center lines to minimize the incorrect alignment of the bottom horizontal shelf and the upper assembly. A number of thumb screws, preferably three or more, are used to secure the assay consumable storage unit together. Additionally, a number of Z-direction adjusting screws, preferably at least three, are provided to level the assay consumable storage unit (1004), if necessary.

An advantage of having the bottom horizontal shelf installed separately from the upper assembly is the ease of removing the assay consumable storage unit (1004) for service and access to the components behind the unit (1004). The alignment pins and the thumb screws further allow for the ease and accurate reattachment of the upper assembly to the bottom horizontal shelf thereafter.

The pipetting subassembly (1021) is supported on gantry (1022) and powered by one or more motors to provide independent X, Y, and Z motions to a probe, such as one or more pipette tips, so as to allow it to access troughs, tubes and/or plates (as required). The pipetting subassembly (1021) also includes the appropriate pumps and valves for controlling the pipettors and/or probes, and optionally, a pipetting tip washing subassembly (not shown). A pump is used to drive fluids through the pipetting subassembly. Preferably, each pipette tip is independently controllable or independently dispensable by the controlling software, controller and motor(s). In other words, one or more pipette tips can dispense or take up liquids independently of the other pipette tips. Additionally, the spacing between adjacent pipette tips can be varied by the controlling software and motors. These degrees of freedom allow the assay machine (1000) to perform a wide range of assays, calibrations, self-diagnostics, etc. One skilled in the art will be able to select appropriate pumps for use in the apparatus including, but not limited to diaphragm pumps, peristaltic pumps, and syringe (or piston) pumps. The pump also includes a multi-port valve to allow the pump to push and pull fluids from different fluidic lines. Alternatively, multiple pumps can be used to independently control fluidics in different fluidic lines. In one specific embodiment, the pipetting subassembly comprises air displacement pipettors. Optionally, the pipetting probes may include fluid sensing capability, e.g., using ultrasonic capacitive or pressure sensors to detect when the probes contact fluid in a tube or well as a means of minimizing the external wetted surface of the probe and detection of the presence of liquid in the container.

In a specific embodiment, the pipetting probe includes a multi-channel pipetting probe enabling fluid transfer to a plurality of wells of a multi-well plate either through all the pipette tips or through a selected number of pipette tips less than all the available pipette tips. For example, the pipetting probe includes an 8-channel pipetting head capable of simultaneous and independent fluid transfer to one or more channels into a multi-well plate or one or more tubes or troughs. Alternatively, the pipetting probe can include a 12-, 96- or 384-channel pipetting head. In a specific embodiment, the pipetting subassembly is supplied by Tecan Group LTD, Switzerland.

In one exemplary example, a capacitance sensor is designed between the pipette tips or pipettor and the pipetting deck to detect contact of the disposable tip with the surface of the liquid contained within a tube, plate or rack found on a pipetting deck. The pipetting deck is preferably conductive and the pipette tips/pipettor is also conductive so that a voltage potential can be applied therebetween.

A common capacitor is a parallel-plate capacitor, which consists of two conductive plates electrically insulated from each other by a dielectric material. In simple, parallel-plate capacitors, the capacitance is inversely proportional to the distance between the two plates. Quantitatively, the capacitance (C) in farads of two overlapping plates is expressed as:

$C = \kappa \varepsilon_o (A/d)$, where $\kappa_i$ the dielectric constant of the substance between the two plates (nondimensional)

$\varepsilon_o$ is the electric constant, which is about $8.854 \times 10^{-12}$ F·m$^{-1}$, A is the overlapping area between the two plates in meters, and d is the distance between the two plates in meters.

For capacitive liquid level sensing, the capacitance of the system takes into account multiple dielectrics that are found in series between the pipette tips and the pipetting deck. Quantitatively, the total capacitance (C) in farads of two overlapping plates that have multiple dielectrics between them (e.g., air, liquid, plastic/glass container) is expressed as:

$1/C = \Sigma 1/C_i$ where the capacitance of each dielectric is accounted for individually as $C = \kappa_i \varepsilon_o (A/d_i)$, and where $\kappa_i$ is the dielectric constant of a given substance between the two plates (nondimensional)

$\varepsilon_o$ is the electric constant, which is about $8.854 \times 10^{-12}$ F·m$^{-1}$, A is the overlapping area between the two plates in meters, and $d_i$ is thickness of a given substance between the two plates in meters.

In a system with multiple dielectrics, the capacitance change that occurs when a single dielectric's thickness (e.g., the air between the pipette tip and the liquid in a plate or rack) approaches zero yields a significant change in capacitance, allowing for the system to recognize that the pipette tip is touching the liquid.

The present inventors have determined that the sensitivity of a particular capacitive sensing system used to detect liquid in conventional tubes and vials can be significantly increased by the use of a conductive plate or rack, made from a plastic with a conductive additive, such as carbon, metal, or metal ions. Using the conductive rack, the liquid levels held in conventional tubes and vials contained in said rack can be determined using the capacitive sensor. Preferably, 500 µl tubes should be filled by at least 50%, preferably at least 40% or 30% and more preferably at least 10%. 2 ml tubes should be filled by at least 20%, preferably at least 15% or 10% and more preferably at least 5%. 4 mL vials with flat bottoms should be filled by at least 25%, more preferably at least 12.5%. 4 mL vials with concave bottoms should be filled by at least 10%, more preferably at least 5%.

In one embodiment, the pipetting probe uses disposable pipetting tips that are stored in a pipetting tip storage compartment (1014, 1026). Disposable pipetting tips can be stored in one or more standard disposable tip box (e.g., 1015 and 1016, available from Tecan Group LTD, Switzerland) and used tips can be stored in a removable waste container (1008) for used pipetting tips. The dimensions of the tips vary according to the dimensions of the pipetting probe, the volume of the sample/reagents dispensed and/or the dimensions of the plates within which the tip is placed. In one embodiment, the tip volume ranges from approximately 1000 µL, to 50 µL. In another embodiment, the tip volume ranges from about 1000 µL, to 350 µL.

As stated above, the pipetting subassembly (1021) provides independent X, Y, and Z motions for a probe or pipette tips so as to allow them to access troughs, tubes, vials, racks and/or plates. The present inventors have invented a training plate designed to initialize the assay system (1000) before first use or periodically thereafter, so that the X, Y and Z positions of the pipetting subassembly (1021) and its pipette tips, as well as the X, Y, Z, G (grip distance) and R (rotational) the robotic system (1002) and its gripper pads (1031) can be pin point with higher accuracy and repeatability.

As best illustrated in FIG. 10(*e*), a training or teaching plate (1035) is positioned on platform (1012). Preferably, training plate (1035) has a similar dimensions and size as an industry standard assay plate (ANSI SLAS 1-2004), and is designed to fit into a slot (1036), also known as a plate carrier (1036), that is designed to receive the assay plate. Training plate (1035) can be a solid rectangular prism or preferably is hollow with a rigid perimeter and internal web members designed to provide stiffness and rigidity. Internal web members including curved members (1037) and substantially linear elements (1038) are provided for rigidity and stability. As shown, the curved members (1037) have opposite concavity.

One or more reference points or pads (1040) are defined on a top surface of training plate (1035). During the initialization procedure for assay system (1000), a probe, such as a pipette tip (1042) connected to the robotic system (1002) or preferably to the pipette subsystem or pipettor (1021), is brought into close proximity with a reference pad (1040), or preferably within 0.1 mm of reference pad (1040) to determine a vertical or Z-reference point. Preferably, probe (1042) does not contact reference pad (1040) to ensure that the probe is not deformed or bent by the contact. The capacitance sensor for the pipette subsystem (1021) described above can be used in this initialization process with an electrically conductive training plate (1035) to determine the Z-reference point and the Z-maximum values for the labwares without having probe (1042) touching reference pad (1040).

Alternatively, the initialization process can be completed with a substrate thinner than about 0.1 mm being moved back-and-forth between probe (1042) and reference pads (1040). When the moving substrate is caught between the probe and the reference pad, the Z-reference point is determined. In a further alternative, a proximity sensor based on a magnetic field that varies a function of a distance between probe (1042) and reference pad (1040) can be used. An exemplary magnetic proximity sensor includes the Hall-effect sensor.

In yet another alternative, an optical distance sensor is used. Suitable optical distance sensors are commercially available from Keyence America, Sens® Part, Omega Engineering, among others. The optical sensor is attached to or replaces probe (1042), and is then used to measure the distance to reference pad(s) (1040).

This Z-reference point is selected to be in the middle of a corner well on an X-Y plane in an industry standard ANSI SLAS 1-2004 96-well microplate (8 rows×12 columns) and in the vertical Z-direction at or near a top surface of the an industry standard ANSI SLAS 1-2004 plate. The dimensions and tolerances of an industry standard ANSI SLAS 1-2004 are discussed below. More specifically, the Z-reference point is used to calculate the Z-maximum values or the highest height in the vertical direction for all the labwares. Advantageously, having accurate Z-maximum values for the labwares improves the reliability of the pipetting and placement and movement of the labwares.

The training plate (1035) may be reversible, i.e., the bottom surface has the same features as the top side. In yet another variation, the X-reference and Y-reference points are also determined in addition to the Z-reference point(s). In this variation, probe (1042) is brought into contact with at least two reference pads (1040) and a Cartesian coordinate (x,y,z) is recorded for each reference pad.

Training plate (1035) can also be used to initialize the positions of the gripper pads (1031) or to align the gripper pads to the assay plate(s) on platform (1012). Accurate and consistent alignment are preferred to achieve the proper get (retrieve) and put (insert) coordinates for the assay plates or any other plates, racks, troughs, tubes, etc. Gripping areas (1044) are provided on the long sides and the short sides of training plate (1035) as best shown in FIG. 10(*f*). During initialization or alignments, with training plate (1035) positioned on platform (1012) robotic system (1002) positions its gripper pads (1031) on either the short sides or the long sides of training plate (1035). Gripper pads (1031) would be positioned within the gripping areas (1044), which are the areas defined by a number of raised lines, in order to pick up and move training plate (1035). As the gripper pads (1031) do so, relative distance between the pads (Grip Distance), the location of the training plate in X, Y space, the orientation (in degrees) of the gripper pads (Rotational coordinate), as well as the Z-elevation are also known and recorded by the processor that controls the robotic system (1002) This alignment information is stored and is used to direct the robotic gripper pads (1031) to get or put the labwares in the proper places.

As shown in FIG. 10(*f*), the outer perimeter of a first surface (1043) containing the reference pads (1040) of training plate (1035) is smaller than the outer perimeter of the opposite surface (1045), which has a bead line (1041) surrounding the perimeter to provide the larger outer perimeter. When determining the Z-reference points, preferably opposite surface (1045) with the larger diameter and tighter tolerance is inserted into a nest on platform (1012). This allows for a snug fit and more accurate and repeatable positioning of reference pads (1040). When determining the positions of gripper pads (1031) of robot arm (1002), preferably first surface (1043) with the smaller perimeter is inserted into the nest on platform (1012). This allows gripper pads (1031) to lift training plate (1035) without having to over any frictional force caused by the contacts between the training plate and the nest.

The training plates (1035) can be individually machined, preferably by a computer numerical control (CNC) milling machine, to achieve tight tolerances. The training plates can be machined to a flatness of within 5 thousandth of one inch or 0.127 mm. In the event that there are dimensional differences between different manufactured training plates, their differences or variations are ascertained, e.g., by measuring the dimensions of the training plates on a calibrated Coordinate Measuring Machine (CMM) and using the measured dimensions to adjust the training values of the platform/assay machine (1000). The tolerances can be stored in any memory device and used to reconcile possible differences in measurements when different training plates are used to initialize and re-calibrate one assay machine.

Preferably, training plates (1035) is made from cast aluminum for its rigidity, strength and light weight. A preferred cast aluminum is ATP 5 (Aluminum Tooling Plate 5) or similar metals. For example, a suitable metal should have density in the range of about 2,400 to about 3,000 kg/m$^3$, a hardness in the range of about 60 to about 80 HB, a tensile strength in the range of about 250 to about 300 MPa and a yield strength in the range of about 100 to about 150 MPa. Other suitable materials include but are not limited to stainless steel, brass, titanium and hard polymers such as polycarbonate and polystyrene.

A reference pad (1040) preferably has a diameter about 1.46 mm±10% and the distance from the center of the reference pad (1040) to a side of the training plate (1035) is about 7 mm±10%. As shown in FIG. 10(*e*), the four reference pads (1040) correspond to the center of the four corner wells in a 96-well microplate, discussed above. Preferably, training plate (1035) is anodized and more preferably gold anodized. Each training plate (1035) has a part number and a revision number affixed and preferably edged thereon, and a serial number affixed thereon.

In one embodiment, the training plate may have a barcode with its serial number affixed to it to allow automated access to stored dimensional information for the training plate.

The plate washing subassembly can be any suitable commercial microtitre plate washing system, e.g., a plate washing subassembly available from BioTek Instruments, Inc., Winooski, Vt., including but not limited to the 405 Touch Washer, 405 LS Washer, Elc405x Select Deep Well Washer, or the Elx50 Washer. Likewise, the robotic subsystem can be any suitable tabletop commercial robotic system, e.g., systems available from Tecan Group LTD, Switzerland.

In a specific embodiment, the plate shaking subassembly comprises a counterbalanced assay consumable shaking apparatus as described and claimed in U.S. Ser. No. 62/143,557, filed Apr. 6, 2015, the disclosure of which is hereby incorporated herein by reference in its entirety, and described herein in reference to FIG. 9(*a*). In particular, the shaking subassembly can include a 2×3, 2×4, or 2×6 array of twenty storage units. Preferably, plate shakers (1006) are individual thermo-shakers that have heaters to maintain the assay plates disposed thereon at an elevated temperature. Such thermo-shakers are commercially available as Bio-Shake 3000-T elm shakers from Q. Instruments from Jena, Germany. In one example, plate shakers (1006) can maintain a temperature that is about 3° C. higher than the operating temperature of the assay system and up to about 37° C. with a tolerance of about ±0.5° C. Samples, buffers, reagents, etc. contained in the wells of assay plates can be mixed and incubated on these shakers.

The present inventors have also discovered that during assay runs the reagents contained in troughs (1018) and during the incubation and mixing period the sample/reagent mixture in the assay plates on plate shakers (1006) experience evaporation. Evaporation of reagents in troughs (1018) represents a loss while evaporation from the assay plates on plate shakers (1006) may cause a change in concentration of the materials contained in the assay plates due to evaporation. In accordance to one aspect of the present invention, lids are designed for these vessels.

As illustrated in FIG. 10(*g*), exemplary trough lids (1028) are illustrated. Lids (1028) are shaped and dimensioned to fit firmly over reagent troughs (1018). Lids (1028) have a top (1029) and side walls sized and dimensioned to fit over the top of trough (1018) with a pattern of cuts (1030) created for example by a laser cutter on top (1029). Cuts (1030) are designed to allow top (1029) to flex and to allow pipette subassembly or pipettor (1021) to insert pipette tips into reagent troughs (1018) to retrieve the reagent, as shown. When the pipette tips are withdrawn, cuts (1030) allow the top to return to its original configuration. Any pattern of cuts (1030) can be used so long as the top (1029) flexes to allow the pipette tips to enter and substantially resumes its original configuration when the pipette tips are withdrawn. Exemplary patterns of cuts (1030) are shown in FIG. 10(*h*); however, the present invention is not limited to any particular cut pattern.

Lids (1028) limit the exposure of the reagents contained in troughs (1018) to the internal space in the assay system (1000) only to the combined area of the cuts. Generally, open troughs may contain buffer such as tripropylamine (TPA), which can evaporate resulting in losses. Limiting the exposure limits the evaporation. To further limit the exposure, a second top (1029') with another cut pattern for example in the opposite orientation can be placed on the top or bottom of top (1029) to create a tortuous path for the evaporated gas to escape. Lids (1028) can be made from relatively rigid material or non-elastomeric material, such as polyester, high density polyethylene (HDPE) or polycarbonate, and flexibility of top (1029) is provided by the cut patterns (1030). Alternatively, lids (1028) can be made from an elastomeric material such as natural or synthetic rubber to improve flexibility and optionally the cuts are made with sharp cutting implements instead of laser cutters to minimize the lost material and the combined area of the cuts. Preferably, lids (1028) are thermoformed or vacuum formed and cuts (1030) are die cut. Thermoforming is a process of heating a plastic sheet and forming its shape with air pressure on a mold and vacuum forming is a similar process but vacuum is used instead of air pressure.

To minimize the possibility of troughs (1018) being pullout of the trough carriers, shown without reference number in FIG. 10(*a*), an elastomeric block can be inserted between troughs. Such elastomeric blocks has a main body with a protrusion on each side that faces an adjacent trough. Each block then would have two protrusions, and preferably the protrusion has different size and/or volume depending on the amount of gripping desired. For example, the protrusion facing an end trough should have a larger volume than the protrusion facing a center trough.

Plate lids (1032), as illustrated in FIG. 10(*i*), has no cut pattern since plate lids (1032) are placed on assay plate (1031) after the processing steps are completed and the assay plates (1031) are incubated and mixed on shakers (1006). As discussed above, shakers (1006) may be heated to the proper incubation temperature. Elevated temperatures promote evaporation particularly when exposed to ambient conditions inside assay system (1000). Lids (1032) preferably comprise a plurality of downward facing dimples (1034). Evaporated vapor from the sample/reagent mixture in the wells (1051) within the assay plate (1033) preferably condenses at dimples (1034) and the condensate would drop back into the wells (1051). Preferably, one dimple (1034) is positioned above each well (1051) in the assay plate (1033). For example, for a 96-well assay plate, 96 downward facing dimples are provided on lid (1032).

As best shown in FIGS. 10(*j*)-(*k*), lid (1032) comprises a skirt (1050) dependent on a top surface. When placed on top of a multi-well assay plate (1033), the outer perimeter of the top surface rests on the outer perimeter of assay plate (1033) creating a contact line at (1052). The contact line (1052) provides a flow restriction or a seal to restrict or keep evaporated gas from leaving the enclosure between assay plate (1033) and lid (1032). Preferably, lid (1032) has no structural rib on its bottom surface to interfere with the contacts at contact line (1052).

Additionally, in the embodiment of lid (1032) shown in FIGS. 10(*i*)-(*k*), secondary contact lines (1053) between the bottom surface of lid (1032) and the top surface of each well (1051). These secondary contact lines (1053) present another obstacle discouraging the evaporated vapor from escaping. The effectiveness of secondary contact lines (1053) for each well (1051) depends on the flatness of lid (1032) and the flatness of the top surface of assay plate (1033). Dimples (1034) along with skirt (1050) also help prevent lid (1032) from sliding off assay plate (1051) during the shaking and incubating period on shaker (1006). Additionally, dimples (1034) also act as the condensation enhancers to promote condensation of the evaporation back into the wells (1051).

The plate lid is preferably made of polystyrene, polypropylene or cyclic olefin copolymer (COC) or any other material commonly used in biological studies.

To further minimize inconsistent evaporation and condensation, lid (1032) is preferably made from a hydrophobic polymer or other hydrophobic materials and/or the bottom of lid (1032) is coated with a hydrophobic coating or rendered hydrophobic.

The bottom surface of lid (1032) can be made hydrophobic by microetching the surface to create micro-sized air pockets. These micro-sized pockets can create a rough micro-topography, which acts as a buffer of air that prevents liquids from sticking to the surface. This is also known as the "lotus effect" after the hydrophobic nature of the lotus leaves. This effect was also observed on the skin of geckos. The rough micro-topography does not allow for water to aggregate together preventing wide distribution. Aggregated water would form larger droplets and fall away from the lid thereby promoting condensation. Microetching can be accomplished by a laser source known as TresClean (http://cordis.europa.eu/project/rcn/200832_en.html). Hydrophobic surfaces also have anti-microbial properties due to its ability to repel moisture.

Suitable hydrophobic polymers include, but are not limited to, poly(tetrafluorethene), polypropylene, polyamides, polyvinylidene, polyethylene, polysiloxanes, polyvinylidene fluoride, polyglactin, lyophilized dura matter, silicone, rubber, and/or mixtures thereof.

Suitable hydrophobic coatings may also include, but are not limited to, polyethylene, paraffin, oils, jellies, pastes, greases, waxes, polydimethylsiloxane, poly(tetrafluorethene), polyvinylidene fluoride, tetrafluoroethylene-perfluoroalkyl vinyl-ether copolymer, fluorinated ethylene propylene, poly(perfluorooctylethylene acrylate), polyphosphazene, polysiloxanes, silica, carbon black, alumina, titania, hydrated silanes, silicone, and/or mixtures thereof. Suitable hydrophobic coatings may also include surfactants, such as perfluorooctanoate, perfluorooctanesulfonate, ammonium lauryl sulfate, sodium laureth sulfate, alkyl benzene sulfonate, a sulfated or sulfonated fatty material, salts of sulfated alkyl aryloxypolyalkoxy alcohol, alkylbenzene sulfonates, sodium dodecyl benzenesulfonate, fluorosurfactants, sodium lauryl sulfate, sulfosuccinate blend, sodium dioctyl sulfosuccinate, sodium sulfosuccinate, sodium 2-ethylhexyl sulfate, ethoxylated acetylenic alcohols, high ethylene oxide octyl phenols, high ethylene oxide nonyl phenols, high ethylene oxide linear and secondary alcohols, ethoxylated amines of any ethylene oxide length, ethoxylated sorbitan ester, random EO/PO polymer on butyl alcohol, water soluble block EO/PO copolymers, sodium lauryl ether sulfate, and/or mixtures thereof.

In a variation, materials the outer perimeter of the top of plate (1033) rests on the outer perimeter of assay plate (1051) that form contact line (1052) can be roughened, e.g., by a wire brush or similar instruments to increase the tortuous path for gases and vapors thereby minimizing the amount of vapor escaping. The bottom surface of lid (1032) can be roughened to increase its hydrophobicity, discussed above, to exhibit Cassie-Baxter behavior. It is known that microstructuring a surface amplifies the natural tendency of a surface, and in certain instances if the roughened surface can entrap vapor (such as air or other gases) the hydrophobicity of the surface may be further enhanced (Cassie-Baxter equation). It is also contemplated that the bottom surface of lid (1032) can be microstructured using methods known in the art including, but not limited to, creating patterns or textures on surfaces using micromachining, lithography (photolithographic, soft lithographic (nano imprint lithography, capillary force lithography, micromolding in capillaries, microtransfer molding), e-beam lithography), and plasma etching; as well as chemical bath deposition, chemical vapor deposition, electrochemical deposition, layer-by-layer deposition via electrostatic assembly, colloidal assembly, sol-gel methods, nanosphere lithography, water droplet condensation induced pattern formation, and/or microabrasion. Hydrophobic materials, coatings and surface treatments are disclosed in published international patent application WO 2012/003111, which is incorporated herein by reference in its entirety.

Optionally, a gasket can be placed proximate to contact line (1052), preferably on the outer perimeter of lid (1032) adjacent to skirt (1050). One or more stacking features (1057) can be positioned on the top of the lid (1032) around its perimeter, so that multiple lids (1032) can be stacked on top of each other without sliding off.

The liquid reagent subassembly (1007) includes a plurality of liquid reagent and waste compartments and for use in one or more steps of an assay conducted in the apparatus. A reagent/waste compartment comprises a compartment body that encloses an internal volume and a reagent or waste port for delivering reagent or receiving waste. The volumes of the compartments in the subassembly can adjustable such that the relative proportions of the volumes of the compartment body occupied by reagent and waste can be adjusted, e.g., as reagent is consumed in assays and returned to a compartment as waste. The total internal volume of the compartment body may be less than about 2, less than about 1.75, less than about 1.5, or less than about 1.25 times the volume of liquid stored in the body, e.g., the volume of reagent originally provided in the compartment, thus minimizing the space required for waste and reagent storage, and allowing for convenient one-step reagent replenishment and waste removal. In certain embodiments, the apparatus has a reagent compartment slot configured to receive the compartment, and provide fluidic connection to the waste and reagent ports, optionally via "push-to-connect" or "quick connect" fittings.

Optionally, the reagent and/or waste compartments are removable. In one embodiment, the reagent and/or waste compartments are removable and the apparatus further includes a sensor, e.g., an optical sensor, to monitor the fluid level(s) in the reagent and/or waste compartments. Alternatively, the liquid reagent subassembly may include electronic scales to monitor the weight of fluid in the reagent and waste reservoirs for real-time tracking of reagent use and availability. Once the reagent and/or waste compartments reach a certain minimal or maximal capacity, as detected by the sensor or scale, the apparatus alerts the user to remove the reagent or waste compartment to replenish and/or empty the contents. Other liquid level detectors can be used. One exemplary liquid level detector comprises a plurality of thermistors arranged vertically within each compartment, e.g., at ¼, ½, ¾ and full marks. Due to the different heat capacity of liquid and air/vapor, a thermistor submerged in liquid produces a different electrical signal than one located in air or vapor. Another liquid level detector comprises a capacitor with one conductive plate at the top of the liquid and the other conductive plate at the bottom of the compartment. The measurable capacitance of the liquid between the two plates varies the distance between the two plates, as described above, indicating the amount of liquid contained in the compartment.

In one embodiment, the pump or motor of the pipetting subsystem (1021) is in communication with these sensors or scales and when the reagent and/or waste compartments reach the minimal or maximal capacity, the pipetting probe motor is disabled by the apparatus, e.g., the probe sensor relays information regarding the capacity of the compartment to the instrument software, which then halts further pipetting action.

The reagent and waste compartments may be provided by collapsible bags located in the subassembly body. One of the reagent and waste compartments may be provided by a collapsible bag and the other may be provided by the compartment body itself (i.e., the volume in the compartment body excluding the volume defined by any collapsible bags in the compartment body). Alternatively, the reagent and waste compartments can be housed in the same container and separated by a flexible, movable or elastic membrane or separator. In addition to the first reagent and waste compartments, the reagent cartridge may further comprise one or more additional collapsible reagent and/or waste compartments connected to one or more additional reagent and/or waste ports. Alternatively, one or the other of the reagent and waste compartments may be constructed from blow-molded plastic.

Figure 10A:
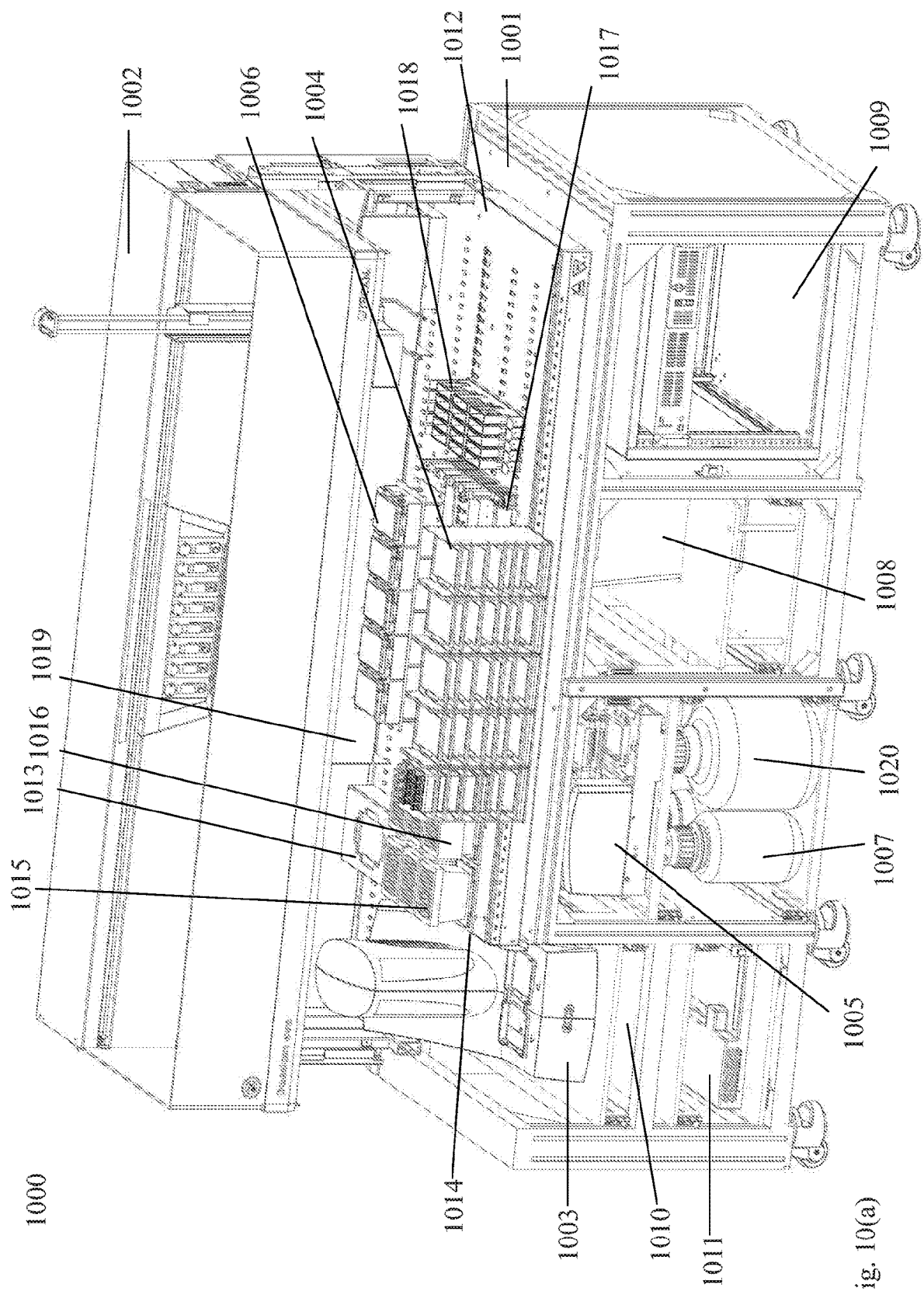
FIGS. 10(a)-(b) illustrate one embodiment of an assay system and various subsystems within the system. The assay system illustrated in FIGS. 10(a)-(b) is configured to conduct all sample processing steps on-board as well as all assay processing steps required in the conduct of an assay, and it is also operatively connected to a user-interface configured to display to the user stepwise instructions for appropriate sample/reagent preparation steps that should be performed manually before the system conducts the assay.
Figure 10B:
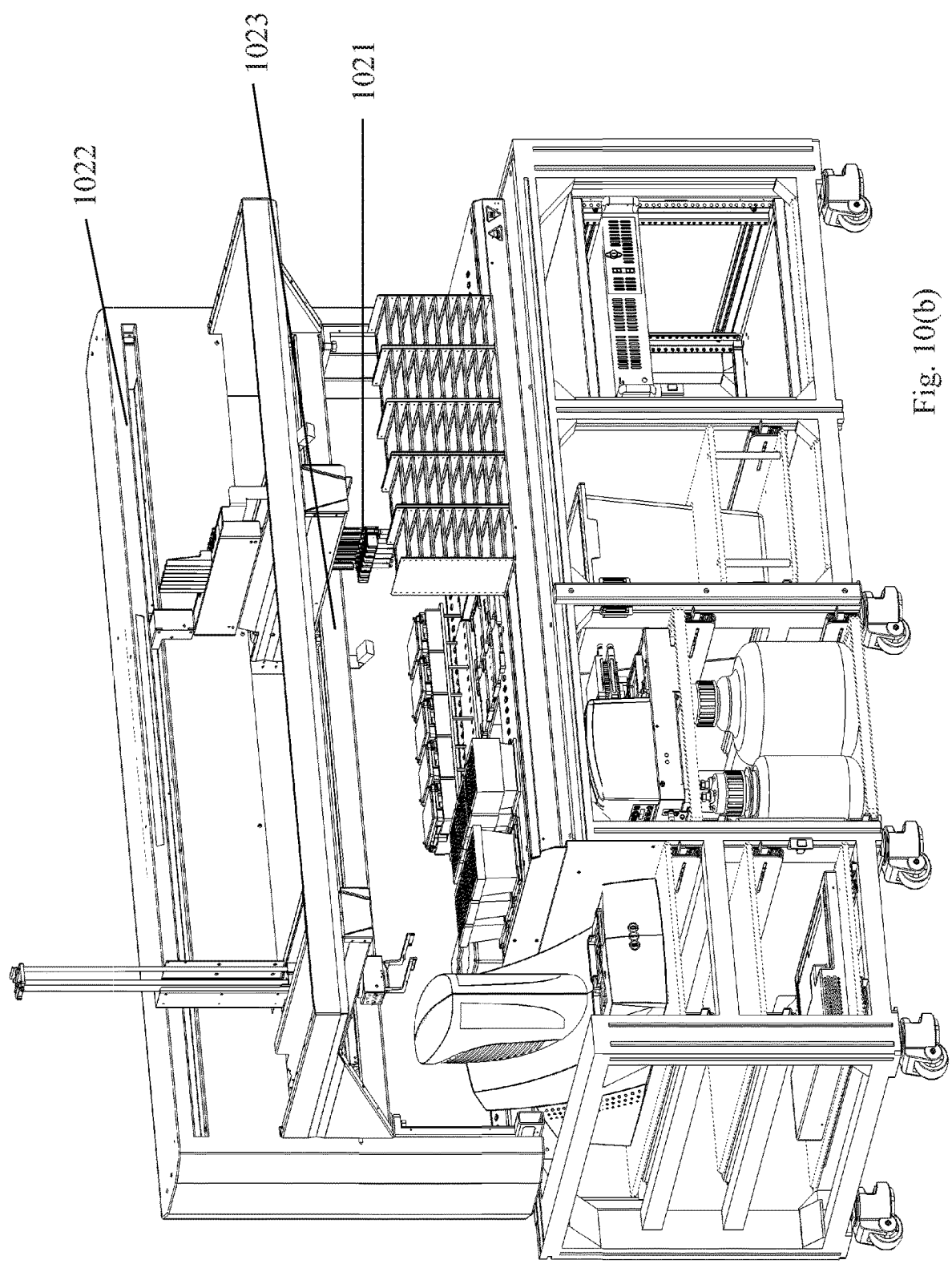
Figure 10C:
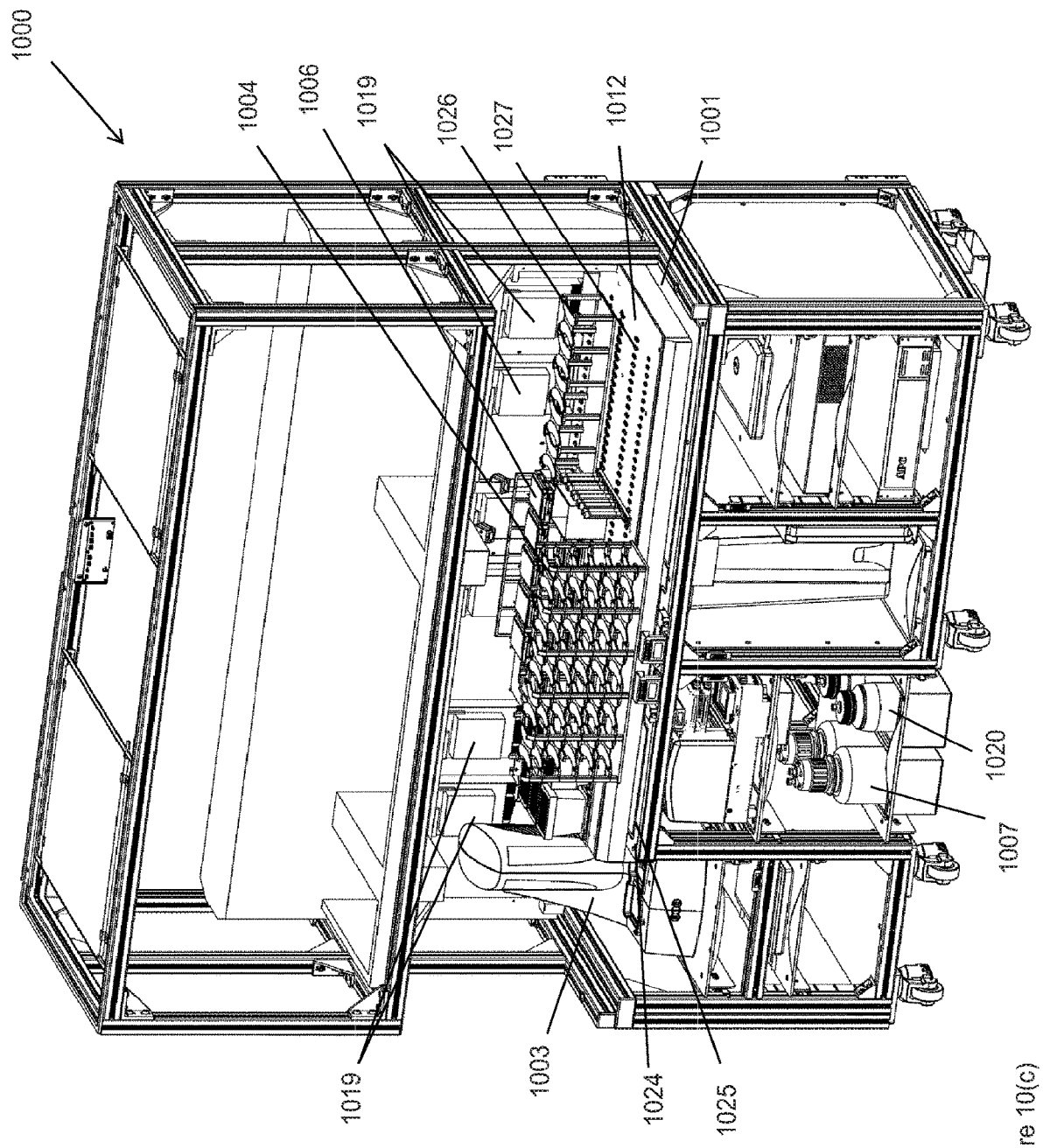
FIG. 10(c) illustrates another iteration of the assay system shown in FIGS. 10(a)-(b).
Figure 10D:
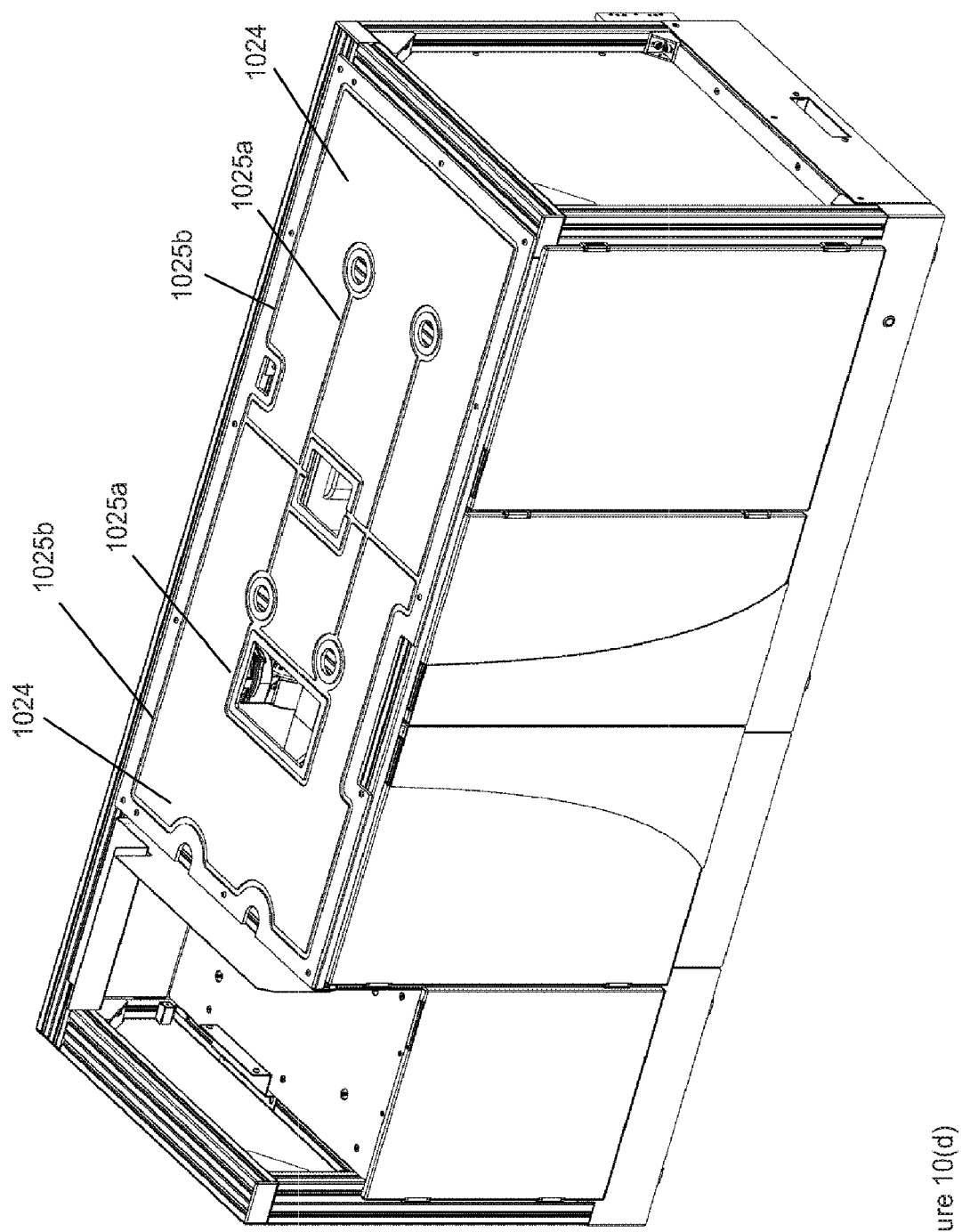
FIG. 10(d) shows a top surface of a table supporting the equipment of the assay system.
Figure 10E:
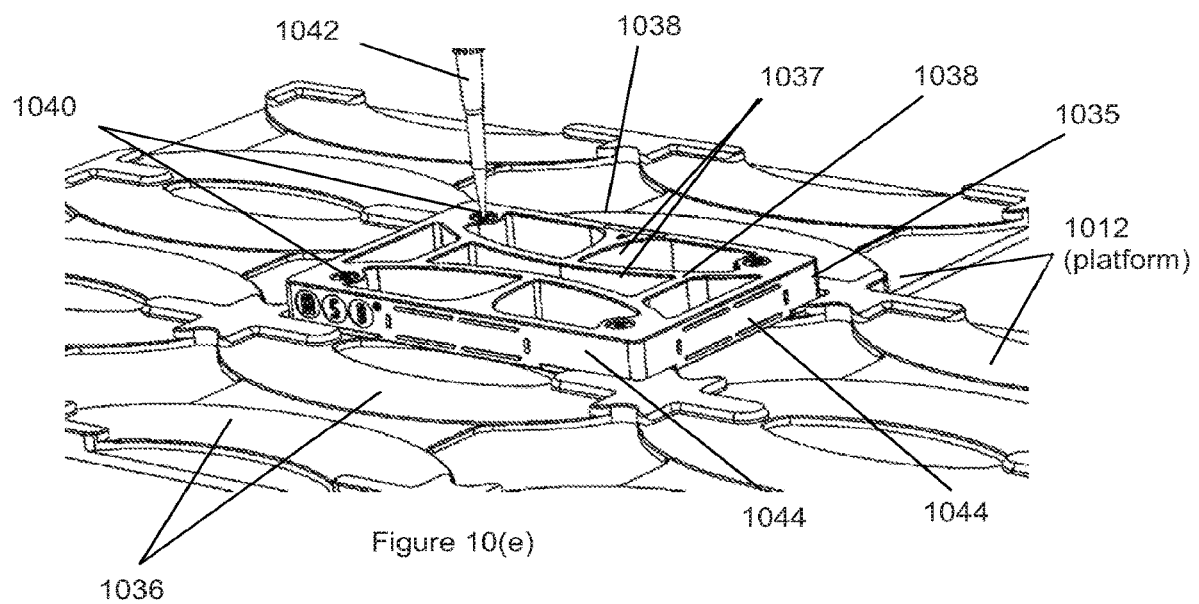
FIGS. 10(e)-(f) are perspective view of a training plate.
Figure 10F:
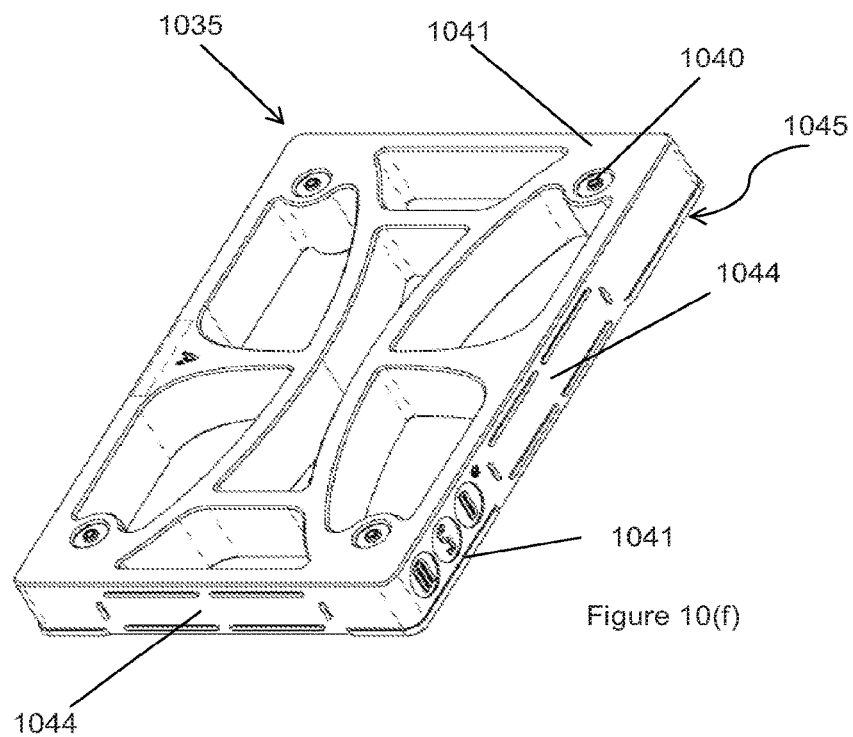
Figure 10L:
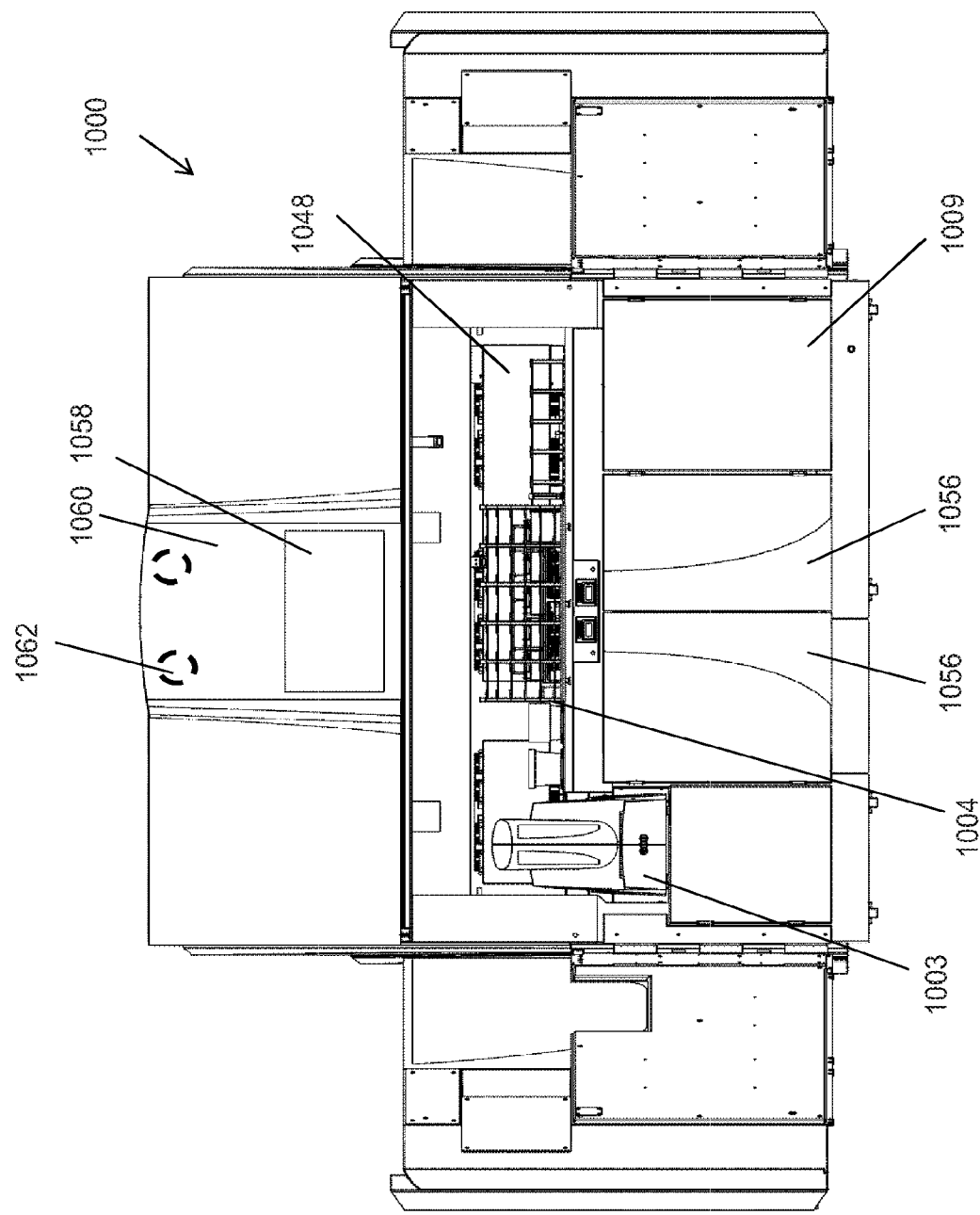
FIG. 10(l) is a front view of the assay system shown in FIGS. 10(a)-(c) with its interior doors closed.
Figure 10Q:
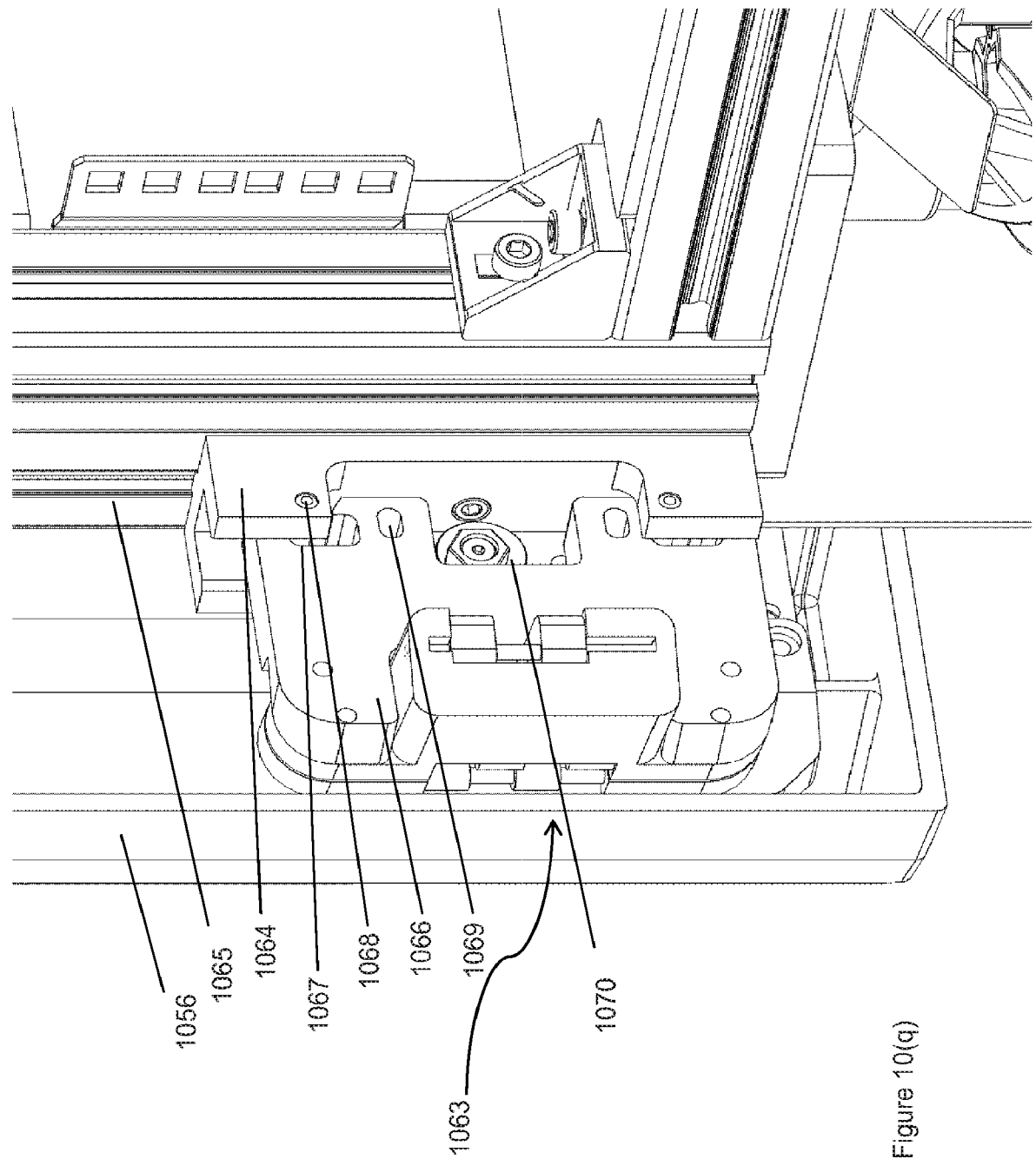
FIG. 10(q) shows an adjustable hinge to the door of the assay system that has two degrees of freedom.
Figure 10R:
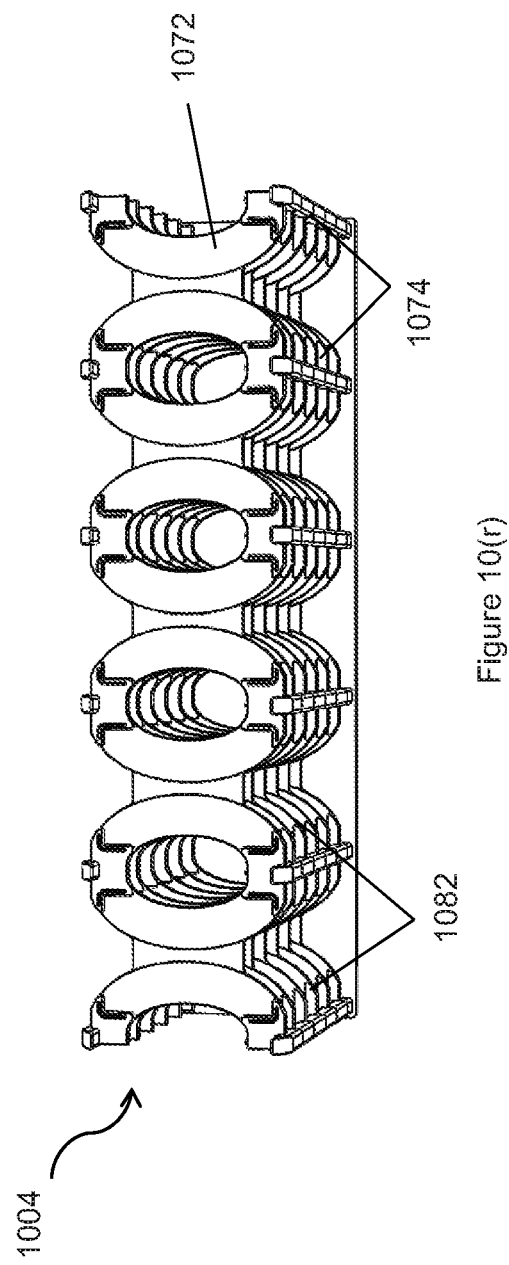
FIG. 10(r) is a top perspective view of the assay consumable storage unit.
Figure 10Z:
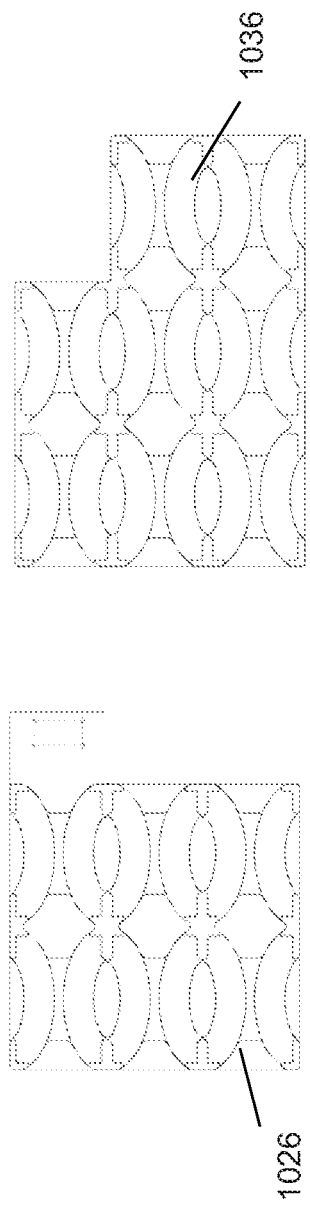
FIG. 10(z) is a top view showing a plate carrier (1036) and a tip carrier (1026).
Figure 10S:
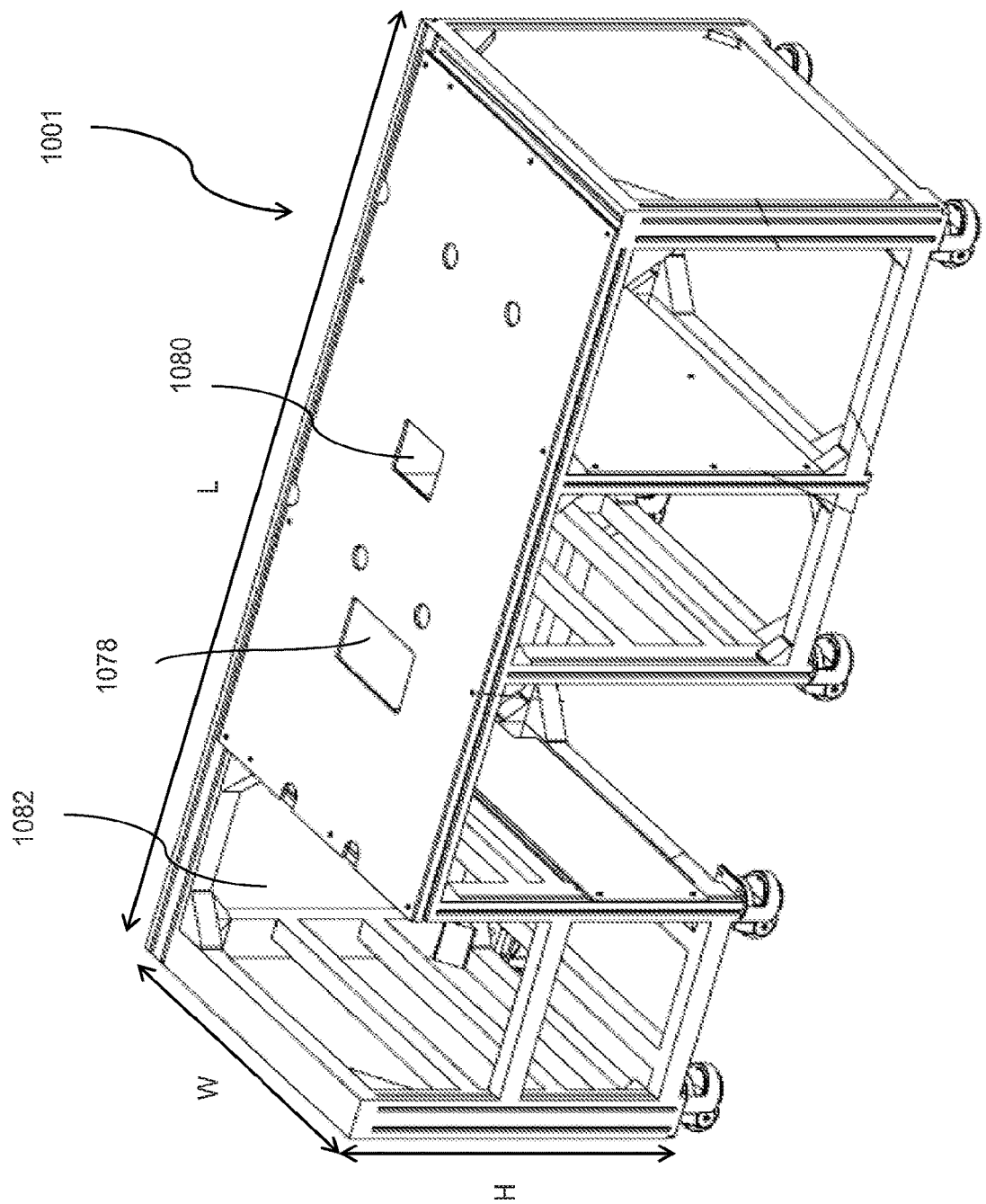
FIGS. 10(s)-(t) show the dimensions of the frames of the assay system.
Figure 10T:
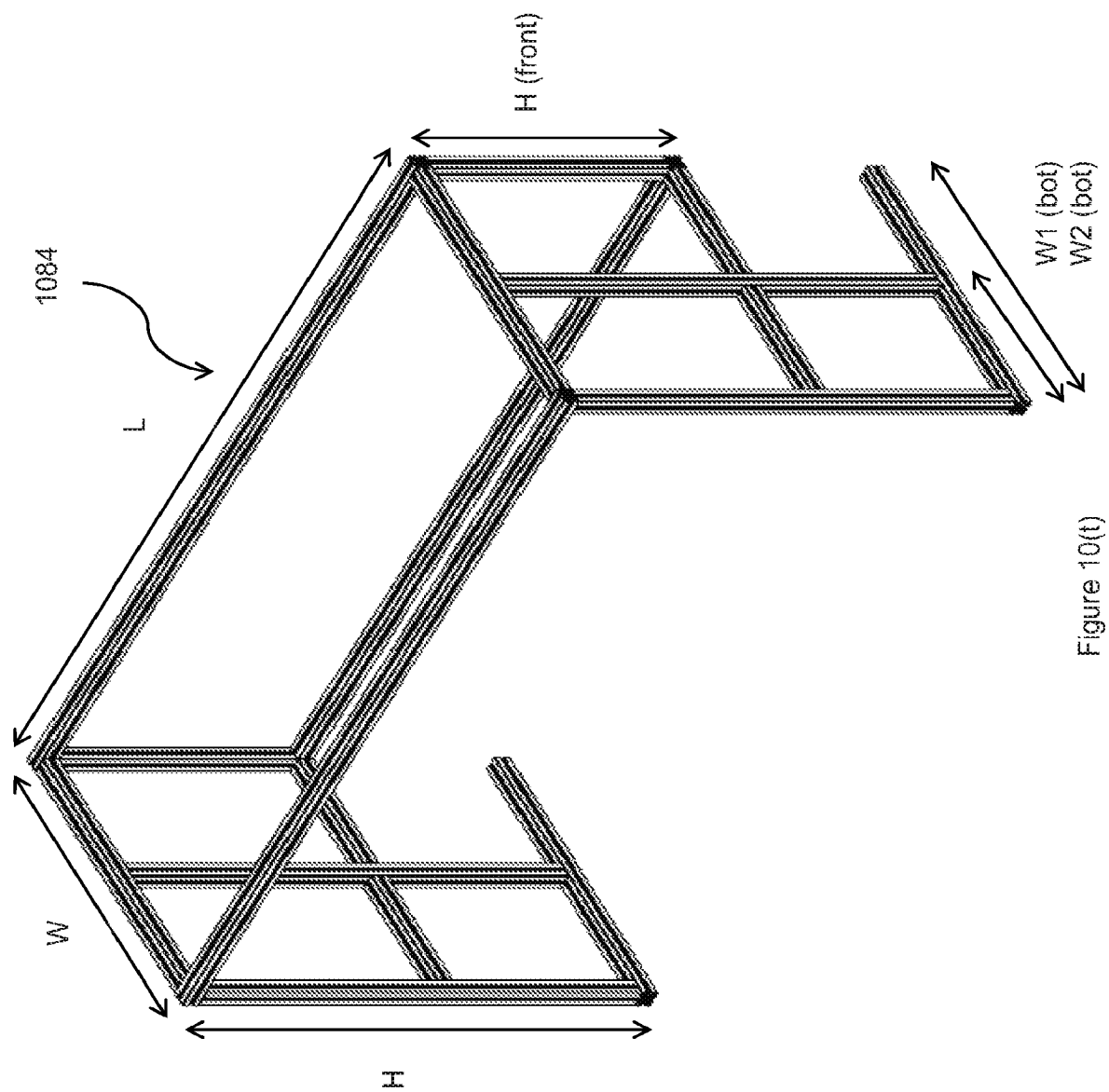
Figure 10U:
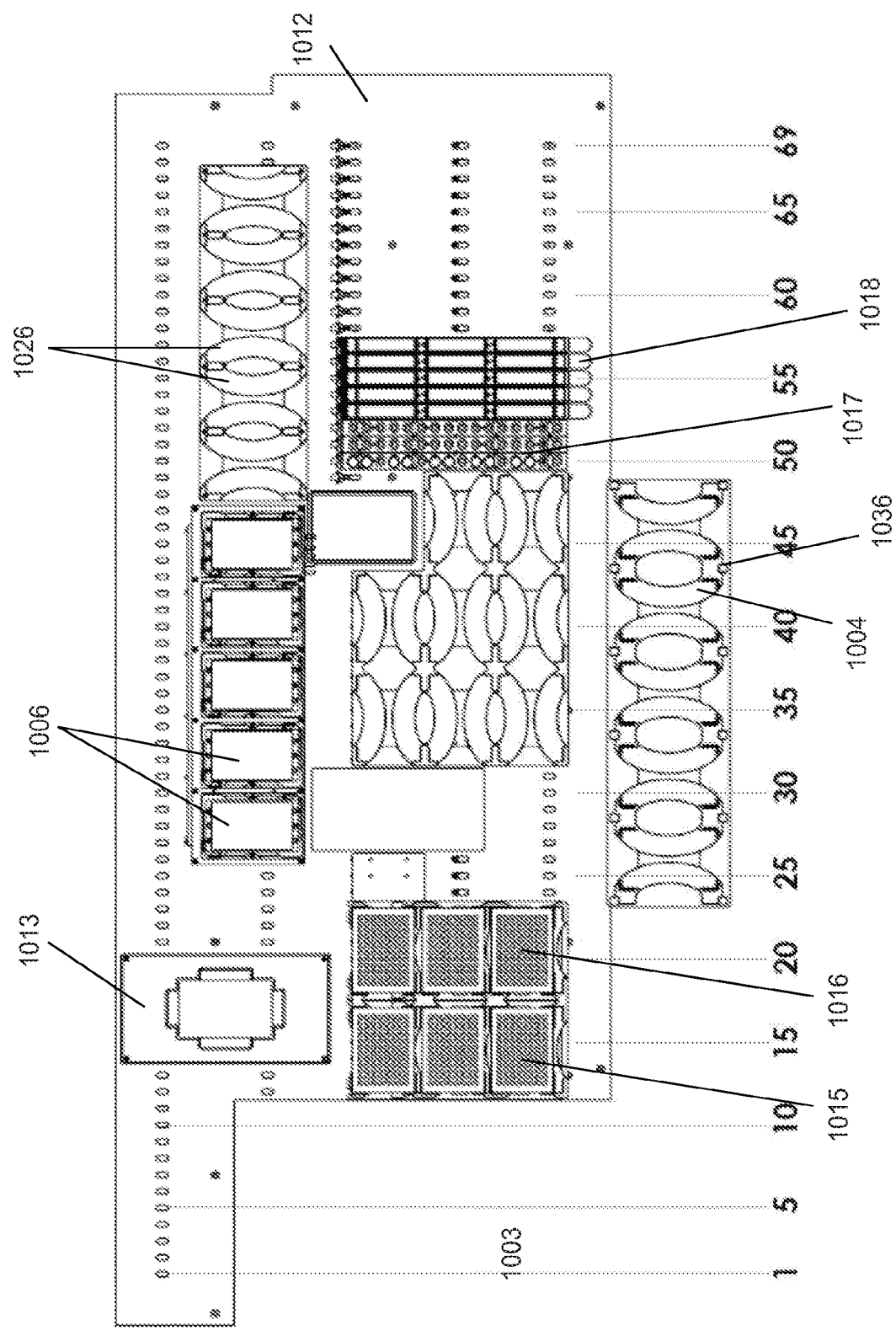
FIG. 10(u) shows a top view of the platform.
Figure 10V:
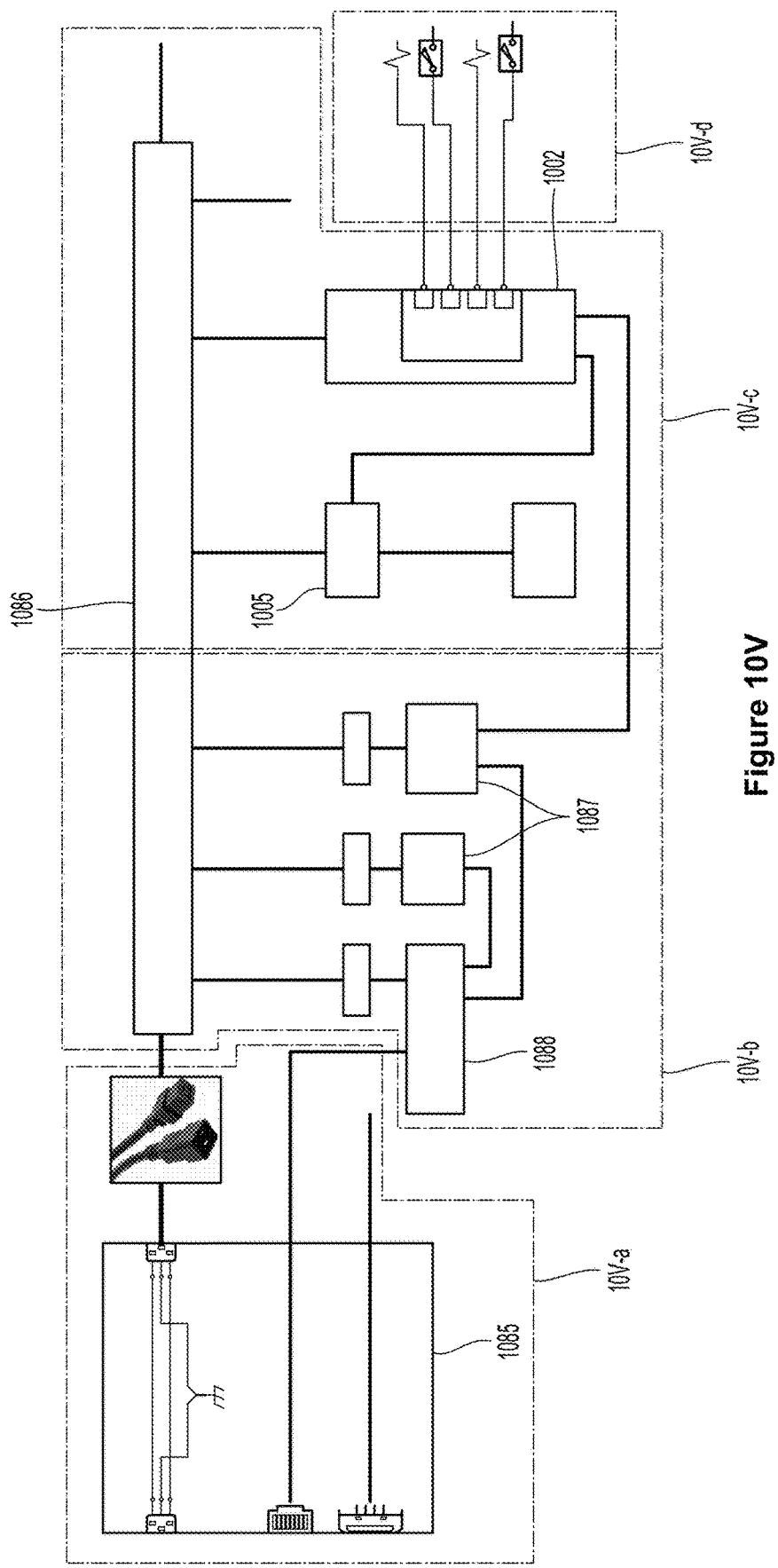
Figure 10W:
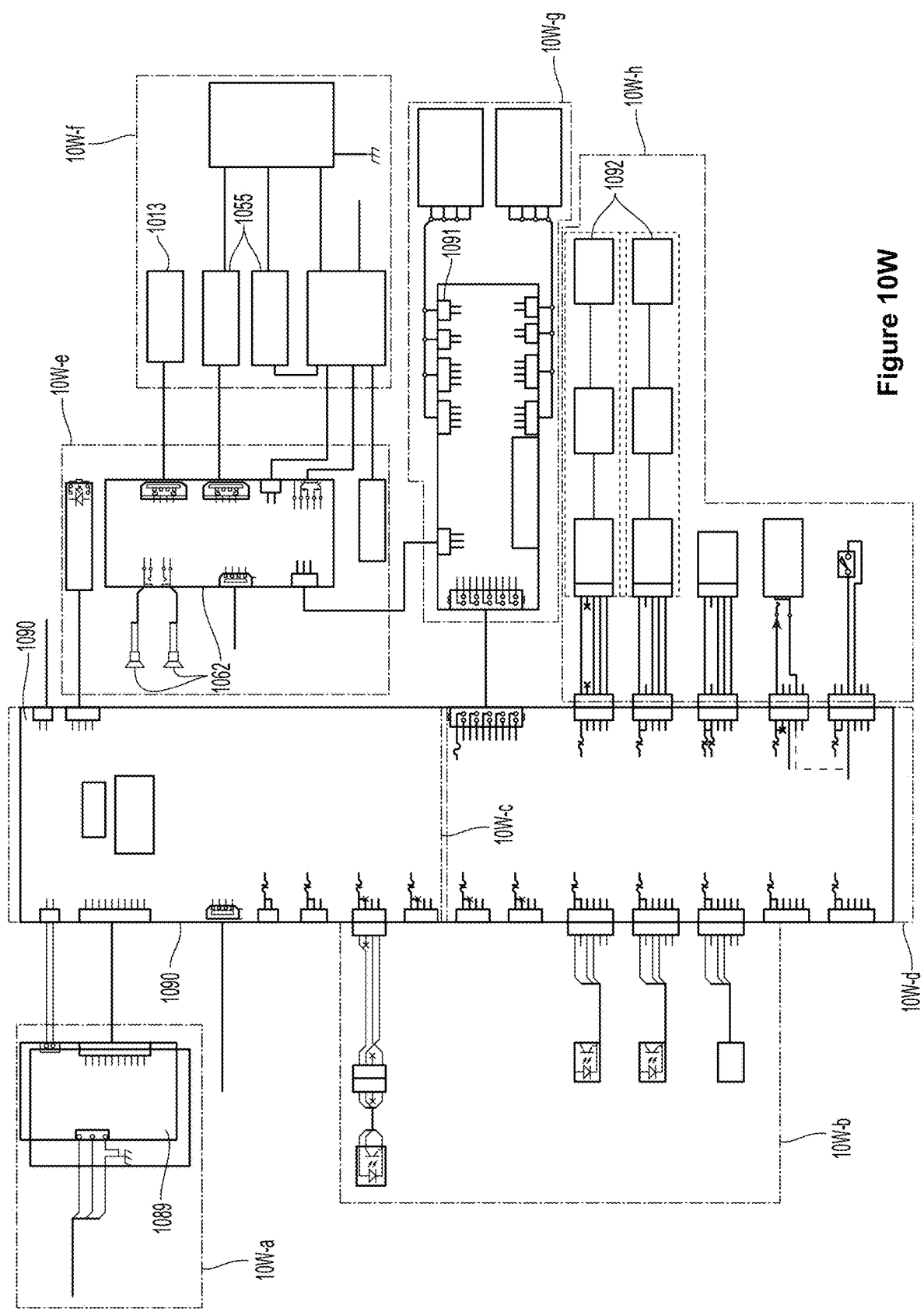
Figure 10Y:
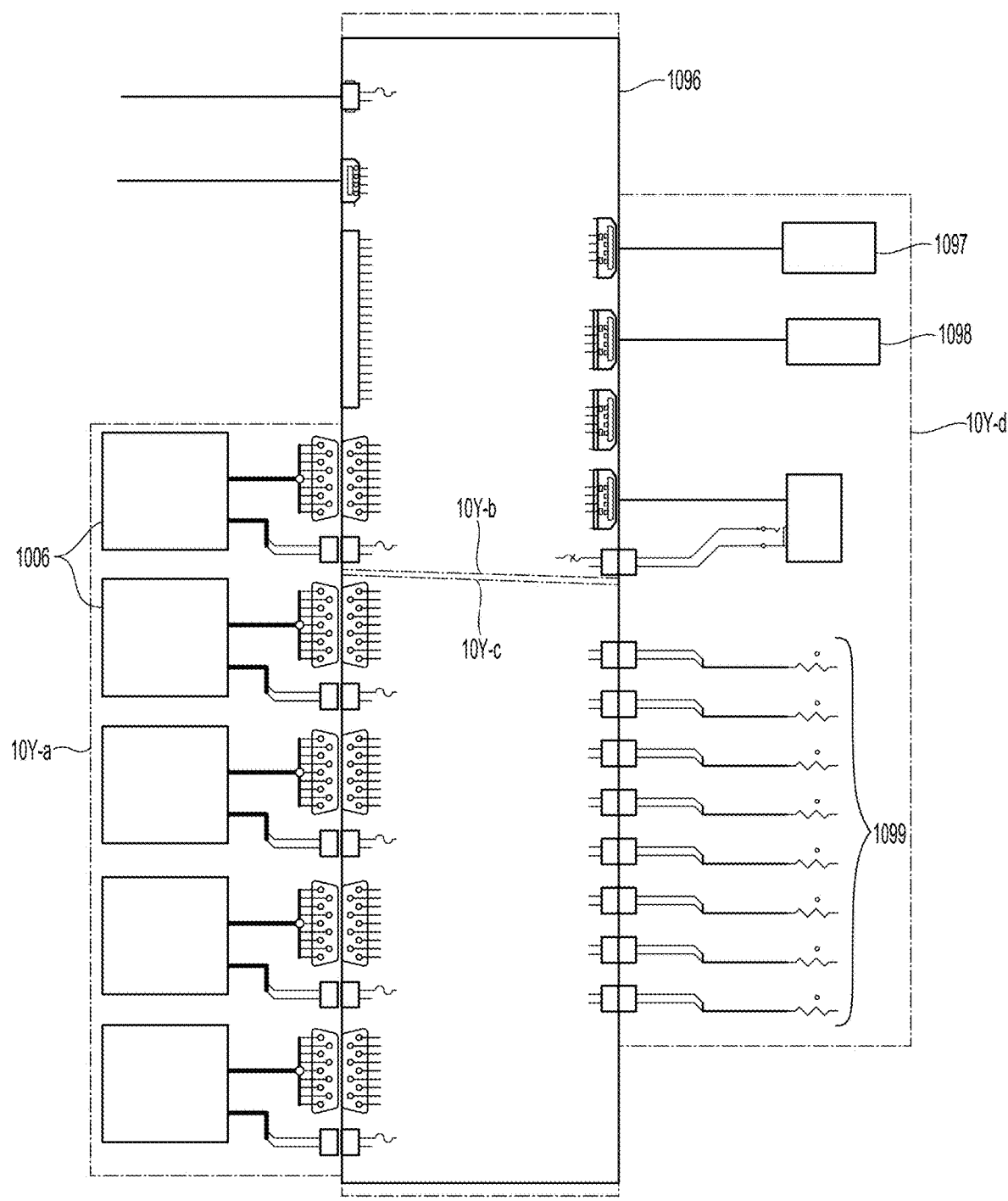

In accordance to another aspect of the present invention, assay system (1000) is capable of controlling the internal temperature when its panels or doors (1056) are closed. While illustrated in FIGS. 10(a)-(c) without its housing and doors in order to show the internal components, assay system (1000) comprises front doors and/or panels designated generally as (1056). These doors and panels are closed before assay system (1000) executes a run. Once the system starts a run, it is preferred that the internal air temperature, in the area above and near the platform where the assay steps are performed, remains within a range of about 20° C. to about 24° C., inclusively. Once an operating temperature is selected depending on the particular assay being run, the selected temperature is preferably maintained within ±1° C. The temperature control area may be defined as from the front of the platform (1012) or assay consumable storage unit (1004) to about six inches in front of the back of the deck or to the back of the deck. The control area may also extend from the left to the right of platform (1012), or from position 26 to position 49, as shown in FIG. 10(u), e.g., to cover the length of all shakers (1006). Assay system (1000) also has temperature sensors located at a number of locations to monitor the temperature(s) inside the assay system. The temperature readings are monitored by the system's software, described herein, and the user is notified if the operating temperature is outside of operating range. The temperature of liquid in a lidded MSD plate placed on the plate shaker with the shaker temperature control turned off should rise by no more than 2° C. above the ambient deck temperature over a duration of two hours.

The selected operating temperature is maintained, notwithstanding the heat produced by plate shaking apparatus (1006), which may also incubate the assay plates at an elevated temperature as discussed above, and assay reader (1003), which contains electromechanical components and thermoelectric coolers for optical sensors such as charge-coupled device (CCD) or complementary metal-oxide semiconductor (CMOS) devices that generate heat. The selected operating temperature is maintained by a number of TECs (1019), as best illustrated in FIG. 10(c). In this particular example, six TECs (1019) are used; however, any number can be deployed. Preferably, two TECs are focused on reader (1003) to dissipate the heat generated by the reader. The remaining TECs are used to control the selected operating temperature and some of the remaining TECs may focus on the optionally heated shakers (1006). Additionally, some of the cooling is directed to the electronic equipment (1010, 1011) or the electronic equipment housed in electronic enclosure (1009), discussed below.

As illustrated in FIG. 10(m), which shows a cross-sectional side view of assay system (1000), TEC (1019) absorbs heat near its midsection, as shown by arrows (1046), and produces cool air at the top and bottom as shown by arrows (1047). Cool air (1047) flows toward the front of assay system (1000) cooling the enclosure, and is turned around by the closed doors or panels (1056) and returns as warm air (1046), where the heat is absorbed by TEC (1019). FIG. 10(n) shows a top view, where all six exemplary TECs (1019) are illustrated. The return warm air is directed toward certain areas proximate the center of the TECs. FIG. 10(o), which is a perspective view, shows with more detail the flow paths of the warm and cool air and baffles (1048). Each baffle (1048) preferably encloses one or more TECs (1019), as shown, forcing cool air (1047) to flow upward and downward, as discussed above. Baffles (1048) also guide the returning warm air to the sides of the baffles where heat is exchanged by the TECs. Additional heat exchange occurs on the hot side of the TECs outside of the enclosure of assay machine (1000), where the heat absorbed from inside the assay machine is exchanged with atmospheric air.

Additionally, shakers (1006) may be raised above platform (1002) to allow air to flow underneath as well as over the top of shakers to improve the convection heat transfer.

FIG. 10(p) illustrates a cooling of electronic equipment (1010, 1011), which preferably are housed in electronic enclosure (1009). Cooling of enclosure (1009) employs chimney effect, by taking cool air (1047) from the bottom and pulling it upward to cool electronic equipment (1010, 1011) and ejects warm air (1046) through cooling channel (1049) to the outside of assay machine (1000). Preferably, cooling channel (1049) is positioned away from the main portion of assay machine (1000) and is positioned adjacent to an outer wall or skin of the system, as shown, for more effective heat removal. One or more fans are used to draw in cool ambient air and to push the air within electronic enclosure (1009) to cool and to eject warmed air through chimney (1049).

Referring back to FIG. 10(l), at least one computer screen or tablet (1058) is attached to a glass surface (1060) of assay system (1000). The pressure transducers commonly used in touch screen are attached or adhered directly to the glass surface (1060) and rely on the glass surface (1060) of assay system (1000) to transmit the pressure exerted by the fingertips of the users to the transducers to generate electrical currents signals to the CPU of the tablet or computer. Also rely on the same glass surface (1060) to generate sound waves are at least one sound exciter (1062). Sound exciter (1062) is also attached or adhered to glass surface (1060). Exciter (1062) vibrates glass surface (1060) to create sound. Both the touch screen and sound exciter can be used for the graphical user interface (GUI) or user interface (UI), described herein.

To minimize or eliminate interference caused by the vibrations generated by exciter (1062) to the pressure transducers of tablet (1058), a minimum distance between the exciter and the pressure transducers/touch screen is preferably established. While human audible frequency ranges from about 20 Hz to about 20 kHz, typical human speech occupies a significantly smaller range, e.g., from about 2048 Hz to about 8192 Hz ($7^{th}$ to $8^{th}$ octave). Preferably, the pressure transducers in tablet (1058) are designed, selected or tuned so that they are not responsive in the human speech range, so that the same glass surface (1060) can be shared by a visual device and an audio device.

Additionally, the glass surface (1060) or other surfaces on the front of assay system (1000) may contain lights, such as LED lights or light strings. Preferably, the LED lights are located on the door handles of the assay system and can also be located on the top of the assay system. These lights may illuminate different colors depending on the status of the immunoassay being run. In one example, the lights may communicate a satisfactory run by emitting a constant green or blue light, flashing or pulsing green or blue while the system is running, emitting yellow or red when an error is detected, and emitting white when the assay is completed. The same colors can also be displayed on tablet (1058).

Another aspect of assay system (1000) relates to how panels and doors (1056), which can be heavy and bulky, are supported on the frame of the system. Referring to FIG. 10(*q*), a flange system (1063), which includes a main hanging part (1066) and a movable bracket (1064) movably mounted on rail (1065) to allow bracket (1064) to be adjusted up and down in the Z-direction. Main hanging part (1066) has a pair of C-shaped openings (1067) adapted to be mounted to support (1068) on bracket (1064). Once the vertical position of door or panel (1056) is satisfactorily established, bolts are threaded into openings ((1069) to fix the vertical position.

The horizontal position (X-Y plane) of door or panel (1056) can also be adjusted by cam (1070). Cam (1070) can have any shape, including a circular lug eccentrically mounted onto bracket (1064). More specifically, cam (1070) is attached via an axis that is spaced apart from the center of the circular lug. A nut, preferably polygonal and more preferably hexagonal, is attached to the lug at the eccentric axis. Rotation of the nut would move main hanging body (1066) horizontally on the X-Y plane. The horizontal movement of the main hanging body (1066) is limited by the shape of opening (1069). In other words, opening (1069) has a horizontal oval shape which allows the connecting bolt a small amount of movement inside the oval shape.

Hence, flange system (1063) allows the door or flange (1056) to be adjusted in two directions to ensure that assay system (1000) can be closed appropriately. Flange system (1063) can be used on any and all doors and panels on the assay system.

Optionally, a video camera is positioned within the enclosure of assay system (1000) to record assay runs and to stream the video to remote locations, where the user or technician can monitor the assay runs, without having to be present at the assay system. The video can also be saved and stored for future reference. The video camera can be mounted on a frame of assay system (1000) described below.

Assay system (1000) is designed to be stable and as shown in FIG. 10(*s*) table (1001) that support platform (1012), all permanent components and labwares/consumables, has a length (L) of 85 inches±n %, a height (H) of about 28 inches±n % not including the caster wheels, and a width (W) of 33 inches±n %. When assembled to table (1001), each caster wheel has a height of about 4.5 inches±n %. The opening (1078) for the plate washer (1005) is about 5.5 inches±n %×10 inches±n %. The opening (1080) for the solid waste storage unit is about 4.5 inches±n %×6 inches±n %. The opening (1082) for the reader (1003) has a length (L direction) of about 16 inches±n %. The tolerance n % is preferably 10%, more preferably 5% and more preferably 2.5%.

Referring to FIG. 10(*t*), frame (1084) has a height (H) of about 52 inches±n %, a front overhang height (H front) of about 30 inches±n %, a length (L) of about 84.5 inches±n %, a width (W) on top of about 34.5 inches±n %. The bottom support has a long width (W2 bot) of about 33 inches±n % and a short width (W1 bot) of about 18 inches±n %. The tolerance n % is preferably 10%, more preferably 5% and more preferably 2.5%.

Reader (1003) is advantageously positioned within recessed opening (1082) and plate washer (1005) is positioned within recessed opening (1078) to provide clearance for the movements of robotic system (1002)'s gripper pads (1031) and pipette system or pipettor (1021) and to make room for the labwares and consumables on platform (1012). Reader (1003) is also positioned away from the center, e.g., on a side of table (1001) so that the heat it generates is kept away from the center of the assay system and is more readily dissipated. Both gripper pads (1031) and pipette system or pipettor (1021) share the same gantry (1022) in order to save space. The assay consumable storage unit (1004) is cantilevered to the front edge of platform (1012) and the shakers (1006) are located toward the back of platform (1012), as discussed above, to make room for the labwares or consumables on the platform, and allows the lab technician to load the consumables from the front and the gripper pads to take and put the consumables from the back. The combination of the dimensions of the table (1001) and frame (1084) and the locations/elevations of the major components described herein provides for the stability and space saving for assay system (1000).

The electrical and electronic connections are shown in FIGS. 10(*v*)-(*y*). FIG. 10(*v*) shows the power and internet connections. Power and ethernet module (1085) is shown on the left and in connection to UPS (1086). UPS (1086) provides emergency power to assay system (1000) when power is cutoff. UPS (1086) is also connected to the processors (1087) for the reader (1003) and the assay system (1000), as well as router (1088). UPS (1086) is also connected to washer (1005) and its pump and to the robotic system (1002).

FIG. 10(*w*) continues the wiring diagram of FIG. 10(*v*) and shows the electrical contact the right side. FIG. 10(*w*) shows that the UPS is connected to another power source (1089), which is a 300 W AC and 24 V DC unit. Power source (1089) supplies a stepped down power to DC power module at 5V DC at 24 A. This 5V power module supplies power to a number of sensors on both sides, such waste bucker sensors, plate washer sensors, etc. on its left side. On its right side, it supplies power to panel (1091) that powers the light panels and to illuminate the left and right doors (1092). Panel (1091) also supplies power and signals to exciter (1062), touch screen (1058) and bar code reader (1013).

FIG. 10(*x*) continues the diagrams of FIG. 10(*w*) and shows a control and power PCB (1093), which is connected to six TECs (1019) and their associated sensors (1094). Control and power PCB (1093) also powers fans (1095) and reader (1003).

FIG. 10(*y*) shows deck control PCD (1096) that powers five shakers (1006), bar code reader (1098) and thermistor sensors (1099) used to monitor temperatures associated with assay reader (1000).

FIG. 10(*z*) is a top view showing a plate carrier (1036) and a tip carrier (1026).

In each of the assay systems depicted in FIGS. 9-10, additional microprocessors and computers in the assay system can interact with the assay consumable identifier by transferring data and commands to/from the identifier to the various microprocessors/controllers throughout the system to perform various operations of the components listed above within the assay system, as described below.

The system can adjust the assay parameters prior to initiating an assay based on the consumable data saved to the identifier and/or stored or provided as consumable data via a direct or indirect interface. Thereafter, the system makes the appropriate electrical, fluidic and/or optical connections to the consumable (making use of electrical, fluidic and/or optical connectors on the consumable and system) and conducts an assay using the consumable. The sample can be introduced into the consumable prior to inserting the consumable in the system. Alternatively, the sample is introduced by a component of the system after the consumable is inserted in the system. The assay can also involve adding one or more assay reagents to the consumable and instructions for adding those various assay reagents can be saved to the identifier and/or provided as consumable data and the system adds those reagents to the consumable before or during the assay according to the instructions saved to the assay consumable identifier and/or provided as consumable data, as further described below.

(iv) Assay Cartridges & Cartridge Reader

Alternatively, the assay consumable is a cartridge and the consumable further comprises an element selected from one or more fluidic components, one or more detection components, one or more assay cells, reagents for carrying out an assay, working electrodes, counter electrodes, reference electrodes, dielectric materials, electrical connections, dried and/or liquid assay reagents, or combinations thereof. The cartridge can further comprise at least one assay cell that comprises a plurality of distinct assay test sites and/or domains, each of these test sites and/or domains comprising reagents for measuring a different analyte.

An example of an assay consumable cartridge that can be used in the present invention is described in U.S. application Ser. No. 2004/0189311, the disclosure of which is incorporated herein by reference in its entirety. The assay consumable described therein is an assay cartridge that incorporates one or more fluidic components such as compartments, wells, chambers, fluidic conduits, fluid ports/vents, valves, and the like and/or one or more detection components such as electrodes, electrode contacts, sensors (e.g. electrochemical sensors, fluid sensors, mass sensors, optical sensors, capacitive sensors, impedance sensors, optical waveguides, etc.), detection windows (e.g. windows configured to allow optical measurements on samples in the cartridge such as measurements of absorbance, light scattering, light refraction, light reflection, fluorescence, phosphorescence, chemiluminescence, electrochemiluminescence, etc.), and the like. Such consumables can also comprise reagents for carrying out an assay such as binding reagents, detectable labels, sample processing reagents, wash solutions, buffers, etc. The reagents can be present in liquid form, solid form and/or immobilized on the surface of solid phase supports present in the cartridge. In this embodiment, the consumables include all the components necessary for carrying out an assay. In addition, the assay consumable is used in connection with a consumable assay reader adapted to receive the consumable and carry out certain operations on the consumable such as controlling fluid movement, supplying power, conducting physical measurements on the cartridge, and the like.

More specifically, such assay consumable cartridges have one or more assay test sites (e.g., wells, compartments, chambers, conduits, flow cells, etc.) that can include one or more assay domains (e.g., discrete locations on a assay test site surface where an assay reaction occurs and/or where an assay dependent signal, such as an electrochemical or an electrode induced luminescence signal is induced) for carrying out a plurality of assay measurements. In this embodiment, assay domains are supported on assay electrodes (in one embodiment, an array of assay electrodes, e.g., a one dimensional array of assay electrodes) so as to permit the conduct of assays based on electrochemical or electrode induced luminescence measurements. The assay domains are, optionally, defined by a dielectric layer deposited on the electrodes. In addition, the assay consumables can have one or more attributes that make them suitable for use in "point of care" clinical measurements, e.g., small size, low cost, disposability, multiplexed detection, ease of use, etc.

The assay consumable cartridge can comprise the necessary electronic components and/or active mechanical components for carrying out an assay measurement, e.g., one or more sources of electrical energy, ammeters, potentiometers, light detectors, temperature monitors or controllers, pumps, valves, etc. Alternatively, some or all of the electronic and/or active mechanical components are arranged within a separate assay reader. The assay reader would also have the appropriate electrical, fluidic and/or optical connections to the assay consumable for carrying out an assay using the consumable. Using such an arrangement, the assay consumable can be designed to be low cost and disposable while the assay reader (which holds the more expensive and complex components) is reusable.

In one embodiment, a cartridge-based biochemical detection system can include a system housing comprising an optical detector wherein the system housing is adapted and configured to receive and position the assay consumable and/or the optical detector for processing. The system can further comprise support subsystems that can include one or more of the following: storage subsystem for storing assay reagents/consumables and/or waste; sample acquisition/preprocessing/storage subsystem for sample handling; fluidic handling subsystem for handling the reagents, sample, waste, etc. and for providing fluids to the detection chamber via a fluid inlet line; electrical subsystem for electrically contacting the cartridge's electrical contacts and supplying electrical energy to the electrodes; and a control subsystem for controlling and coordinating operation of the system and subsystems and for acquiring, processing and storing the optical detection signal. The information associated with the assay consumable identifier and/or provided as consumable data can include information that is used to control or adjust one or more of the assay system components prior to and/or during the conduct of an assay using the assay consumable.

Still further, the assay consumable can be a container holding one or more assay reagents, including but not limited to one or more buffers, diluents, and/or reagents used by the assay system in the conduct of an assay. The assay consumable identifier can be affixed to the container and/or affixed to a packaging for the container.

B. Assay Consumable Identifier

In one embodiment, the assay consumable identifier comprises memory for storing information related to the consumable, its history and/or its use. In one embodiment, the memory is non-volatile memory. Non-volatile memory is computer memory that can retain the stored information without power. Examples of non-volatile memory which can be used in the consumable identifier include, but are not limited to, electronic non-volatile memory (e.g., read-only memory and flash memory), magnetic memory (e.g., hard disks, floppy disk drives, and magnetic tape), optical memory (optical disc drives) and hybrids of these approaches (e.g., magneto-optical memory).

In one embodiment, the assay consumable identifier comprises EPROM (erasable programmable read-only memory), a type of programmable read-only memory that can be erased by exposing it to ultraviolet light. Once erased, it can be reprogrammed with new or modified data. In another embodiment, the assay consumable identifier comprises EEPROM (electronically erasable programmable read-only memory) a class of non-volatile electronic memory that can be electrically erased and reprogrammed without exposure to UV light. An EEPROM can be written to or programmed more than once and can be selectively programmed (the customer can alter the value of certain cells without erasing the programming of the other cells). Therefore, sections of data can be erased and replaced without needing to alter or reinstall the rest of the chip's programming.

In another embodiment, the assay consumable identifier comprises flash memory, a specific type of EEPROM that is erased and programmed in large blocks. Although flash memory is technically a type of EEPROM, the term "EEPROM" is generally used to refer specifically to non-flash EEPROM which is erasable in small blocks, typically bytes. Because erase cycles are slow, the large block sizes used in flash memory erasing give it a significant speed advantage over conventional EEPROM when writing large amounts of data.

In another embodiment, the assay consumable identifier comprises a smart card, chip card, or integrated circuit card (ICC) (referred to collectively as "ICCs"). These are small cards with embedded integrated circuits which can process and store data. There are two broad categories of ICCs; i) "memory cards" that contain non-volatile memory storage components and, optionally, some specific security logic but do not contain microprocessors and ii) "microprocessor cards" that combine non-volatile memory components with microprocessor components and enable the processing of information being read into or out of the ICC. The ICC electronic components are supported on a card that is, typically, made of plastic such as PVC or ABS. The card can include an embedded hologram to avoid counterfeiting. Contact ICCs have conductive contact pads. When inserted into a assay reader, the contact pads on the ICC make contact with electrical connectors in the identifier controller to allow for transfer of information between the identifier controller and the ICC, for example, allowing the identifier controller to read, erase or write information on the ICC.

Another method of transferring information is via an RFID, i.e., radio frequency identification, which is similar in theory to bar code identification. With RFID, the electromagnetic or electrostatic coupling in the RF portion of the electromagnetic spectrum is used to transmit signals. An RFID system consists of an antenna and a transceiver, which read the radio frequency and transfers the information to a processing device, and a transponder, or tag, which is an integrated circuit containing the RF circuitry and information to be transmitted.

Identification can also be accomplished by reading a consumable identifier (e.g. bar code). One of the key differences between RFID and bar code technology is that RFID eliminates the need for line-of-sight reading that bar coding depends on. Also, RFID scanning can be done at greater distances than bar code scanning. High frequency RFID systems (850 MHz to 950 MHz and 2.4 GHz to 2.5 GHz) offer transmission ranges of more than 90 feet, although wavelengths in the 2.4 GHz range are absorbed by water (the human body) and therefore has limitations.

In one embodiment, the non-volatile memory used in the present invention is comprising an EEPROM, flash memory, ICC or combinations thereof. In one embodiment, the non-volatile memory is an EEPROM. In an alternate embodiment, the non-volatile memory is an RFID. In a specific embodiment, the non-volatile memory is a consumable identifier (e.g. bar code), including but not limited to a one- or two-dimensional consumable identifier (e.g. bar code), or combinations thereof.

In an additional alternative embodiment, two or more non-volatile memory components can be used in the present invention. For example, a first assay consumable comprising a first identifier can be used in the assay system, and an additional assay consumable comprising an additional identifier can also be used in the assay system. Each identifier can include the same or different type of memory. However, for each different form of memory, there will be a separate identifier controller. And certain consumable data can be stored on one identifier and other consumable data on an additional identifier of the same or different type. For example, one assay consumable used in the system can comprise an EEPROM or RFID as an identifier, whereas the system can also use an additional assay consumable comprising, e.g., a consumable identifier (e.g. bar code) as an identifier. The assay system would comprise an identifier controller capable of interfacing with the first identifier, i.e., the EEPROM or RFID, and the system will further comprise an additional controller that will interface with the consumable identifier (e.g. bar code).

The assay system of the present invention includes an identifier controller that controls the operation of the non-volatile memory and other components of the assay system. The identifier controller optionally includes a micro-controller to interface with the non-volatile memory over a communication interface, which can incorporate conventional interface architectures and protocols such as I$^2$C, a two line serial bus protocol. The microcontroller addresses the non-volatile memory and performs write, read and erase operations on the memory.

The consumable identifier can be located on the consumable or it can be a separate component. In either case, the system can be designed to have a unique identifier for each consumable. Alternatively, the system can be configured so that one separate consumable identifier is used to hold information relating to a plurality of consumables. In one example, each package of consumables has a package-specific identifier mounted on the package (or, alternatively, supplied in the package) that holds information relating to the plurality of consumables in the package. Optionally, each consumable also carries an additional unique consumable-specific identifier attached to the consumable. This consumable-specific identifier is used primarily to uniquely identify the consumable and link it to information on the package-specific identifier. In this embodiment, lot information content and/or non-editable identifiers such as consumable identifiers (e.g. bar codes) can be used.

The various components of the assay system can be housed together in a single unit or can be housed separately. For example, the assay system can include an assay reader and an identifier controller as separate units. The assay system provides for communication (which can be wired or wireless communication) directly between the assay reader and identifier controller or, alternately, indirectly through additional components of the assay system. In an alternative embodiment, the identifier controller is housed within the assay reader. In such an embodiment, the assay reader can be configured such that insertion of the consumable into the assay reader during the conduct of an assay also enables communication between the consumable identifier and the identifier controller (e.g., a port into which the consumable is inserted includes components for processing and/or reading the consumable and also includes components, such as electrical contacts or a radio transmitter, for communicating with the consumable identifier). In one example, when the consumable is loaded into the assay system, electrical contacts are made between the controller and the identifier. The controller is then able to read, erase and/or write consumable data from/to the identifier. Alternatively, the assay reader can have separate ports for processing/reading a consumable and for communicating with the consumable identifier. The customer places the assay consumable or packaging in or in proximity to the controller port such that the controller makes electrical contact with the identifier to enable the controller to read, erase and/or write consumable data.

In one embodiment, the identifier comprises non-volatile memory comprising an RFID tag, a consumable identifier (e.g. bar code), an EPROM, an EEPROM or combination thereof. Still further, the identifier can comprise an EEPROM comprising flash memory and ICC. In a specific embodiment, the identifier is a consumable identifier (e.g., a one- or two-dimensional bar code).

C. Consumable Data

The identifier is programmed, e.g., during the manufacturing process or when the consumable is prepared for shipment. The identifier is associated with consumable data which can be used before, during or after an assay or a step of a multi-step assay to control the operation of the assay system, assay reader or a component of the assay system. In addition or alternatively, some or all of the information required for use of a given consumable can be provided as consumable data. The term "consumable data" can include any information used to uniquely identify a particular assay or assay step, assay consumable, consumable domain(s), biological reagent or sample or to distinguish a particular assay, assay step, assay consumable, consumable domain(s), biological reagent or sample from other assay consumables, consumable domains, biological reagents or samples. Consumable data can include consumable information, sample information, chain of custody information, consumable/test site information, assay process information, consumable security information, or combinations thereof. Consumable data can further include information related to one or more analytical tools that can be applied by the system to analyze data generated during and/or after the conduct of an assay, assay system maintenance information, system-consumable promotional information, and/or system and/or consumable technical support information.

Each type of consumable data is described in more detail below and it should be understood that each type of consumable data can be associated with the consumable identifier and/or provided as consumable data.

(i) Consumable Identification & Configuration Information

Consumable data can include consumable identification and configuration information that includes but is not limited to lot identification information, lot specific analysis parameters, manufacturing process information, raw materials information, expiration date, Material Safety Data Sheet (MSDS) information, product insert information (i.e., any information that might be included or described in a product insert that would accompany the assay consumable, e.g., the assay type, how the assay is performed, directions for use of the assay consumable, assay reagents, or both, etc.), threshold and/or calibration data for one or more reagents used in the assay consumable or in an assay or a step of a multi-step assay, and the location of individual assay reagents and/or samples within one or more test sites of the assay consumable.

The consumable data can also include lot identification information, i.e., information that is used to identify a particular lot of assay consumables, which is distinct from lot-specific analysis parameters, which includes that information that is unique to a given lot that can be used by the system, e.g., to conduct an assay with a consumable from that lot or to analyze assay results derived from a consumable from that lot. In one embodiment, if the assay consumable is a multi-well assay plate or a cartridge, the lot-specific analysis parameters can include, but are not limited to, the following: (i) the revision level that determines the schema used to interpret the information; (ii) the consumable type; (iii) the date of manufacture; (iv) the lot number; (v) the date of expiration; (vi) a cross-talk correction matrix, to account for chemical cross-reactivity; (vii) a threshold for assays to be conducted in the consumable and each internal negative control; (viii) a range for each internal positive control; (ix) ranges for each assay to be conducted in the cartridge for the positive control sample; (x) a software checksum to ensure integrity of the data; (xi) in-well (or in-test site) control acceptance ranges; (xii) assay names and/or identifiers; (xiii) information concerning assay quality control, including negative and positive quality control materials that are used to verify the operation of the assay reader and the consumable; (xiv) calibration information such as a master calibration curve; and (xv) number and names of assay calibrators and/or assay calibrator acceptance ranges.

Consumable data can include sample information, such as the location of samples within at least one test site of the assay consumable, assay results obtained on the assay consumable for the sample, and the identify of samples that have been and/or will be assay in the assay consumable.

The consumable data can also relate to chain of custody, e.g., information regarding the control, transfer and/or analysis of the sample and/or an assay consumable. Chain of custody information can be selected from customer identification, sample identification, time and date stamp for an assay, the location of the assay system in a laboratory during the assay, calibration and QC (quality control) status of the assay system during the assay, custody and/or location information for the assay consumable before and after the conduct of the assay, assay results for a given sample, as well as customer created free text comments input before, during or after an assay is processed by the system. Still further, chain of custody information can include time, date, manufacturing personnel or processing parameters for one or more steps during the manufacture of the assay consumable, custody, location and/or storage conditions for the assay consumable following manufacture and/or between steps during the manufacture of the assay consumable.

Consumable data can also include consumable/test site information, such as consumable type and structure, the location and identity (e.g., the structure, composition, sequence, concentration and/or origin) of assay reagents included within an assay consumable, and the location and identity of assay reagents within an assay test site of the assay consumable. The consumable data can be used to distinguish a first test site within that consumable from a different test site within the consumable. Still further, the consumable data can include sample information comprising the location of samples within at least one test site of the assay consumable; assay results obtained on the assay consumable for the sample; identity of samples that have been and/or will be assayed in the assay consumable; or combinations thereof. Additionally, the consumable data is consumable/test site information comprising consumable type and structure; location and identity of assay reagents included with the assay consumable; location and identity of assay reagents within an assay test site of the assay consumable; or combinations thereof.

In an additional embodiment, consumable/test site information can include information concerning assays previously performed by an assay reader or system on one or more test sites of the consumable, and information concerning assays to be performed by a assay reader on one or more test sites within the consumable. Therefore, once the assay is conducted by the system, the controller can be used to write the results of the assay to the identifier. Such information includes, but is not limited to raw or analyzed data collected by the system during the assay (wherein analyzed data is data that has been subjected to statistical analysis after collection and raw data is data that has not been subjected to such statistical analysis), a list of test sites and/or domains within the assay consumable used during a given assay, a schedule of events to be conducted on an assay consumable or a test site and/or domain within an assay consumable, a list of those test sites and/or domains of the assay device that have not be subjected to an assay, assay or system errors that resulted during a given assay or assay step, or combinations thereof.

Still further, consumable data can be used as a security mechanism, e.g., to confirm that the correct assay consumable is being used in the system (referred to herein as "consumable security information"). The consumable data can include a digital signature to prove that the consumable was manufactured by the designated vendor. In one embodiment, if an inappropriate assay consumable is present in the system, e.g., a counterfeit consumable or a consumable that is otherwise incompatible with the assay system, the controller will disable the system, assay reader or a component thereof. In addition or alternatively, the consumable data can be used to detect the proper placement of the assay consumable in the system, e.g., the proper orientation of the assay consumable or a portion thereof, in the assay system, such that the controller will disable the system, assay reader or a component thereof until the assay consumable is placed in the correct orientation. Still further, the consumable data can also be used to detect a defect in the assay consumable or an assay test site and/or domain and the controller will disable the system, assay reader or a component thereof accordingly. For example, depending on the nature of the defect in the assay consumable or domain, the controller can disallow the use of the assay consumable in its entirety or direct the assay reader to disallow the use of a test site and/or domain or a set of test site and/or domain in the assay consumable. In one embodiment, the assay reader can perform a diagnostic analysis on the assay consumable and/or a test site and/or domain therein to identify defects therein and the controller will write the results of that diagnostic analysis to the identifier on the consumable. If the consumable is later used in a different assay reader, the results of this diagnostic analysis will be read by the controller and used by the assay reader to adjust the use of that consumable or a test site and/or domain in that consumable accordingly. In a further embodiment, the assay consumable can be subjected to a quality control process during or after its manufacture and the results of that quality control analysis can be written to the identifier for later use and/or verification by the customer of the assay consumable in an assay reader.

The consumable data can also include authorization information for consumables or test site and/or domain thereof or biological reagents, such as information regarding whether a particular customer has a valid license to use a particular consumable or biological reagent, including the number of times the customer is permitted to use the particular consumable or biological reagent in a particular assay and the limitations, if any, on that use, e.g., whether the customer's license is for research purposes only. Such information can also include validation information regarding whether a particular consumable or biological reagent has been subject to a recall or has otherwise become unsuitable or unauthorized for use. The recall information and an optional last recall check date and/or timestamp can be written to the identifier and/or provided as consumable data.

The consumable data can further include information regarding the origin of a biological reagent used in an assay consumable, test site and/or domain, including for example an identification of an original sample from which it was derived or the number of generations removed it is from an original sample. For example, if an assay reagent used in an assay is an antibody, the consumable data can include the identification of the hybridoma from which the antibody was derived, e.g., the ATCC accession number for that hybridoma.

According to various embodiments, biological samples or reagents that are provided in or with the consumables described above can be licensed separately from systems designed to operate on the biological reagents. In various embodiments the assay system, assay reader or a component thereof is coupled to a network that allows the system to communicate over public and/or private networks with computer systems that are operated by or on behalf of the customers, manufacturers and/or licensors of the biological reagents, consumables or systems. In various embodiments, a limited license can provide for the use of licensed biological reagents, consumables or systems for a particular biological analysis on only licensed systems. Accordingly, a system can authenticate a biological reagent, consumable or system based on, for example, a digital signature contained in the identifier associated with a particular consumable and/or provided as consumable data, if a particular customer has a valid license. In various embodiments, the identifier and/or consumable data can also be used to provide for a one time use such that biological reagents cannot be refilled for use with the same authentication.

In certain embodiments, when the identifier is read by a system, assay reader or component thereof that has access to a public or private data network operated by or on behalf of the customers, manufacturers and/or licensors of the biological reagents, consumables or systems, certain consumable data can be communicated to the assay system and read, written or erased locally via the identifier/controller on the assay system. For example, recall and/or license information can be a subset of consumable data that is available via a direct and/or indirect interface, whereas additional consumable data e.g., lot-specific information, expiration date, calibration data, consumable specific information, assay domain information, assay results information, consumable security information, or combinations thereof, can be stored locally on the identifier and otherwise unavailable via the network connections on the assay system. In one embodiment, recall, license and/or consumable security information can be available via the network connections on the assay system and/or stored to the storage medium as consumable data and the remaining consumable data is stored locally on the identifier. The assay system or assay reader includes system hardware, system firmware, system data acquisition and control software, and method or consumable data. In various embodiments, the system hardware includes electronic control and data processing circuitry, such as a microprocessor or microcontroller, memory, and non-volatile storage. In various embodiments, the system hardware also includes physical devices to manipulate biological reagents such as robotics and sample pumps. In various embodiments, the system firmware includes low-level, computer-readable instructions for carrying out basic operations in connection with the system hardware. In various embodiments, the system firmware includes microprocessor instructions for initializing operations on a microprocessor in the system hardware.

The system data acquisition and control software is higher-level software that interfaces with the system firmware to control the system hardware for more specific operations such as operating a charge coupled device (CCD) to acquire visual luminescence information regarding a particular biological analysis. In various embodiments the data acquisition and control software includes a software-implemented state machine providing, for example, the following states: (i) idle; (ii) running; (iii) paused; and (iv) error. In various embodiments, when the state machine is in the idle state, it can receive an instruction from the general purpose machine to perform a particular data acquisition or system control operation. In various embodiments, the general purpose computer opens a TCP/IP socket connection to the system, determines whether the system is in the idle state and then begins transmitting instructions and/or parameters. In various embodiments, an encrypted TCP/IP connection is established, using, for example, the SSH protocol. The instructions and/or parameters can be in the form of ASCII encoded, human readable consumable and/or method information that defines the behavior of the biological system. In various embodiments, the consumables and/or methods are stored in the form of ASCII text files. In various embodiments, the general purpose computer uses the FTP protocol to transfer the ASCII text files to the system. In various other embodiments the method and/or consumable information is stored in and read from the identifier. The method and/or consumable information can be stored in the form of an ASCII text file in the identifier, but it is understood that the information can be represented in other data formats without departing from the present teachings.

According to various embodiments, the consumable, macro, and/or method information includes parameters that can be used by the system data acquisition and control software to perform specific data acquisition and system control operations. In various embodiments, the method and/or consumable information contains sequences of operations to be performed by the system or control parameters for use in connection with the data acquisition or control software.

(ii) Assay Process Information

In addition, the consumable data can include assay process information concerning the individual assay parameters that should be applied by the system or assay reader during the assay. For example, such consumable data can include a sequence of steps for a given assay, the identity, concentration and/or quantity of assay reagents that should be used or added during the assay or during a particular step of an assay, e.g., buffers, diluents, and/or calibrators that should be used in that assay. The consumable data can also include the type or wavelength of light that should be applied and/or measured by the system or assay reader during the assay or a particular step of a multi-step assay; the temperature that should be applied by the system or assay reader during the assay; the incubation time for an assay; and statistical or other analytical methods that should be applied by the system or assay reader to the raw data collected during the assay.

In one embodiment, one or more steps of an assay protocol can be tailored to an individual consumable or lot of consumables. One or more steps of a protocol can differ from consumable lot to lot and/or from individual consumable to consumable within a given lot and the consumable data stored to the system includes instructions to tailor those steps of the assay protocol. This type of consumable data can be used by the system to adjust one or more operations performed by the system before, during and/or after the conduct of an assay by the system. Moreover, this type of consumable data can optionally be adjusted by the system user at the user's discretion. For example, dilution steps in an assay protocol can be adjusted to account for lot to lot or consumable to consumable differences. The amount of diluent added and/or the nature of the diluent can be altered based on such differences. Similarly, the amount of a given reagent that can be added during the conduct of an assay, an incubation period and/or temperature for one or more steps of an assay can also be dependent on lot to lot or consumable to consumable differences. Each of these are non-limiting examples of consumable data that can be saved to the storage medium of the system.

Moreover, the consumable data comprises information that directly or indirectly controls a component of the assay system, e.g., one or more photodetectors, a light tight enclosure; mechanisms to transport the assay consumables into and out of the assay reader; mechanisms to align and orient the assay consumables with the one or more photodetector(s) and/or with electrical contacts in the assay reader; additional mechanisms and/or data storage media to track and/or identify assay consumables; one or more sources of electrical energy to induce luminescence; mechanisms to store, stack, move and/or distribute one or more consumables; mechanisms to measure light from a consumable during the assay sequentially, substantially simultaneously or simultaneously from a plurality of test sites of the consumable; or combinations thereof.

The consumable data can also include assay process information comprising assay parameters to be applied by the assay reader during the assay; a sequence of steps to be applied by the assay reader during the assay; the identity, concentration, and/or quantity of assay reagents to be used or added during the assay; the type or wavelength of light to be applied and/or measured by the assay reader during the assay; the temperature to be applied by the assay reader during the assay; an incubation time for the assay; statistical or analytical methods to be applied by the assay reader to raw data collected during the assay; or combinations thereof (such assay process information can optionally be adjusted by the user). In one specific embodiment, the assay conducted with the consumable is a multi-step assay and the assay process information relates to a step or step(s) of the multi-step assay. In this embodiment, the consumable/test site information comprises information concerning assays previously performed by a assay reader on one or more test sites of the consumable; information concerning assays to be performed by an assay reader or a component thereof on one or more test sites within the consumable; or combinations thereof.

The consumable data can additionally include information regarding a consumable, test site, domain, sector, or a biological reagent or sample as individual operations are performed on that consumable, test site, domain, sector, or biological reagent or sample, for example during manufacture of the consumable, test site, domain, sector, or biological reagent or while an assay or step is being performed on the consumable, test site, domain, sector, or biological reagent or sample. For example, if an assay consumable includes a plurality of assay test sites, domains, and/or sectors, the assay system can perform an assay or step of a multi-step assay on a single test site, domain and/or sector of the assay consumable. Once that assay or assay step is completed by the assay system, the controller records the results of that assay, e.g., the raw or analyzed data generated during the assay or assay step, to the identifier, and/or the controller records which test site, domain and/or sector of the assay consumable were used during the assay or assay step and/or which test site, domain and/or sector of the assay consumable have yet to be used. The assay consumable can be stored for later use and when the customer is ready to use another test site, domain and/or sector of the assay consumable, the controller reads the consumable data stored on the identifier of the assay consumable to identify which test site, domain and/or sector has been used, has yet to be used, and/or the results of those assays. The controller can then instruct the assay system, assay reader or component thereof to conduct an assay or assay step on an unused test site, domain and/or sector.

In addition, a given assay protocol can require a set of consumables of a particular type. Therefore, if the customer inputs a specific type of assay consumable, e.g., a multi-well assay plate, for use in a particular assay protocol, one or more additional assay consumables can be required to carry out that assay protocol in the system, e.g., one or more reagents can be required for use with that multi-well assay plate. Each of the required consumables can include a consumable identifier with information concerning the consumable requirements for an assay protocol. When one of the required consumables is input into the assay system and the identifier controller interacts with the consumable identifier for that consumable, the system will take an inventory of the components present in the system and compare the results to the consumable requirements associated with the consumable identifier and/or stored to the storage medium and/or provided as consumable data. If any required consumables are not present or are present in insufficient supply, the system will prompt the customer to input the additional required consumables for that assay protocol based on the information stored on the required consumable identifier. If two or more assay consumables are used in the system, the instrument will correctly identify a first assay consumable and any associated consumables based on the consumable requirements associated with the identifiers associated with each consumable. The system will verify that the assay consumable and associated consumables are loaded on the system before the sample is run. In the case where only the first assay consumable is loaded into the system without the corresponding associated consumable, the system will prompt the customer to load the associated consumable if the instrument does not identify the associated consumable within the system within a predefined period of time. The system will notify the customer if mismatched assay consumables are loaded on the instrument. The system will not run samples if there are no available matched sets of assay consumables (e.g., multi-well assay plates and given reagents for a particular assay). The system will check for assay consumable expiration prior to the start of an assay and the system will alert the customer and prevent the use of an expired consumable. The system will not process a sample if the consumables have expired prior to sample aspiration. If a partially used assay consumable is installed into a different instrument, consumable usage will automatically start with the next available unused well.

The identifier can also be used to track the time a given assay consumable is present in the assay system. Therefore, when an assay consumable is inserted into or contacted with an assay system, a timer is initiated in the assay system and the start time is recorded to the identifier. When the assay is initiated by the system on the consumable or a test site, domain and/or sector within the consumable, the time is also recorded to the identifier. If the instrument, system or a component thereof is shutdown (e.g., by turning the power off), the timer is stopped and that time is recorded to the identifier. Thus, whenever the timer is stopped, the accumulated onboard time is recorded to the identifier.

(iii) Analytical Tools

In another embodiment, the consumable data further includes one or more analytical tools that can be applied by the system to analyze data generated during and/or after the conduct of an assay. In addition, such analytical tools can include instructions for the customer and/or the system to generate a specific output by the system software after the conduct of an assay, e.g., a tailored data report and/or format for the results of the analysis based on the consumable data. Alternatively or additionally, the analytical tools can further include one or more statistical algorithms that can be applied by the system to the data. For example, the consumable data can include a selection of two or more statistical algorithms that can be used to analyze data resulting from use of a given consumable and the customer can optionally select the appropriate algorithm for the desired data analysis. The consumable data can also include information that can be used by the customer to select the appropriate algorithm for his or her needs, e.g., technical notes or literature references related to algorithm selection.

Analytical tools can differ from consumable lot to lot and/or from individual consumable to consumable within a given lot. In this embodiment, the consumable data is used by the system to adjust the analytical processing tools applied by the system software in the conduct of an assay or after the assay is completed and the results are generated and/or displayed. Such analytical processing tools include but are not limited to assay thresholds and/or calibration curves that can be applied to one or more steps of an assay protocol that can also be altered based on consumable differences. In a specific embodiment, for a given consumable type and/or desired use, the consumable data can include a project management tool that schedules the conduct of one or more assays or steps thereof using a given consumable in the system or with a set of consumables. Still further, such analytical processing tools can optionally be adjusted by the system user at the user's discretion. Analytical tools can be sent to the customer via a direct or indirect interface between the system and the customer.

(iv) Assay System Maintenance Information

Consumable data can further comprise system maintenance information to the customer, including but not limited to system monitoring reports, system components usage, service history, system troubleshooting information, the results of diagnostics run on the system, control charting, periodic maintenance scheduling, warranty information regarding the system and/or a components thereof, or combinations thereof. The system software can be programmed to monitor various components of the system and automatically or when prompted, send monitoring reports to a remote computing system and/or to a service technician. If a direct interface is not enabled, the system can prompt the customer to send monitoring reports to the CD server via an indirect interface. In addition or alternatively, such system monitoring reports can be accessed by a service technician charged with the task of maintaining and/or servicing the system on site or remotely. In this embodiment, a service technician can communicate with a customer regarding service of or assistance with an instrument via a direct or indirect interface. In a specific embodiment in which a direct interface is enabled, the CD server monitors system component usage and/or warranty information and based on standard system component lifetimes and/or warranty terms, schedules periodic system/component maintenance and/or upgrades by a service technician. However, the system can be programmed to automatically monitor such information on the system and it can periodically prompt the customer to send the CD server the output of such monitoring activities via an indirect interface if a direct interface is not enabled to enable a service technician to assess the status of the system and to determine if system service or maintenance is required. In addition, the CD server can maintain a log of the service history for a given assay system and schedule a service call by a service technician (this can be done using either a direct or indirect interface). The remote computing system can also send an individual assay system software upgrades via a direct or indirect interface.

(v) System-Consumable Promotional Information

In another embodiment, consumable data includes promotional materials, e.g., when a new type or lot of consumables becomes available, especially those products historically used by a given customer. Such promotional materials can also relate to new assay systems, modifications to a current system, and/or optional attachments or improvements to a current system, especially those modifications, attachments or improvements that specifically relate to a system the customer owns or operates and/or those modifications, attachments or improvements that might be of interest to the customer based on that customer's prior usage. Consumable data of this type can also include literature references, brochures, product inserts, technical and application notes, technical presentations, conference information, and promotional seminars, especially those that can relate to one or more consumables/systems used by a given customer. Such promotional information can be provided to the customer via a direct or indirect interface between the customer and vendor.

(vi) Technical Support Information

Consumable data also includes technical support information that can assist the customer in the use of a consumable or system, e.g., product insert and data sheet information, information related to associated products intended to be used with that consumable, instructions for use, training materials, tutorials, recommended usage and/or storage information, data analysis templates, template reports, calibration curves, lot specific QC data, verified limits of quantitation, and trouble-shooting methods and/or algorithms. For consumables that include or are provided with one or more additional consumables, e.g., reagents, the consumable data can also include a reagent catalog number, reagent lot specific information, reagent manufacture dates, reagent expiration dates, instructions for use, training materials, tutorials, recommended usage and/or storage, and the like. Technical support information can also include receiving feedback or assistance via a direct or indirect interface with a technical support representative, e.g., customer training modules, consulting services, and/or live customer service assistance capabilities to facilitate the customer experience (i.e., live-chatting). It will be understood that technical support information can relate to a consumable, system, or both.

In a specific embodiment, Table 1 includes a list of consumable data that can be associated with a consumable identifier and/or exchanged between a CD server and a system via a direct or indirect interface.

TABLE 1

| Types of Consumable Data | Examples of Consumable Data |
|---|---|
| Consumable identification and/or configuration information | Consumable type<br>Consumable description/configuration<br>Consumable lot number<br>Consumable expiration date<br>Certificate of analysis<br>Lot specific quality control data<br>Catalog number<br>Associated consumables<br>Verified limits of quantitation<br>Shipping manifest for complete order<br>Recommended storage conditions<br>Product insert<br>Chain of custody information |
| Assay protocol steps Analytical tools that can be applied by the system | Instructions for use in the system<br>Data analysis templates<br>Report templates<br>Calibration curves<br>Statistical analyses that can be applied to a data set<br>Control Charting<br>Assay thresholds<br>Project management scheduler |
| Assay system maintenance information | Preventative maintenance tips & reminders for system or components thereof<br>Service reminders & scheduling for service visits<br>Warranty information for system or components thereof<br>System software upgrades/patches<br>Service history information<br>Individual system component monitoring and remote maintenance |
| System-consumable promotional information | New consumable and/or system offerings<br>Literature references that relate to customer-system use |
| System and/or consumable technical support information | Product insert<br>Training materials<br>Access to customer support representatives<br>Usage recommendations, e.g., sample type and sample preparation procedures<br>Recommended usage configuration<br>Trouble shooting algorithms<br>Concentration ranges for controls<br>Expected calibration curve data for consumable<br>Recommended calibration curve concentrations for consumable |

D. Specific Embodiments of Data Association Workflows

A specific embodiment of a data association workflow, a process in which certain data are associated with and stored to a consumable identifier, is illustrated in FIG. 11. In the first step of FIG. 11, the vendor receives a request for a consumable, either from a sales order or from an internal request to replenish existing inventory. The vendor maintains a central database (1100) for various types of data, as described herein and the central database also includes one or more processors (1101) configured to process data queries, extract data from one or more databases or data tables within the central database, and generate, send, and/or store data sets in response to a data query. The order (1102) has a unique identifier associated with it, e.g., an order number (1103), and that order number is stored in one or more vendor data tables, e.g., an order data table (1104). Each customer, whether external or internal, is also associated with a unique identifier, e.g., a customer number (1105), and each customer number is stored to a customer data table. The customer data table includes customer contact information, shipping address(es), etc., for one or more individuals or organizations associated with that customer. For example, if the customer is a company with many locations, that customer can be uniquely identified by a single customer number, each associated in the customer data table with the various locations of the company, or each location of the company can be uniquely identified by a single customer number. If the customer is internal, e.g., a department within the vendor's organization, requesting replenishment of consumable inventory, the customer data table can also include one or more subdirectories or data tables for internal departments. Therefore, the customer data table includes the unique customer number for a customer (e.g., customer X), the order data table includes each unique order number (e.g., order Y), and there is also a customer-order association data table (1106) that stores an association between each customer and its orders (e.g., customer X-order number Y).

The order is received by a manufacturing technician and a unique consumable identifier for that specific consumable is created (e.g., as described hereinabove, a consumable identifier (e.g. bar code)) and the consumable identifier is stored to a consumable identifier data table (1107). Therefore, in one embodiment, all data uniquely associated with that consumable is associated with the consumable identifier and it is also stored in the consumable identifier data table. Alternatively, different types of data related to a product, e.g., quality-related data or manufacturing-related data can be stored in individual data-specific data tables and each entry is indexed by the consumable identifier. Thus, either all data uniquely associated with that consumable are stored to the consumable identifier data table or data is stored to a series of individual data-specific data tables indexed by a consumable identifier and if data are needed about that consumable, the consumable identifier is scanned via a consumable identifier controller and the data associated with that consumable are downloaded to a computing system requesting data about that consumable. The system also includes a customer number-order number-consumable identifier association data table (1108), such that for each customer, order and consumable, there is a unique association stored to the data table between customer X, order number Y and consumable identifier Z (customer X-order number Y-consumable identifier Z). Additional unique identifiers can also be associated with an order, e.g., a catalog number, a sales person number, order subcomponents, etc. Each association with the order number can be stored in one or more additional data tables in the system. Based on the type of consumable requested in the order, the technician queries one or more manufacturing and/or order fulfillment data tables in the system to identify the set of consumable data required for the manufacture of that consumable or fulfillment of that order (consumable specification data table (1109)). The data is associated with the consumable identifier, the consumable is manufactured or the order is fulfilled, and an additional set of consumable data associated with the manufacture of that consumable or fulfillment of that order is associated with the consumable identifier. The consumable data associated with that consumable or lot thus far in the manufacturing process is saved to the consumable identifier data table. The manufacturing process can also include a quality control system in which the product is subjected to one or more quality control steps. Unique data stemming from each quality control step performed on the consumable or lot are associated with the consumable identifier and the consumable identifier data table and/or a quality data-specific data table are updated to include this data. The consumable or lot (1110) is then transferred to a shipping department, shipping event-data is associated with the consumable identifier, e.g., packaging date, shipping date, etc., and the consumable identifier data table and/or a shipping-specific data table are updated accordingly.

It should be evident that while FIG. 11 and the accompanying description pertains to a consumable, consumable data, etc., the same process outlined in FIG. 11 can be used to associate data with an instrument, a kit that includes a plurality of components, etc. For example, if the consumable is a kit containing a plurality of components, when the order is transferred to manufacturing and the manufacturing technician queries the consumable specification data table for data concerning how the kit is manufactured, the consumable specification data table will provide a list of the components of the kit and each component of the kit will include a unique component identifier that is associated with the kit identifier in the system.

As described above in reference to FIG. 1, consumable (lot and/or instrument) data is generated by a vendor before, during and/or after the individual consumable and/or lot of consumables are made and/or distributed. The CD creation system generates a database of CD information for that consumable or lot, i.e., a CD database, to which consumable data is stored. The CD database is sent to a CD Server (104) which includes a master repository of all consumable data. In addition, the CD creation system stores information that is used to associate a given consumable identifier with consumable data in the master repository. The CD creation system and/or CD Server are located on a remote computing system, i.e., a computing system remote from the assay system and/or the customer or customer, e.g., a site maintained by the vendor. In one embodiment, the remote computing system is a data hub or cloud-based computing system, e.g., a system hosted by a third party (e.g., Amazon Web Services) but maintained by the vendor. The data hub can include any suitable data structure, e.g., each customer can have a separate data structure on the data hub which is secured and distinct from other customer data structures on the data hub. As illustrated in FIG. 2, upon receipt of an order from a customer or when the consumable or lot is manufactured (step i), the vendor generates, stores and sends a CD database to the CD server (201) on the data hub (step ii). The CD database can include order fulfillment information, i.e., a summary of the components of the order for a given customer so that the system can verify that all components of the order have been supplied to the customer. The customer receives the consumable (202), including consumable identifier (203), and contacts the consumable with the assay system (204) in preparation for the conduct of an assay (step iii), the system reads the information associated with the consumable identifier (203) and that information is used by the system to identify the consumable (202) (step iv). The system reviews the consumable data stored locally on the system in a local storage medium (referred to in FIG. 2 as "local CD") to identify that consumable data stored to the storage medium that can be used for the conduct of an assay using a given consumable. If the storage medium includes the consumable data for that consumable or lot, the consumables can be used in the system (step v). If the storage medium does not include consumable data for that particular consumable or lot of consumables, the system can query the customer for that consumable data and the customer can communicate with the vendor to receive the requisite consumable data, e.g., via email, compact diskette, memory card/stick, flash drive, web data storage service, etc. (step vi). The vendor sends consumable data binary files (including but not limited to encrypted XML files) to the customer, e.g., as an email attachment to a customer email account, the customer loads that file attachment to the assay system and the system software stores the consumable data to the local system consumable data repository. The consumable/lot of consumables can then be used in the instrument (step vii).

In an alternative embodiment, the CD server can be connected to the system via a direct interface which can automatically obtain the consumable data from the CD server if it is not available on the system locally. In this embodiment, the vendor generates, stores and sends a CD database to the CD server for a consumable order and/or lot of consumables, as shown in FIG. 2 and as described above. Thereafter the customer receives the consumable, order and/or lot and contacts the system with the consumable identifier to enable the system to identify the consumable or lot. The system software queries the system consumable data repository for the consumable data associated with that consumable identifier and if that consumable data is available locally on the system, the software will adjust the system based on the consumable data, if necessary. If the consumable data is not present in the system consumable data repository, the system will either (i) prompt the customer to manually obtain the consumable data from the vendor, or (ii) automatically, via a direct interface with the CD server, obtain the consumable data from the CD server and store that information locally on the system consumable data repository. Once the consumable data is available locally on the system, the software adjusts the system based on the consumable data, if necessary, and conducts an assay. Once the consumable data is available locally on the system, the consumable or lot can be used in the system to conduct an assay and display the assay results to the customer. In a specific embodiment, the system software adjusts the output to the customer based on the consumable data.

As described above, consumable and/or instrument data can be sent to the data hub via the software so that the vendor can collect data relevant to the customer, instrument, consumable, and/or vendor. The software can be programmed on the instrument to automatically collect this data and/or it can be an optional element selected by the customer upon installation of the instrument. In one embodiment, the following consumable data is collected by the instrument and sent to the data hub: specific consumable identifiers used on an instrument at a customer location as well as the analysis layout for experiments performed using one or more specific consumables. For instruments that are installed on a networked system, i.e., a customer-maintained computer network to which two or more instruments are connected, the software can collect the following consumable data: consumable statistics, e.g., detection signal, CVs, averages, image centers; performance of controls and calibrators, e.g., % recovery, detection signal data; the identity of consumable identifiers uploaded on one or more instruments connected to the network; audit logs; and/or instrument logs.

Figure 11A:
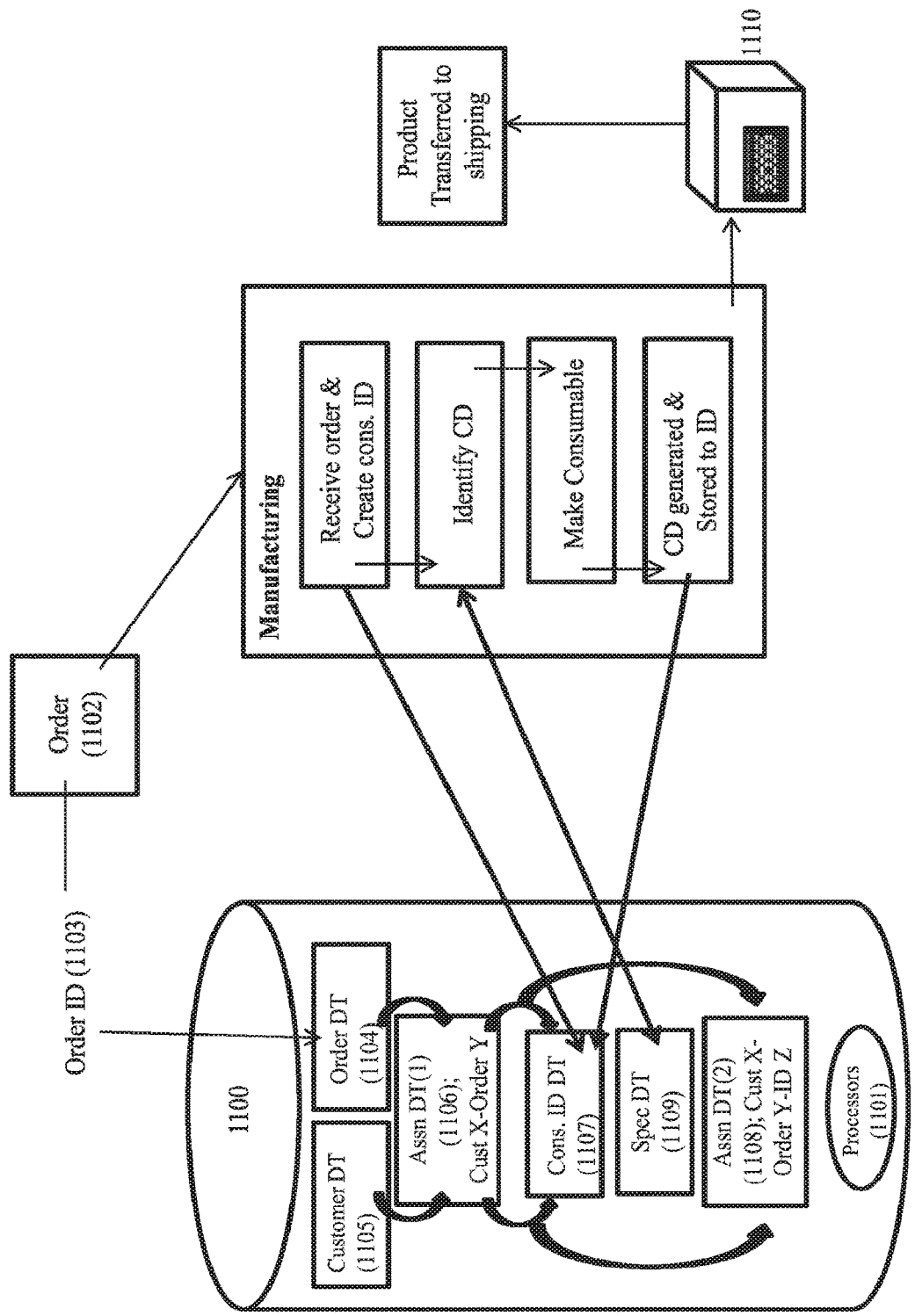
FIG. 11(a) illustrates a specific embodiment of a data association workflow, a process in which certain data is associated with a consumable identifier.
Figure 11B:
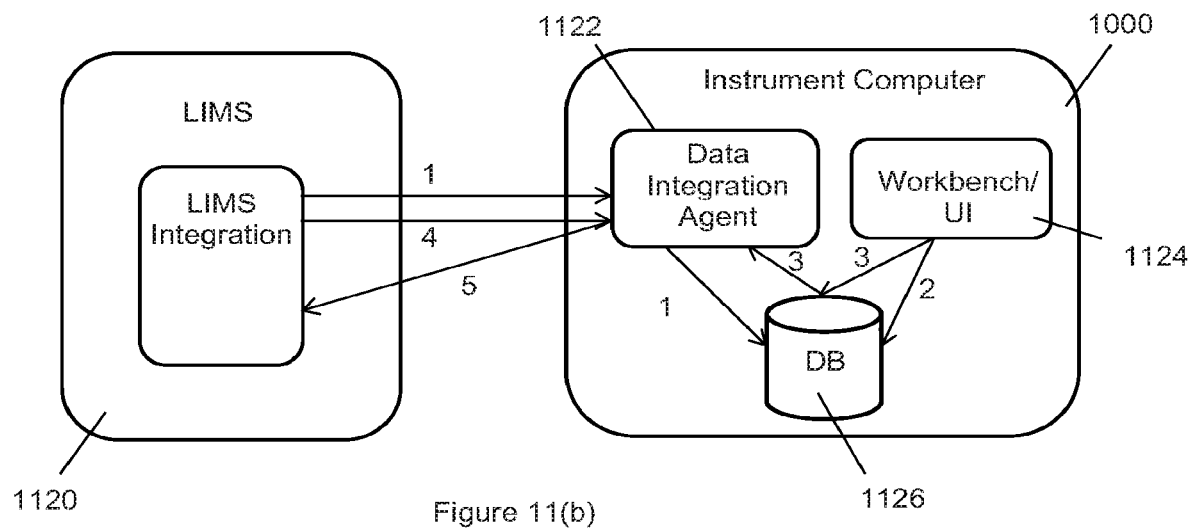
FIG. 11(b) is a diagram showing the interaction between the assay system's computer system and the customer's computer system.

In another embodiment, an exemplary system that coordinates the communication between the processors present in assay system (1000) and the computer located at the user's facilities, also known as the Lab Information Management System (LIMS), is shown in FIG. 11(b). LIMS (1120) is linked to the various processors in assay system (1100) through Data Integration Agent (DIA) (1122). DIA (1122) is preferably an API (Application Programming Interface) and is the interface between LIMS (1120) and the Workbench software (1124), such as the user interface (UI) and the database (DB) (1126).

To initiate an assay run, LIMS (1120) sends a request (arrow 1) to DIA (1122). DIA (1122) then forwards and/or translates request (arrow 1) to DB (1126). Workbench (1124), which is connected to DB (1126), uses the UI to guide the user/lab technician through the assay protocol(s), and assay system (1000) or another assay system (900) runs the immunoassay and reports the results to DB (1126) as raw ECL data (arrow 3) and/or as ECL data with analysis (arrow 2) from reader (1003). DIA (1122) retrieves ECL data from DB (1126) and converts the ECL data to XML (Extensible Markup Language) and sends to LIMS (1120) (arrow 5). LIMS (1120) may send queries to DIA (1122) through connection (arrow 4) concerning the status of the assay run.

Figure 11C:
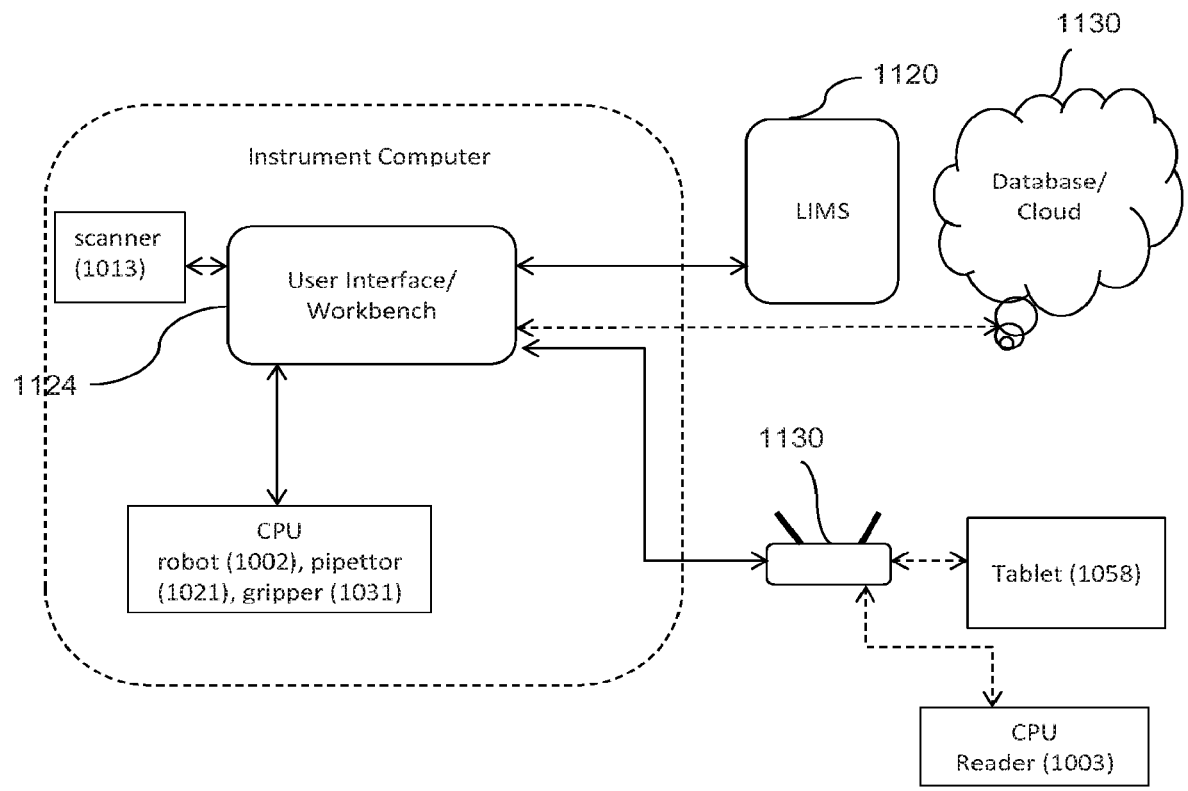
FIG. 11(c) is a diagram of the components of the assay system's computer system.

FIG. 11(c) illustrates the relationship between Workbench/UI (1124) with the other systems and processors in assay system (1000). Workbench/UI (1124) is connected to the components that have their own processors, such as robotic system (1002) which includes pipettor (1021) and gripper pads (1031). Workbench/UI (1124) is also connected to tablet (1058), which actually displays the UI, and the processor of reader (1003), either by wires or preferably wirelessly through router (1130). As discussed above, Workbench/UI (1124) is also connected to LIMS (1120). A bar code scanner or consumer ID controller (1013) would read a consumable identifier (e.g. bar code) or unique ID from any labwares or assay kit. As discussed further below, the consumable identifier (e.g. bar code) or unique ID would inform Workbench/UI of the type of labware or assay to be run from the kit. If any additional information or data is necessary, it can be downloaded from an external server or the cloud (1130).

The software that runs assay system (1000) comprises three major components:

(i) the user interface (UI), which guides the user through the process of selecting, loading and running an immunoassay, described herein (ii) the instrument control system, which controls the workings of the robotic system (1002) and the operational and performance qualification, as well as the reported errors, and (iii) the data services, which save the ECL results and user preferences, described above in connection with FIG. 11(b).

Figure 11D:
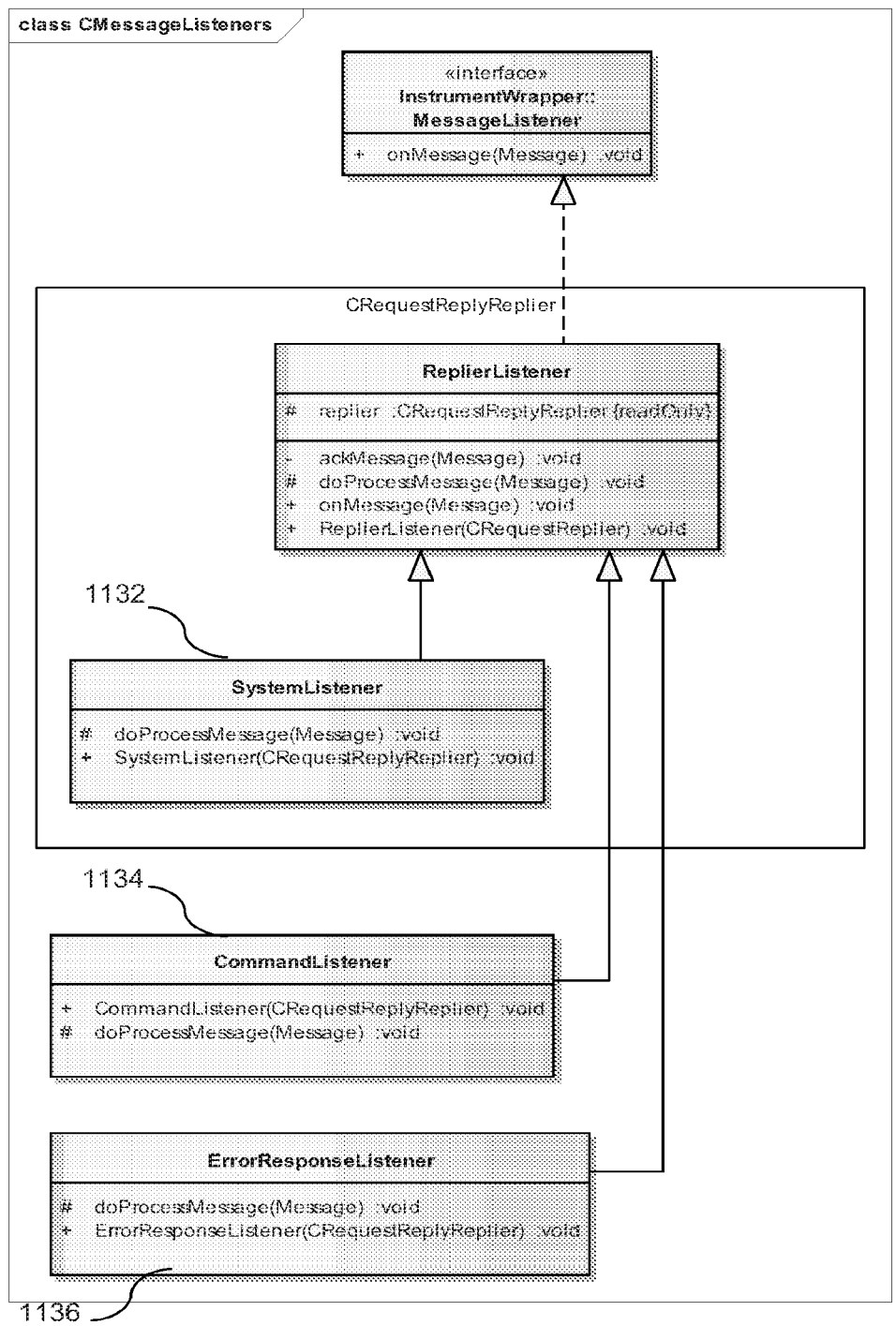
FIG. 11(d) is a flow chart of the instrument control portion of the software.

Referring to FIG. 11(d), the Workbench/UI would send a request to the instrument control system, which has three listening modules: (i) the system listener (1132), the command listener (1134) and the error command listener (1136). System listener (1132) listens for requests during the qualification of the assay system before use and during regular maintenance, which are described below in connection with the operational and performance qualification system. Command listener (1134) listens for requests to instruct the robotic system, including pipettor (1021) and robotic gripper pads (1031) to perform the steps of the immunoassay. Error Response Listener (1136) listens for error codes broadcast from the various components of the assay system (1000).

Errors are classified into three types: (i) unrecoverable errors that result in data losses, such as communication error with reader (1003), (ii) unattended recoverable errors, which are errors detected by software but does not require user intervention to recover, such as single sample not detected and (iii) interactive recoverable errors, such as the doors to assay system (1000) were not properly closed. Preferably, an error would return a flag in the result file and would produce a visual or audio alert. In the event of a power loss, the instrument control portion of the software would take control of shutting down the instrument using a universal power system (UPS), which should be stored in the instrument.

In accordance with another aspect of the present invention, the UI portion of the software is built using plug-ins, also known as applications or applets. Once an assay system is validated or qualified, operators generally do not want to re-validate or re-qualify the system due to a software update. Re-validation is necessary when the components of a software system are interconnected. In other words, when one component depends on inputs or instructions from other components in order to function then the components are interconnected. Hence, an inventive feature of the UI or Workbench is that its components are decoupled from each other. This means that each component can be a standalone piece of software. These standalone pieces only need minimal instructions from a master organizer to execute.

Figure 11E:
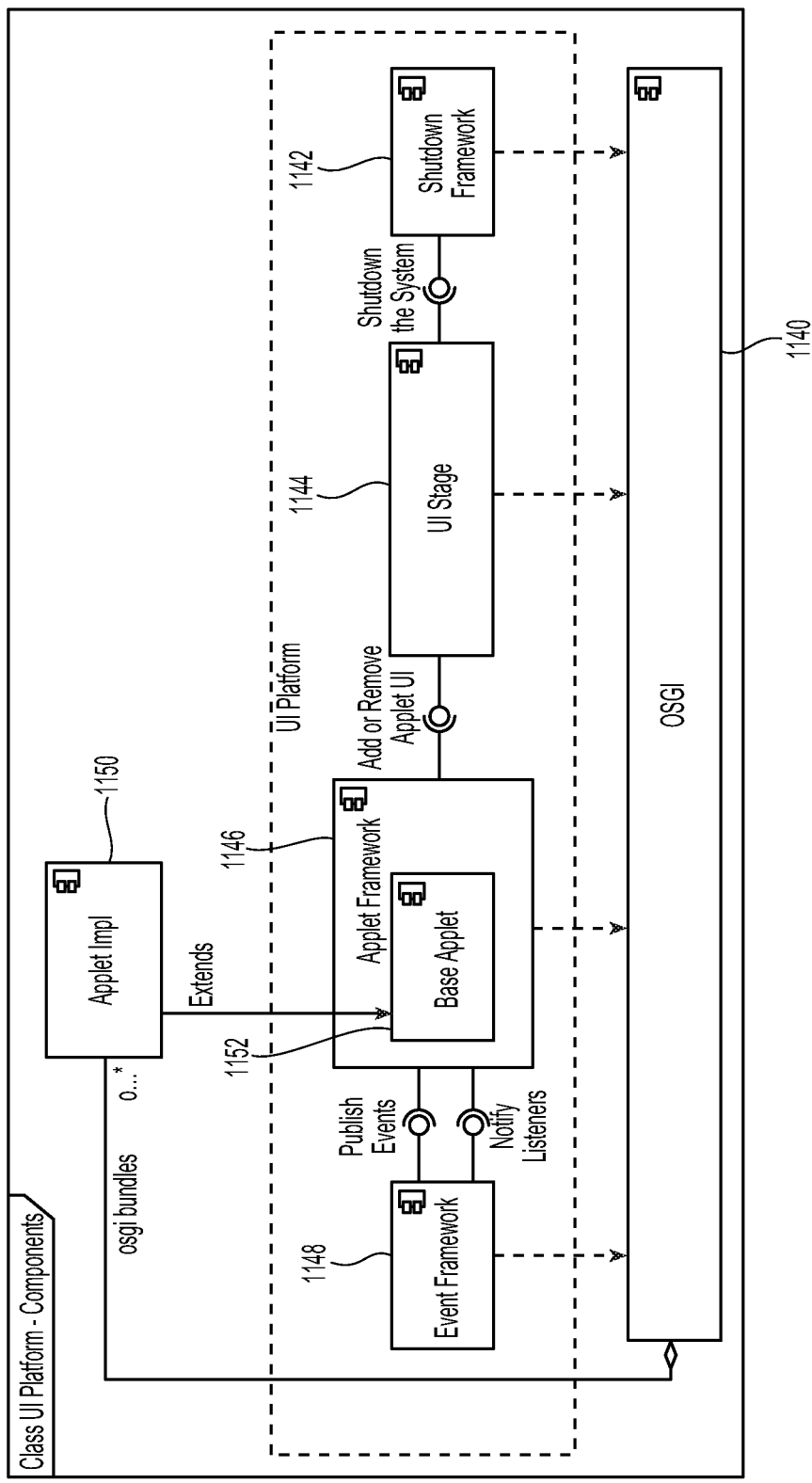
FIG. 11(e) is a diagram showing an example of the software architecture.

Referring to FIG. 11(e), a master organizer (labeled as OSGI) (1140) is connected to the components of the UI platform. In this embodiment, master organizer (1140) is shown as a bus or a message bus, and is connected to a number of components, such as security/log-in/log-off component (1142), UI (1144), application framework (1146) and event framework (1148). Other components, such as the instrument control component and data services component discussed above, can connect to the master organizer bus (1140).

Master organizer (1140) operates similar to a traffic controller and sends start or shutdown request to each component when it is necessary to operate or shutdown that component. Communications among the components are conducted through the master organizer bus, except that master organizer (1140) may instruct components to send information or data to each other. For example, in FIG. 11(e), the event frame work (1148), which creates and maintains a log file of events during an assay run, may publish or notify significant events, such as the reading of an assay plate, to the application framework (1146), when directed or requested by master organizer (1140). The publication or notification would not occur without master organizer (1140).

These communications between components do not rise to the level of connectedness that requires a revalidation of the Workbench/UI platform if one component requires a software update. Alternatively, master organizer (1140) may also act as a conduit to pass through data from one component to another.

An application can be created by an application implementation (1150) which obtains the codes from a storage medium, such as base application (1152) which may reside in application framework (1146). Base application (1152) stores codes that can be accessed by application implementation (1150) to be used by the UI during an assay run. The application created by application implementation (1150) may be kept or removed when master organizer (1140) directs shutdown framework (1142) to shut down, as illustrated in FIG. 11(e). Application implementation (1150), which is shown to be outside of the UI platform, can be another software component connected to the master organizer bus.

Due to this decoupling architecture, if one component needs a software update, that one component should be revalidated, but not the entire software system.

In another embodiment, the other major components may have a similar architecture. For example, the instrument control component may have its own internal master organizer to control the traffics among its internal components that have a processor, such as robotic system (1002), pipettor (1021), robotic grippers (1031), plate washer (1005), tablet (1058), reader (1003), etc. A software update to one of the instrument control's internal components would not require a revalidation of the instrument control and not require a revalidation of the assay system (1000)'s software.

The major software components, i.e., the workbench/UI, the instrument control and the data services, can also be connected to the master organizer and share the same software architecture.

An example of a UI is shown below.

| | |
|---|---|
| START | Create new Assay Run, or Continue an in-progress Run |
| DEFINE | a. Identify Assay Methods to Run<br>b. Identify Samples to be Processed |
| EXECUTE | Collect/Gather components required for Run from various storage locations, cold-storage and non-cold storage |
| PREPARE | a. Lead user through a step-by-step process of preparing an Assay Method to be ran with a set of Samples<br>b. Lead user in loading up the Sample Cart |
| LOAD | a. Lead user through a step-by-step process of loading the P5 hotel with the components previously prepared and loaded on Sample Cart<br>b. Lead user through a step-by-step process of loading/prepping bulk solutions and emptying waste |
| RUN | a. Run the Samples with the associated Assay Methods on the P5<br>b. Provide status and error updates on device and via message (on P5 computer, as well as email or text message for remote notification)<br>c. Present time remaining in Run |
| UNLOAD | Lead user through a step-by-step process of unloading the P5 hotel and emptying waste |
| REVIEW | a. Present data to the user for 1 or more plates<br>b. Provide "heat map"<br>i. Either as Signal or Concentration in the case where calibrators were ran<br>ii. Provide data in log or linear |

The major components of the UI are shown on the left column, and the steps within each component are shown on the right column. The UI walks the users through these steps to conduct an assay.

FIGS. 12(a)-(l) illustrate an exemplary software framework for collection, deployment and location of Global Product Data (GPD) for multi-well assay kits and plates available from Meso Scale Discovery, Rockville, Md. While the following description and the accompanying figures specifically relate to plates and kits, it will be understood that the software framework and methods described herein are also applicable to assay systems, instruments, and additional assay consumables beyond plates and kits.

The GPD is associated with a consumable identifier, e.g., a Global Product Identifier (GPI). A GPD is a flexible data container comprising a set of consumable data as described herein, which can include the following non-limiting list of data for a given consumable, e.g., a plate, assay reagent container (reagent rack), or assay kit:

Physical consumable properties, e.g., plate properties like plate type, geometry, graph
Image processing parameters
Detection parameters
Plate coating, assay assignment
Partial plate information
Recommended sample layout
Assay protocol
Assay workflows or scripts and instrument parameters associated with GPI
Contents of a test kit like product insert, reagents
Recommended analytical information like fit curves Recommended reports Customer order information like expiration of consumables, consumable lot information, etc.

As shown in FIG. 12(a), a data deployable bundle (DDB) is a container configured to organize and collect related consumable data, e.g., data related to an individual consumable. A DDB is assembled by a vendor and deployed to vendor software products. DDB provides a framework to deploy new information or data to a customer, e.g., the software package operating on a customer assay system. A GPD is one example of a DDB. Some additional examples of DDBs include but are not limited to new assays, new plate types, new consumable types, etc. Different types of products, e.g., consumables and instruments or assay systems, are each associated with a different DDB. For example, an assay system includes a unique identifier, as described above, and that identifier is associated with a DDB for that assay system, which can include but is not limited to, system identifier authentication, assay system information, and other technical data related to the assay system, for example:

Physical system properties, e.g., system components, configuration, etc.

Subsystem properties, configuration, etc.

Associated consumable types

Workflow wizard used to guide user through system use

Customer order information like system manufacturing information, etc.

Each DDB has a DDB identifier (UID), a version number and a deployable bundle description file. The UID and version number together uniquely identify a DDB. The description file describes the DDB contents and the instructions for processing the DDB, including a description of steps required to integrate the DDB into the local assay system software package. The DDB provides the deployment framework for distributing a GPD. Data contained within the DDB can be in separate file structures or in one file structure. The format of the files can be XML, key-value pairs, etc. The DDB can be distributed via multiple forms such as a vendor e-commerce site or an email attachment.

As shown in FIG. 12(b), to install the DDB, the file is placed in the specified directory locally on the assay system. Using a Plug and Play framework, the local software system detects the bundle, and processes it for incorporation into the software. The local software contains a registry which is a directory that lists information about services and data available on the software. The DDB registers what data is available from itself with the registry and the DDB instructs the local software how it should be processed. The DDB also includes a filtering processor that controls the data that is exposed in the registry and the properties of the exposed data, e.g., in order to resolve or remove data conflicts that might occur from one DDB to another, e.g., from one plate to another.

The DDB includes a unique DDB UID and version. As shown in FIG. 12(c), a DDB can include data that will be persisted to the local data store, e.g., the DDB UID and version. Data is persisted in order to efficiently access types of data required during system operation if the DDB includes a large dataset. Data is persisted by identifying one or more data types in a DDB and storing that data in a local database that is structured for a type(s) of data. In one embodiment, the entire contents of a DDB are persisted, i.e., locally restructured in separate datasets. In a specific embodiment, the DDB UID, version, plate static data (data about the plate type), and/or plate processing data (data used to process and/or run a plate) is persisted. In a further specific embodiment, the DDB UID, version, and plate static data is persisted. During DDB installation, the software determines if a DDB has data to persist and if the data has already been persisted by using the DDB UID and version. After persisting DDB data that needs persistence to the data store, the DDB UID and version is saved to track what has been stored. This eliminates unnecessary data store operations on the same DDB by detecting that the data has already been stored.

In general, software understands and works with a specific version of data format. The DDB framework supports different versions of data format and different versions of software working together for easier maintenance. FIG. 12(d) illustrates how different software versions of DDB can coexist in the software. As shown in FIG. 12(d), the software is configured to upgrade previous data format versions and the software is backward compatible with older DDB versions. Likewise, the DDB may provide downgrades to previous data format versions. By providing downgrades, the DDB can be backward compatible with previous software versions. Thus, in the framework illustrated in FIG. 12(d), DDBs do not need to be re-released to work with new software versions and one DDB can be created that works on multiple versions of software. The DDB files are upgraded and/or downgraded, as needed, one or more files are locally stored and/or persisted, and a DDB processor (factory) transforms the raw class data into a data type or format that can be used by the software to perform an assay or assay step on the assay system.

As shown in FIG. 12(e), a typical DDB for a plate can include the following consumable data:

The plate static data contains data about the plate type. These are the properties associated with a physical plate regardless of the type of instrument that will be used to process it. Some example properties:

Number of columns/rows of wells

Number of spots per well

The plate processing data contains data used to process/run a plate. The plate processing data is typically instrument specific. Some example properties:

Number of sectors/circuits

Detection parameters used to read the plate, e.g. camera binning, waveform, etc.

Image processing properties used to produce ECL results

Plate type gain

Spot gain

Optical cross talk matrix

The kit contains data such as assays, and the kit information. Some example data would be:

Assay spot assignment

Assay protocol

Data analysis parameters

Product insert

The lot contains specific data for a test kit or plate created for an order.

Figure 12F:
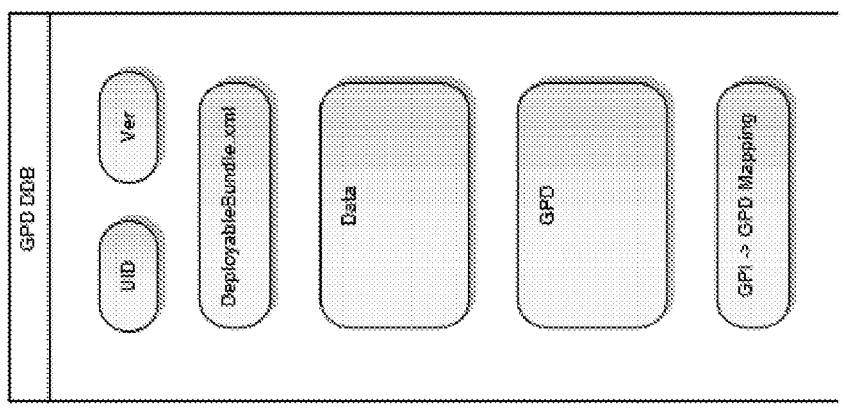
FIGS. 12(a)-(l) show one embodiment of the software architecture for deployment and use of a data deployable bundle (DDB).
Figure 12G:
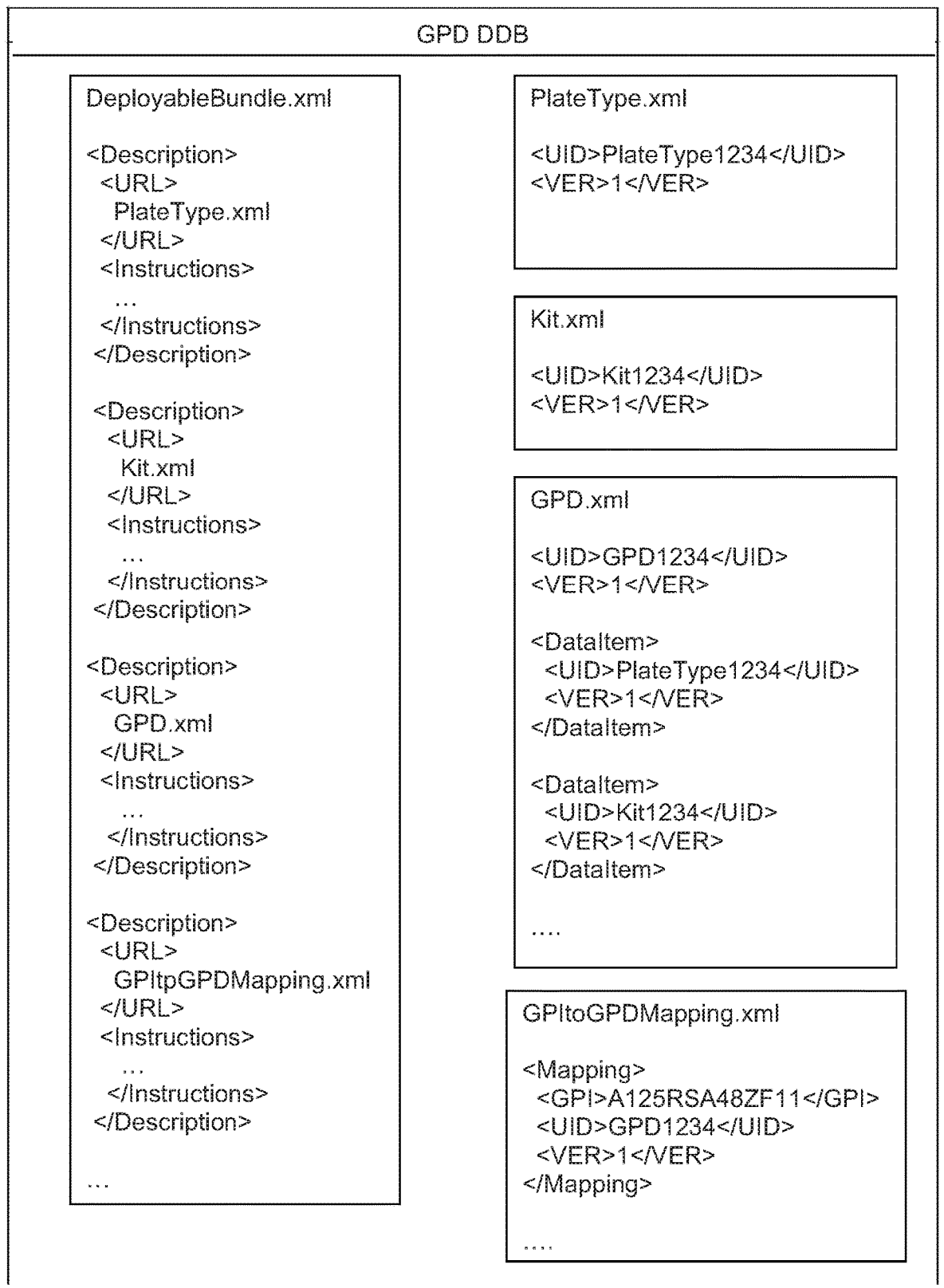

FIG. 12(f) illustrates an example of how a GPD DDB is deployed and FIG. 12(g) is a diagram of one example of the DDB xml and the files within a GPD DDB. As illustrated in FIG. 12(g), the DDB xml describes the data within the DDB and how to process it, the GPD is a container of data that references the data by UID and version, and the GPI to GPD mapping provides the indexing data for the associated GPI. In addition, FIG. 12(g) shows that other data can also be bundled inside the DDB.

Figure 12I:
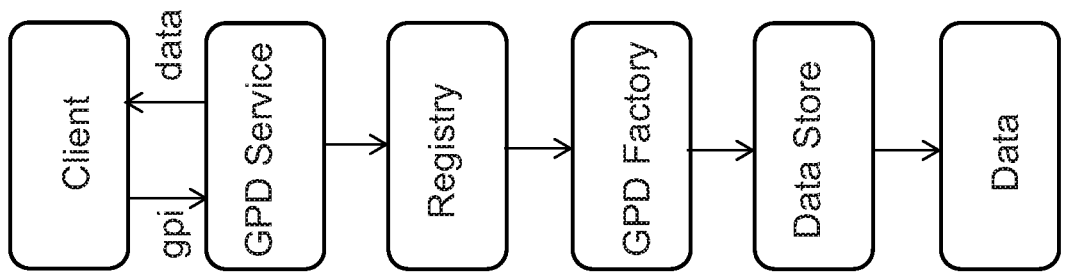
Figure 12H:
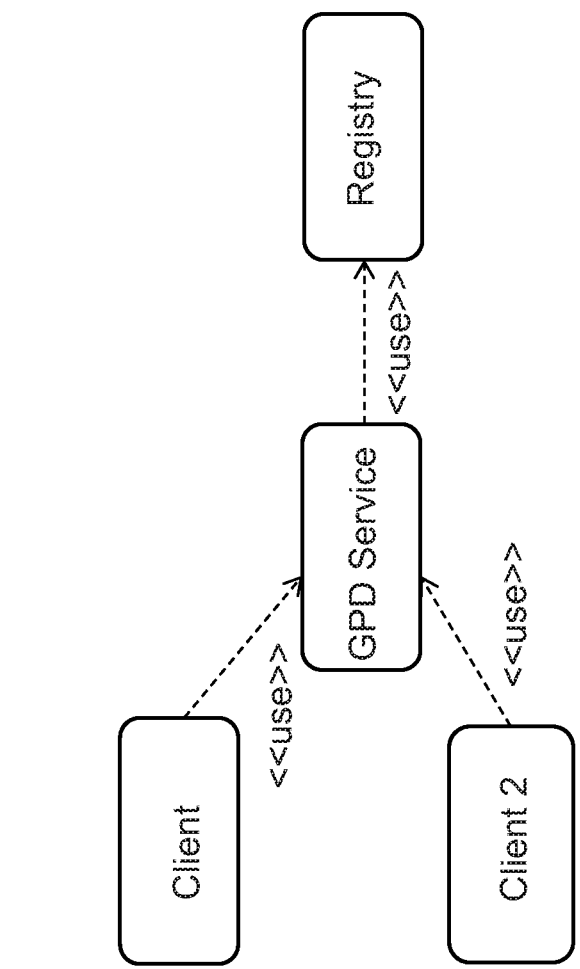
Figure 12I:
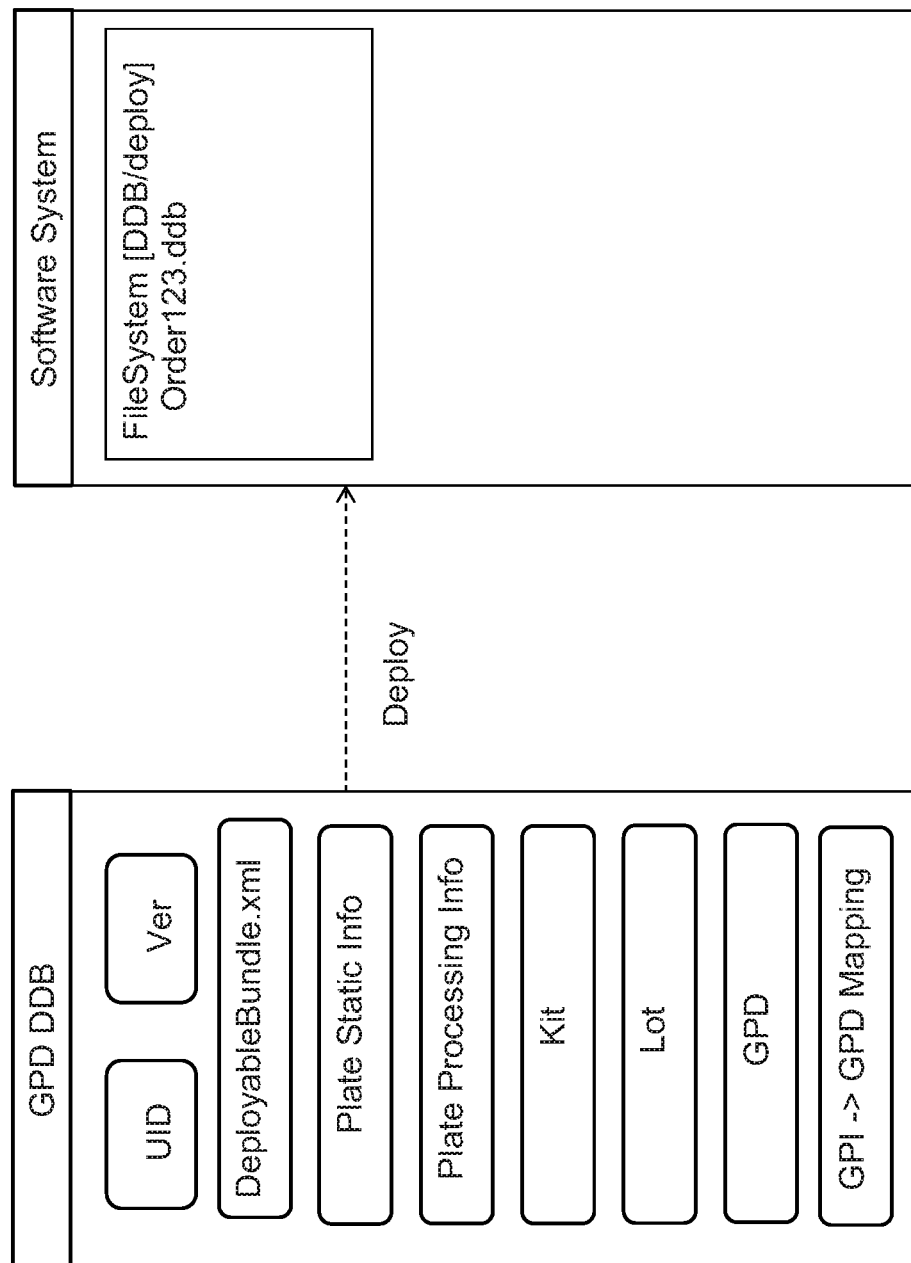

FIG. 12(h) shows how GPD data is located. The software includes a GPD service processor that interacts with the registry to locate GPD data. Using the GPD, the software identifies the type of data needed for a given consumable and the properties of the data and filters the registry for the required data. As described above, if the required data is not included in the local registry, the GPD service queries the Master Repository for the required data and downloads that data locally. Most searches use the UID as a search criterion and a UID can be obtained from the GPI to GPD mappings. A GPD factory takes a UID and retrieves the GPD data from the appropriate data store for the system software (in the example illustrated in FIG. 12(h), Client 1 is e.g., assay system software, and Client 2 is, e.g., an associated stand-alone software system that provides the user-interface functionality of the software in Client 1, e.g., at a remote laptop or desktop computer). Below are two possible options of how the search for data can occur:

(a) A DDB registers all the data it provides. The GPD Service asks the registry for matches. Some aspects of this searching approach include but are not limited to:
- The registry contains many entries and all data is directly accessible through the registry.
- Search may be slow depending on the registry implementation.

(b) A DDB only directly registers a select subset of data items. It also registers a search provider which can be used to locate data instead of exposing all available data directly. The GPD Service indirectly uses a DDB's search provider by going through the registry. The aspects of this searching approach include but are not limited to:
- The DDB manages the data it provides, hiding or filtering details it does not need to expose.
- Less information is published to the registry making it smaller.
- This approach is well suited for factories and resource constrained systems.

These search options are not mutually exclusive. A GPD service implementation can support both and allow each DDB to define what is exposed.

FIG. 12(i) illustrates option (b), in which a factory is responsible for accessing the final data. In this example, the assay system software interacts with the GPD Service to access the data and the GPD Service internally uses a registry to search for the requested data or a GPD Factory that can provide the data. The GPD Factory is registered as a provider of the data and it retrieves the data from a data store and returns it.

For example, a vendor manufactures a lot of consumables, e.g., plates, each plate having a GPI. There will be a DDB for that lot of consumables and that DDB has a single UID and all GPI within that lot, no matter how large the lot, will be associated with that individual lot-specific UID. When a consumer purchases a plate that is a member of that lot and the plate GPI is read by the assay system, the software identifies the type of data needed for that plate and the properties of the data and filters the registry for the required data. As described above, if the required data is not included in the local registry, the GPD service queries the Master Repository for the required data and downloads that data locally. Using the GPI, the software queries the local and remote databases for that UID and it locally installs the required GPD which can be immediately used to process that individual plate or used at a later time if another plate from the same lot is processed by the system.

Figure 12K:
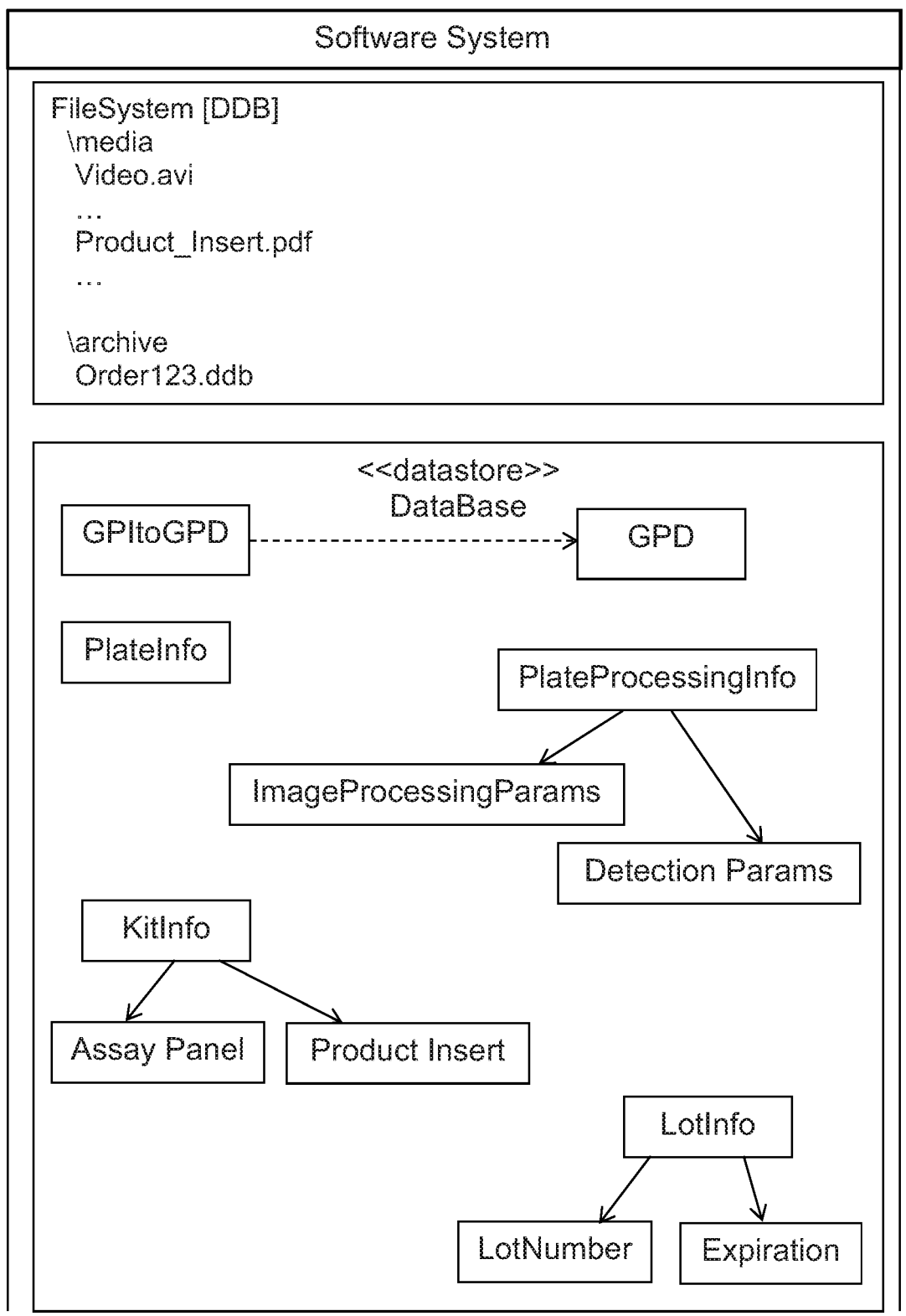
Figure 12I:
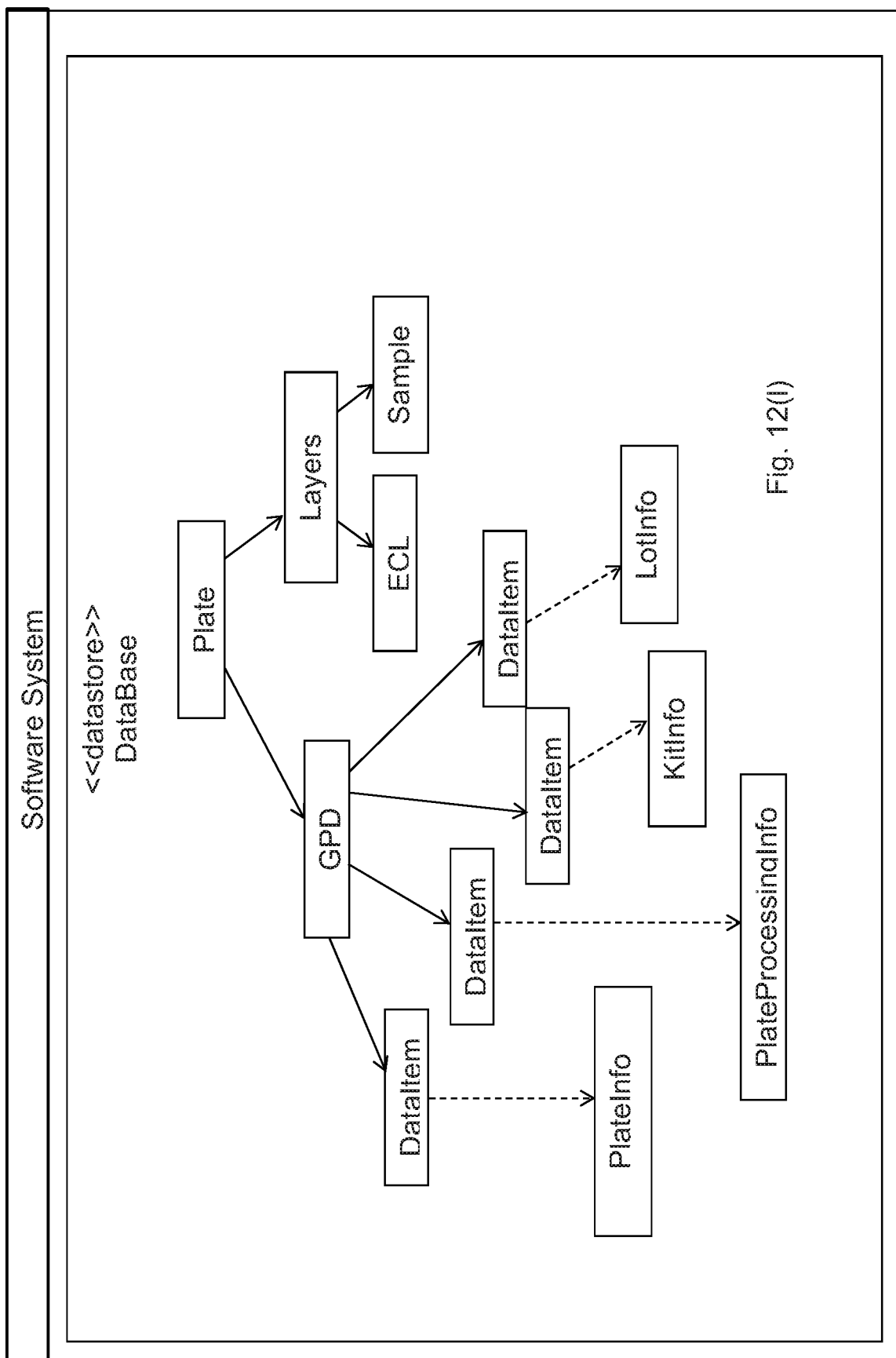

As shown in FIGS. 12(j)-(l), a GPD goes through different stages in its lifecycle from installation to retirement of the data. These stages include but are not limited to:

All data for the DDB is gathered and packaged into one DDB file for deployment.

The DDB file is delivered to the software in an agreed upon directory.

The DDB instructs the software on what needs to be done. It controls how it should be processed.

The GPD data is extracted and stored in the software system according to the instructions. The UID and version are used to track whether the GPD data has been previously processed and can be skipped.

Some GPD data will be extracted to the file system as appropriate and the location of the data is saved in the database.

The rest of the data is placed in the database.

Once the file is processed, it no longer has any data that is not already in the system and it will be moved from the deploy directory to an archive/backup directory.

Software clients use the GPD Service to retrieve GPD data.

Using the GPI to GPD mapping, the software is able to determine which GPD data should be used with a given plate.

After a read, the software plate data storage will contain a read-only copy of data from the GPD for the plate and the generated data from processing it.

An example of the interaction between GPD-DDB and GPI is discussed below.

The GPD may include a generic assay protocol, e.g., the steps in an assay, that contains all the steps for a number of assays preferably within one type of assay, e.g., immunoassays which include pharmacokinetic assays, immunogenicity assays, U-PLEX, V-PLEX assays and other types of assay. Certain specific assay protocols within one type of assays may not need all of the steps in the generic assay protocol. Instead of preparing unique assay protocol for each specific assay, the inventive GPD includes a generic assay protocol as well as an instrument parameter file associated with the GPI of the specific assay.

Figure 12P:
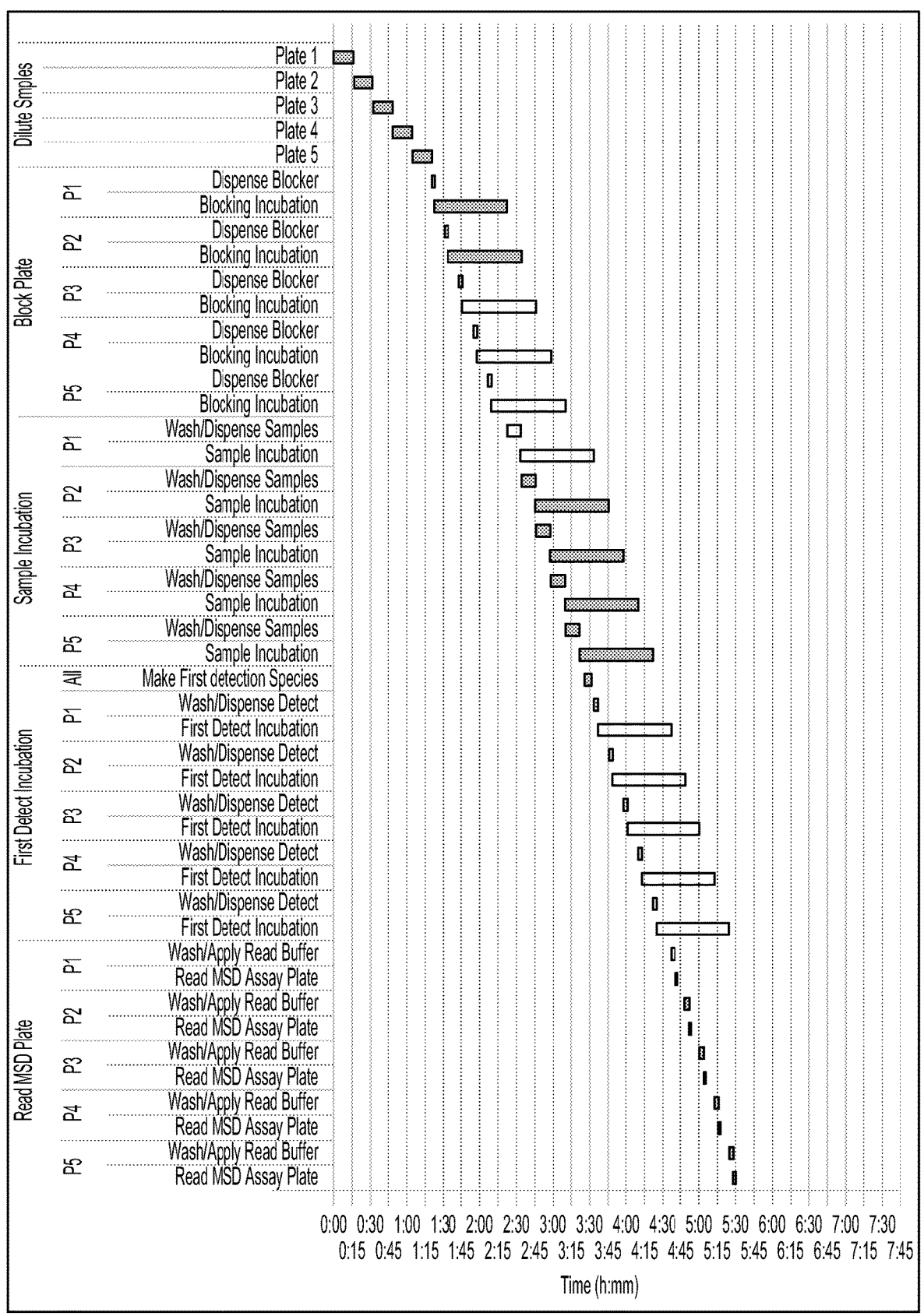
FIG. 12(m) is a script showing an exemplary generic protocol.
FIGS. 12 (n)-(p) show the scripts of FIG. 12(m) with selected steps in the protocol turned OFF.
FIG. 12(q) is an exemplary instrument parameter file showing the ON/OFF status of certain steps in a protocol.
FIG. 12(r) is another example of a generic protocol.
FIG. 12(s) is the generic script with certain steps turned OFF.

As shown in FIG. 12(m), a protocol or script of a streptavidin plate, indirect assay is shown. This protocol or script contains a number of steps, including but not limited to dilute samples for plates 1-5, blocking plates, coating plates, incubating samples, preparing first detect incubation, preparing second detect incubation and reading assay plate. For another assay in this type of assays, the second detect steps are not activated, as shown in FIG. 12 (n). Another assay may not need the coating plate steps, as shown in FIG. 12(o), and another assay in this type of assays may not need the coating plate steps and the second detect steps are not needed, as shown in FIG. 12(p). The table below summarizes the assay protocols in FIGS. 12(m)-(p).

|  |  | Assay 1 FIG. 12(m) | Assay 2 FIG. 12(n) | Assay 3 FIG. 12(o) | Assay 4 FIG. 12(p) |
| --- | --- | --- | --- | --- | --- |
| Dilute samples | Dilute samples in plates 1-5 | ON | ON | ON | ON |
| Block plates | Dispense blocker | ON | ON | ON | ON |
|  | Blocker incubation | ON | ON | ON | ON |
| Coat plate | Create coating species | ON | ON | OFF | OFF |
|  | Wash-dispense coating solution | ON | ON | OFF | OFF |

-continued

|  |  | Assay 1 FIG. 12(m) | Assay 2 FIG. 12(n) | Assay 3 FIG. 12(o) | Assay 4 FIG. 12(p) |
|---|---|---|---|---|---|
|  | Coating incubation | ON | ON | OFF | OFF |
| Sample incubation | Wash-dispense sample | ON | ON | ON | ON |
|  | Sample incubation | ON | ON | ON | ON |
| First detect incubation | Make first detection species | ON | ON | ON | ON |
|  | Wash-dispense first detect | ON | ON | ON | ON |
|  | First detect incubation | ON | ON | ON | ON |
| Second detect incubation | Make second detection species | ON | OFF | ON | OFF |
|  | Wash-dispense second detect | ON | OFF | ON | OFF |
|  | Second detect incubation | ON | OFF | ON | OFF |
| Read assay plate | Wash-apply read buffer | ON | ON | ON | ON |
|  | Read plate 1-5 | ON | ON | ON | ON |

Assay 1: Custom assay, Sreptavidin plate, Indirect assay
Assay 2: Custom assay, Streptavidin plate, Direct assay
Assay 3: Custom assay, Uncoated plate, Indirect assay, Coating offline
Assay 4: Custom assay Uncoated plate, Direct assay, Coating offline In this embodiment, since all the steps in Assay 1 are executed, this protocol could serve as the generic protocol for custom sandwich immunoassay, which includes pharmacokinetic assays. The generic protocol is preferably a part of the GPD. Accompanying the GPD is the instrument parameter file associated with the GPI unique to Assay 1. The instrument parameter file would include a number of flags or switches. Each flag or switch would be ON ("1" or "true") or OFF ("0" or "false"). For Assay 1, all the flags in the instrument parameter files would be ON. For Assay 2, the flags associated with the second detect would be OFF, while the remaining flags would be ON. For Assay 3, the flags associated with the coating of the plates would be OFF, while the remaining flags would be ON. For Assay 4, the flags associated with the coating of the plates and the second detect would be OFF, while the remaining flags would be ON.

The generic protocol would be the same for all of these exemplary Assays 1-4, and other compatible assays in this type of assays, but the instrument parameter files of Assays 1-4, which are much smaller file in size than the generic protocol, are different. An exemplary instrument parameter file is illustrated in FIG. 12(q), which is a computer readable file in text format. A number of flags are located at the bottom of this text file. Some of the flags are ON or true and some are OFF or false. Assays 1-4 include pharmacokinetic assays.

In this embodiment, before a particular assay is run the GPI of this particular assay, e.g., the consumable identifier (e.g. bar code) on the outer box of the kit containing the labwares and consumables for this particular assays, such as the assay kits available from Meso Scale Diagnostics, is read by a bar code reader or other processor. The GPI is mapped onto its associated GPD by the assay system's processor. This processor would then determine whether the generic protocol or script is included in the assay system's processor/memory and whether the instrument parameter file associated with the GPI is already stored in the system's memory. If not, the processor can download the generic protocol, which is preferably stored in binary format to minimize its size, and the instrument parameter file, which can be stored in text format from an external system or server, or from the cloud.

Another table below illustrates another example of the generic protocol or script for the bridging immunogenicity assays and a specific instrument parameter file associated with the GPI for IG assay with acid treatment and another specific instrument parameter file associated with the BPI for IG assay without acid treatment.

|  |  | IG assay with acid treatment- - 5 plate run FIG. 12 (r) | IG assay without acid treatment-- 5 plate run FIG. 12(s) |
|---|---|---|---|
| Setup | Apply acid to all plates | ON | OFF |
|  | Creating drug blend | ON | ON |
|  | Apply drug blend to all plates | ON | ON |
| Sample dilution | Create dilutions for each plate | ON | ON |
|  | Mix on shakers | ON | OFF |
| Block plates | Apply blocker to each plate | ON | ON |
|  | Incubate each plate | ON | ON |
| Interleave acid treatment and sample incubation |  | ON | OFF |
| Acid treatment | Acid treatment set up | ON | OFF |
|  | Acid incubation for plates | ON | OFF |
| Sample incubation | Sample incubation set up | ON | ON |
|  | Sample incubation | ON | ON |
| Test plate incubation | Wash-apply dilutions to test plate | ON | ON |
|  | Sample incubation 1-5 | ON | ON |
| Read assay plate | Wash-apply read buffer | ON | ON |
|  | Read plate 1-5 | ON | ON |

Using the generic protocol for a plurality of assays with individual instrument parameter files with ON/OFF flags uniquely associated with GPI of specific assays provides improvements to the specific computer technology used with immunoassays and more particularly with immunoassays using ECL and with automated immunoassays.

The embodiment of the protocol or scripts shown in connection with FIGS. 12(m)-(s) may represent best practices recommended to the user. The user interface may allow further fine tuning to the user/lab technician by allowing the user a number of options to turn other features ON or OFF immediately before the commencement of an assay run. For the sandwich immunoassays, such as Assays 1-4 discussed above, the user interface may allow one or more of the following non-limiting options to the user/lab technician.

assay type: direct or indirect
plate type
standard curve setup, including number of points on curve, dilution factor, etc.
control setup including number of controls per plate, dilution factor for each control
sample setup, including number of replicates for each unknown and dilution factor for each wash plate: Y/N blocking: Y/N, including blocking volume, incubation time, wash plate afterward coating: Y/N, including coating volume, online/offline incubation, incubation time, wash plate afterward (Y/N)

sample incubation, including sample volume, online/offline incubation, incubation time, wash plate afterward (Y/N)

FOR INDIRECT assays: unlabeled/biotinylated detection species incubation: detection species volume, online/offline incubation, incubation time, wash plate afterward (Y/N)

STAG-labeled detection species incubation: detection species volume, online/offline incubation, incubation time, wash plate afterward (Y/N)

Read buffer incubation: ON/OFF, incubation time

For the bridging immunogenicity assay, the following are some of the user-selectable options.

plate type standard curve setup including number of points on curve and dilution factors, etc.

control setup including number of controls per plate, dilution factor for each control sample setup, including number of replicates for each unknown and dilution factor for each acid treatment (Y/N), including ratio of acid to diluted samples and incubation time sample incubation time, including ratio of mastermix to sample wash late before start (Y/N)

blocking (Y/N), including blocking volume and wash plate afterward (Y/N)

sample incubation on plate, including sample volume, online/offline incubation, incubation time, wash plate afterward (Y/N)

Read buffer incubation: ON/OFF, incubation time

One embodiment of an assay conducted in an assay system illustrated in FIG. 10 and its subparts is shown in FIGS. 13(*a*)-(*f*). FIG. 13(*a*) shows a schematic representation of certain of the subsystems in the assay system (1300) involved in the conduct of an assay positioned on a table or platform (1301), wherein each subsystem is operatively connected to a robotic subsystem (not shown). The plurality of subsystems include an assay reader (1302); an assay consumable storage unit (1303); a plate washing subassembly (1304); a plate shaking subassembly (1305); The platform comprises a consumable identifier controller (e.g., a bar code reader (1306)) configured to read assay consumable identifiers, e.g., positioned on a multi-well plate; a pipetting tip storage compartment (1307) configured to house pipetting tip boxes of varying size tips, as needed (e.g., 1308 and 1309, 1000 μl and 350 μl tips, respectively) and further including a pipetting tip disposal chute (1310) connected to a waste compartment (not shown); and one or more sample/reagent tube carriers (1311).

As shown in FIG. 13(*b*), when an assay consumable, e.g., a multi-well plate, is inserted into the assay system (1300), the bar code reader (1306) reads the consumable identifier (1313) on the consumable and downloads the available consumable data associated with that identifier (1314) (alternatively or additionally, the system can query the data hub for additional consumable data, as described hereinabove). A representative list of consumable data that can be associated with the identifier is provided in FIG. 13(*b*), including but not limited to, a list of components, calibrator values, control values, recipient customer number, order number, catalog number, the relevant assay protocol for that consumable, etc. The assay protocol (1315) comprises one or more steps performed by the user and/or by a component of the assay system during the conduct of an assay. For those steps performed by the user (1316), the software displays those steps to the user via the user-interface of the assay system (1317). All of the manual steps can be displayed simultaneously on the user-interface or each manual step can be displayed on the user-interface individual and the software will prompt the user to confirm completion of that step on the user-interface before displaying the next manual step. Once the manual steps are completed, the software will proceed to the next step in the assay protocol. Each step of the assay protocol that should be performed by an assay subsystem can comprise one or more sub-steps (1318 and 1319, respectively), and each sub-step can comprise one or more assay subsystem operations (e.g., 1320-1322, respectively). For example, if a step of the assay protocol is to incubate a test plate in the plate shaking subsystem, that step can include at least the following sub-steps: (a) moving the test plate to the plate shaking subsystem and (b) initiating the plate shaking subsystem for a specified duration. Each of these sub-steps require the software to send one or more commands to a subsystem or a component thereof to complete the required sub-step, e.g., moving the test plate to the plate shaking subsystem requires the software to command one or more motors in the robotic subsystem to move to and collect the test plate and move that test plate to a designated position in the plate shaking subsystem. Each of the subsystem operations are identified in the protocol script in the software.

The assay system should then be prepared for the conduct of an assay before manual assay steps can be completed (if any). For example, the software can instruct the assay reader to evaluate a demonstration multi-well assay plate to ensure proper performance of the assay reader. Wash buffers can be filled or replenished, as needed (manually), and waste containers or reservoirs can be emptied, if necessary (manually). The software can also instruct the plate washing subsystem to perform a maintenance script, if needed, and prime the washing subsystem. Moreover, the user can manually refill or replace disposable tip boxes in the assay system. The user can also prepare the software for the conduct of an assay, either on a remote, networked computer or directly on the assay system user interface. The consumable, e.g., kit, can be selected by the user in the user-interface, and the number of samples to be run in the assay can be selected. The user can also review the list of required consumable for an assay (displayed on the user-interface by the software) and confirm that all required consumables are available. The user can then submit the defined experiment to the system software for initiation and completion. As described above, the software will prompt the user to complete any manual steps, as needed, and follow any software prompts to prepare the system for the conduct of an assay. The user initiates an assay run on the user-interface, the system is locked, and the software script for the protocol is initiated.

In one embodiment of a V-PLEX, e.g., cytokine, assay conducted on the assay system of FIG. 13(*b*), the following manual steps are required and the software displays each step on the user-interface, optionally requiring the user to confirm via the user-interface that each step has been completed:

a) Unpack consumable kit;

b) Thaw reagents per consumable instructions;

c) Dilute ECL read buffer to 2X using deionized water;

d) Dilute wash buffer to 1X using deionized water;

e) Reconstitute lyophilized calibrators by adding 1000 uL of Diluent A and mix well by vortexing;

f) Reconstitute lyphilized controls by adding 250 uL of Diluent A to the vials and mix well by vortexing.

Calibrators are samples with known concentration of analytes relevant to the assay used to determine the fit curve to apply to the unknown samples. Calibrators are generally provided in high concentration and is diluted to prepare solutions of lower concentration. Typically, up to eight (8) points are used to prepare the fit curve. Control are also samples with known concentration of analyte relevant to the assay used to determine the system performance and whether the assay is performing accurately. Either calibrators or controls are used in the immunoassays, and in some assays both calibrators and controls are used.

Figure 13A:
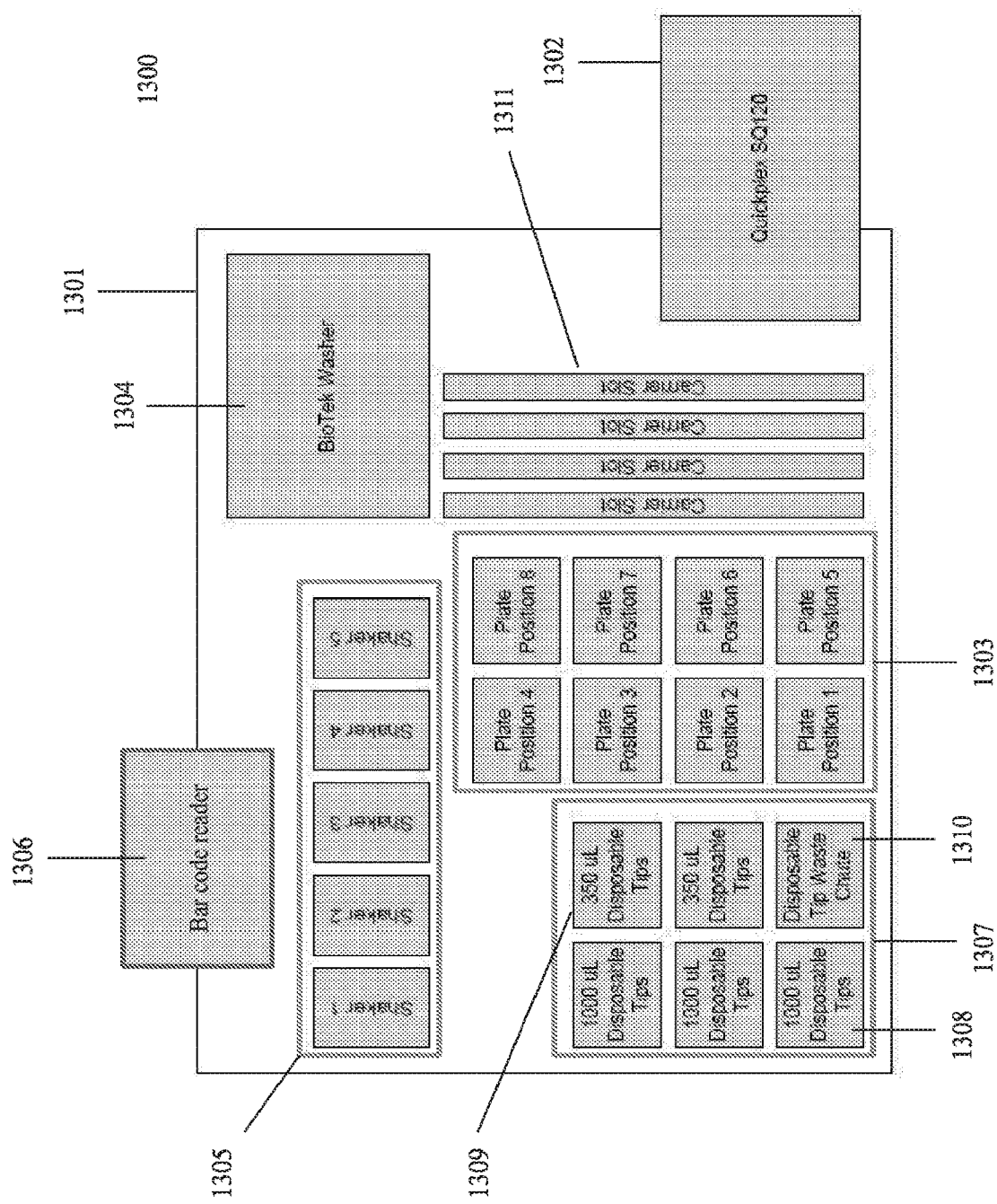
Figure 13B:
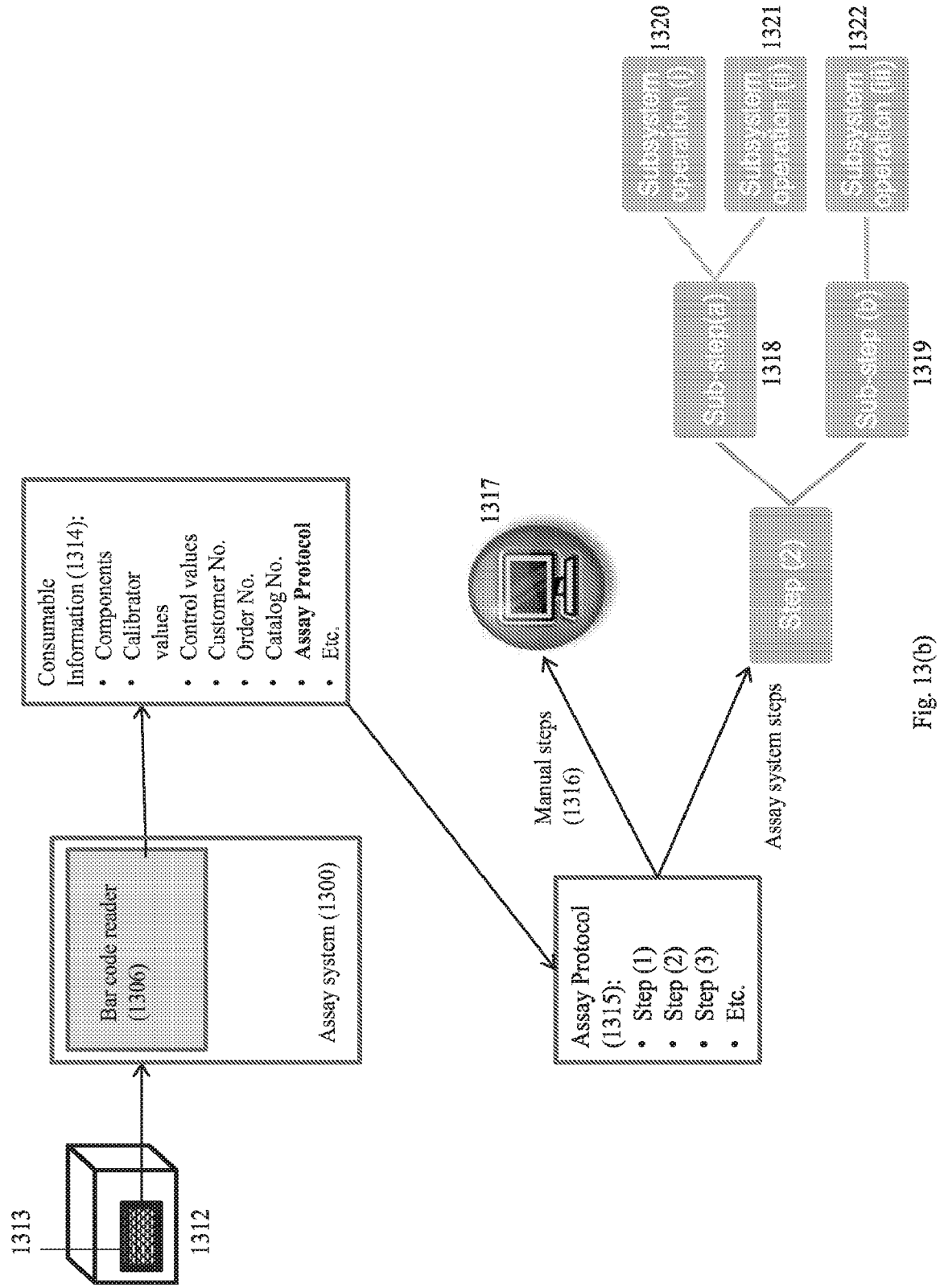
Figure 13C:
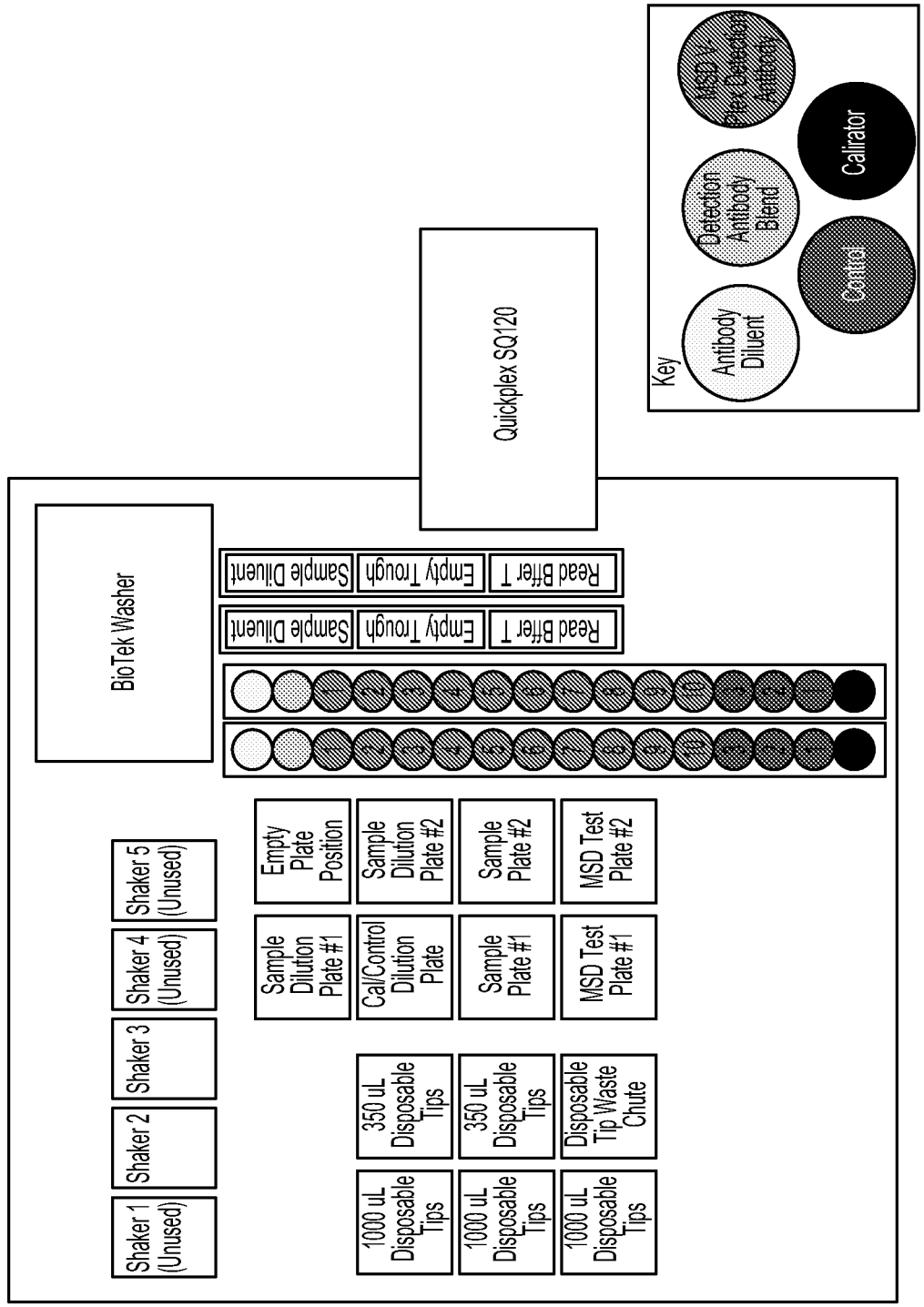

The appropriate consumables and reagents are loaded onto the assay system, as depicted in FIG. 13(c). Briefly, disposable pipetting tips are loaded onto the platform, empty dilution plates, empty test plates, and pre-loaded sample plates are loaded onto the platform, troughs are filled with ECL read buffer and sample diluent and loaded into the trough carriers on the platform, and the reagent rack is loaded with empty antibody blend tubes, control vials, calibrator vials, detection antibody tubes, and antibody diluent tubes. The software can display the subsystem layout depicted in FIG. 13(c) on the user-interface, highlighting each subsystem to aide in the proper placement of each consumable or reagent in the subsystem. Once the loading steps are completed, the software prompts the user to close the doors to the assay system, the software locks the doors to the system and initiates a loading confirmation script that is configured to confirm that each consumable and reagent has been properly loaded in the instrument in the correct position and orientation. If any consumable or reagent has been improperly loaded, the system doors will unlock and the software will display a warning on the user-interface, instructing the user to manually adjust the improperly loaded consumable or reagent.

The protocol for the conduct of a V-PLEX, e.g., cytokine, assay, on the assay system is shown in FIG. 13(d). As described above in reference to FIG. 13(b), each step of the protocol corresponds to one or more substeps and subsystem operations, and the software includes the required scripts and subscripts needed to instruct the system to perform each step, substep and operation required to complete the assay. The sequence of steps in the assay protocol and timing of events is shown in FIG. 13(e) and a summary of the steps is provided in FIG. 13(f).

Figure 14A:
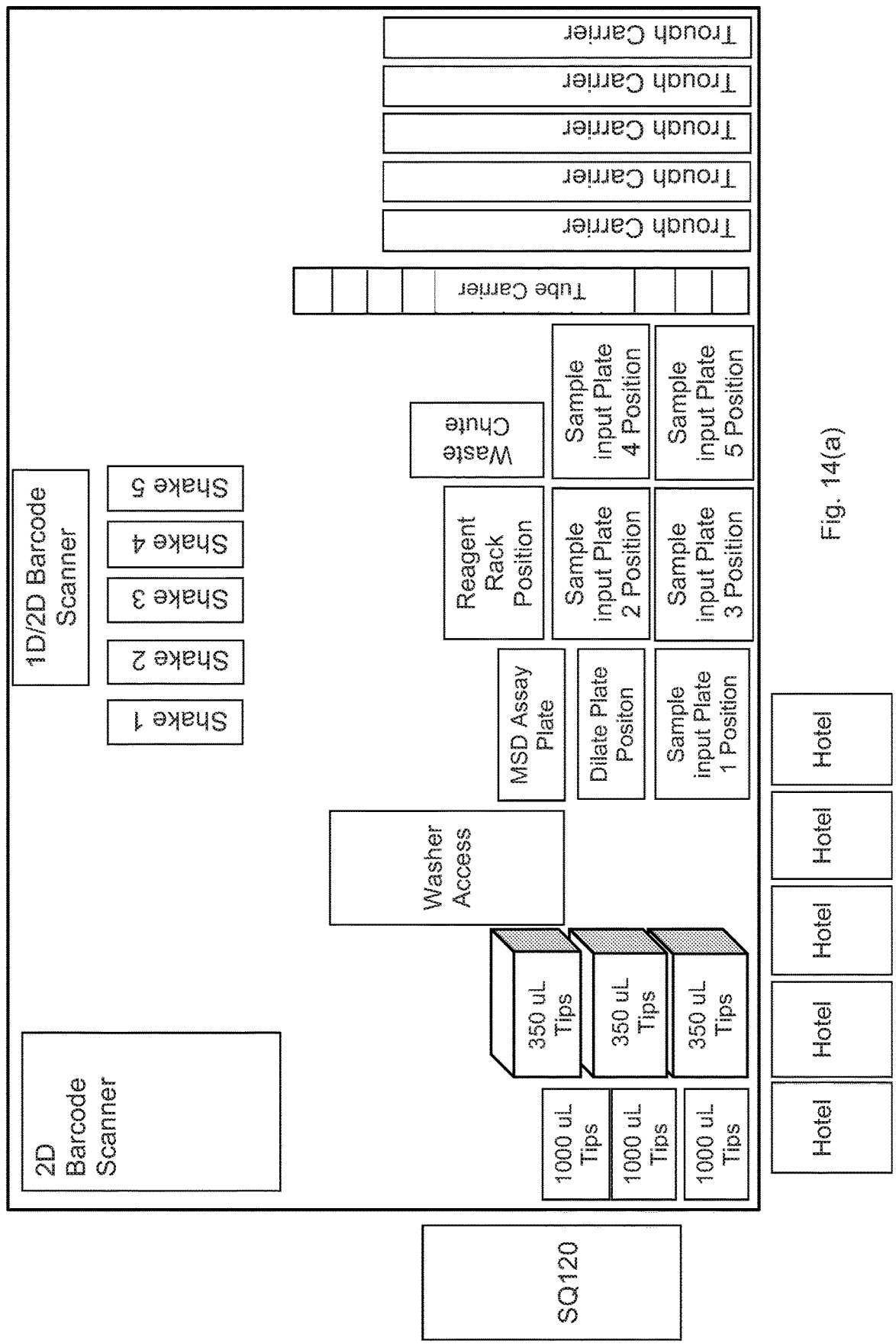
Figure 14I:
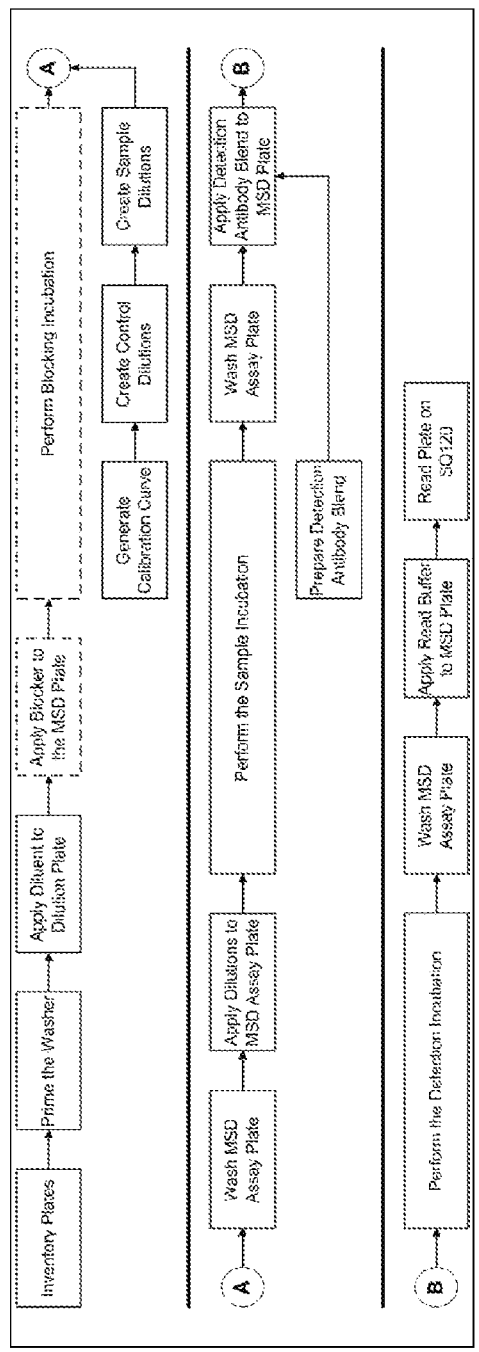

FIGS. 14(a)-(i) illustrate the conduct of a V-PLEX assay on the assay system depicted in FIG. 14. V-PLEX assays are commercially available from Meso Scale Discovery, LLC. (Rockville, Md.). As in FIG. 13(a), FIG. 14(a) illustrates the layout of various subsystems in the assay system. FIG. 14(b) shows the configuration of the plate storage subassembly for the conduct of one or more V-PLEX assays in the assay system and likewise, FIG. 14(c) shows the orientation of reagent tubes and troughs in the tube carrier (panel (i)), trough carrier (panel (ii)), and reagent racks (panel (iii)). FIGS. 14(d)-(i) show various assay protocols for V-PLEX kits, and as described above, the protocol that should be used with a given item number or catalog number is consumable data that is associated with the consumable identifier of the kit and the kit subcomponents. FIGS. 14(j) and (k) show two exemplary timing sequences or scripts for the V-PLEX protocols. FIG. 14(l) shows an updated protocol for Sthe V-PLEX step-wise protocol sequence shown in FIG. 14(d).

Figure 15B:
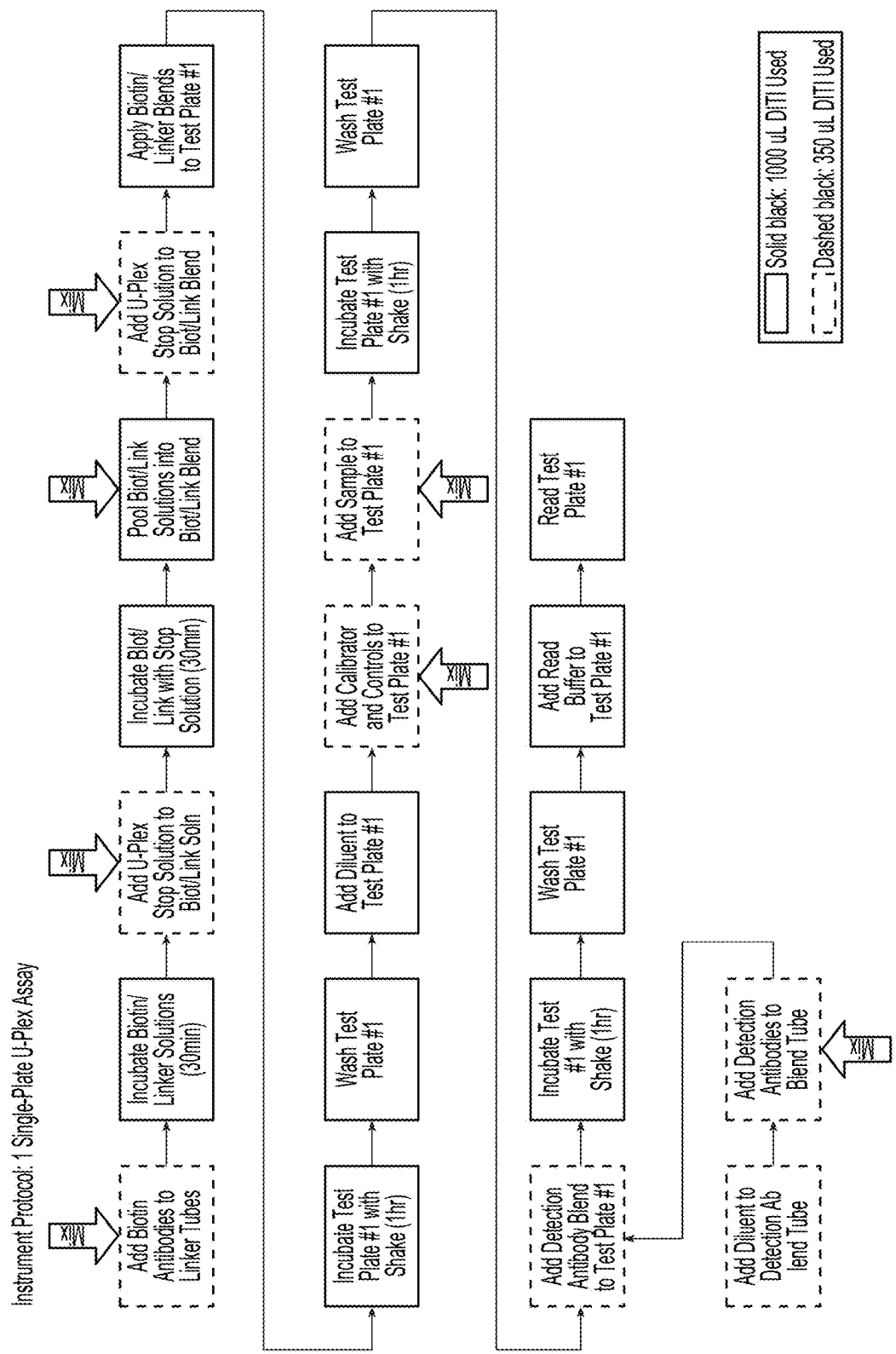

The assay system and software described herein can be configured to conduct a plurality of different types of assays and based on the type of assay and protocol, the user-interface is configured to display step by step instructions to the user for the appropriate preparation of samples and/or reagents for use in the assay system. For example, in addition to the V-PLEX assays described in detail above, the assay system and software are also configured to conduct U-PLEX and S-PLEX assays (available from Meso Scale Discovery, Rockville, Md.). Both U-PLEX and S-PLEX assays require a certain number of preparation and optional optimization steps, the software is configured to display individualized stepwise protocols to the user for those preparation and optimization steps. For example, the U-PLEX protocol requires one or more reagents to be prepared according to a specific reagent preparation protocol and those steps are displayed to the user via the user-interface prior to conducting the assay on the assay system. FIGS. 15(a)-(b) illustrate the assay protocol as conducted on the assay system for a single plate U-PLEX assay, and FIGS. 15(c)-(f) illustrate the assay protocol as conducted on the assay system for a multi-plate U-PLEX assay. FIGS. 15(g) and (h) show two exemplary timing sequences or scripts for the U-PLEX protocols. In addition to the specific assay protocols identified herein above, the assay system can be configured to perform the following types of assays and the software is configured to lead the user through the sample/reagent preparation steps via the user-interface:

Pharmacokinetic assays, preparation, optimization, and assay execution

Immunogenicity assays, preparation, optimization, and assay execution

Custom sandwich immunoassays: preparation, optimization and assay execution

Kinetic measurements

Assay development panels

Antibody screening

Calibration curve titrations

Manually reading prepared consumable test plates

Plate incubations

IQ/OQ/PQ (Installation Qualification (IQ); Operational Qualification (OQ); Performance Qualification (PQ))

Figure 16B:
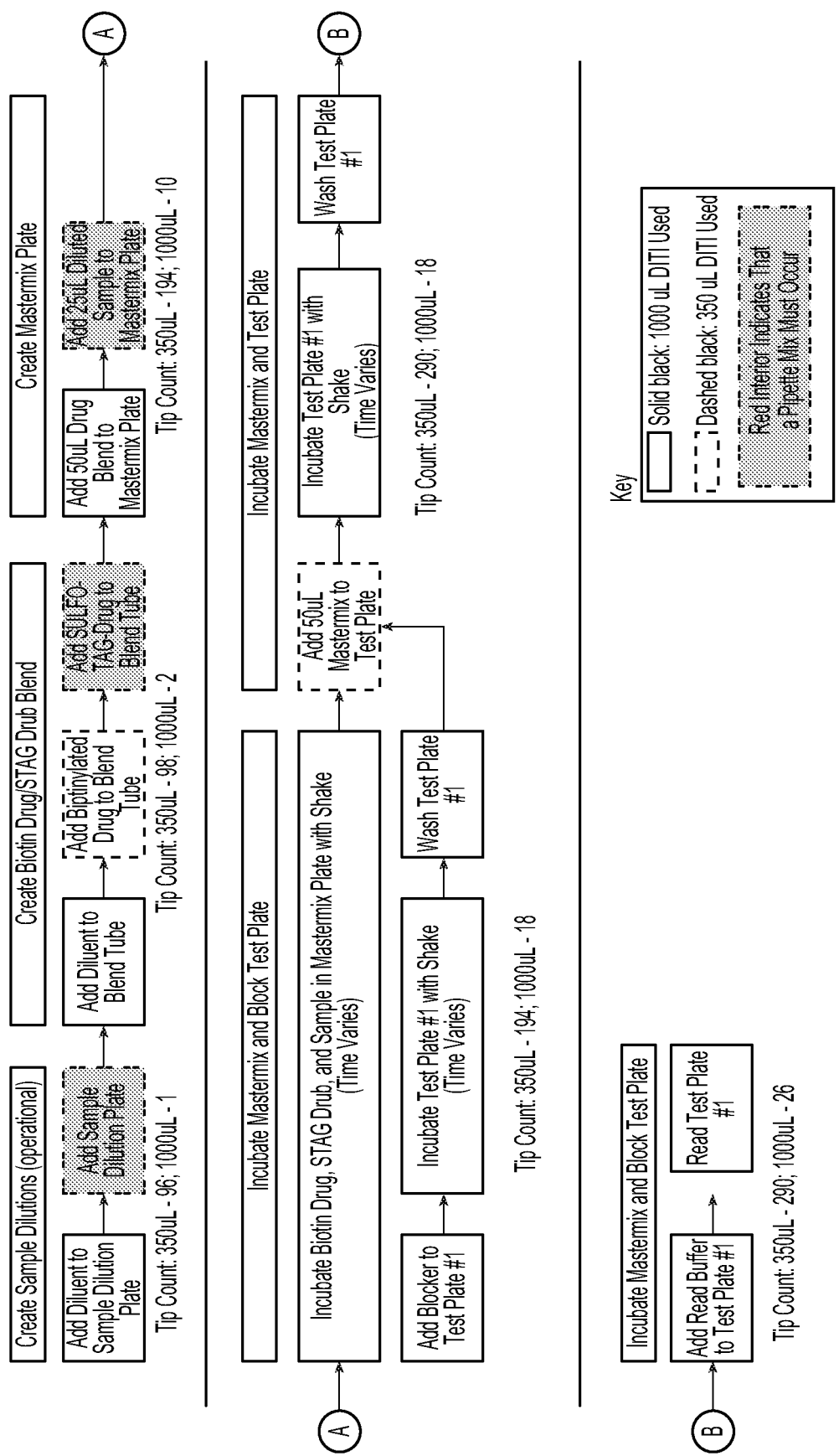
Figure 16C:
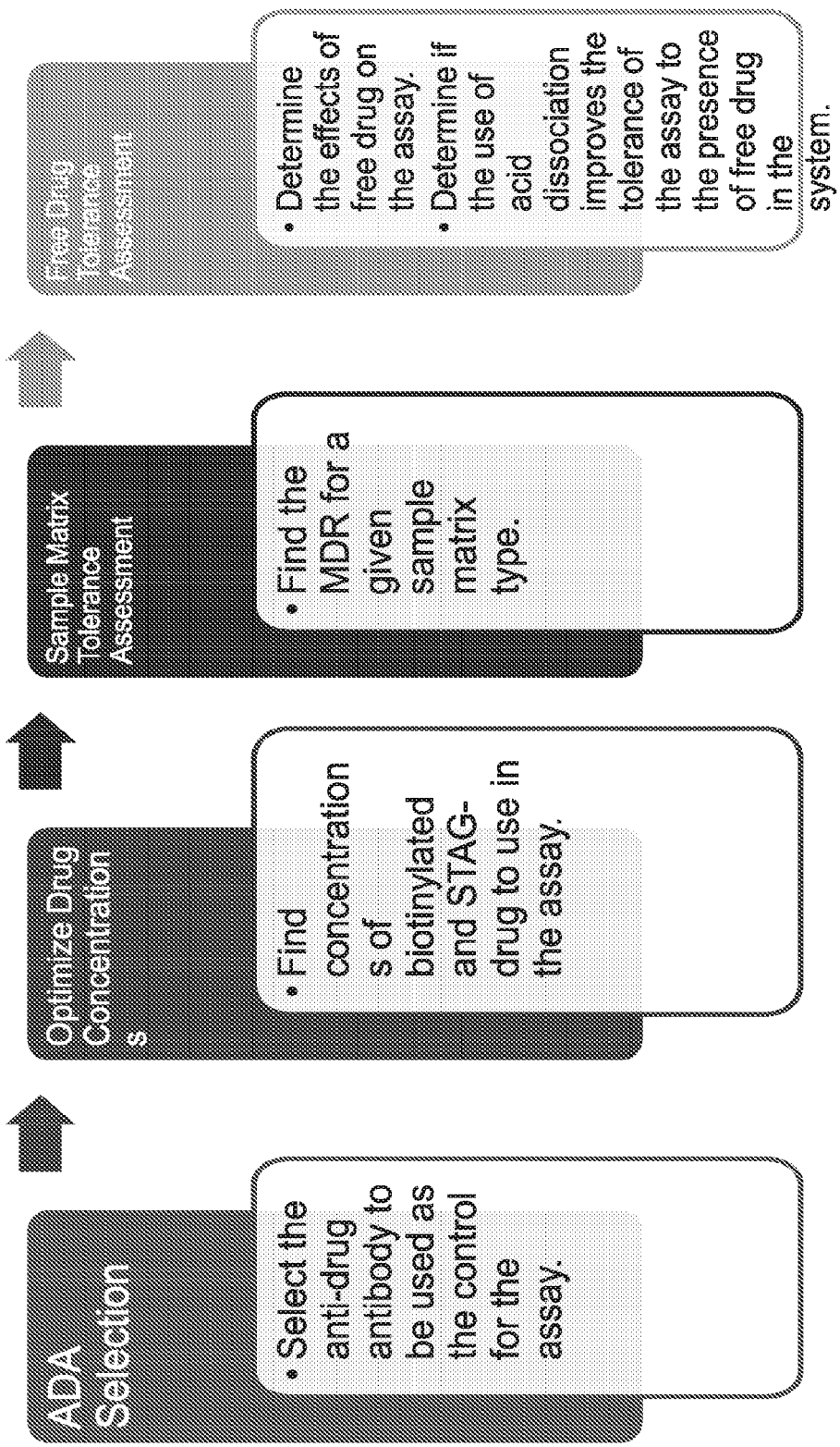
Figure 16D:
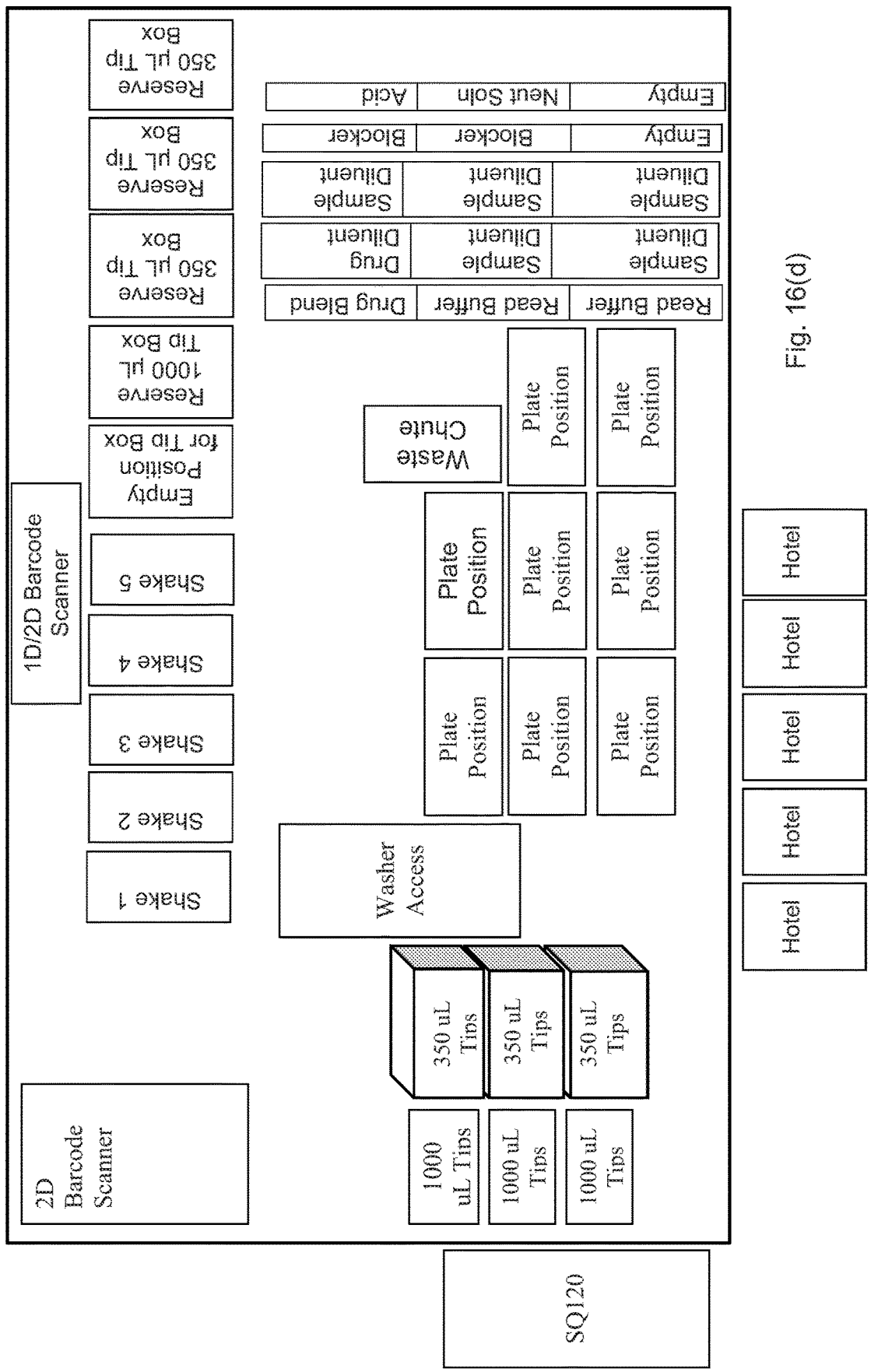

U-PLEX AND V-PLEX assays when automated to run in an assay system, such as assay system (1000) or (900) may have the following steps:

Automated Assay Sequence
1 Inventory Plates
2 Prime the Washer
3 Couple Antibodies to U-PLEX Linkers
4 Incubate Capture Antibodies with Linkers
5 Add Stop Solution to Coupled Antibody Linker Solution
6 Incubate Stop Solution
7 Prepare Capture Antibody Blend
8 Prepare Capture Antibody Dilution
9 Apply Capture Antibody Blend to the MSD Plate
10 Perform the Coating Incubation
11 Apply Blocker to the MSD Plate
12 Apply Sample Diluent to the MSD Plate
13 Perform Blocking Incubation
14 Apply Diluent to the Dilution Plate(s)
15 Generate Calibration Curve
16 Dilute Control Vials
17 Create Control Dilutions
18 Create Sample Dilutions
19 Wash the MSD Assay Plate
20 Apply Dilutions to MSD Assay Plate
21 Perform the Sample Incubation 22 Prepare Detection Antibody Blend
23 Prepare Detection Antibody Blend with Blocker
24 Apply Detection Antibody Blend to the MSD Plate
25 Perform the Detection Incubation
26 Apply Detection Antibodies and Dilutions to the MSD Plate
27 Perform the Homogeneous V-PLEX Assay Incubation
28 Apply Read Buffer to Plate
29 Read Plate on ECL reader
30 Clean Up Process (i) Immunogenicity Assay Preparation, Optimization & Execution Immunogenicity is the property of enabling a substance to provoke an immune response by generating an anti-drug antibody or the degree to which a substance possesses this property. Bridging IG assays are used to detect the presence of these anti-drug antibodies in samples in order to characterize an immune response to a drug substance. FIG. 16(a) shows a complex used to in a bridging immunogenicity (IG) assay on the Meso Scale Discovery's MULTI-SPOT® or MULTI-ARRAY® platforms (available from Meso Scale Discovery, LLC., Rockville, Md.). To form the complex, a biotinylated drug, SULFO-TAG™ labeled (STAG) drug, and the anti-drug antibody (ADA) are incubated together and the biotinylated drug and STAG drug each bind to different sections of the ADA. Drug/ADA complex is incubated on an MSD test plate containing spots of streptavidin or avidin and biotinylated drug binds to the streptavidin or avidin in the plate spots (FIG. 16(a)). A standard IG assay protocol block diagram is shown in FIG. 16(b). FIG. 16(d) illustrates an exemplary deck layout is to be used for bridging IG assays performed on the assay system (1000) that do not include acid treatment.

IG assays are preferably optimized prior to implementation in a laboratory. The standard IG protocol includes multiple parameters that can be assessed during optimization, including but not limited to: (i) duration of incubations; (ii) plate type(s); (iii) anti-drug antibody selection; (iv) concentration of biotinylated drug; (v) concentration of STAG-drug; (vi) determination of minimum dilution ratio (MDR); (vii) assessment of assay response to free drug in the sample; and/or (viii) assessment of acid dissociation to improve free drug tolerance. Each of these parameters is important to the overall determination of the final protocol.

In order to optimize an IG assay on the assay system shown in FIG. 10 and its subparts, a user is provided a System Development Pack, which includes set of sample incubation plates (0.3 mL), sample dilution plates (1.1 mL), plate lids, reagent tubes, and a kit that may include the following components:

TABLE 1

| |
|---|
| QUICKPLEX ® 96 Well STREPTAVIDIN GOLD ™ Plate (10 Plates) |
| QUICKPLEX ® 96 Well High Bind Avidin Gold Plate (10 Plates) |
| MSD SULFO-TAG NHS Ester 150 nMoles |
| Anti Mouse Antibody (Goat) Sulfo-TAG Labeled, 50 ug |
| Anti Rabbit Antibody (Goat) Sulfo-TAG Labeled, 50 ug |
| MSD Blocker A, 1L |
| MSD Phosphate Buffer (5X) 200 ml |
| MSD Blocker B, 2 g |
| MSD Read Buffer T (4x), 200 ml |
| Zeba 40K Columns, 2 mL |

The Development Pack, itself, as well as each component within it includes a consumable identifier (e.g. bar code) with consumable data associated therewith. The system bar code reader reads the consumable identifiers (e.g. bar codes), and downloads and installs the DDB stored to that consumable identifier (e.g. bar code). The DDB includes a DDB unique identifier, DDB version, a DDB xml file, consumable static information, consumable processing information, and combinations thereof. For example, if the components include a multi-well assay plate, the consumable type information includes the number of columns of wells; the number of rows of wells; the number of binding domains per well; and combinations thereof; and the consumable processing information comprises data used by the assay system in the conduct of an assay using the plate and/or the processing of assay data resulting from the conduct of an assay using the plate. In a specific embodiment, the consumable processing information comprises the number of sectors per plate, the number of circuits per plate, detection parameters used by said assay system to read said plate; image processing properties use to produce ECL results; plate type gain; binding domain gain; optical cross talk matrix; and combinations thereof.

The system then identifies relevant consumable data from the local data repository and/or from one or more remote consumable data databases required to process that consumable, adjusts one or more operations performed or that will be performed by the system before, during and/or after the conduct of an assay based on that consumable data, including but not limited to the appropriate protocols and optimization parameters for an IG assay. A specific embodiment of an IG optimization workflow is shown in FIG. 16(c), and includes the following steps: (i) screen various anti-drug antibodies; (ii) optimize biotinylated drug and STAG-labeled drug concentrations; (iii) perform sample matrix tolerance assessment; and/or (iv) perform free drug tolerance assessment. At each step, the user may also evaluate whether or not to use an acid dissociation protocol as part of the final protocol; additionally, users may evaluate multiple assay plate types at each step of the process (e.g., QUICKPLEX® 96 Well STREPTAVIDIN GOLD™ Plate vs. QUICKPLEX® 96 Well High Bind Avidin Gold Plate). The user may elect to skip one or more of these steps and the software allows the user to skip one or more steps and/or manually enter parameters/data, e.g., drug concentration, which would be generated in the skipped step.

The consumable data for the Development Pack includes the protocol for the IG optimization workflow and each of the steps or sub-protocols that are conducted for that consumable. The first step of this embodiment of the IG optimization workflow is ADA Selection and the system prompts the user in the design of an experiment on the system that is used by the system to determine the proper ADA as a control for the assay. The user-interface will prompt the user to enter the following data on the anti-drug antibodies to be tested:

Number of dilutions of each ADA to test (either 8 or 12 dilutions)
Number of ADAs to test (2-6 different ADAs per plate, dependent on the number of dilutions selected)
Name of each ADA to test (for tracking purposes)
User will select whether or not to include zeroth dilutions
Concentration of dilutions to test The user-interface also prompts the user to (i) select the length of incubations (30 min to 4 hours on-instrument or a user-determined length of time off-instrument), (ii) whether to include an acid dissociation step, (iii) add plates of varying types, if needed, (iv) select whether or not to apply the same reagents to all plates. The experiment can be conducted on up to 5 plates. The system then conducts the ADA selection experiment and displays the results of that experiment on the user-interface to enable the user to select the ADA most suitable as an assay control.

The user-interface then prompts the user to conduct a second experiment to determine the concentration of biotinylated drug and STAG-labeled drug to use in the assay (the relative affinities of biotinylated drug and SULFO-TAG labeled drug for the ADA can differ). The user interface prompts the user to make the following selections for this optimization experiment:

Enter the following data on the detection species to be tested:
Number of detection species dilutions (4 concentrations of biotinylated drug and 4 concentrations of STAG-labeled drug per plate)
Dilution factor for each detection species
User will select whether or not to include zeroth dilutions
Enter the following data on the ADA samples to be tested:
Number of ADA dilutions (Up to 3 dilutions per plate)
Concentration of ADA dilutions
Select length of incubations (30 min to 4 hours on-instrument or a user-determined length of time off-instrument).
Select whether to include an acid dissociation step.
Add plates of varying types.
Select whether or not to apply the same reagents (i.e. the same reagent sources) to all plates.

The experiment can be conducted on up to 5 plates. The system then conducts the drug concentration optimization experiment and displays the results of that experiment on the user-interface.

Then the user-interface prompts the user to conduct a third experiment to determine the minimum dilution ratio (MDR) for each sample matrix which enables the user to evaluate the signal produced by the assay in the presence of differing sample matrix concentrations. The user interface prompts the user to make the following selections for the MDR optimization experiment:

Enter the following data on the ADA samples to be tested:
Number of dilutions of ADA to test (either 8 or 12 dilutions per plate)
Concentration of ADA dilutions
User will select whether or not to include zeroth dilutions
Enter the following data on the sample matrices to be tested:
Number of matrix dilutions (2-6 dilutions per plate, dependent on the number of ADA dilutions that are being tested.)
Dilution factor for each dilution
User will select whether or not to include zeroth dilutions
User can use different sample matrices for each plate (e.g. serum, citrate plasma, EDTA plasma, etc.)
Select length of incubations (30 min to 4 hours on-instrument or a user-determined length of time off-instrument).
Select whether to include an acid dissociation step.
Add plates of varying types, assuming there is adequate capacity in the run.
Select whether or not to apply the same reagents (i.e. the same reagent sources) to all plates.

The experiment can be conducted on up to 5 plates. The system then conducts the MDR optimization experiment and displays the results of that experiment on the user-interface.

Finally, the user-interface prompts the user to conduct a fourth free drug tolerance assessment experiment to determine the effects of free drug on the assay and whether the use of acid dissociation is necessary to improve the free drug tolerance of the assay. For the free drug tolerance assessment, the user has the option to perform the protocol with or without acid dissociation and/or to perform a comparison between an untreated and an acid-treated plate. The user interface prompts the user to make the following selections for the free drug tolerance assessment experiment:

Enter the following data on the ADA samples to be tested:
Number of dilutions of ADA to test (either 8 or 12 dilutions per plate)
Concentration of ADA dilutions
User will select whether or not to include zeroth dilutions
Enter the following data on the free drug to be tested:
Number of free drug dilutions (2-6 dilutions per plate, dependent on the number of ADA dilutions that are being tested.)
Dilution factor for each dilution.
User will select whether or not to include zeroth dilutions.
Select length of incubation (30 min to 4 hours on-instrument or a user-determined length of time off-instrument).
Select whether to use acid dissociation and/or whether to perform a comparison between acid-treated and untreated plates.
Add plates of varying types, assuming there is adequate capacity in the run.
Select whether or not to apply the same reagents (i.e. the same reagent sources) to all plates.

The experiment can be conducted on up to 5 plates. The system then conducts the free drug tolerance assessment experiment and displays the results of that experiment on the user-interface.

Figure 17A:
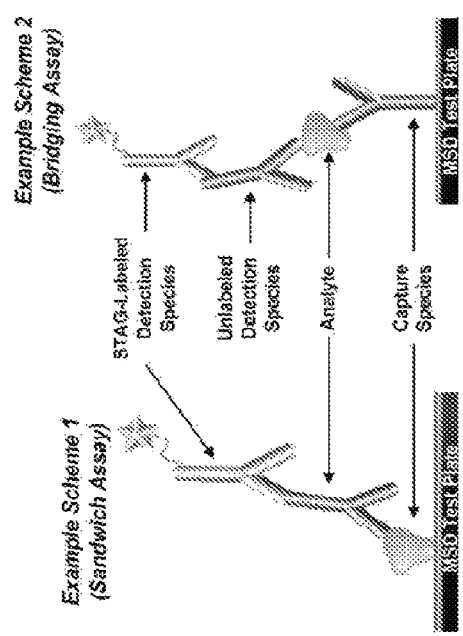
Figure 17B:
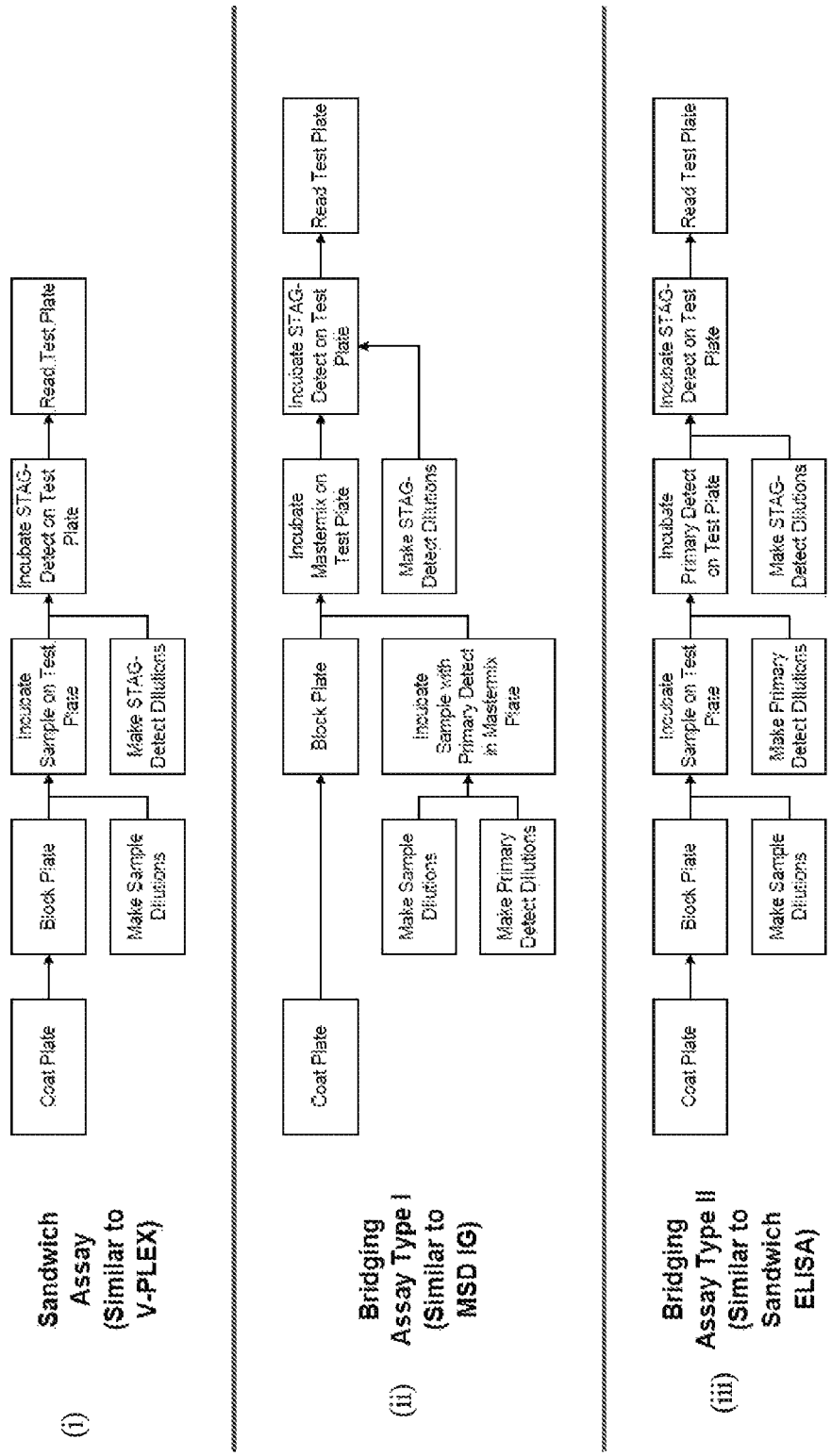

Immunogenicity (IG) assays when automated to run in an assay system, such as assay system (1000) or (900) may have the following steps:

Automated Assay Sequence
1 Inventory Plates
2 Prime the Washer
3 Create Drug Blend
4 Apply Drug Blend to Sample Incubation Plate
5 Apply Diluent to the Dilution Plate(s)
6 Generate Standard Curve
7 Create Control Dilutions
8 Create Sample Dilutions
9 Apply Blocker to the MSD Plate
10 Perform Blocking Incubation
11 Apply Dilutions to Sample Incubation Plate
12 Perform Sample Incubation
13 Wash the MSD Test Plate
14 Apply Incubated Sample to MSD Test Plate
15 Perform the MSD Test Plate Incubation
16 Apply Read Buffer to Plate
17 Read Plate on ECL reader
18 (lean U Process (ii) Pharmacokinetic Assay Preparation, Optimization & Execution Pharmacokinetics is the study of time course of drug absorption, distribution, metabolism and excretion. Pharmacokinetic (PK) assays are used to measure concentrations of a drug in samples from the same patient over time. These assays can be direct or indirect immunoassays and they are preferably optimized prior to implementation in a lab. A standard PK assay conducted on the Meso Scale Discovery's MULTI-SPOT® or MULTI-ARRAY® platforms is shown in FIG. 17(a). First an MSD plate is coated with capture species. The capture species is immobilized to the MSD plate and can be an antibody, protein, antigen, carbohydrate, lysate, etc. Detection species and analyte are applied to the coated MSD test plate. Detection species can include STAG-labeled antibody by itself (direct format), STAG-labeled streptavidin and biotinylated detection antibody (indirect format), STAG-labeled anti-species antibody and unlabeled detection antibody, etc. (indirect format). The detection species can be premixed with the analyte or it can be applied to the test plate directly. Block diagrams for the conduct of a direct PK assay and two different types of indirect PK assays are shown in FIG. 17(b) (panels (i)-(iii), respectively).

Figure 17C:
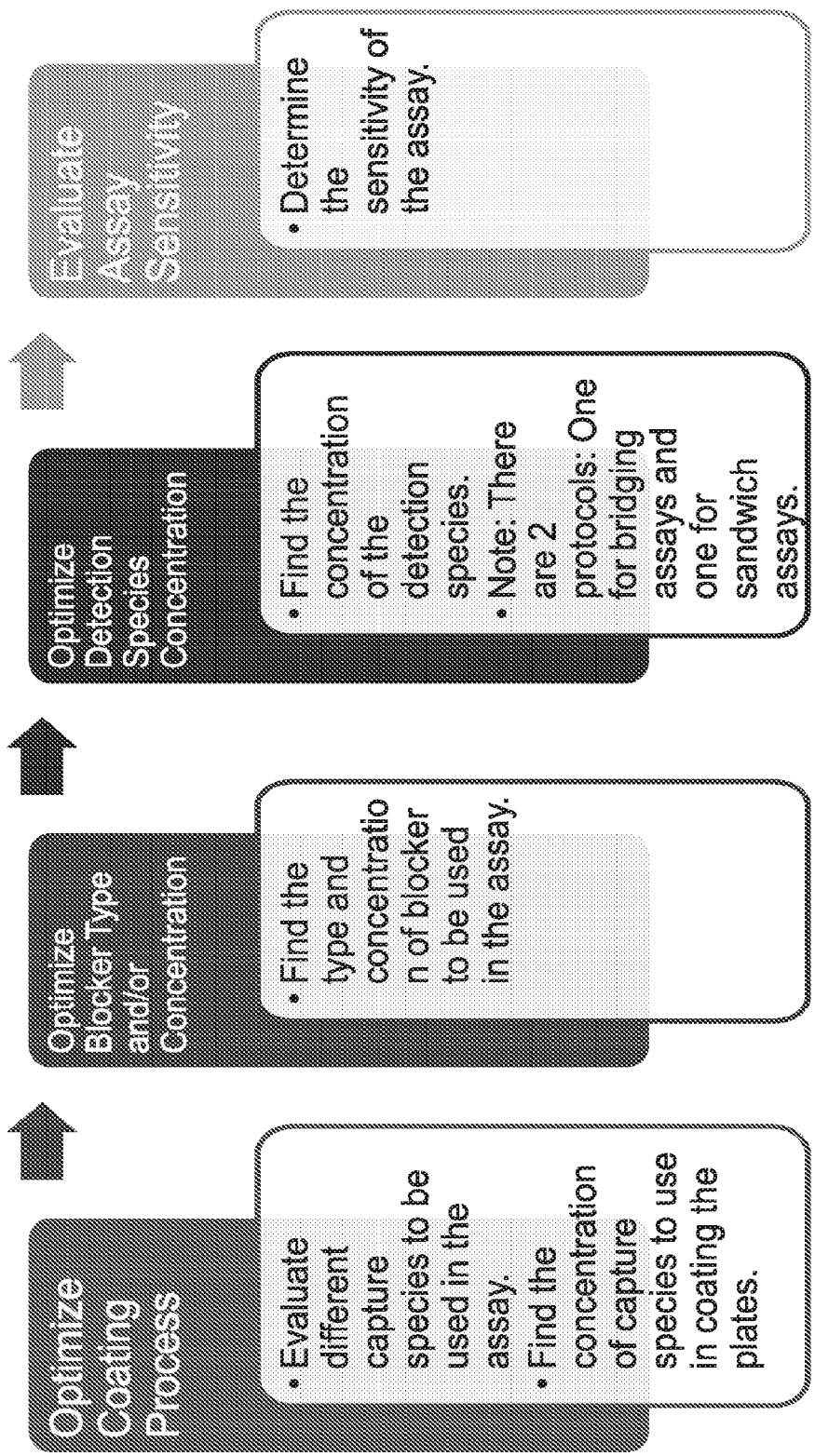
Figure 17I:
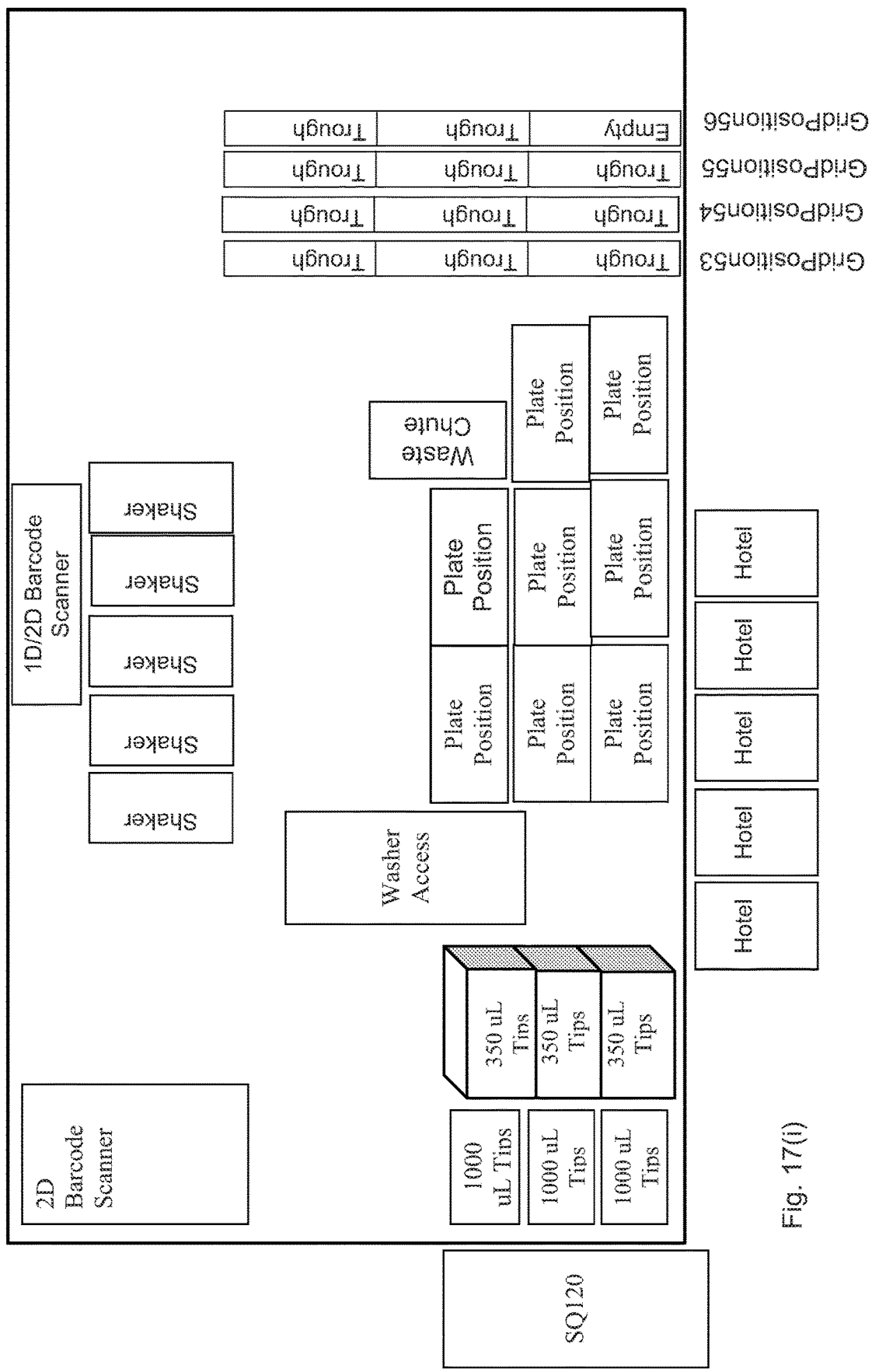
Figure 18A:
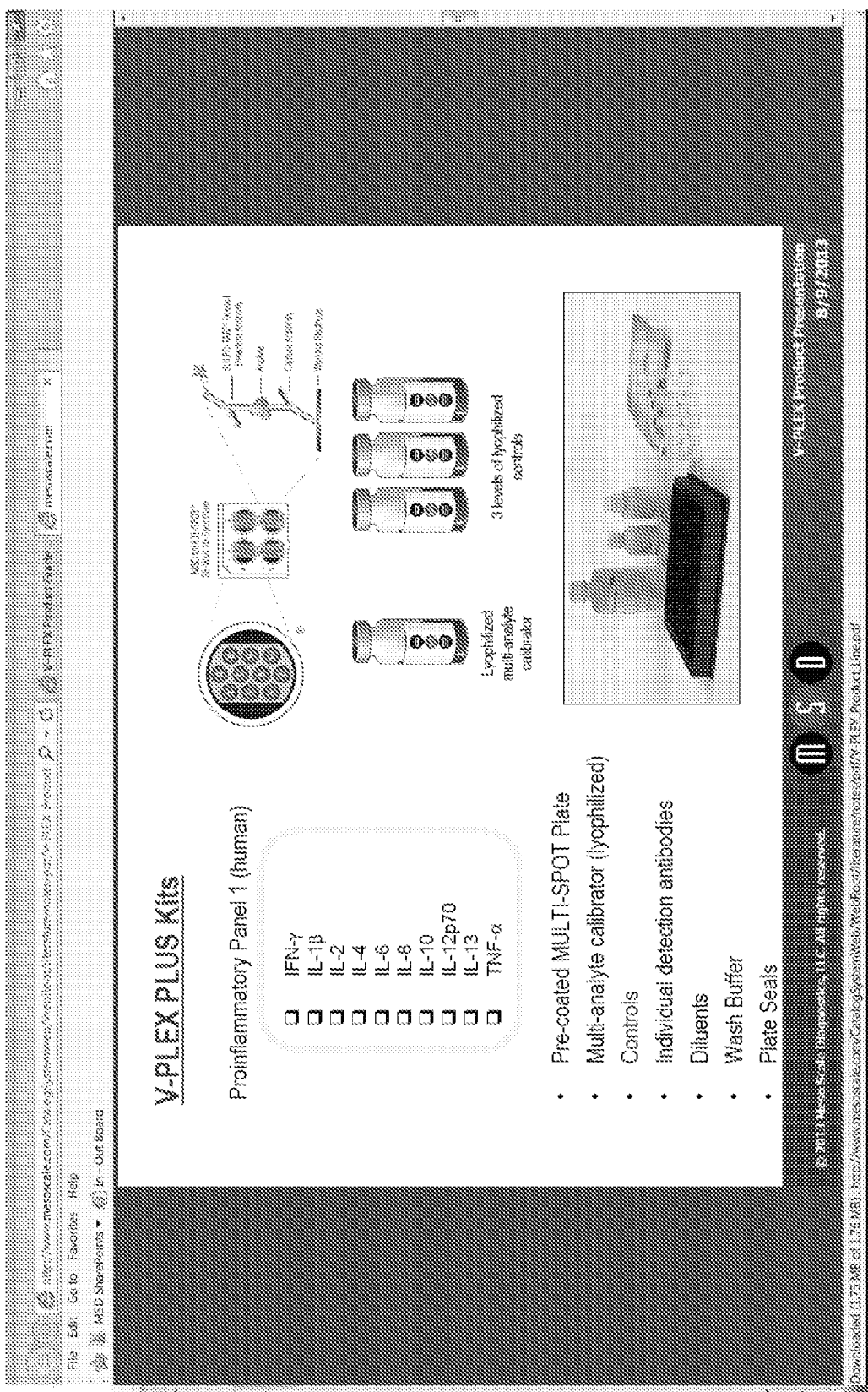
FIGS. 18(a)-(n) illustrate a consumable assay kit usable with the assay systems described herein.
Figure 18B:
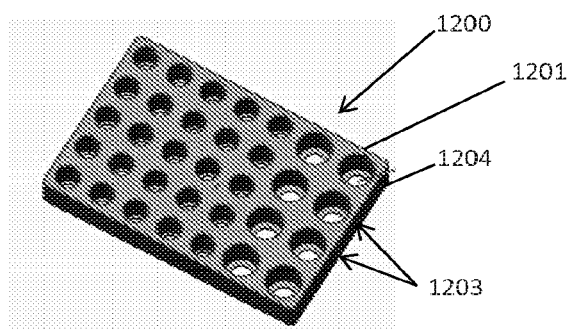
Figure 18C:
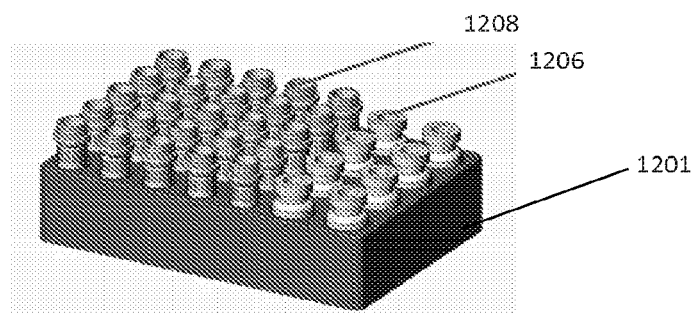
Figure 18D:
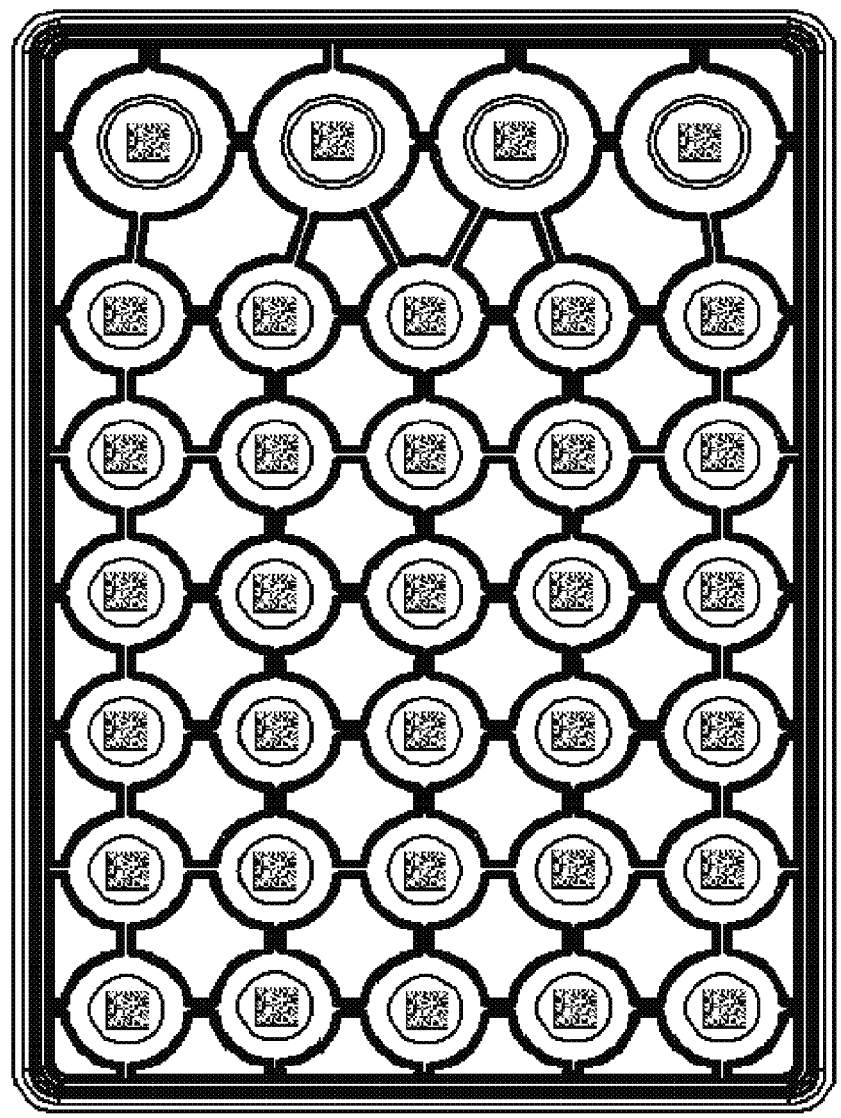
Figure 18E:
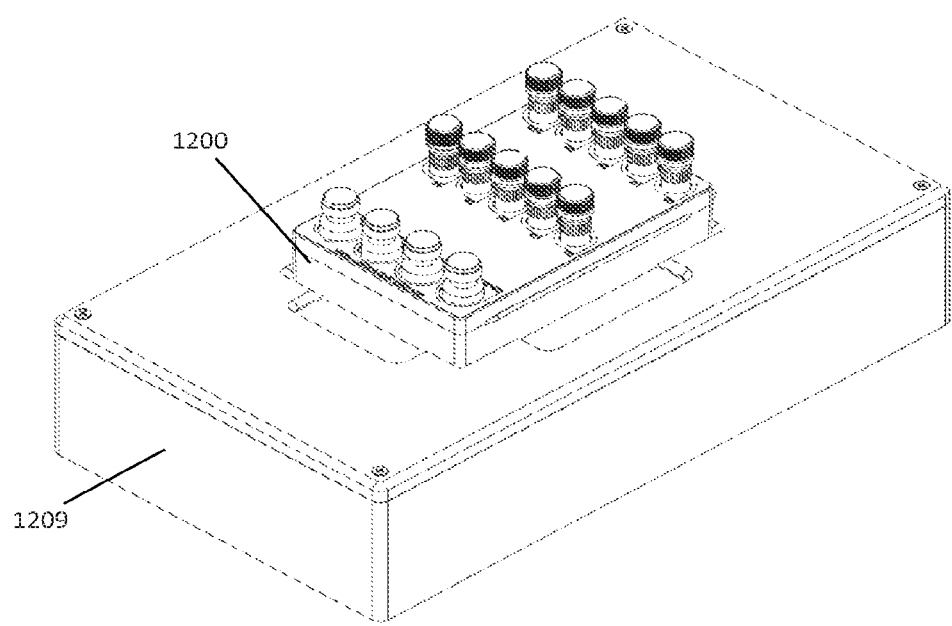
Figure 18F:
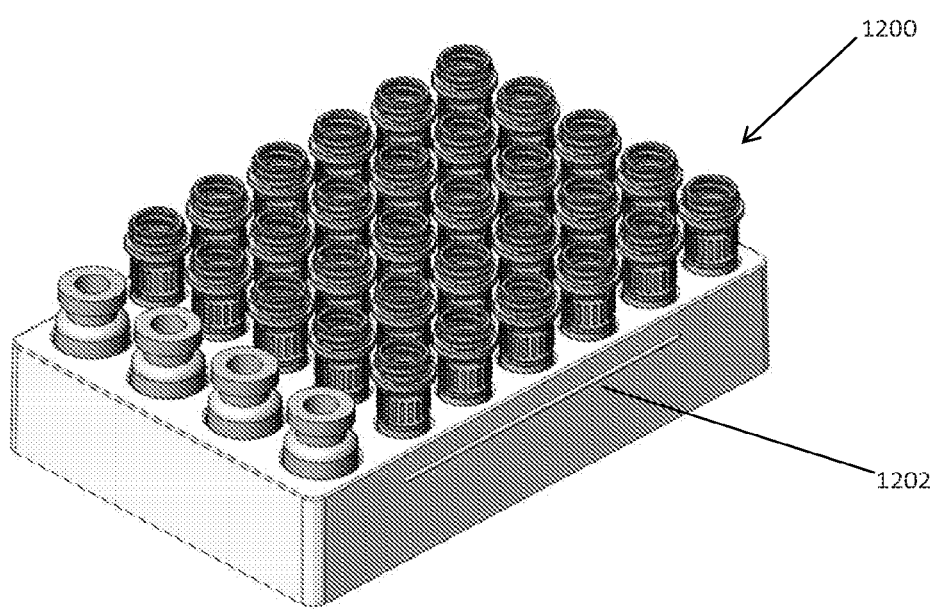
Figure 18G:
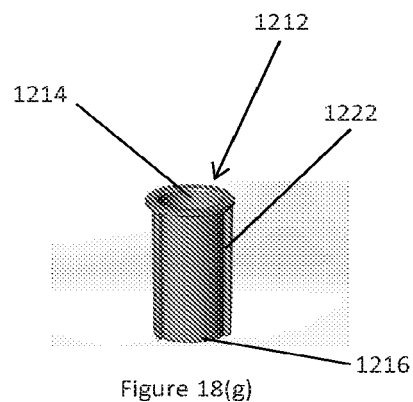
Figure 18H:
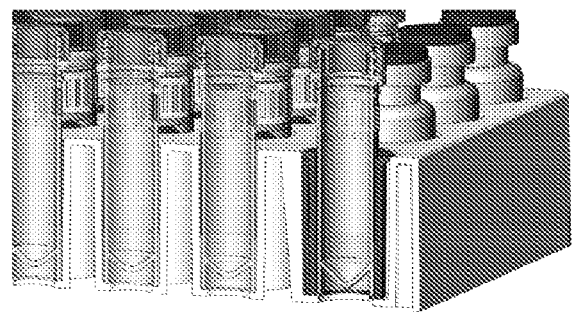
Figure 18I:
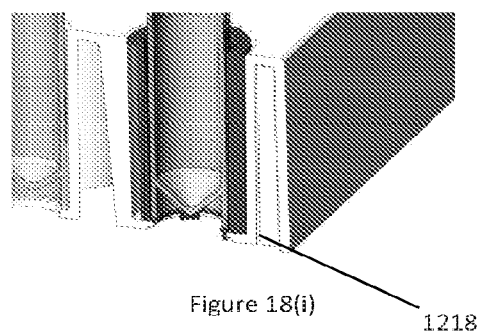
Figure 18J:
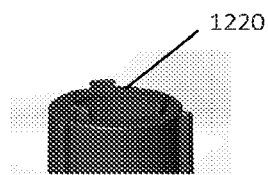
Figure 18L:
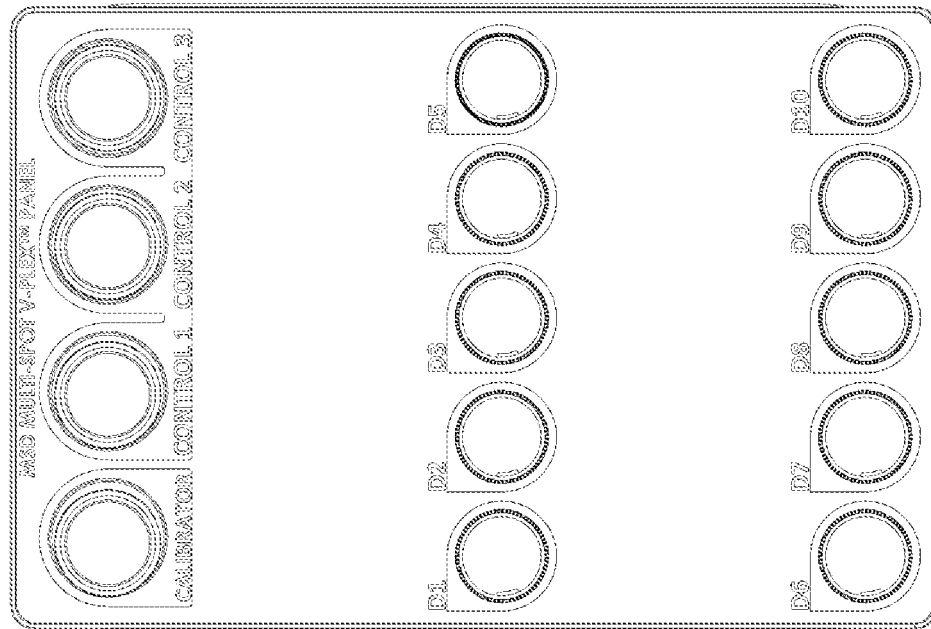
Figure 18K:
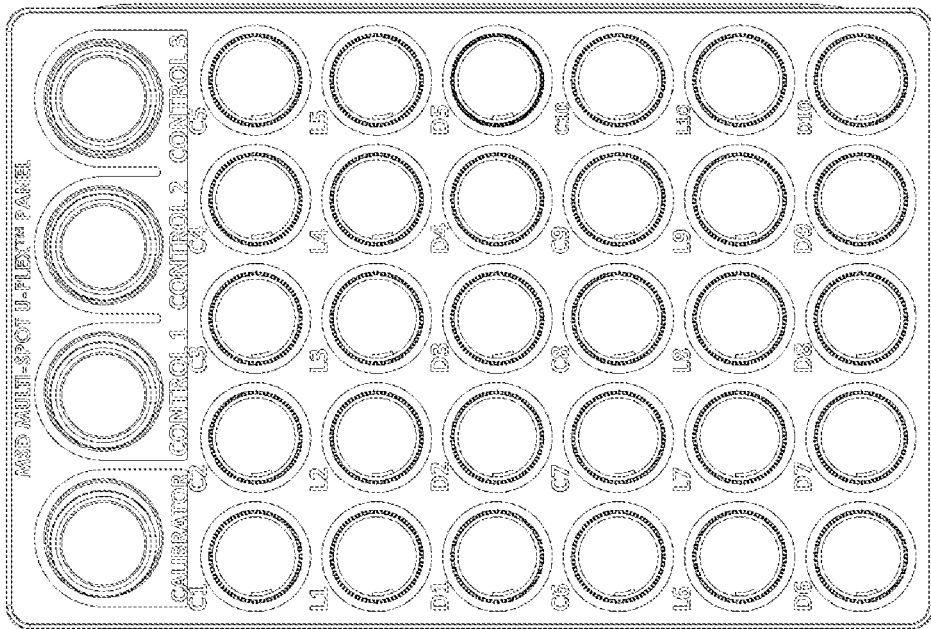
Figure 18N:
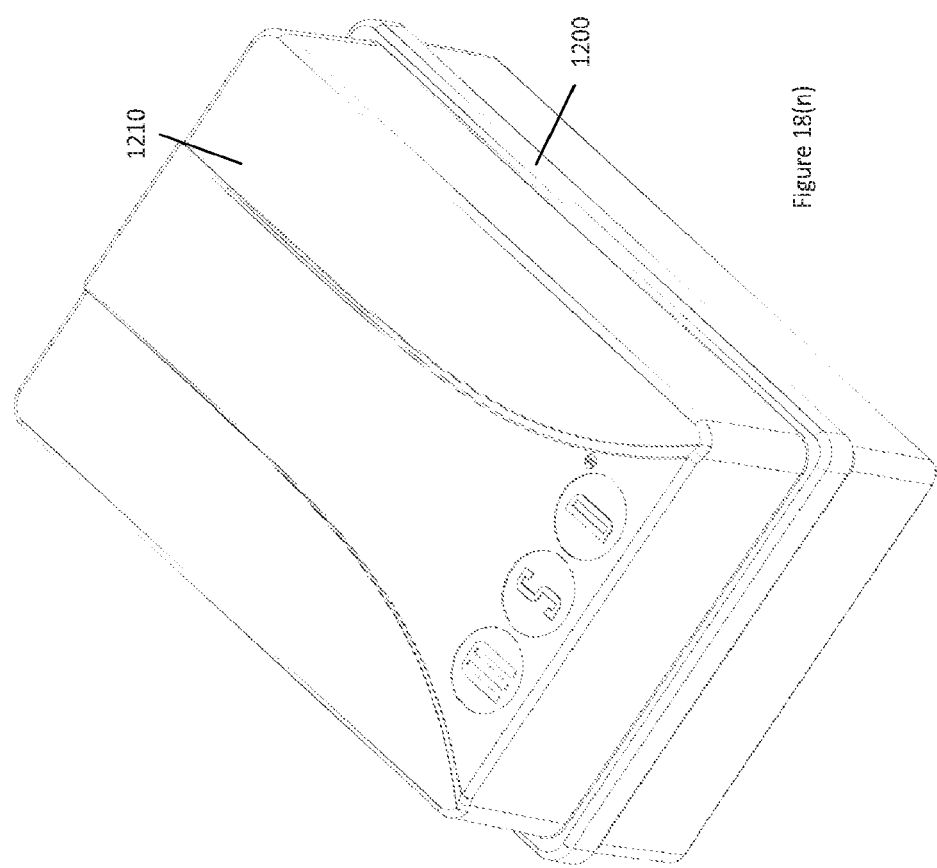
Figure 19D:
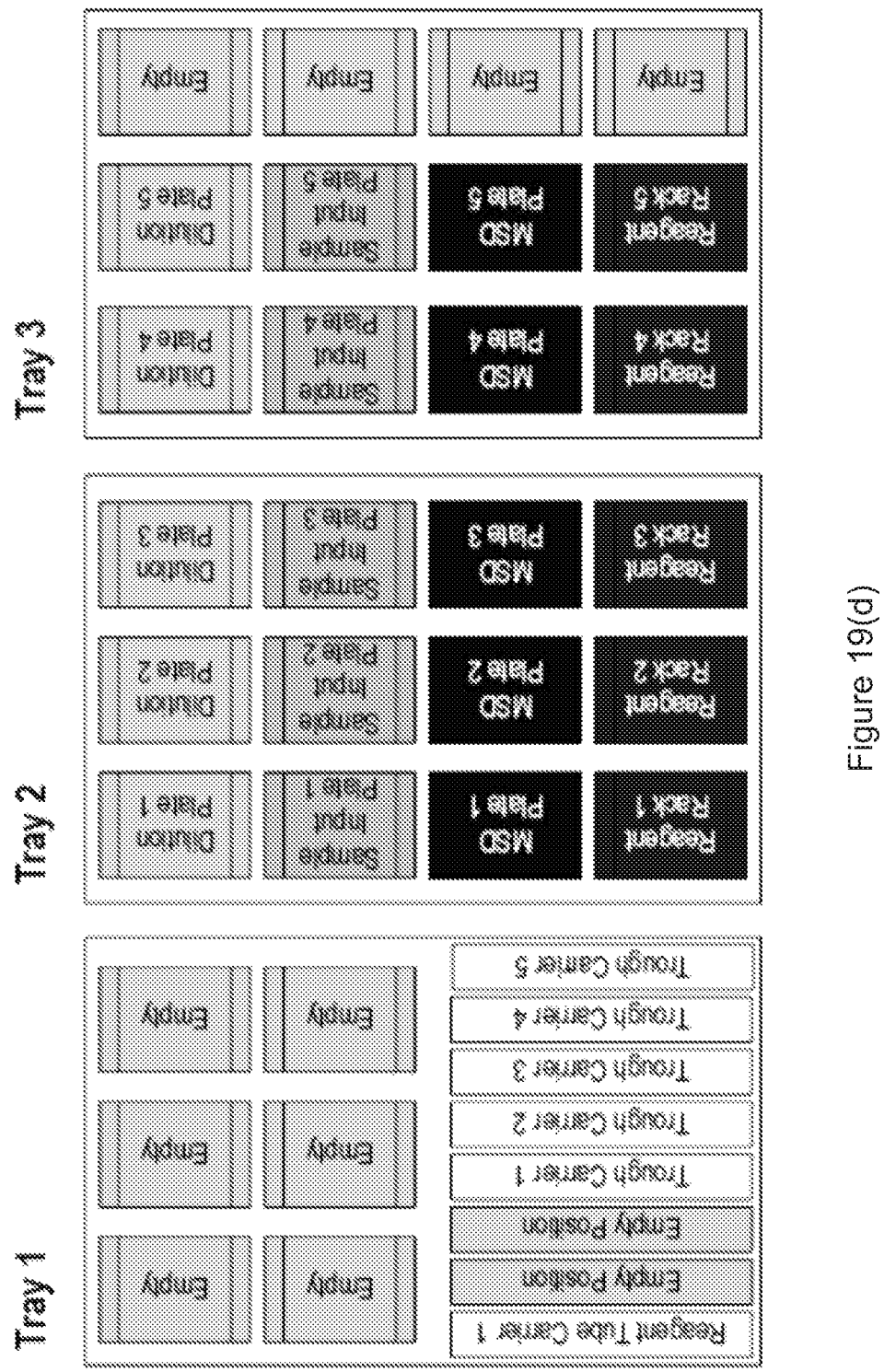
FIGS. 19(d)-(h) are exemplary top view of the trays loaded with assay consumables.
Figure 19E:
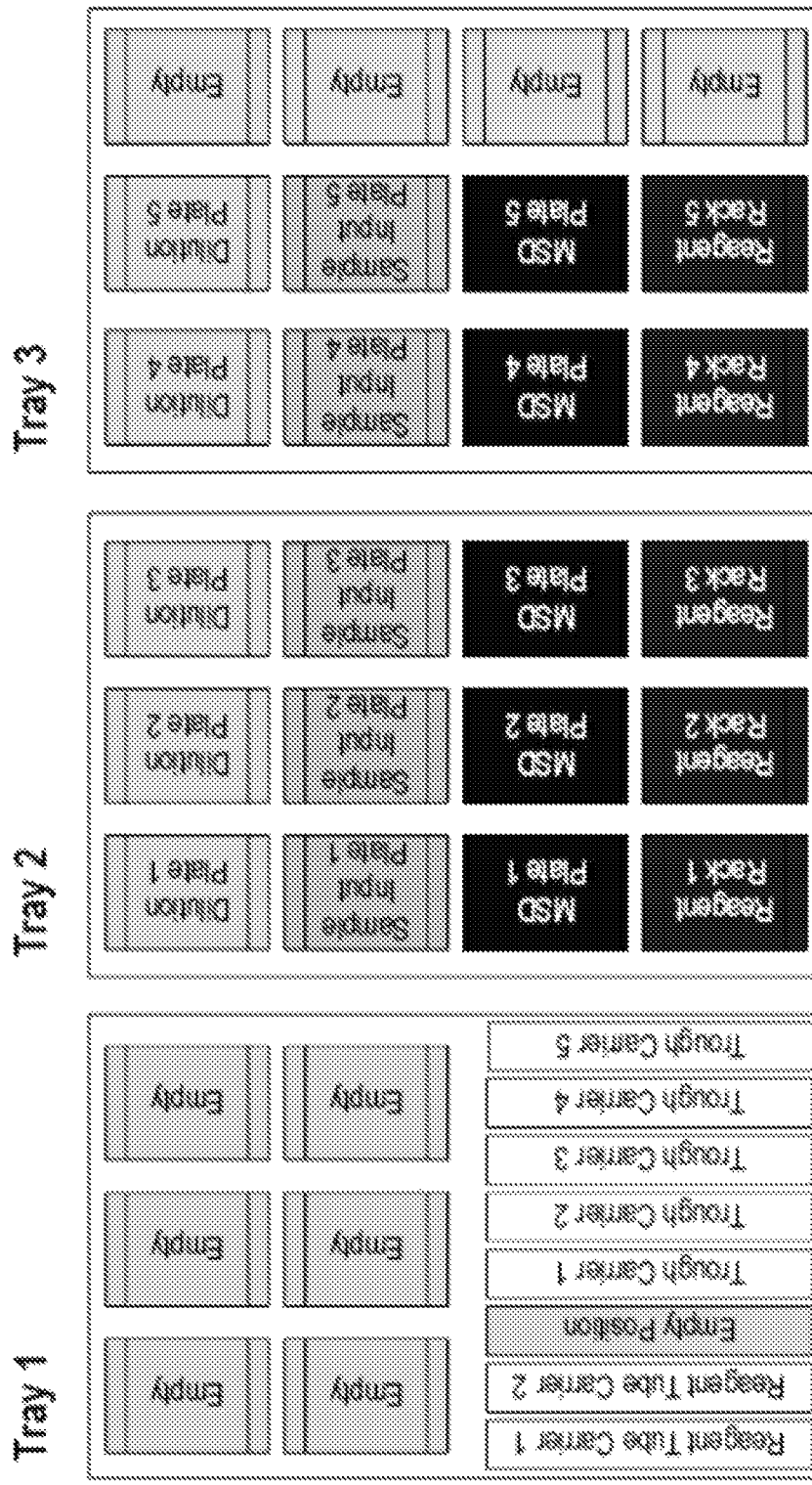
Figure 19F:
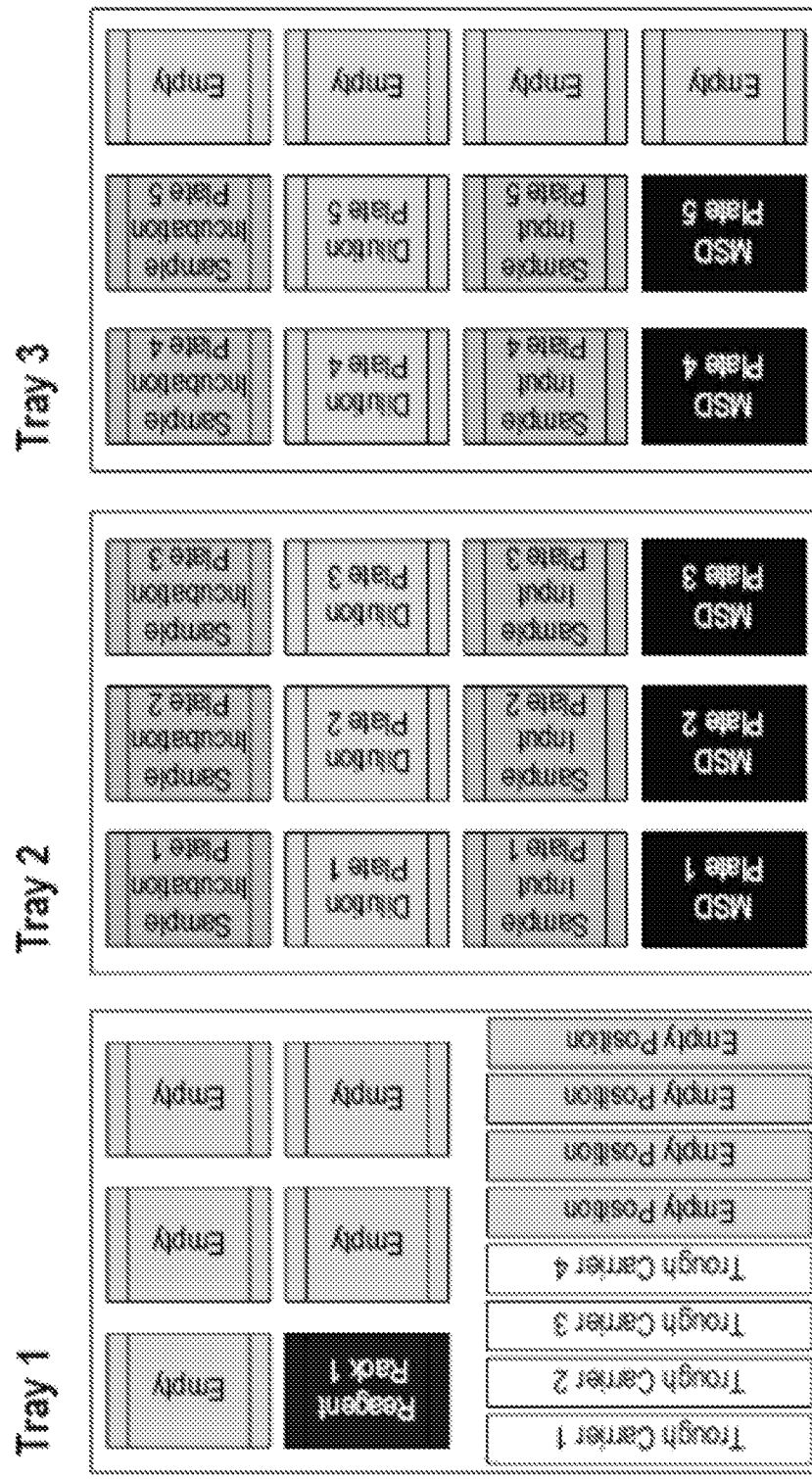
Figure 19G:
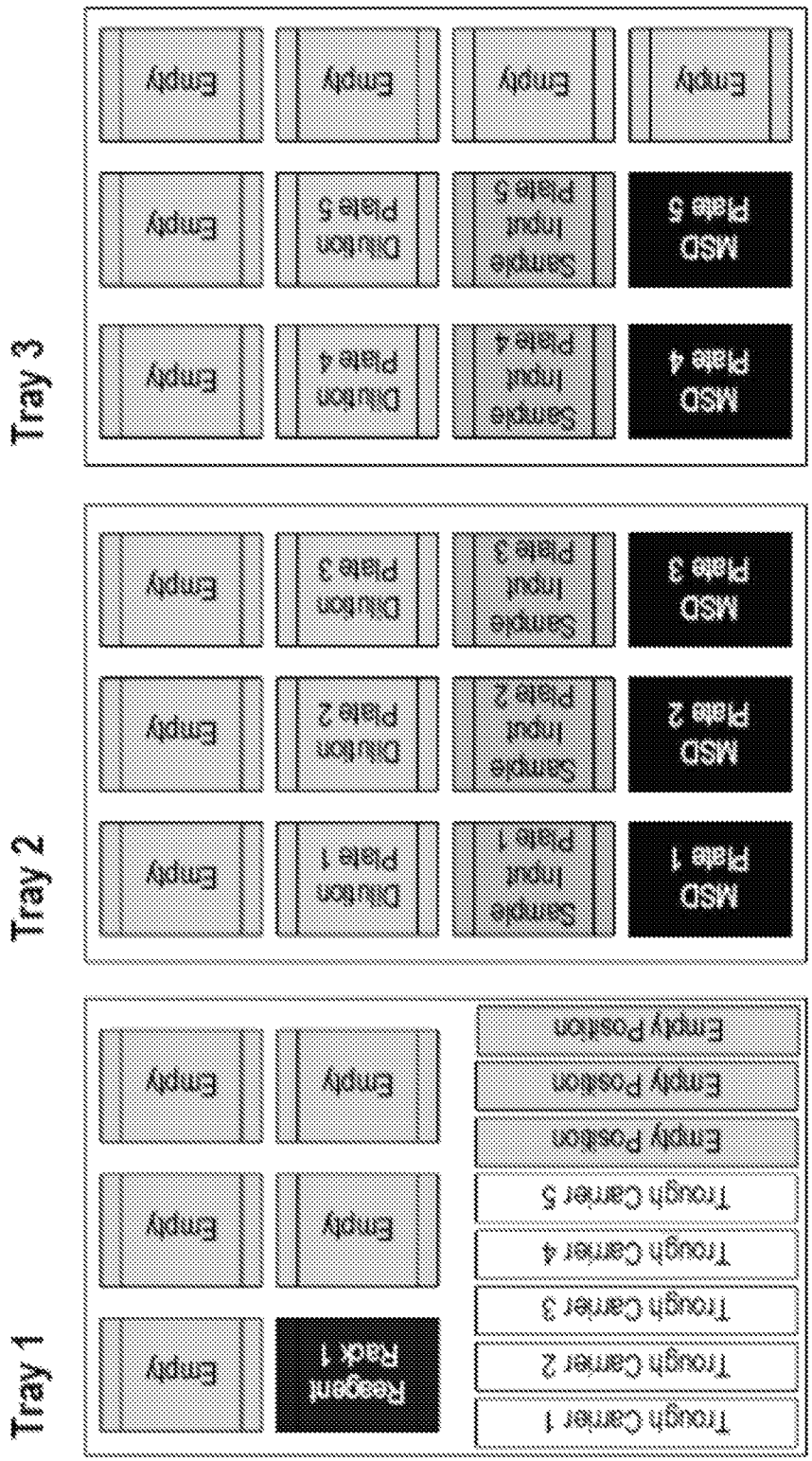
Figure 19H:
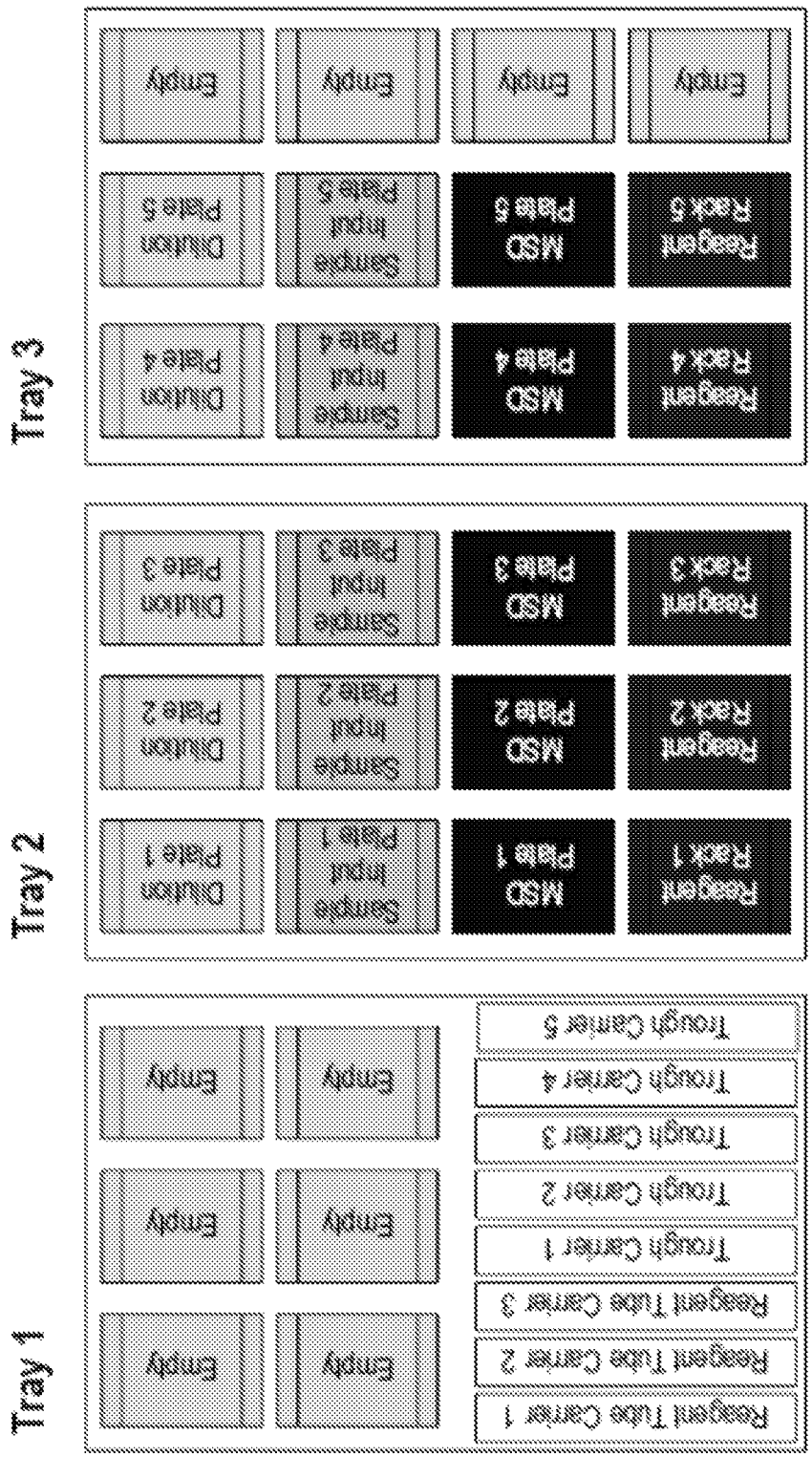
Figure 19I:
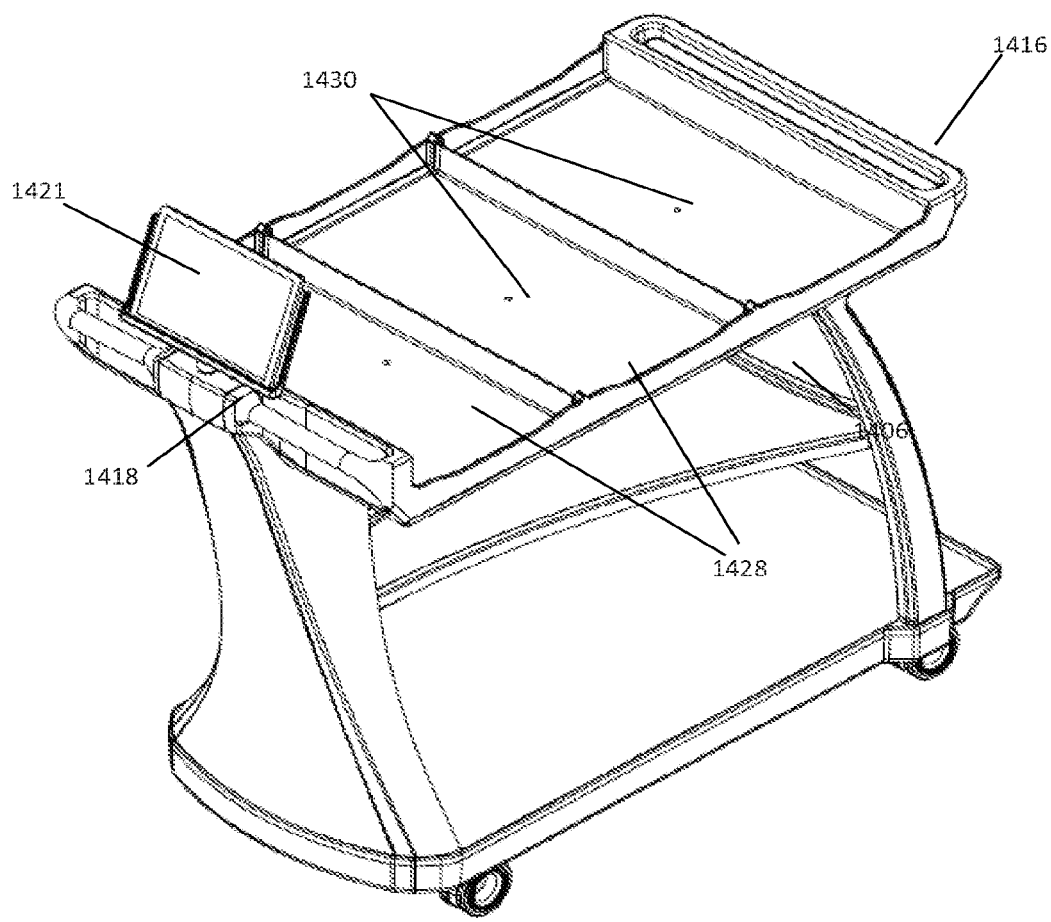
FIG. 19(i) shows cooling compartments under the trays.

FIG. 17(d) shows a general protocol sequence for Custom Sandwich Immunoassays. FIGS. 17(e)-(h) show protocols and reagent racks as labeled, and FIG. 17(i) shows a deck layout for these assays.

The standard PK protocol includes multiple parameters that can be optimized, including but not limited to:
Duration of incubations (1 hour to overnight)
Plate type
Type and/or concentration of capture species
Type and/or concentration of blocker
Concentration of unlabeled/biotinylated detection species (indirect assay only)
Concentration of STAG-labeled detection species
Assessment of assay sensitivity by varying known concentration of drug in a sample In order to optimize a PK assay on the assay system shown in FIG. 10 and its subparts, a user is provided a System Development Pack, which includes set of sample dilution plates (1.1 mL), plate lids, reagent tubes, and a kit that may include the following components:

TABLE 2

QUICKPLEX ™ 96-Well High Bind Plate Pack (10 Plate) and QUICKPLEX ™ 96-Well Plate Pack (10 Plate)
OR
QUICKPLEX ® 96 Well STREPTAVIDIN GOLD ™ Plate (10 Plate) and QUICKPLEX ® 96 Well High Bind Avidin Gold Plate (10 Plate)
MSD SULFO-TAG NHS Ester 150 nMoles
Streptavidin Sulfo-TAG Labeled 50 ug
Anti Mouse Antibody (Goat) Sulfo-TAG Labeled, 50 ug
Anti Rabbit Antibody (Goat) Sulfo-TAG Labeled, 50 ug
MSD Blocker A, 1L
MSD Phosphate Buffer (5X) 200 ml
MSD Blocker B, 2 g
MSD Read Buffer T (4x), 200 ml
Zeba 40K Columns, 2 mL The Development Pack, itself, as well as each component within it includes a consumable identifier (e.g. bar code) with consumable data associated therewith. The system bar code reader reads the consumable identifiers (e.g. bar codes), and downloads and installs the DDB stored to that consumable identifier (e.g. bar code). The DDB includes a DDB unique identifier, DDB version, a DDB xml file, consumable static information, consumable processing information, and combinations thereof. For example, if the components include a multi-well assay plate, the consumable type information includes the number of columns of wells; the number of rows of wells; the number of binding domains per well; and combinations thereof; and the consumable processing information comprises data used by the assay system in the conduct of an assay using the plate and/or the processing of assay data resulting from the conduct of an assay using the plate. In a specific embodiment, the consumable processing information comprises the number of sectors per plate, the number of circuits per plate, detection parameters used by said assay system to read said plate; image processing properties use to produce ECL results; plate type gain; binding domain gain; optical cross talk matrix; and combinations thereof.

The system bar code reader reads the consumable identifiers (e.g. bar codes) and downloads the appropriate protocols and optimization parameters for PK assay. A specific embodiment of a PK optimization workflow is shown in FIG. 17(c), and includes the following steps: (i) optimize the plate coating process; (ii) optimize the blocker type and/or concentration; (iii) optimize the detection species concentration; and/or (iv) evaluate the assay sensitivity. The user may elect to skip one or more of these steps and the software allows the user to skip one or more steps and/or manually enter parameters/data that would be generated in the skipped step.

The proposed sequence of assay optimization experiments for indirect assays is as follows:
Step 1: Optimize capture species type and/or concentration
Step 2: Optimize blocker type and/or concentration
Step 3A: Optimize biotinylated/unlabeled detection species and Sulfo-TAG-labeled detection species concentration
Step 4: Test for drug sensitivity The proposed sequence of assay optimization experiments for direct assays is as follows:
Step 1: Optimize capture species type and/or concentration
Step 2: Optimize blocker type and/or concentration
Step 3B: Optimize Sulfo-TAG labeled detection species concentration
Step 4: Test for drug sensitivity In order to optimize the capture process, the software will prompt the user to enter the following data in preparation for an experiment:
User will enter the following data on the samples to be tested:
Number of sample dilutions (either 8 or 12 dilutions per plate)
Dilution factor for samples
User will select whether or not to include zeroth dilutions
User will enter the following data on the capture species to be tested:
Number of capture species types and/or dilutions (up to 6 per plate, dependent on the number of sample dilutions that are being tested)
Dilution factor for each type of capture species (if more than one dilution per type is used)
User will select whether or not to include zeroth dilutions
User will select length of incubations (1 hour to 4 hours on-instrument or a user-determined length of time off-instrument).
User may add plates of varying types, assuming there is adequate capacity in the run.

User will select whether or not to apply the same reagents (i.e. the same reagent sources) to all plates.

The experiment can be conducted on up to 5 plates. The system then conducts the experiment and displays the results of that experiment on the user-interface.

In order to optimize the blocking process, the software will prompt the user to enter the following data in preparation for an experiment:

User will enter the following data on the samples to be tested:
Number of sample dilutions (either 8 or 12 dilutions per plate)
Dilution factor for samples
User will select whether or not to include zeroth dilutions User will enter the following data on the blockers to be tested:
Number of blocker types and/or dilutions (up to 6 per plate, dependent on the number of sample dilutions that are being tested)
Dilution factor for each type of blocker (if more than one dilution per type is used)

User will select length of incubations (1 hour to 4 hours on-instrument or a user-determined length of time off-instrument).

User may add plates of varying types, assuming there is adequate capacity in the run.

User will select whether or not to apply the same reagents (i.e. the same reagent sources) to all plates.

The experiment can be conducted on up to 5 plates. The system then conducts the experiment and displays the results of that experiment on the user-interface.

In order to optimize the detection species concentration for an indirect assay, the software will prompt the user to enter the following data in preparation for an experiment:

User will enter the following data on the samples to be tested:
Number of sample dilutions (either 8 or 12 dilutions per plate)
Dilution factor for samples User will enter the following data on the detection species to be tested:
Number of detection species and/or dilutions (4 concentrations of unlabeled/biotinylated detection species and 4 concentrations of STAG detection species per plate)
Dilution factor for each type of detection species
User will select whether or not to include zeroth dilutions User will select length of incubations (1 hour to 4 hours on-instrument or a user-determined length of time off-instrument).

User may add plates of varying types, assuming there is adequate capacity in the run.

User will select whether or not to apply the same reagents (i.e. the same reagent sources) to all plates.

The experiment can be conducted on up to 5 plates. The system then conducts the experiment and displays the results of that experiment on the user-interface.

In order to optimize the detection species concentration for a direct assay, the software will prompt the user to enter the following data in preparation for an experiment:

User will enter the following data on the samples to be tested:
Number of sample dilutions (either 8 or 12 dilutions per plate)
Dilution factor for samples User will enter the following data on the detection species to be tested:
Number of STAG-detection species and/or dilutions (up to 6 per plate, dependent on the number of sample dilutions that are being tested)
Dilution factor for STAG-detection species
User will select whether or not to include zeroth dilutions User will select length of incubations (1 hour to 4 hours on-instrument or a user-determined length of time off-instrument).

User may add plates of varying types, assuming there is adequate capacity in the run.

User will select whether or not to apply the same reagents (i.e. the same reagent sources) to all plates.

The experiment can be conducted on up to 5 plates. The system then conducts the experiment and displays the results of that experiment on the user-interface.

Finally, in order to evaluate the assay sensitivity, the software will prompt the user to enter the following data in preparation for an experiment:

User will enter the following data on the samples to be tested:
Number of sample dilutions (up to 12 dilutions per plate)
Dilution factor for samples
User will select whether or not to include zeroth dilutions User will select length of incubations (1 hour to 4 hours on-instrument or a user-determined length of time off-instrument).

User may add plates of varying types, assuming there is adequate capacity in the run.

User will select whether or not to apply the same reagents (i.e. the same reagent sources) to all plates.

The experiment can be conducted on up to 5 plates. The system then conducts the experiment and displays the results of that experiment on the user-interface.

Pharmacokinetic (PK) assays when automated to run in an assay system, such as assay system (1000) or (900) may have the following steps:

Automated Assay Sequence
1 Inventory Plates
2 Prime the Washer
3 Apply Diluent to the Dilution Plate(s)
4 Generate Standard Curve
5 Create Control Dilutions
6 Create Sample Dilutions
7 Apply Blocker to the MSD Plate
8 Perform Blocking Incubation
9 Wash the MSD Assay Plate
10 Create Coating Solution
11 Apply Coating Solution to MSD Plate
12 Perform the Coating Incubation
13 Apply Dilutions to MSD Assay Plate
14 Perform Sample Incubation
15 Create Detection Solution
16 Create Secondary Detection Solution
17 Apply Secondary Detection Solution to MSD Plate
18 Perform the Secondary Detection Incubation
19 Apply Detection Solution to MSD Plate
20 Perform the Detection Incubation
21 Apply Read Buffer to Plate
22 Read Plate on ECL reader
23 Clean up process

E. The Consumable Holders and Kits

The capabilities of assay system (1000) allow the system to run a wide number of assays. These capabilities provide the users with the ability to order all necessary reagents in a specialized assay reagent holder or all necessary consumables in a kit at the same time to run a particular assay. Such assay reagent holders and kits are available from Meso Scale Diagnostics in Rockville, Md. Exemplary assay reagent holders include, but are not limited to, holders for assay reagents (e.g., Custom Racks for MSD Kitted Reagents). Kits specialized for use in the disclosed instruments, systems, and methods contain an assay reagent holder and other consumables such as troughs, tubes, and assay plates (e.g., multi-well assay plates). A V-PLEX kit is described below; however, suitable kits may include kits for any assays including V-PLEX, U-PLEX, S-PLEX, pharmacokinetic (PK), immunogenicity (IG), and custom.

MSD Kits, such as the V-PLEX Plus kits, require packaging and shipment of lyophilized calibrator and control materials in glass vials and detection reagents in plastic tubes. These items are typically inserted into a foam insert that is packaged into a cardboard box for shipment. The contents of a V-PLEX kit are shown in FIG. 18(*a*). 10 plastic tubes containing different detection reagents are typically included with each V-PLEX kit. The number of plastic tubes that a user must manage is multiplied 3-fold for U-PLEX kits, where up to 30 vials containing linker, capture and detection reagents would be required to run a fully populated 10-spot plate. The possibility of mix-ups with such a large number of tubes can be significant. Hence, there is a need for positive identification of each tube and its contents. Equally important is the ability to ship and present the tubes in an automated friendly and compact format.

The present invention provides inventive custom industry-standard format (see American National Standards Institute/Society for Laboratory Automation and Screening standard for microplates available at http://www.slas.org/default/assets/File/ANSI_SLAS_1-2004_FootprintDimensions.pdf, which is incorporated herein by reference in its entirety) racks that can hold the control and calibrator vials and all of the plastic tubes containing reagents, and methods of using or operating such racks. The rack (1200) is sized and dimensioned to conform to the ANSI-SLAS standard for microplates. The rack (1200) has a body or frame (1201), which is designed to have a plurality of hollow columns (1203) adapted to receive vials (1206) and tubes (1208). Each hollow column (1203) has an opening (1204) at the bottom below each vial (1206) and tube (1208). Hollow columns (1203) and openings (1204) may have different sizes or diameters, as shown in FIGS. 18(*b*)-(*c*), to accommodate different sized vials, tubes, as well as other liquid containers, and openings (1204) may be covered by a transparent or translucent cover or may be left uncovered. The vials and tubes have identification barcodes on the bottom, and openings (1204) allow the consumable identifiers (e.g. bar codes), whether 1-D or 2-D, to be shown through the bottom of rack (1200), as best shown in FIG. 18(*d*). A bar code reader (1209) with its field-of-view (FOV) looking upward can scan these consumable identifiers (e.g. bar codes). These openings provide viewing access for such a 2-D barcode reader, so that rack (1200) and its contents (1206, 1208) can be placed directly on top of the platen of the bar-code reader (1209) and can be read without having to maneuver each tube or vial to be read, as illustrated in FIG. 18(*e*). Rack (1200) may have its own consumable identifier (e.g. bar code) affixed to any surface thereof, including the bottom, top or one or more sides.

The rack is designed to be grippable with robotic grippers for compatibility with automated plate handling systems, such as gripper pads (1031) of robotic subsystem (1002) shown in FIGS. 10(*a*)-(*c*). As best shown in FIG. 18(*f*), rack (1200) has ledges (1202), which are similar to ledges (1044) on teaching or training plate (1035). Ledges (1202) are sized and dimensioned to be gripped, lifted and moved by gripper pads (1031) within the enclosure of assay system (1000).

Rack (1200) also includes snap-in inserts (1212) for compatibility with different types or sizes of tubes and vials, as shown in FIGS. 18(*g*)-(*j*). Insert (1212) has a generally cylindrical shape with a top opening (1214) adapted to receive the tube or vial and a bottom opening (1216). Bottom opening (1216) abuts bottom rim (1218) of opening (1204) to keep insert (1212) within hollow column (1203). Bottom opening (1216) also has a rim to prevent the tube or vial from being pushed out of the bottom of rack (1200), as best shown in FIG. 18(*i*). Additionally, insert (1212) also has a plurality of snaps (1220) to latch to bottom rim (1218) of opening (1204), and external ribs (1222) to provide structural support to the insert.

The consumable identifiers (e.g. bar codes) can be printed or affixed directed onto a tube or vial, if the bottom is relatively flat. For tube or vial that has a hollow skirted bottom, such as those shown in FIGS. 18(*h*) and (*i*), the consumable identifiers (e.g. bar codes) can be printed or affixed on a solid plug or puck sized and dimensioned to fit into the skirted bottom of these tubes or vials. Alternatively, the consumable identifier (e.g. bar code) can be printed on a membrane, such as a metal foil or polymeric membrane, that is adhered to the skirted bottom for example by induction sealing.

In addition to the consumable identifiers (e.g. bar codes) on the bottom of the tubes and vials, the top surface of rack (1200) can have color codes or alphanumeric texts indicative of the content(s) of the tubes or vials, readable to lab technicians or other user of the assay machines, as best shown in FIGS. 18(*k*) and (*l*).

Before running an assay, the user or lab technician would reconstitute the lyophilized calibrators typically contained in one or more glass vials (1206) and remove the caps from tubes (1208) and load rack (1200) onto assay consumable storage unit (1004). Gripper pads (1031) on robotic system (1002) can grip rack (1200) by ledge (1202) to place rack (1200) on top of bar code reader (1209), where the consumable identifiers (e.g. bar codes) of the tubes and vials can be read. Thereafter, gripper pads (1031) moves rack (1200) onto platform (1012) and make the reagents, calibrator, controls, detection antibodies, diluents, and wash buffers contained on rack (1200) available to the assay run.

Preferably, rack (1200) may have a mask (1224) with a plurality of mask apertures (1226) defined thereon. The number of mask apertures (1226) is less than or equal to the number of hollow columns (1203). Mask apertures (1226) restrict access to hollow columns (1203) that are not being used. As shown in FIG. 18(*m*), rack (1200*a*) has mask (1224) that covers some of hollow columns (1203) and mask apertures (1226) are present only where vials (1206) and tubes (1208) are present for the V-PLEX assay. Rack (1200*b*) has mask (1224) that has the same number of mask apertures (1226) and hollow columns (1203) for the U-PLEX assay. Mask (1226), which may be color coded as described above, minimizes the possible operator errors in conducting assays. Rack (1200) also has a lid (1210) to prevent the tubes (1208) and vials (1206) from falling out during shipment, as best shown in FIG. 18(*n*). Lid (1210) is preferably removed before rack (1200) is placed into assay consumable storage unit (1004).

An advantage provided by inventive rack (1200) is that in use bar code reader (1209) can read all the consumable identifiers (e.g. bar codes) of the tubes (1208) and vials (1206) while rack (1200) is placed directly on the bar code reader. No robotic or manual manipulation of the individual tubes and vials is necessary to read their individual consumable identifiers (e.g. bar codes). An inventive method of the present invention described above includes this advantage.

Alternatively, the bar code reader may read one consumable identifier (e.g. bar code) at a time, or read one row of bar code, or one column of bar code. The present invention is not limited to any particular type of bar code reader.

F. The Loading Cart

Another aspect of the present invention that minimizes possible operator errors is a loading cart designed to work in conjunction with assay system (1000) shown in the subparts of FIG. 10. However, the inventive loading cart can be used with other assay systems, including but not limited to those illustrated in FIG. 8 and FIGS. 9(a)-(d), and other commercially available assay systems. The inventive loading cart is (1400) illustrated in the subparts of FIG. 19. Loading cart (1400) may have two or more shelves for storing consumables and labwares. Although three shelves or levels are shown, any number of shelves can be used. Bottom shelf (1402) is designed to store liquid reagent storage (1007), liquid waste storage (1020) and other larger or heavier storages or bottles. Middle shelf (1404) is designed to hold any labwares, such as extra pipette tips, such as 1000 µl tips (1015) and 350 µl tips (1016). Top shelf (1406) is specifically designed to handle a large number of consumables such as tubes, tube carriers (1017), rack (1200), assay plates, troughs (1018), etc. The bottom and middle shelves are preferably coated or lined with a non-slip material. The shelves are preferably made from cast urethane Loading cart (1400) preferably has light weight frame comprising rear supports (1410) and tapered front support (1412), as the main weight bearing members. Rear supports (1410) are preferably made from lightweight aluminum, and tapered front support (1412) also has aluminum or metal frame wrapped by a polymeric skin. Loading cart (1400) is supported by four caster wheels (1414), preferably hubless wheel casters that contain ball bearings to reduce friction. Such hubless casters can carry significantly higher load than standard caster wheels, e.g., up to 275 lbs. or 125 kg. Alternatively, self-braking casters can be used. Preferably, the back two casters (1414) do not rotate during transport.

Loading cart (1400) also has a rear handle (1416) and front handle (1418). Front handle (1418) also contains a mount and support (1420) designed to support a computer or computer tablet (1421), such as an iPad or Surface tablet. Mount (1420) can be rotated 360° and the tablet can be tilted through a limited range to adjust to the user's reading height.

Loading cart (1400) may also include a hand-held or fixed mount barcode scanner (not shown) for scanning barcodes on consumables.

In one example, the loading cart weighs about 133 lbs. (60 kg) when unloaded and about 154 lbs. (69 kg) when the top shelf (1406) is loaded with consumables. Loading cart (1400) stand 41 inches tall (104 cm) to top tray (1406), a width of 27 inches (69 cm) and a length of 52 inches (132 cm). Loading cart (1400) has considerably more utility and is more ergonomic than conventional assay carts, such as the two-shelf AKRO-MILS carts (http://www.mscdirect.com/product/details/00677666), which measures 32 inches tall× 24 inches wide and 44 inches long and weighs 77 lbs. unloaded.

Preferably, top shelf (1406) is designed to receive a number of trays (1408). Although three trays (1408) are shown, any number of trays of any size can be used and the present invention is not limited to any number of trays or any tray sizes. Each tray (1408) can have any configuration. Three exemplary configurations are illustrated in FIG. 19(c). Tray (1408a) has a plurality of slots (1422) that can store tube carriers (1017) and carriers for troughs, such as troughs (1018), shown in FIG. 10(a) and square slots (1424) for labwares such as assay plates, dilution plates, sample plates, reagent racks, carriers for pipette tips (1015, 1016), etc. Tray (1408b) also has slots (1422) and slots (1424), as well as circular slots (1426) adapted to carry tubes, such as vials (1206) and tubes (1208), shown in FIGS. 18(c) and (f). Tray (1408c) has a plurality of square slots (1424). It is noted that an inventive tray can have any combination of slots (1422, 1424, 1426) and slots of any shape and sized. The trays can be reversible, i.e., the trays may have slots on the top and bottom surfaces.

In one example, tray configurations for V-Plex, U-Plex, Immunogenicity (IG), pharmacokinetic (PK) and S-Plex are illustrated in FIGS. 19 (d)-(h). It is noted that these tray configurations are for illustrative purpose only and the present invention is not limited thereto. Certain reagents, buffers or diluents may have to be kept cool while the assay run is being setup. Another improvement built into top shelf (1406) is compartments (1428) that built below trays (1408), as best shown in FIG. 19(i). Preferably, one compartment (1428) is provided below each tray (1408), as shown. Compartments (1428) may be filled with a coolant such as ice or dry ice. The bottom surface of compartments (1428) is concave with a minimum point proximate its center. A drainage hole (1430) can be provided near the minimum point to drain melted water.

Possible errors can occur while loading an assay system, such as assay systems (900) and (1000). These assay systems have robotic systems, pipettors, assay consumable storage units, readers, optionally heated shakers, plate washers, etc. These equipment present obstacles to placing the labwares on the platform and may cause confusions. Additionally, the different assay runs require different placements and/or configurations of labwares on the system's platform, as illustrated in FIGS. 13(a) 13(c), 14(a), 14(b), 15(a) and 15(c). The variety of different placements and configurations can also cause confusion. An inventive method of loading the assay systems utilizing loading cart (1400) is described below.

A lab technician when starting an assay run may use the tablet computer on loading cart (1400) to select the assay to be run, e.g., V-Plex, U-Plex, S-Plex, PK or IG, and any specific subset of the assay. The user interface would advise the technician how to arrange the trays (1408a, 1408b, 1408c) on top shelf (1206). Trays (1208) can be color coded and/or labelled to assist the lab technician in loading the labwares including one consumable kit (1200) discussed above, for example as shown in FIGS. 19(d)-(h). Such arrangements preferably match exactly the arrangements on platform (1012) of assay system (1000) as shown in FIGS. 10(a)-(c). Other consumables such as liquid reagent (1007) and the liquid waste container (1020) should be loaded on bottom shelf (1402) and containers of pipette tips (1015, 1016) are loaded on middle shelf (1404). Preferably, the arrangements of labwares on loading cart (1400) are check against the display by the user interface on the tablet on loading cart (1400). Thereafter, loading cart (1400) is pushed to an assay machine, such as assay system (1000). The technician would then open the system, activate computer screen (1058), and optionally sound generator (1062) as shown in FIG. 10(*k*). The technician would then follow the user interface on computer screen (1058) and transfer the labwares on loading cart (1400) to assay system (1000), preferably by following the same configurations and placements of the labwares on trays (1408).

G. Operational and Performance Qualifications

Assay systems such as those shown in FIGS. 9 and 10 and their subparts are preferably qualified, i.e., to ascertain that all their major components, such as the ECL reader, the robotic system including gripper pads and pipettor, plate washers, etc. function within acceptable ranges. The present invention also includes methods for qualifying the operation and performance of the assay systems. The inventive method generally comprises a number of steps described below. This method can be automated and executed by the assay systems (900, 1000) without human assistance, once all reagents, buffers and consumables are loaded into the systems. Furthermore, qualification kits which contain all necessary reagents and buffers for an operational and performance qualification can be purchased from Meso Scale Diagnostics of Rockville, Md.

Preferably, the steps to qualify the ECL reader should be completed together and at the beginning of the qualification process, because having an operational ECL reader is necessary for any assay runs. The ECL qualification includes the step of running the ECL reader with an electronic plate, which measures the electrical current applied to the plate. This ensures that the applied electrical current is adequate and uniform. Another step, which may be the next step, is to run the ECL reader with an empty assay microplate, e.g., a MSD 96-well plate, to measure the level of electronic noise or background/dark noise within the ECL reader. Another step, which may follow the other two steps, is to fill an assay tray with a reagent consisting of unbound SULFO-TAG in Meso Scale Diagnostics Read Buffer (hereafter referred to as "free tag") to verify that the ECL reader is reading the expected count. For example, a 300,000 count free tag may be used as a detection reagent to generate ECL signals. Hence, the ECL reader should read about 300 k count from each well within a small predetermined range. The 300 k free tag is available from Meso Scale Diagnostics.

To verify the plate washer's aspiration, the assay plate with the free tag from the ECL reader qualification is aspirated by the plate washer. In other words, the plate washer evacuates all the wells in the assay plate. Thereafter, an amount of about 150 µl of read buffer is pipetted from a read buffer trough into each well and shaken to mix before the assay plate is read by the ECL reader. This qualification step checks to see how much residual free tag remains in the assay plate, since the residual free tag would be read by the ECL reader. Low ECL reading means good aspiration from the plate washer.

Another qualification step checks on the ability of the pipettor, such as pipette system (1021) to pipette a predetermined amount. In one example, a 96 well assay tray with 12 columns and 8 rows of wells is used. The first column of wells holds 300 µl of 300 k free tag in each well. A partial amount, e.g., 120 µl, is pipetted to the second column of wells along with another amount of read buffer, e.g., 180 µl. Another partial amount of liquid from the second column of wells is pipetted into a third column of wells along with an amount of read buffer. This continues until the penultimate column. The last or $12^{th}$ column contains no free tag and all read buffer. When the pipetting process is completed, the concentration of free tag should be the highest in the $1^{st}$ column and lowest or zero in the final column. The concentration of free tag from one column to the next is a geometric series where the concentration is decreased by a factor of N, where N is less than 1.0. In the example, the concentration from column to column from the first to the penultimate column decrease by a multiple of 0.4. Thereafter, the assay plate is read by the ECL reader, which preferably is already qualified. Consistent readings that also decreased by a factor of N from column to column from the ECL reader would qualify the pipettor.

In another qualification step, the plate washer's dispensing function is tested. The washer dispenses a predetermined amount of wash buffer, e.g., 300 µl, into each well in an assay plate. Since the amount of wash buffer and the volume and shape of each well are known, the liquid level in each well should also be known. The pipettor using the capacitive liquid level sensing, discussed above, is used to gauge the liquid levels in the well. In one example, an eight-pipette system can check the liquid level from one column to the next until all 12 columns in a 96-well assay plate are checked. Consistent reading of the liquid level in each well would qualify the plate washer's dispensing capability.

Preferably, if one of the above qualification steps fails, the entire qualification process may stop to conserve qualification consumables. Also, preferably the above qualification process should be completed before the assay system (900, 1000) is first used, and should be repeated about once a year. More frequent re-qualification, e.g., monthly, quarterly, semi-annually, is preferred for certain applications. The operation and performance qualification can be automated and the user/technician can be guided or prompted by the user interface on the assay system to load the consumable, preferably from a qualification kit, and activate the qualification. Preferably, the operation and performance qualification of the system may be evaluated for PASS/FAIL criteria by the software running the assay system, without requiring user interaction.

H. Adjusting Timing of Adding Read Buffer to Timing of ECL Reader

The present inventors have discovered that for certain assays the wait time from the time the read buffer is added to the wells in the multi-well assay plate to the time the wells are read by the ECL reader needs to be monitored. For these certain assays, the difference in wait time from well to well should not be more than a relatively short period, e.g., 1 minute or less, preferably 50, 40, 30, or 20 seconds.

Figures 20C, 20D:
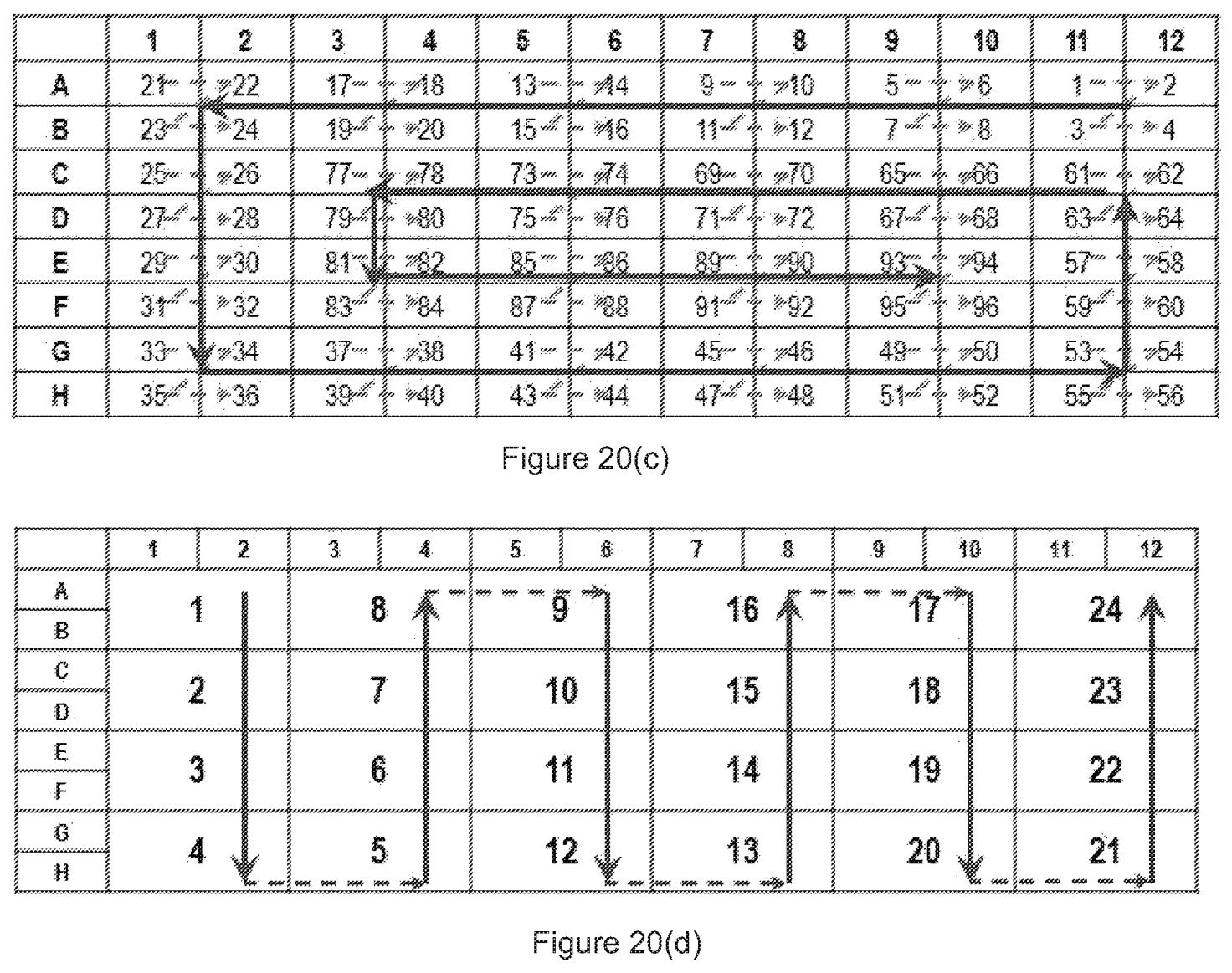
Figure 20E:
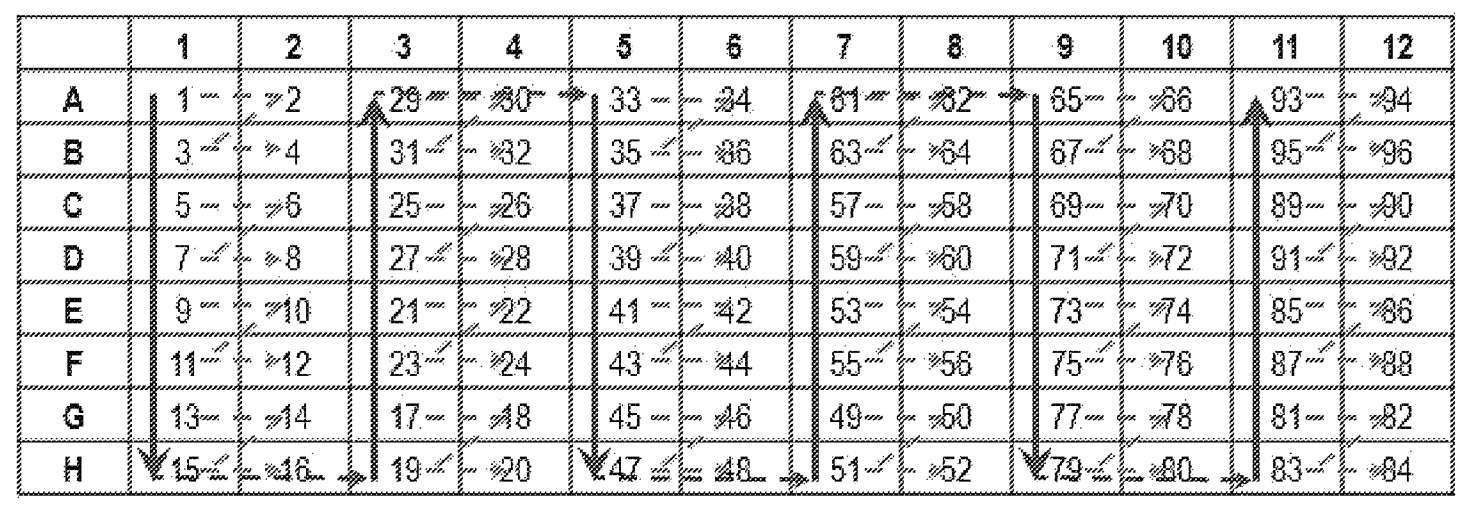

For assay system (1000), the preferred pipettor with eight tips deposits the read buffer in a 8×12 multi-well assay plate one column at a time for 12 times from left to right, as illustrated in FIG. 20(*a*). The preferred reader, the SQ 120, reads the same assay plate in blocks of four wells in a counterclockwise spiral from the upper right corner, as illustrated in FIG. 20(*b*). This counterclockwise spiral superimposed on the read pattern for individual wells in the well blocks is illustrated in FIG. 20(*c*).

To achieve more uniform wait time from well to well, the present inventors revised the reading pattern from counterclockwise spiral to column to column as shown in FIGS. 20(*d*)-(*e*) to better match the pattern of read buffer pipetting. Additionally, the timing of pipetting the read buffer is stretched out to take into account the speed of the ECL reader. More specifically, about 15 seconds pause were inserted between pipetting the read buffer from column 2 to column 3, from column 4 to column 5, from column 6 to column 7, from column 8 to column 9, and from column 10 to column 11 on the plate These adjustments allowed the differences in wait time between pipetting read buffer and reading ECL values to be within the accepted margin, thereby improving the reliability and repeatability of the ECL results.

I. Example: Reproducibility of Timing or Assay Runs

Three substantially identical assays were conducted on assay system (900) on three consecutive days. Two plates were used in each assay run. Each assay run used an 8-point calibration curve in triplicate, 3 controls run in duplicate and 29 samples run in duplicate. As noted below, the second assay run was delayed for a total of 13 minutes and 44 seconds during sample dilutions due to a shortage of pipette tips. The issue was remedied and the run continued. The time delay is included in the data below. The data show that the three runs were completed in substantially the same amount of time.

TABLE

Timing for Key Sequence Operations

| | Time to Complete Operation ([h]:mm:ss) | | | | | |
|---|---|---|---|---|---|---|
| | Run 1 | | Run 2 | | Run 3 | |
| Operation | Plate 1 | Plate 2 | Plate 1 | Plate 2 | Plate 1 | Plate 2 |
| Create Standard Curve | 4:28 | 4:27 | 4:23 | 4:25 | 4:26 | 4:25 |
| Dilute Controls | 1:31 | 1:31 | 1:30 | 1:29 | 1:26 | 1:26 |
| Dilute Samples | 3:58 | 4:21 | 4:04 | 4:22 | 3:57 | 4:37 |
| Total Time for Dilution Prep | 9:57 | 10:19 | 9:57 | 10:16 | 9:49 | 10:28 |
| Add Cal Curve and Dilutions to MSD Assay Plate | 4:30 | 4:28 | 4:48 | 4:30 | 4:11 | 4:16 |
| Sample Incubation | 2:00:00 | 2:00:00 | 2:00:01 | 2:00:00 | 2:00:00 | 2:00:00 |
| Prepare Detection Antibody Blend | 4:33 | 4:48 | 4:33 | 4:47 | 4:34 | 4:54 |
| Dispense Detection Antibody Blend to MSD Assay Plate | 2:09 | 2:11 | 2:09 | 2:09 | 2:15 | 2:11 |
| Detection Incubation | 2:00:00 | 1:59:59 | 2:00:00 | 2:00:00 | 2:00:00 | 2:00:00 |
| Dispense Read Buffer to MSD Assay Plate | 1:30 | 1:30 | 1:33 | 1:33 | 1:30 | 1:31 |
| Read MSD Assay Plate | 1:32 | 1:32 | 1:32 | 1:32 | 1:32 | 1:32 |
| Total Run Time | 5:01:49 | | 5:11:42*** | | 5:01:41 | |

For the second run, the total time duration excluding the delay time was 4:57:58, which was within 4 minutes for the first and third runs. The first and third runs were within seconds of each other.

Across all six plates, the differences in time durations from the longest to the shortest for key sequences in the assay were in the order of seconds, as shown below.

TABLE

Comparison of Timing for Key Sequence Operations

| Operation | Maximum Time ([h]:mm:ss) | Minimum Time ([h]:mm:ss) | Jitter (Max − Min) |
|---|---|---|---|
| Create Standard Curve | 4:28 | 4:23 | 0:05 |
| Dilute Controls | 1:31 | 1:26 | 0:05 |
| Dilute Samples | 4:37 | 3:57 | 0:40 |
| Add Cal Curve and Dilutions to MSD Assay Plate | 4:48 | 4:11 | 0:37 |
| Sample Incubation | 2:00:01 | 2:00:00 | 0:00:01 |
| Prepare Detection Antibody Blend | 4:54 | 4:33 | 0:21 |
| Dispense Detection Antibody Blend to MSD Assay Plate | 2:15 | 2:09 | 0:06 |
| Detection Incubation | 2:00:00 | 1:59:59 | 0:00:01 |
| Dispense Read Buffer to MSD Assay Plate | 1:33 | 1:30 | 0:03 |
| Read MSD Assay Plate | 1:32 | 1:32 | 0:00 |
| Total Run Time | 5:01:42 | 5:01:41 | 0:00:01 |

Hence, the data shows that the time durations for key sequence operations in the same assay runs are highly reproducible, and that the time durations for running the same assay over multiple days are substantially the same. "Substantially the same" includes, but is not limited, that the time duration are close so that the ECL reading are accurate or repeatable or both. Another time duration data is presented in FIG. 13(f) and shows similar results.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the claims. Various publications are cited herein, the disclosures of which are incorporated by reference in their entireties.

The invention claimed is:

1. An assay system configured to use an assay consumable for conducting an assay, said assay consumable associated with a consumable identifier wherein said assay system comprises:
   (a) a storage medium configured to store data describing a plurality of steps of a generic assay protocol applicable to a plurality of assays, and configured to store a data deployable bundle (DDB) associated with the consumable identifier, wherein the DDB includes information describing a specific assay protocol to be performed, the specific assay protocol including all or a portion of the plurality of steps of the generic assay protocol;
   (b) a controller adapted to:
   read the information in the DDB to determine the specific assay protocol to be performed when conducting the assay; and
      cause all or a portion of the steps of the generic assay protocol to be performed based on the specific assay protocol associated with the DDB.

2. The assay system of claim 1, wherein the controller is further configured to persist one or more data files of the DDB to the storage medium.

3. The assay system of claim 2, wherein the one or more data files comprise a DDB unique identifier, a DDB version, consumable static information, consumable processing information, and combinations thereof.

4. The assay system of claim 3, wherein the consumable static information comprises consumable type information.

5. The assay system of claim 4, wherein the assay consumable is a multi-well assay plate and the consumable type information includes a number of columns of wells; a number of rows of wells; a number of binding domains per well; and combinations thereof.

6. The assay system of claim 3, wherein the assay consumable is a multi-well assay plate and the consumable processing information comprises data used by the assay system in the conduct of the assay using the multi-well assay plate and/or the processing of assay data resulting from the conduct of the assay using the multi-well assay plate.

7. The assay system of claim 6, wherein the consumable processing information comprises the number of sectors per multi-well assay plate, the number of circuits per multi-well assay plate, detection parameters used by the assay system to read the multi-well assay plate; image processing properties use to produce ECL results; plate type gain; binding domain gain; optical cross talk matrix; and combinations thereof.

8. The assay system of claim 3, wherein the assay consumable is a kit comprising a multi-well assay plate and one or more reagents used in the conduct of the assay using the multi-well assay plate and the DDB further comprises assay binding domain information, assay protocol, data analysis parameters, a product insert, and combinations thereof.

9. The assay system of claim 2, wherein the one or more data files comprise a DDB unique identifier, a DDB version, and consumable static information.

10. The assay system of claim 1, wherein the assay system further comprises a DDB version compatibility processor configured to downgrade and/or upgrade incompatible DDB software.

11. The assay system of claim 1, wherein the assay system further comprises a DDB factory adapted to transform raw classified data into assay system configured data suitable for use by the assay system in the conduct of the assay.

12. The assay system of claim 1, wherein the DDB comprises a DDB xml file including data description information and data processing information.

13. The assay system of claim 1, wherein the specific assay protocol includes only a portion of the plurality of steps of the generic assay protocol.

14. A non-transitory computer readable medium having stored thereon a computer program which, when executed by a computer system operatively connected to an assay system, causes the assay system to perform all or some of the steps of a method of conducting an assay on said assay system, wherein said assay system is configured to use an assay consumable in the conduct of said assay, said assay consumable comprising an assay consumable identifier including a data deployable bundle (DDB), and said assay system comprises:
   (a) a storage medium including a consumable data repository comprising local consumable data, a data registry, and data describing a plurality of steps of a generic assay protocol applicable to a plurality of assays;
   (b) a consumable identifier controller adapted to read and install said DDB to said storage medium; and
   (c) a consumable data service processor adapted to query said data registry and one or more remote consumable data databases to identify and download the local consumable data required for the conduct of the assay by the assay system using said assay consumable;
   said method comprising the steps of:
   (a) causing the DDB to be read from said assay consumable identifier to determine a specific assay protocol to be performed when conducting the assay;
   (b) causing the DDB to be stored to said consumable data repository;
   (c) causing the local consumable data to be identified from said consumable data repository and
   optionally, causing the local consumable data to be downloaded from one or more remote consumable data databases;
   (d) causing all or a portion of the plurality of steps of the generic assay protocol to be selected to be performed based on the specific assay protocol associated with the DDB; and
   (e) conducting said assay using said assay consumable.

15. The computer readable medium of claim 14, wherein the method further comprises the step of persisting one or more data files of the DDB to the storage medium.

16. The assay system of claim 15, wherein the one or more data files comprise a DDB unique identifier, a DDB version, consumable static information, consumable processing information, and combinations thereof.

17. The assay system of claim 16, wherein the consumable processing information comprises data used by the assay system in the conduct of the assay using a multi-well assay plate or the processing of assay data resulting from the conduct of the assay using the multi-well assay plate.

18. The assay system of claim 17, wherein the consumable processing information comprises the number of sectors per multi-well assay plate, the number of circuits per multi-well assay plate, detection parameters used by the assay system to read the multi-well assay plate; image processing properties use to produce ECL results; plate type gain; binding domain gain; optical cross talk matrix; and combinations thereof.

19. The assay system of claim 15, wherein the one or more data files comprise a DDB unique identifier, a DDB version, and consumable static information.

20. The assay system of claim 19, wherein the consumable static information comprises consumable type information.

21. The assay system of claim 14, wherein selecting all or a portion of a plurality of steps of the generic assay protocol includes selecting only a portion of the plurality of steps.

22. The assay system of any of claim 14, wherein the DDB comprises a DDB xml file including data description information and data processing information.

23. An automated assay system configured to use assay consumables in the conduct of an assay, said assay system comprises at least one processor and at least one storage medium,
   wherein said storage medium stores instructions to conduct said assay by said at least one processor,
   wherein said instructions are separated into a plurality of components, said plurality of components comprises:
   a security component,
   a user interface component,
   an instrument control component, and
   a data services component,
   wherein each component operates substantially independently of each other and has substantially no interaction with each other,
   wherein said plurality of components are connected to a master organizer and the master organizer instructs each component when to operate.

24. The assay system of claim 23, wherein the system comprises more than one component and an update to one component does not require a revalidation of all the components.

25. The assay system of claim 23, wherein the master organizer serves as a conduit to pass information among the plurality of components.

26. The assay system of any of claim 23, wherein at least one of said components is further separated into sub-components, wherein each sub-component operates substantially independently of each other and has substantially no interaction with each other, and wherein a sub-master organizer is connected to the sub-components and the sub-master organizer instructs each sub-component when to operate.

27. The assay system of claim 26, wherein an update to one sub-component does not require a revalidation of all the sub-components.

28. An assay system configured to use assay consumables in the conduct of a first assay, wherein the first assay comprises a unique assay identifier, said assay system comprises:
   a reader adapted to read the unique assay identifier, and
   a processor that accesses a general protocol file and an instrument parameter file,
   wherein the general protocol file contains a general assay protocol comprising assaying steps that are applicable to a plurality of assays including the first assay,
   wherein the instrument parameter file contains a plurality of flags that are either ON or OFF, and
   wherein the processor turns the assaying steps in the general assay protocol either ON or OFF according to said plurality of flags to conduct the first assay.

29. The assay system of claim 28, wherein the general assay protocol contains assaying steps for a V-PLEX assay.

30. The assay system of claim 28, wherein the general assay protocol contains assaying steps for a U-PLEX assay.

31. The assay system of claim 28, wherein the general assay protocol contains assaying steps for an immunogenicity assay.

32. The assay system of claim 28, wherein the general assay protocol contains assaying steps for a pharmacokinetic assay.

33. The assay system of claim 28, wherein the general assay protocol contains assaying steps for a custom sandwich assay.

* * * * *